US006756477B1

(12) United States Patent
Jiang et al.

(10) Patent No.: US 6,756,477 B1
(45) Date of Patent: Jun. 29, 2004

(54) COMPOSITIONS AND METHODS FOR THE THERAPY AND DIAGNOSIS OF BREAST CANCER

(75) Inventors: Yuqiu Jiang, Kent, WA (US); Davin C. Dillon, Issaquah, WA (US); Jennifer L. Mitcham, Redmond, WA (US); Jiangchun Xu, Bellevue, WA (US); Susan L. Harlocker, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/590,751

(22) Filed: Jun. 8, 2000

Related U.S. Application Data

(63) Continuation-in-part of application No. 09/551,621, filed on Apr. 17, 2000, which is a continuation-in-part of application No. 09/433,826, filed on Nov. 3, 1999, now Pat. No. 6,579,973, which is a continuation-in-part of application No. 09/389,681, filed on Sep. 2, 1999, now Pat. No. 6,518,237, which is a continuation-in-part of application No. 09/339,338, filed on Jun. 23, 1999, now Pat. No. 6,573,368, which is a continuation-in-part of application No. 09/285,480, filed on Apr. 2, 1999, now Pat. No. 6,590,076, which is a continuation-in-part of application No. 09/222,575, filed on Dec. 28, 1998, now Pat. No. 6,387,697.

(51) Int. Cl.[7] .......................... C07K 14/00; C07K 1/00; A61K 39/00

(52) U.S. Cl. ................. 530/350; 424/184.1; 424/185.1; 424/192.1; 424/277.1; 530/806; 530/828

(58) Field of Search .............................. 536/23.5, 23.1; 530/350, 806, 828; 424/184.1, 192.1, 277.1, 185.1

(56) References Cited

U.S. PATENT DOCUMENTS

| | | | |
|---|---|---|---|
| 5,215,926 A | 6/1993 | Etchells, III et al. | 436/501 |
| 5,240,856 A | 8/1993 | Goffe et al. | 435/299 |
| 5,891,857 A | 4/1999 | Holt et al. | |
| 5,986,170 A | 11/1999 | Subjeck | 800/2 |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/21331 | 5/1998 |
| WO | WO 98/33915 | 8/1998 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |
| WO | WO 01/51628 | 7/2001 |
| WO | WO 01/57270 | 8/2001 |
| WO | WO 02/59377 | 8/2002 |

OTHER PUBLICATIONS

L Anderson et al.,Electrophoresis, "A comparison of selected mRNA and protein abundances in human liver, "1997, 18,pp. 533–537.*

Genseq Database (Thomson Derwent), Accession No. AAL25059, Dec. 7, 2001.

Chang and Shu, "Current status of adoptive immunotherapy of cancer," *Critical Reviews in Oncology/Hematology* *22*(3):213–228, Apr. 1996.

Cheever and Chen, "Therapy with cultured T cells: principles revisited," *Immunological Reviews, 157*: 177–194, 1997.

Cheever et al., "Potential uses of interleukin 2 in cancer therapy," *Immunobiol, 172*:365–382, 1986.

Chen et al., "T–cells for tumor therapy can be obtained from antigen–loaded sponge implants," *Cancer Research* *54*(4):1065–1070, Feb. 15, 1994.

Cole et al., "Characterization of the functional specificity of a cloned T–cell receptor heterodimer recognizing the MART–1 melanoma antigent," *Cancer Research,* *55*:748–752, Feb. 15, 1995.

Durrant L., "Cancer vaccines," *Anti–Cancer Drugs,* *8*:727–733, 1997.

Eshhar Z., "Tumor–specific T–bodies: toward clinical application," *Cancer Immunol Immnother, 45*:131–136, 1997.

Hwu et al., "In vivo antitumor activity of T cells redirected with chimeric antibody/T–cell receptor genes," *Cancer Research, 55*:3369–3373, Aug. 1, 1995.

Porter–Jordan and Lippman, "Overview of the biologic markers of breast cancer," *Breast Cancer 8*:(1):73–100, Feb. 1994.

Wei et al., "Protection against mammary tumor growth by vaccination with full–length, modified human ErB–2 DNA," *Int. J. Cancer, 81*:748–754, 1999.

GenBank Accession No. AA864891, Feb. 20, 1998.

GenBank Accession No. AA398925, Apr. 25, 1997.

Geneseq Accession No. V84525 (Dec. 10, 1998).

Stratagene 1991 product catalog, Prime–It™ Random Labeling Kit, catalog No. 300387, p. 66.

GenBank Accession No. AC069200, May 24, 2000.

(List continued on next page.)

*Primary Examiner*—Sean McGarry
*Assistant Examiner*—Janet L. Epps-Ford
(74) *Attorney, Agent, or Firm*—Seed IP Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

9 Claims, 1 Drawing Sheet

OTHER PUBLICATIONS

Figure 1:
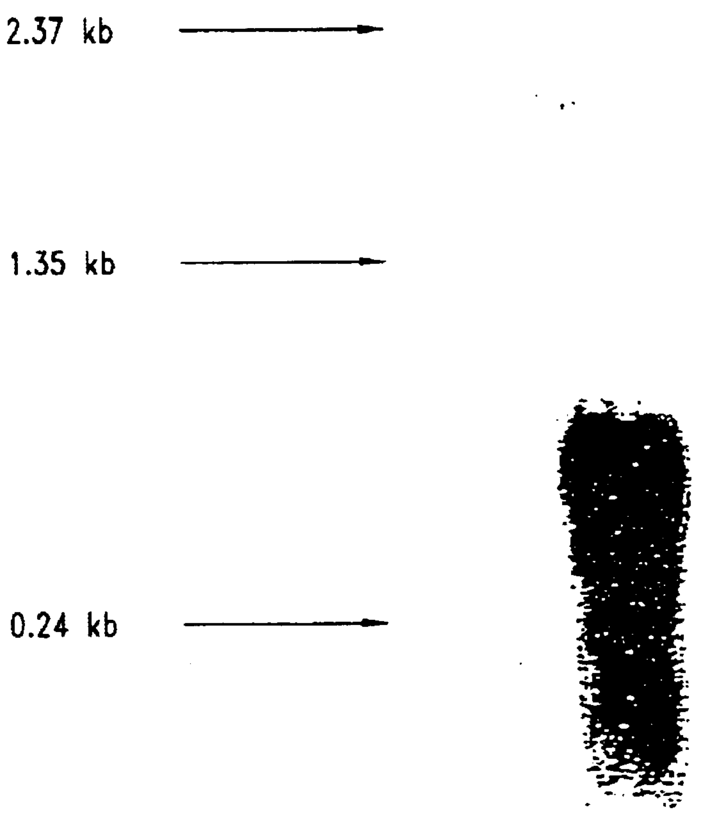

Sulston et al., "Toward a complete human genome sequence," *Genome Research 8*(11):1097–1108, 1998.
GenBank Accession No. AL157387, Feb. 18, 2000.
GenBank Accession No. AC036170, Apr. 9, 2000.
Jäger, D. et al, "Identification of a Tissue–specific Putative Transcription Factor in Breast Tissue by Serological Screening of a Breast Cancer Library," *Cancer Research 61*(5): 2055–2061, Mar. 1, 2001.
GenBank Accession No. AF269087, Mar. 28, 2001.
GenBank Accession No. AAK27325, Mar. 28, 2001.
GenBank Database, Accession No. AA219147, Feb. 7, 1997.
GenBank Database, Accession No. AI272025, Nov. 17, 1998.
GenBank Database, Accession No. AI687645, May 27, 1999.
GenBank Database, Accession No. AL049911, Oct. 22, 1999.
GenBank Database, Accession No. AQ280806, Nov. 22, 1998.
Geneseq (Derwent) Database, Accession No. AAV41453, Oct. 12, 1998.
Genseq (Derwent) Database, Accession No. AAV90219, Feb. 15, 1999.

* cited by examiner

SYN18C6 NORTHERN BLOT

SEQUENCE LISTING

```
<160> NUMBER OF SEQ ID NOS:  479

<210> SEQ ID NO 1
<211> LENGTH: 281
<212> TYPE: DNA
<213> ORGANISM: Homo sapien

<400> SEQUENCE: 1

caatgacagt caatctctat cgacagcctg cttcatattt agctattgtt cgtattgcct     60

tctgtcctag gaacagtcat atctcaagtt caaatgccac aacctgagaa gcggtgggct    120

aagataggtc ctactgcaaa ccacccctcc atatttccgt acgcaattac aattcagttt    180

ctgtgacatc tctttacacc actggaggaa aaatgagata ttctctgatt tattctacta    240

taacactcta catagagcta tggtgagtgc taaccacatc g                        281


<210> SEQ ID NO 2
<211> LENGTH: 300
<212> TYPE: DNA
```

-continued

<213> ORGANISM: Homo sapien

<400> SEQUENCE: 2
gaggtcctgg gctaacctaa tggtttatta ttggtggaga gaaagatctg gaaatacttg 60
aggttattac atactagatt agcttctaat gtgaaccatt tttcttttaa cagtgataaa 120
ttattatttc cgaagttaac tgttcccttg gtcgtgatac acactcgatt aacaaacata 180
ctgttgtatt ttttccagtt ttgtttggct atgccaccac agtcatcccc agggtctata 240
catactatgt ctcaactgta ttatttgcca tttttggcat tagaatgctt cgggaaggct 300

<210> SEQ ID NO 3
<211> LENGTH: 302
<212> TYPE: DNA
<213> ORGANISM: Homo sapien

<400> SEQUENCE: 3
ggccgaggta attggttaag tctaaagaga ttattattcc ttgatgtttg ctttgtattg 60
gctacaaatg tgcagaggta atacatatgt gatgtcgatg tctctgtctt ttttttgtc 120 tttaaaaaat aattggcagc aactgtattt gaataaaatg atttcttagt atgattgtac 180
agtaatgaat gaaagtggaa catgtttctt tttgaaaggg agagaattga ccatttattg 240
ttgtgatgtt taagttataa cttatcgagc acttttagta gtgataactg tttttaaact 300
tg 302

<210> SEQ ID NO 4
<211> LENGTH: 293
<212> TYPE: DNA
<213> ORGANISM: Homo sapien

<400> SEQUENCE: 4
tgtaccaatc ctttggcaca agaatatgta agaactatag ttgtttttat tggtttttgt 60
tcttgagatt gttttcattc tgtttttgac tgtatctctt taggaggctg aggatggcat 120
tattgcttat gatgactgtg gggtgaaact gactattgct tttcaagcca aggatgtgga 180
aggatctact tctcctcaaa tacgagataa ggcaagataa ttctgctcat tcgagagagg 240
gttaagagtt gtcatcttaa tcataaatcc tgcaggatgg gttcttcaaa ttt 293

<210> SEQ ID NO 5
<211> LENGTH: 275
<212> TYPE: DNA
<213> ORGANISM: Homo sapien

<400> SEQUENCE: 5
cgaggtttgg aatcagactt ctgtgtccag taaaaaactc ctgcactgaa gtcattgtga 60
cttgagtagt tacagactga ttccagtgaa cttgatctaa tttcttttga tctaatgaat 120
gtgtctgctt accttgtctc cttttaattg ataagctcca agtagttgct aattttttga 180
caactttaaa tgagtttcat tcacttcttt tacttaatgt tttaagtata gtaccaataa 240
tttcattaac ctgttctcaa gtggtttagc tacca 275

<210> SEQ ID NO 6
<211> LENGTH: 301
<212> TYPE: DNA
<213> ORGANISM: Homo sapien

<400> SEQUENCE: 6
gaggtctggt ttcctgggta tgcctggact gttgcccagt gtaagatctg tgcaagccat 60

-continued

```
attggatgga agtttacggc caccaaaaaa gacatgtcac ctcaaaaatt ttggggctta    120

acgcgatctg ctctgttgcc cacgatccca gacactgaag atgaaataag tccagacaaa    180

gtaatacttt gcttgtaaac agatgtgata gagataaagt tatctaacaa attggttata    240

ttctaagatc tgctttggaa attattgcct ctgatacata cctaagtaaa cataacatta    300

a                                                                    301
```

<210> SEQ ID NO 7
<211> LENGTH: 301
<212> TYPE: DNA
<213> ORGANISM: Homo sapien

<400> SEQUENCE: 7

```
gtccagtttg tacacagtga ttccttatgc acgccgaaag ggtttccgta aaaatgacat     60

tatatacaaa tctgtacacc catccaccag agcgattctc cagctcccag agggagttat    120

caacttaaag caggatacct gaggtttcat gtctttagtt gccttatcat aatcccaaat    180

atacatttca gggtttgttt ttgtttttaa agacactttc ctggaatatg tgcactatgg    240

ttaaaattaa aaacaaaagt aataaaataa aatgatcgct ggaaggactg acctccccac    300

c                                                                    301
```

<210> SEQ ID NO 8
<211> LENGTH: 301
<212> TYPE: DNA
<213> ORGANISM: Homo sapien

<400> SEQUENCE: 8

```
ctgtcctcat ctctgcaaag ttcagcttcc ttccccaggt ctctgtgcac tctgtcttgg     60

atgctctggg gagctcatgg gtggaggagt ctccaccaga gggaggctca ggggactggt    120

tgggccaggg atgaatattt gagggataaa aattgtgtaa gagccaaaga attggtagta    180

gggggagaac agagaggagc tgggctatgg gaaatgattt gaataatgga gctgggaata    240

tggctggata tctggtacta aaaaagggtc tttaagaacc tacttcctaa tctcttcccc    300

a                                                                    301
```

<210> SEQ ID NO 9
<211> LENGTH: 301
<212> TYPE: DNA
<213> ORGANISM: Homo sapien

<400> SEQUENCE: 9

```
gaggtctgcc taagtagagg acaaagactt cctcctttca aaggagaact gagcccagga     60

ttggtaagtt taaggcactt aaccttgacc agctctgtag gtctggagca ttctggtccc    120

tggccgcttt caccaccagg cccttctcac ttatccacct cacatactgc cccagcattc    180

ctttggcatt gcgagctgtg acttgacaca ttttaatgac aagattgaag tagctacctt    240

gcaggataga ttttctgggg tataggggac aaaccaacag tgccatcagg tgtcttaaca    300

c                                                                    301
```

<210> SEQ ID NO 10
<211> LENGTH: 301
<212> TYPE: DNA
<213> ORGANISM: Homo sapien

<400> SEQUENCE: 10

-continued ggcaggtcca acagttcttc cagttctggt cgagctttga atcgtccctt gaagtcttct 60
tcagtgtgct ccttcactga cagtctgact ccttcaggaa gactgctttg gattatttcc 120
aagaaaattt ctgcaaacgt agcactcaaa ccgctgatct gaaccactcg ctcatgggtg 180
gtaagcactg agtccaggag cattttgctg ccttggtcct gcaactgcaa cacttctatg 240
gttttggttg gcattgcata actttcctcg actttaatgg agagagattg cagaggttgt 300
g 301

<210> SEQ ID NO 11
<211> LENGTH: 301
<212> TYPE: DNA
<213> ORGANISM: Homo sapien

<400> SEQUENCE: 11
aggtctgtga ctttcaccca ggacccagga cgcagccctc cgtgggcact gccggcgcct 60
tgtctgcaca ctggaggtcc tccattacag aggcccagcg cacatcgctg gccccacaaa 120
cgttcagggg tacagccatg gcagctcctt cctctgccgt gagaaaagtg cttggagtac 180
ggtttgccac acacgtgact ggacagtgtc caattcaaat ctttcagggc agagtccgag 240
cagcgcttgg tgacagcctg tcctctcctg ctctccaaag gccctgctcc ctgtcctctc 300
t 301

<210> SEQ ID NO 12
<211> LENGTH: 301
<212> TYPE: DNA
<213> ORGANISM: Homo sapien

<400> SEQUENCE: 12
gaggtctggg attacaggca cgtgccacca cacctagcta atttttgagc atggggctca 60
aaggaactgc tctctggggc atgtcagatt tcggatttgg ggctgcacac tgatactctc 120
taagtggtgg aggaacttca tcccactgaa attcctttgg catttggggt tttgtttttc 180 ttttttttcct tcttcatcct cctcctttttt taaaagtcaa cgagagcctt cgctgactcc 240
accgaagaag tgcaccactg ggagccaccc cagtgccagg cgcccgtcca gggacacaca 300
c 301

<210> SEQ ID NO 13
<211> LENGTH: 256
<212> TYPE: DNA
<213> ORGANISM: Homo sapien

<400> SEQUENCE: 13 tttttggca taaaaaacac aatgatttaa tttctaaagc acttatatta ttatggcatg 60
gtttgggaaa caggttatta tattccacat aggtaattat gcagtgcttc tcatggaaaa 120
aatgcttagg tattggcctt ttctctggaa accatatttt tcctttttta ataatcaact 180
aaaatgtata tgttaaaaag cctcatcttt tgattttcaa tatacaaaat gctttcttta 240
aaagaacaag attcaa 256

<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc 60

-continued atcctctacc tttcctgtcc ccagaggtat gagatagacc ccctggcctg gttcctgcac 120
tgtgctaggc ccacagtgga cacttccacc ttaatggaga ataggcccca tggagtggag 180
gtccctcctc catggcctgc aacccaatga ctatgggggt gacacaagtg acctctgccc 240
tgtgatggct caacaccatc acacgcaact gtccagacaa gccccctcaa cgggctgctg 300
t 301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct 60
ctctttctgc ttttctgatc atcctaaagg ctgaatacat cctcctcctg tgtggaggac 120
acgaagcaat actaaaatca atacactcga tcaggtcttc atcagatacc acgtcactgt 180
gggtagagtg ctaattttca acaaatgtgg tgttcttagg gccccacaag gtagtccttt 240
ctcaaggtcg ctgggccac 259

<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc 60
agtgttattc agtgctatgc ctccttgtaa tgggtagtta ttaattattt tcagagcttt 120
ctggaaatac tgtcctaact ggctatgttt aggatctttg ttatctctga agacaaagaa 180
agaactagga ctcttaattt tggggtgctt cttgactctt agttgggaaa ctgaaaatat 240
ttccaacctt ttacccacgt caatggcata ttctgggaat caccaccacc accaccacta 300
c 301

<210> SEQ ID NO 17
<211> LENGTH: 301
<212> TYPE: DNA
<213> ORGANISM: Homo sapien

<400> SEQUENCE: 17
gcccgggcag gtctggggcc tagggtggct ctttgcaaag ctgaggggca agctaaggaa 60
gccaggcagg tcaggggccc tttcggcctt ctcaagcctc cacctgagtt ctcgtcaatg 120
ccagtctccc tggtatgatt ggggacatta tcagagaaac atctaatagc gcacatctgg 180
gcacccacac tctgcttcag ttgcatccat cctcccaccc caaattcaac tcctgaccca 240
atacaaaaga ctttttttaac caggatttct tcttgcagga aagctgactt ggaaacacgg 300
g 301

<210> SEQ ID NO 18
<211> LENGTH: 301
<212> TYPE: DNA
<213> ORGANISM: Homo sapien

<400> SEQUENCE: 18
attacaggca cgtgccacca cacctagcta atttttgagc atggggctca aaggaactgc 60

-continued

```
tctctggggc atgtcagatt tcggatttgg ggctgcacac tgatactctc taagtggtgg    120

aggaacttca tcccactgaa attcctttgg catttggggt tttgtttttc tttttttcct    180

tcttcatcct cctccttttt taaaagtcaa cgagagcctt cgctgactcc accgaagaag    240

tgcaccactg ggaccaccc agtgccaggc gcccgtccag ggacacacac agtcttcact    300

g                                                                   301
```

<210> SEQ ID NO 19
<211> LENGTH: 301
<212> TYPE: DNA
<213> ORGANISM: Homo sapien

<400> SEQUENCE: 19

```
agaatctctg cactgtcatc aggtacaaca aaagatcaaa cccctgtccc gatgttaact     60

ttttaactta aaagaatgcc agaaaaccca gatcaacact ttccagctac gagccgtcca    120

caaaggccac ccaaaggcca gtcagactcg tgcagatctt attttttaat agtagtaacc    180

acaatacaca gctctttaaa gctgttcata ttcttccccc attaaacacc tgccccgggc    240

ggccaagggc gaattctgca gatatccatc acactggcgg ccgctcgagc atgcatctag    300

a                                                                   301
```

<210> SEQ ID NO 20
<211> LENGTH: 290
<212> TYPE: DNA
<213> ORGANISM: Homo sapien

<400> SEQUENCE: 20

```
aggttttttt tttttttttt tttttttttt tttttccctt tcaattcatt taatttcaac     60

aatctgtcaa aaaacagcca ataaacaaat actgaattac attctgctgg gtttttttaaa    120

ggctctaaac tataaaaaca tcttgtgtct cccaccctga ccaccctgct acttttccat    180

ataccacagg ccacccataa acacaaagcc agggggtgaa gctgacatgg tctatttgga    240

gccagtaaac aggagggcga taagtcctga taagcactta tggacaatat              290
```

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag     60

actctttaaa aaaaaaaaat acccagggtt tgtcatcatt ttcagaggca gagtgccaaa    120

tatcacccaa agctcttgtg tctttttttt accccttat tttattttta tttattaatt    180

ttttgtgcaa acatcaaatg tcactggtgt tcacagaagg cttttttgac tagccttaaa    240

ttcctgagtc aaaagattaa tcagattttc aggcagtgtt taatcaggtg ctttgtcctg    300

t                                                                   301
```

<210> SEQ ID NO 22
<211> LENGTH: 301
<212> TYPE: DNA
<213> ORGANISM: Homo sapien

<400> SEQUENCE: 22

```
gacgccatgc accctccggt aaccagcagc cgcctgtcca tcccccaaga ccggaaaggc     60

agcagcagcc cccgggagcc cagggctgtc ctcggtgcat ctggctgcag agggaaattg    120
```

-continued

```
atgaccttac acagcaacta gcggccatgc agtccttcac tgacaagttc caggaccttt    180

gaagttggag ccagcgtccg gagctgcagc caagcgagtt tcctccttat cctccttagc    240

cagggctttt tctcttccgc tgcatttgcc cccttcccaa cgcaattcaa agcagttgtg    300

a                                                                     301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac     60

attatttgtc tgtcacagaa gagagctgct tatgattttg aaggggtcag ggagggtggg    120

agttggtaaa gagtagggta tttctataac agatattatt cagtcttatt tcctaagatt    180

ttgttgtaac ttaaggtatc ttgctacagt agacagaatt ggtaatagca acttttaaaa    240

ttgtcattag ttctgcaata ttagctgaaa tgtagtacag aaaagaatgt acatttagac    300

atttgggttc agttgcttgt agtctgtaaa tttaaaacag cttaatttgg tacaggttac    360

acatatggac ctcccgggcg g                                               381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg     60

caaagggtct cattggtcct gatgaataat cttgtgactg tacatattcc tgggtgcatg    120

tccacaaata ctgaggtata gcctgcatgc cactaaaaat aacaaaggtt tcaggggtgg    180

aaacattgtc caccacactg tcatgaccat cttt                                 214
```

<210> SEQ ID NO 25
<211> LENGTH: 302
<212> TYPE: DNA
<213> ORGANISM: Homo sapien

<400> SEQUENCE: 25

```
gggggcactg agaactccct ctggaattct tggggggtgt tggggagaga ctgtgggcct     60

ggagataaaa cttgtctcct ctaccaccac cctgtaccct agcctgcacc tgtcctcatc    120

tctgcaaagt tcagcttcct tccccaggtc tctgtgcact ctgtcttgga tgctctgggg    180

agctcatggg tggaggagtc tccaccagag ggaggctcag gggactggtt gggccaggga    240

tgaatatttg agggataaaa attgtgtaag aagccaaaga aattggtagt agggggggaga    300

ac                                                                    302
```

<210> SEQ ID NO 26
<211> LENGTH: 301
<212> TYPE: DNA
<213> ORGANISM: Homo sapien

<400> SEQUENCE: 26

```
ttggagaacg cgctgacata ctgctcggcc acagtcagtg aagctgctgc atctccatta     60

tgttgtgtca gagctgcagc caggattcga atagcttcag ctttagcctt ggccttcgcc    120
```

-continued

```
agaactgcac tggcctctcc tgctgcctga tttatctgtg cagccttttc tgcttcggag    180

gccaggatct gggcctgttt cttcccttct gccacattga tggccgactc tcgggtcccc    240

tcagactcta gaactgtggc ccgtttccgc cgctctgcct ccacctgcat ctgcatagac    300

t                                                                    301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg     60

accattttat tagacaccct ctattagtgt taacagacaa agatgaaggt taagttgaaa    120

tcaaattgaa atcatcttcc ctctgtacag attgcaatat ctgataatac cctcaacttt    180

cttggtgcaa attaattgcc tggtactcac agtccagtgt taacaggcaa taatggtgtg    240

attccagagg agaggactag gtggcaggaa aataaatgag attagcagta tttgacttgg    300

a                                                                    301
```

<210> SEQ ID NO 28
<211> LENGTH: 286
<212> TYPE: DNA
<213> ORGANISM: Homo sapien

<400> SEQUENCE: 28

```
tttttttttg cacaggatgc acttattcta ttcattctcc cccacccttc ccatatttac     60

atccttagag gaagagaggg gtaaggtgat aaagtaactg aaggaccgca agacgggtat    120

gtcccttgtt caccaaatgg tcaaagggtc aaagatcgga ggaggtcagg gggtaacgca    180

ggaacaggtg agggcgtttc gccctctctc cctctcccct tttcaacctc ttaatcactg    240

gctaactcgc gacctcatgg gttaattcgt aagcttacac gcgttg                   286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga     60

ttttcctttg ttcaaaggat ttattcctac catttcacaa atccgaaaat aattgaggaa    120

acaggttaca tcattccaat tttgccttgg gtttgaagag tctctcatgg tggcacagtc    180

ctccagggta gctatgttgt tgggctcccc tacatcccag aagctcagag actttgtcaa    240

aggtgtgccg tccacccatt gccactgacc ctcgacaacc tggtctgaca gtccaataaa    300

a                                                                    301
```

<210> SEQ ID NO 30
<211> LENGTH: 332
<212> TYPE: DNA
<213> ORGANISM: Homo sapien

<400> SEQUENCE: 30

```
gagcagaatt gatgcctatg gctccaagtc aaatactgct aatctcattt attttcctgc     60

cacctagtcc tctcctctgg aatcacacca ttattgcctg ttaacactgg actgtgagta    120

ccaggcaatt aatttgcacc aagaaagttg agggtattat cagatattgc aatctgtaca    180
```

-continued

```
gagggaagat gatttcaatt tgatttcaac ttaaccttca tctttgtctg ttaacactaa    240

tagagggtgt ctaataaaat ggtcaaattt gtgatctcat ttgttataac tagcactctt    300

ttcacagatg tgatgactga tttccagcag ac                                  332
```

<210> SEQ ID NO 31
<211> LENGTH: 141
<212> TYPE: DNA
<213> ORGANISM: Homo sapien

<400> SEQUENCE: 31

```
aaaggctatc aagtactttg aaggacagga aggaatgaac acacccaggt ggacgtttgg     60

tttcatttgc aggggttcag ggagggttgc aggggttcag ggagggctct tgtcccacaa    120

ccgggggaag ggagagggca c                                              141
```

<210> SEQ ID NO 32
<211> LENGTH: 201
<212> TYPE: DNA
<213> ORGANISM: Homo sapien

<400> SEQUENCE: 32

```
gagctgatct cacagcacat acagaatgat gctactatgt agaccctcac tcccttggga     60

aatctgtcat ctaccttaaa gagagaaaaa agatggaaca taggcccacc tagtttcatc    120

catccaccta cataaccaac atagatgtga ggtccactgc actgatagcc agactgcctg    180

gggtaaacct tttcagggag g                                              201
```

<210> SEQ ID NO 33
<211> LENGTH: 181
<212> TYPE: DNA
<213> ORGANISM: Homo sapien

<400> SEQUENCE: 33

```
tttcaaaaca ctcatatgtt gcaaaaaaca catagaaaaa taaagtttgg tgggggtgct     60

gactaaactt caagtcacag acttttatgt gacagattgg agcagggttt gttatgcatg    120

tagagaaccc aaactaattt attaaacagg atagaaacag gctgtctggg tgaaatggtt    180

c                                                                    181
```

<210> SEQ ID NO 34
<211> LENGTH: 151
<212> TYPE: DNA
<213> ORGANISM: Homo sapien

<400> SEQUENCE: 34

```
atgtcctgca cagtatagct tggacctctg ggcctgaacc agggtgagca tcaaggcccc     60

catttctcct caccacgggg tcgcttgtca gctccaagaa ccagtctggc cccactgaga    120

acttttcagt cgagggcctg atgaatcttg g                                   151
```

<210> SEQ ID NO 35
<211> LENGTH: 291
<212> TYPE: DNA
<213> ORGANISM: Homo sapien

<400> SEQUENCE: 35

```
tctttagggc aaaatcatgt ttctgtgtac ctagcaatgt gttcccattt tattaagaaa     60

agctttaaca cgtgtaatct gcagtcctta acagtggcgt aattgtacgt acctgttgtg    120
```

-continued

```
tttcagtttg tttttcacct ataatgaatt gtaaaaacaa acatacttgt ggggtctgat    180

agcaaacata gaaatgatgt atattgtttt ttgttatcta tttattttca tcaatacagt    240

attttgatgt attgcaaaaa tagataataa tttatataac aggttttctg t             291


<210> SEQ ID NO 36
<211> LENGTH: 201
<212> TYPE: DNA
<213> ORGANISM: Homo sapien

<400> SEQUENCE: 36

ctgatacaat tataataacg gttccctgaa ccttttagag tgcaattaag aacaaaaact     60

aaattttgtt tacatgaata tggaataaat acaataatca aaatatgact ctccctaaaa    120

gtgaaacaca caagccaatc cggaactgct gtgcgaaaga taaaatcgag aaaggcaagg    180

tttcggtagg aggacgcgat g                                              201


<210> SEQ ID NO 37
<211> LENGTH: 121
<212> TYPE: DNA
<213> ORGANISM: Homo sapien

<400> SEQUENCE: 37

catcacactg gcggccgctc gagcatgcat ctagagggcc caattcgccc tataatgagt     60

cgtattacaa ttcactggcc gtcgttttac aacgtcgtga ctgggaaaac cctggcgtta    120

c                                                                    121


<210> SEQ ID NO 38
<211> LENGTH: 200
<212> TYPE: DNA
<213> ORGANISM: Homo sapien

<400> SEQUENCE: 38

aaacatgtat tactctatat ccccaagtcc tagagcatga cctgcatgtt ggagatgttg     60

tacagcaatg tatttatcca gacatacata tatgatattt agagacacag tgattctttt    120

gataacacca cacatagaac attataatta cacacaaatt tatggtaaaa gaattaatat    180

gctgtctggt gctgctgtta                                                200


<210> SEQ ID NO 39
<211> LENGTH: 760
<212> TYPE: DNA
<213> ORGANISM: Homo sapien

<400> SEQUENCE: 39

gcgtggtcgt cggccgaggt cctgggctag acctaatggt ttattattgg tggagagaaa     60

gatctggaaa tacttgaggt tattacatac tagattagct tctaatgtga accatttttc    120

ttttaacagt gatcaaatta ttatttcgaa gttaatcgtt cccttggtgg ctgcatacac    180

atcgcattaa caaacatact gttgtatttt ttcccagttt tgtttggcta tgccaccaca    240

gtcatcccca gggtctatac atactatgtt tcaactgtat tatttgccat ttttggcatt    300

agaatgcttc gggaaggctt aaagatgagc cctgatgagg gtcaagagga actggaagaa    360

gttcaagctg aattaaagaa gaaagatgaa gaagtaagcc atggcactgt tgatctggac    420

caaaaaggca ctcaactagg aataaacact ctacagaggt ttctcagtgg ccccatctgt    480

gtgatatgcg gggctacaca aaaatagctt cttttgcttt gttctgttct tatacctgtc    540

tgtgatctga cttggggttg gtgtgaatgt agtagagaaa ggaagctgac agatgaatac    600
```

-continued tgaacacagg taatcagttt ccttaattag gttgattata agctcctgaa aagcaggaac 660
tgtattttat aattttacct gtttctcccg tggtgtctag gatagtaagt gagcagagca 720
gtaaatactg tttggtttgt tcagacctgc ccgggcggcc 760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgtttttct 60
tttattaaca ggaattttga ttcttcaagg aagtggctca atttcaattt caggtgacca 120
ggtttatcgt gacttttcct tcttgtttac ttttcgctag gaaggggagt tgtaggggca 180
gattcaggta ttggaatagg aaaattacgt ctaaaccatg gaaatcttgg aaatggaatt 240
ggtggaagtg ggcgaaatgg atatgggtaa gggaacacaa aaaaccctga agctaattca 300
tcgctgtcac tgatacttct tttttctcgt tcctggtctt gagagactgg gaaaccaaca 360
gccactgcca agatggctgt gatcaggagg agaactttct tcatctcaaa cgtttcagtc 420
agttctttct ctcacctcgg ccgcgaccac gc 452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc 60
aagatacata gcaatgatag caggtttctt tttaaagctt agtattaata ttaaatattt 120
ttccccattt aaattttaca ttacttgcca agaaaaaaaa aaaattaaaa ctcaagttac 180
ttgaagcctg gacacacttc catgattagc cgggctaggt aaaagttggt ggctttattc 240
ttcctgctct ataagcagat ccaggcccta gaaagatggg accagggtat ataattgttt 300
ttgaaaagtg tgctacaaaa atggatggcc tgttataagc caggatacaa agttaaggat 360
gggggtaagg gagggacatt ttcttccaga agaaaagaca gaatttctga agagtcccag 420
tccataattt tcccaaaatg gttggaggag agggtaaaat ctcaacatga gtttcaaagt 480
actgtctctg tgaggggccg gtagatgcct tgctgaggag ggatggctaa tttggaccat 540
gccccatccc cagctaggag aatggaaatg gaaactttaa ttgcccagtg ggtgtgaaag 600
tgggctgaag cttggttggt actgaattct ctaagaggtt tcttctagaa acagacaact 660
cagacctgcc cgggcg 676

<210> SEQ ID NO 42
<211> LENGTH: 468
<212> TYPE: DNA
<213> ORGANISM: Homo sapien

<400> SEQUENCE: 42
agcgtggtcg cggccgaggt ttggccggga gcctgatcac ctgccctgct gagtcccagg 60
ctgagcctca gtctccctcc cttggggcct atgcagaggt ccacaacaca cagatttgag 120
ctcagccctg gtgggcagag aggtagggat ggggctgtgg ggatagtgag gcatcgcaat 180
gtaagactcg ggattagtac acacttgttg attaatggaa atgtttacag atccccaagc 240

-continued

```
ctggcaaggg aatttcttca actccctgcc ccccagccct ccttatcaaa ggacaccatt    300

ttggcaagct ctatgaccaa ggagccaaac atcctacaag acacagtgac catactaatt    360

aaaacccccct gcaaagccca gcttgaaacc ttcacttagg aacgtaatcg tgtcccctat    420

cctacttccc cttcctaatt ccacagacct gcccgggcgg ccgctcga                 468


<210> SEQ ID NO 43
<211> LENGTH: 408
<212> TYPE: DNA
<213> ORGANISM: Homo sapien

<400> SEQUENCE: 43

atcatatcaa aacactatct tcccatctgt ttctcaatgc ctgctacttc ttgtagatat     60

ttcatttcag gagagcagca gttaaacccg tggattttgt agttaggaac ctgggttcaa    120

acctctttcc actaattggc tatgtctctg gacagttttt tttttttttt tttttttaa    180

acccttctg aactttcact ttctatggct acctcaaaga attgttgtga ggcttgagat    240

aatgcatttg taaagggtct gccagatagg aagatgctag ttatggattt acaaggttgt    300

taaggctgta agagtctaaa acctacagtg aatcacaatg catttacccc cactgacttg    360

gacataagtg aaaactagcc cgaagtctct ttttcaaatt acttacag                 408


<210> SEQ ID NO 44
<211> LENGTH: 160
<212> TYPE: DNA
<213> ORGANISM: Homo sapien

<400> SEQUENCE: 44

tggtcgcggc cgaggtcttg tgtgccctgt ggtccagggg accaagaaca acaagatcca     60

ctctctgtgc tacaatgatt gcaccttctc acgcaacact ccaaccagga ctttcaacta    120

caacttctcc gctttggcaa acaccgtcac tcttgctgga                         160


<210> SEQ ID NO 45
<211> LENGTH: 231
<212> TYPE: DNA
<213> ORGANISM: Homo sapien

<400> SEQUENCE: 45

cgagcggccg cccgggcagg tctggggagg tgattccatc cagagtcata tctgttgtca     60

ccccaataag tcgatcagca aggctgacag gctgtgagga aaccccggcc ttgtagcctg    120

tcacctctgg ggggatgatg actgcctggc agacgtaggc tgtgatagat ttgggagaaa    180

acctgactca ccctcaggaa tccggaggtc ggtgacattg tcggtgcaca c             231


<210> SEQ ID NO 46
<211> LENGTH: 371
<212> TYPE: DNA
<213> ORGANISM: Homo sapien

<400> SEQUENCE: 46

cccgggcagg tctgtgtaac atgccaaggc tttgcacttt ctgcagagca gttttttatt     60

ttccttatca ggtacaggtt ttggtttttc ttgactatct ctgatgaatt tttcatgagt    120

ctgtatatgc agaatctttt ccctaaatac tgcttcgtcc catgtctgaa ggcgtaaaat    180

aaagtcattc atcatttttt ctttgtacat gtttatttgt tctttttcaa ttacaccaag    240

cattactagt cagaaggaag cacttgctac ctcttgctct tcctctgcct ctggtttgga    300

tcattttgat gacattgccc acattactca tgaaggatga caagattgca ctgtgcaatg    360
```

-continued tcaattgcct t 371

<210> SEQ ID NO 47
<211> LENGTH: 261
<212> TYPE: DNA
<213> ORGANISM: Homo sapien

<400> SEQUENCE: 47
gccctgtttt tatacacttc acatttgcag aaatataatg atgccctcat tatcagtgag 60
catgcacgaa tgaaagatgc tctggattac ttgaaagact tcttcagcaa tgtccgagca 120
gcaggattcg atgagattga gcaagatctt actcagagat ttgaagaaaa gctgcaggaa 180
ctagaaagtg tttccaggga tcccagcaat gagaatccta aacttgaaga cctctgcttc 240
atcttacaag aagagtacca c 261

<210> SEQ ID NO 48
<211> LENGTH: 701
<212> TYPE: DNA
<213> ORGANISM: Homo sapien

<400> SEQUENCE: 48
cgagcggccc ccgggcaggt ccaattagta caagtctcat gatataatca ctgcctgcat 60
acatatgcac agatccagtt agtgagtttg tcaagcttaa tctaattggt taagtctcaa 120
agagattatt attcttgatg tttgctttgt attggctaac aaatgtgcag aggtaataca 180
tatgtgatgt ccgatgtctc tgtctttttt tttgtcttta aaaaataatt ggcagcaact 240
gtatttgaat aaaatgattt cttagtatga ttgtaccgta atgaatgaaa gtggaacatg 300
tttctttttg aaagggagag aattgaccat ttattattgt gatgtttaag ttataactta 360
ttgagcactt ttagtagtga taactgtttt taaacttgcc taataccttt cttgggtatt 420
gtttgtaatg tgacttattt aacccccttt tttgtttgtt taagttgctg ctttaggtta 480
acagcgtgtt ttagaagatt taaatttttt tcctgtctgc acaattagtt attcagagca 540
agagggcctg attttataga agccccttga aaagaggtcc agatgagagc agagatacag 600
tgagaaatta tgtgatctgt gtgttgtggg aagagaattt tcaatatgta actacggagc 660
tgtagtgcca ttagaaactg tgaatttcca aataaatttg a 701

<210> SEQ ID NO 49
<211> LENGTH: 270
<212> TYPE: DNA
<213> ORGANISM: Homo sapien

<400> SEQUENCE: 49
agcggccgcc cgggcaggtc tgatattagt agctttgcaa ccctgataga gtaaataaat 60
tttatgggcg ggtgccaaat actgctgtga atctatttgt atagtatcca tgaatgaatt 120
tatggaaata gatatttgtg cagctcaatt tatgcagaga ttaaatgaca tcataatact 180
ggatgaaaac ttgcatagaa ttctgattaa atagtgggtc tgtttcacat gtgcagtttg 240
aagtatttaa attaaccact cctttcacag 270

<210> SEQ ID NO 50
<211> LENGTH: 271
<212> TYPE: DNA
<213> ORGANISM: Homo sapien

<400> SEQUENCE: 50

-continued

```
atgcatttat ccatatgaac ttgattattc tgaattactg actataaaaa ggctattgtg     60

aaagatatca cactttgaaa cagcaaatga attttcaatt ttacatttaa ttataagacc    120

acaataaaaa gttgaacatg cgcatatcta tgcatttcac agaagattag taaaactgat    180

ggcaacttca gaattatttc atgaagggta caaacagtct ttaccacaat tttcccatgg    240

tcttatcctt caaaataaaa ttccacacac t                                   271
```

<210> SEQ ID NO 51
<211> LENGTH: 241
<212> TYPE: DNA
<213> ORGANISM: Homo sapien

<400> SEQUENCE: 51

```
tggtcgcggc cgaggtgtga ggagatgaac tttgtgttaa tggggggcac tttaaatcga     60

aatggcttat ccccaccgcc atgtaagtta ccatgcctgt ctcctccctc ctacacattt    120

ccagctcctg ctgcagttat tcctacagaa gctgccattt accagccctc tgtgattttg    180

aatccacgag cactgcaggc cctccacagc gttactaccc agcaggcact cagctcttca    240

t                                                                    241
```

<210> SEQ ID NO 52
<211> LENGTH: 271
<212> TYPE: DNA
<213> ORGANISM: Homo sapien

<400> SEQUENCE: 52

```
tccaagactt aaaacttagg aaacacctat gatgccactt taactggaag taatggagac     60

atctgattcc aaattcacat tttaaatgcc tatttgcaat cagcaaagag ccaggtatgc    120

tgcatgctgc ttgctgtaag ttacgatttg gcttcactag ctcaaatttt ttcactccac    180

caaaagataa ggcacaggcc cgtttgtcca atcaagtttg ctgaaaatac tgcagcctga    240

gtgtagacaa acttcccctg aatttgctag a                                   271
```

<210> SEQ ID NO 53
<211> LENGTH: 493
<212> TYPE: DNA
<213> ORGANISM: Homo sapien

<400> SEQUENCE: 53

```
ttagcgtggt cgcggtccga ggtctggcct gactagctca ctctgaagag tgtctttcac     60

atggattaac caaaaaatgc attactgcct ttggcacact gtcttgaata ttctttctga    120

caatgagaaa atatgattta atggagtcgt tcaataacct cacaatctcg ctgttccgag    180

cagatagttt tcgtgccaac aggaactggc acatctagca ggttcacggc atgacctttt    240

tgtggactgg ctggcataat tggaatgggt tttgattttt cttctgctaa taactcttca    300

agcttttgaa gttttcaagc attcctctcc agttgcctgt ggttggttct tgaacaccat    360

ctccaacccc accacctcca gatgcaacct tgtctcgtga tacagacctg cccgggcggc    420

cctcaagggc gaattctgca gatatccatc acactggcgg ccgctcgagc atgcatctag    480

agggcccaat tcg                                                       493
```

<210> SEQ ID NO 54
<211> LENGTH: 321
<212> TYPE: DNA
<213> ORGANISM: Homo sapien

<400> SEQUENCE: 54

-continued cgtggtcgcg gccgaggtct gtttgcttgt tggtgtgagt ttttcttctg gagactttgt 60
actgaatgtc aataaactct gtgattttgt taggaagtaa aactgggatc tatttagcca 120
ctggtaagct tctgaggtga aggattcagg gacatctcgt ggaacaaaca ctccccactg 180
gactttctct ctggagatac ccttttgaat atacaatggc cttggctcac taggtttaaa 240
tacaaacaag tctgaaaccc actgaagact gagagattgc agcaatattc tctgaattag 300
gatcgggttc cataactcta a 321

<210> SEQ ID NO 55
<211> LENGTH: 281
<212> TYPE: DNA
<213> ORGANISM: Homo sapien

<400> SEQUENCE: 55
ttgcaaatga aactgtggat gtataataag aaaacacaag ggtttattct taacactaaa 60
attaacatgc cacacgaaga ctgcattaca gctctctgtt tctgtaatgc agaaaaatct 120
gaacagccca ccttggttac agctagcaaa gatggttact tcaaagtatg gatattaaca 180
gatgactctg acatatacaa aaaagctgtt ggctggacct gtgactttgt tggtagttat 240
cacaagtatc aagcaactaa ctgttgtttc tccgaagatg g 281

<210> SEQ ID NO 56
<211> LENGTH: 612
<212> TYPE: DNA
<213> ORGANISM: Homo sapien

<400> SEQUENCE: 56
gcgtggtcgc ggccgaggtc ctgtccgggg gcactgagaa ctccctctgg aattcttggg 60
gggtgttggg gagagactgt gggcctggag ataaaacttg tctcctctac caccaccctg 120
taccctagcc tgcacctgtc ctcatctctg caaagttcag cttccttccc caggtctctg 180
tgccactctg tcttggatgc tctggggagc tcatgggtgg aggagtctcc accagaggga 240
ggctcagggg actggttggg ccagggatga atatttgagg gataaaaatt gtgtaagagc 300
caaagaattg gtagtagggg gagaacagag aggagctggg ctatgggaaa tgatttgaat 360
aatggagctg ggaatatggc tggatatctg gtactaaaaa agggtcttta agaacctact 420
tcctaatctc ttccccaatc caaaccatag ctgtctgtcc agtgctctct tcctgcctcc 480
agctctgccc caggctcctc ctagactctg tccctgggct agggcagggg aggagggaga 540
gcagggttgg gggagaggct gaggagagtg tgacatgtgg ggagaggacc agacctgccc 600
gggcggccgt cg 612

<210> SEQ ID NO 57
<211> LENGTH: 363
<212> TYPE: DNA
<213> ORGANISM: Homo sapien

<400> SEQUENCE: 57
gtcgcggccg aggtcctgag cgtcacccta gttctgcccc tttttagctg tgtagacttg 60
gacaagacat ttgacttccc tttctccttg tctataaaat gtggacagtg gacgtctgtc 120
acccaagaga gttgtgggag acaagatcac agctatgagc acctcgcacg gtgtccagga 180
tgcacagcac aatccatgat gcgttttctc cccttacgca ctttgaaacc catgctagaa 240
aagtgaatac atctgactgt gctccactcc aacctccagc gtggatgtcc ctgtctgggc 300

-continued

```
ccttttctg tttttattc tatgttcagc accactggca ccaaatacat tttaattcac    360

cga                                                                 363
```

<210> SEQ ID NO 58
<211> LENGTH: 750
<212> TYPE: DNA
<213> ORGANISM: Homo sapien

<400> SEQUENCE: 58

```
cgtggtcgcg gccgaggtct aattccacct gactggcaga acctgcgccc ctcgcctaac     60

ctgcgccctt ctcccaactc gcgtgcctca cagaacccag gtgctgcaca gccccgagat    120

gtggcccttc ttcaggaaag agcaaataag ttggtccaag tacttgatgc ttaaggaata    180

cacaaaggtg cccatcaagc gctcagaaat gctgagagat atcatccgtg aatacactga    240

tgtttatcca gaaatcattg aacgtgcatg ctttgtccta gagaagaaat ttgggattca    300

actgaaagaa attgacaaag aagaacacct gtatattctc atcagtaccc ccgagtccct    360

ggctggcata ctgggaacga ccaaagacac acccaagctc ggtctcttct tggtgattct    420

gggtgtcatc ttcatgaatg gcaaccgtgc cagtgaggct gtcttttggg aggcactacg    480

caagatggga ctgcgtcctg ggtgagaca tcccctccct tggagatcta aggaaacttc    540

tcacctatga gtttgtaaag cagaaatacc tggactacag acgagtgccc aacagcaacc    600

ccccggagta tgagttcctc tggggcctcc gtccctacca tgagactagc aagatgaaaa    660

tgctgagatt cattgcagag gttcagaaaa gagaccctcg tgactggact gcacagttca    720

tggaggctgc agatgaggac ctgcccgggc                                     750
```

<210> SEQ ID NO 59
<211> LENGTH: 505
<212> TYPE: DNA
<213> ORGANISM: Homo sapien

<400> SEQUENCE: 59

```
tggccgcccg ggcaggtcca gtctacaagc agagcactct catggggagc accagatgag     60

ttccagccgc agttctttta taagctttaa gtgcctcatg aagacgcgag gatctcttcc    120

aagtgcaacc tggtcacatc agggcacatt cagcagcaga agtctgtttc cagtatagtc    180

cttggtatgg ctaaattcca ctgtcccttt ctcagcagtc aataatccat gataaattct    240

gtacaacact gtagtcaata acagcagcac cagacagcat attaattctt ttaccataaa    300

tttgtgtgta attataatgt tctatgtgtg gtgttatcaa aagaatcact gtgtctctaa    360

atatcatata tgtatgtctg gataaataca ttgctgtaca acatctccaa catgcaggtc    420

atgctctaag acttggggat atagagtaat acatgtttcg tggacctcgg ccgcgaccac    480

gctaagggcg aattctgcag atatc                                          505
```

<210> SEQ ID NO 60
<211> LENGTH: 520
<212> TYPE: DNA
<213> ORGANISM: Homo sapien

<400> SEQUENCE: 60

```
cgtggtcgcg gccgaggtcc tcaggacaag gaaacaggta tcagcatgat ggtagcagaa     60

accttatcac caaggtgcag gagctgactt cttccaaaga gttgtggttc cgggcagcgg    120

tcattgcctg cccttgctgg agggctgatt ttagtgttgc ttattatgtt ggccctgagg    180

atgcttcgaa gtgaaaataa gaggctgcag gatcagcggc aacagatgct ctcccgtttg    240
```

-continued

```
cactacagct ttcacggaca ccattccaaa aaggggcagg ttgcaaagtt agacttggaa    300

tgcatggtgc cggtcagtgg gcacgagaac tgctgtctga cctgtgataa aatgagacaa    360

gcagacctca gcaacgataa gatcctctcg cttgttcact ggggcatgta cagtgggcac    420

gggaagctgg aattcgtatg acggagtctt atctgaacta cacttactga acagcttgaa    480

ggacctgccc gggcggccgc tcgaaagggg cgaattctgc                          520


<210> SEQ ID NO 61
<211> LENGTH: 447
<212> TYPE: DNA
<213> ORGANISM: Homo sapien

<400> SEQUENCE: 61

agagaggtgt ttttattctt tggggacaaa gccgggttct gtgggtgtag gattctccag     60

gttctccagg ctgtagggcc cagaggctta atcagaattt tcagacaaaa ctggaacctt    120

tctttttttcc cgttggttta tttgtagtcc ttgggcaaac caatgtcttt gttcgaaaga   180

gggaaaataa tccaaacgtt tttcttttaa cttttttttt aggttcaggg gcacatgtgt    240

aggcttgcta tataggtaaa ttgcatgtca ccagggtttg ttgtacagat tatttcatca    300

tccagataaa aagcatagta ccagataggt agttttttga tcctcaccct ccttccatgc    360

tccgacctca ggtaggcccc agtgtctgac ctgcccggcg gcccgctcga aagggccaat    420

tctgcagata tccatcacac tggccgg                                        447


<210> SEQ ID NO 62
<211> LENGTH: 83
<212> TYPE: PRT
<213> ORGANISM: Homo sapien

<400> SEQUENCE: 62

Lys Lys Val Leu Leu Leu Ile Thr Ala Ile Leu Ala Val Ala Val Gly
1               5                   10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys


<210> SEQ ID NO 63
<211> LENGTH: 683
<212> TYPE: DNA
<213> ORGANISM: Homo sapien

<400> SEQUENCE: 63

acaaagattg gtagctttta tatttttttta aaaatgctat actaagagaa aaaacaaaag    60

accacaacaa tattccaaat tataggttga gagaatgtga ctatgaagaa agtattctaa    120

ccaactaaaa aaaatattga aaccactttt gattgaagca aaatgaataa tgctagattt    180

aaaaacagtg tgaaatcaca ctttggtctg taaacatatt tagctttgct tttcattcag    240

atgtatacat aaacttattt aaaatgtcat ttaagtgaac cattccaagg cataataaaa    300

aaagwggtag caaatgaaaa ttaaagcatt tattttggta gttcttcaat aatgatrcga    360
```

-continued gaaactgaat tccatccagt agaagcatct ccttttgggt aatctgaaca agtrccaacc 420
cagatagcaa catccactaa tccagcacca attccttcac aaagtccttc cacagaagaa 480
gtgcgatgaa tattaattgt tgaattcatt tcagggcttc cttggtccaa ataaattata 540
gcttcaatgg gaagaggtcc tgaacattca gctccattga atgtgaaata ccaacgctga 600
cagcatgcat ttctgcattt tagccgaagt gagccactga acaaaactct tagagcacta 660
tttgaacgca tctttgtaaa tgt 683

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64
ctgttcattt gtccgccagc tcctggactg gatgtgtgaa aggcatcaca tttccatttt 60
cctccgtgta aatgttttat gtgttcgcct actgatccca ttcgttgctt ctattgtaaa 120
tatttgtcat ttgtatttat tatctctgtg ttttccccct aaggcataaa atggtttact 180
gtgttcattt gaacccattt actgatctct gttgtatatt tttcatgcca ctgctttgtt 240
ttctcctcag aagtcgggta gatagcattt ctatcccatc cctcacgtta ttggaagcat 300
gcaacagtat ttattgctca gggtcttctg cttaaaactg aggaaggtcc acattcctgc 360
aagcattgat tgagacattt gcacaatcta aaatgtaagc aaagtaagtc attaaaaata 420
caccctctac ttgggcttta tactgcatac aaatttactc atgagccttc ctttgaggaa 480
ggatgtggat ctccaaataa agatttagtg tttattttga gctctgcatc ttancaagat 540
gatctgaaca cctctccttt gtatcaataa atagccctgt tattctgaag tgagaggacc 600
aagtatagta aaatgctgac atctaaaact aaataaatag aaaacaccag gccagaacta 660
tagtcatact cacacaaagg gagaaattta aactcgaacc aagcaaaagg cttcacggaa 720
atagcatgga aaaacaatgc ttccagtgg 749

<210> SEQ ID NO 65
<211> LENGTH: 612
<212> TYPE: DNA
<213> ORGANISM: Homo sapien

<400> SEQUENCE: 65
acagcagcag tagatggctg caacaacctt cctcctaccc cagcccagaa aatatttctg 60
ccccacccca ggatccggga ccaaaataaa gagcaagcag gccccccttca ctgaggtgct 120 gggtagggct cagtgccaca ttactgtgct ttgagaaaga ggaaggggat ttgtttggca 180
ctttaaaaat agaggagtaa gcaggactgg agaggccaga gaagatacca aaattggcag 240
ggagagacca tttggcgcca gtcccctagg agatgggagg agggagatag gtatgagggt 300
aggcgctaag aagagtagga ggggtccact ccaagtggca gggtgctgaa atgggctagg 360
accaacagga cactgactct aggtttatga cctgtccata cccgttccac agcagctggg 420
tgggagaaat caccattttg tgacttctaa taaaataatg ggtctaggca acagttttca 480
atggatgcta aaacgattag gtgaaaagtt gatggagaat tttaattcag gggaattagg 540
ctgataccat ctgaaaccat ttggcatcat taaaaatgtg acaacctggt ggctgccagg 600

-continued

```
gaggaagggg ag                                                     612

<210> SEQ ID NO 66
<211> LENGTH: 703
<212> TYPE: DNA
<213> ORGANISM: Homo sapien

<400> SEQUENCE: 66

tagcgtggtc gcggccgagg tacattgatg ggctggagag cagggttggc agcctgttct    60

gcacagaacc aagaattaca gaaaaaagtc caggagctgg agaggcacaa catctccttg   120

gtagctcagc tccgccagct gcagacgcta attgctcaaa cttccaacaa agctgcccag   180

accagcactt gtgttttgat tcttcttttt tccctggctc tcatcatcct gcccagcttc   240

agtccattcc agagtcgacc agaagctggg tctgaggatt accagcctca cggagtgact   300

tccagaaata tcctgaccca caaggacgta acagaaaatc tggagaccca agtggtagag   360

tccagactga gggagccacc tggagccaag gatgcaaatg gctcaacaag gacactgctt   420

gagaagatgg gagggaagcc aagacccagt gggcgcatcc ggtccgtgct gcatgcagat   480

gagatgtgag ctggaacaga ccttcctggc ccacttcctg atcacaagga atcctgggct   540

tccttatggc tttgcttccc actgggattc ctacttaggt gtctgccctc aggggtccaa   600

atcacttcag gacaccccaa gagatgtcct ttagtctctg cctgaggcct agtctgcatt   660

tgtttgcata tatgagaggg tacctgcccg ggcggccgct cga                     703

<210> SEQ ID NO 67
<211> LENGTH: 1022
<212> TYPE: DNA
<213> ORGANISM: Homo sapien

<400> SEQUENCE: 67

cttgagaaag caggattgtt ttaagttcca agatttaaca aacttactgt tcagcatcat    60

attcaagcct aaaaggaaga taggattttc aagatatatt tccaacttct ttaacatggc   120

accatggatg aactgtttct cagcactgtg ctgcttcact tggaattaag gatgaattgg   180

gaggagacag tatgacatag gtgggtaggt tgggtggtga ggggaaccag ttctaatagt   240

cctcaactcc actccagctg ttcctgttcc acacggtcca ctgagctggc ccagtccctt   300

tcactcagtg tgtcaccaaa ggcagcttca aggctcaatg gcaagagacc acctataacc   360

tcttcacctt ctgctgcctc tttctgctgc cactgactgc catggccatc tgctatagcc   420

gcattgtcct cagtgtgtcc aggccccaga caaggaaggg gagccatggt gagactccaa   480

ttcccaggcc ttaatcctta accctagacc tgttgcctct agcatcattt atttatctac   540

ctacctaata gctatctacc agtcattaaa ccatggtgag attctaacca tgtctagcac   600

ctgatgctag agataatttt gttgaatccc ttcaattata aacagctgag ttagctggac   660

aaggactagg gaggcaatca gtattattta ttcttgaaca ccatcaagtc tagacttggt   720

ggcttcatat ttctatcata atccctgggg gtaagaaatc atatagcccc aggttgggaa   780

ggggaaaacg gtttgcaaca ttctcctcct tgtaggaggc gagctctgtc tcactagcta   840

tgcccctcca tcaattcacc ctatactcag atcagaagct gagtgtctga attacagtat   900

attttctaaa ttcctagccc ctgctggtga atttgccctc ccccgctcct ttgacaattg   960

tccccgtgtt cgtctccggg ccctgagact ggccctgctt atcttgctga ccttcatcct  1020

ct                                                                1022
```

-continued

<210> SEQ ID NO 68
<211> LENGTH: 449
<212> TYPE: DNA
<213> ORGANISM: Homo sapien

<400> SEQUENCE: 68
ccagatccat tttcagtggt ctggatttct ttttattttc ttttcaactt gaaagaaact 60
ggacattagg ccactatgtg ttgttactgc cactagtgtt caagtgcctc ttgttttccc 120
agagatttcc tgggtctgcc agaggcccag acaggctcac tcaagctctt taactgaaaa 180
gcaacaagcc actccaggac aaggttcaaa atggttacaa cagcctctac ctgtcgcccc 240
agggagaaag gggtagtgat acaagtctca tagccagaga tggttttcca ctccttctag 300
atattcccaa aaagaggctg agacaggagg ttattttcaa ttttattttg gaattaaata 360 ctttttttccc tttattactg ttgtagtccc tcacttggat atacctctgt tttcacgata 420
gaaataaggg aggtctagag cttctattc 449

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69
gcccttagcg tgggtcgcgg cncgangtct ggagcntatg tgatncctat ggtncncagg 60
cnnatactgc tantctcatt tattctcctg cnacctantc ctctnctctg gaatcacacc 120
attattgcct gttaacactg gactgtgagt accangcaat taatttgcac caanaaagtt 180
gagggtatta tcanatattg caatctgtac agagggaaga tgatttcaat ttgatttcaa 240
cttaaccttc atctttgtct gttaacacta atagagggtg tctaataaaa tggcaaattt 300
gngatctcat tnggtataac tacactcttt ttcacagatg tgatgactga atttccanca 360
acctgcccgg gcggncgntc naagggc 387

<210> SEQ ID NO 70
<211> LENGTH: 836
<212> TYPE: DNA
<213> ORGANISM: Homo sapien

<400> SEQUENCE: 70
tattccattt acaaaataaa ttcagccctg cactttcttt agatgccttg atttccagaa 60
tggagcttag tgctactgaa taccctggcc acagagccac ctcaggatat tcttttctcc 120
accctagttt atttatttat agatatctgt ttacaaagtc tgtagtaaat cctgatgctg 180
accatctgaa atgtactttt tttctgaatg ctgtttcaat ctaaaatagc agcttttgag 240
aaaacaatga tgtaaattcc ttatgataaa aggatgattc tatatattct ttaatgatat 300
taaatatgcc gaagccaagc acacagtctt tctaaagtgt gtgtatgttt gtgtgaatgt 360
gaatgatact gatcttatat ctgttaaaag ttgttttaaa aagctgtggc atcccattgt 420
tcatatttgc caagtcttct gtaaagatgt ctaggacgaa atattttatg tgctaatgca 480
tgtatttgta aaccagattt gtttaccact caaaattaac ttgttttctt catccaaaaa 540
agtttatttc ttccacgtac ttaaattttc tgtgtgggta taatatagct ttctaatttt 600
tttctttcac aaaggcaggt tcaaaattct gttgaaagaa aaatgctttc tgaaactgag 660

-continued

```
gtataacacc agagcttgct gtttaaagga ttatatgatg tacatcagtt ctataaatgt    720

gctcagcagt ttaacatgtg aatcctgttt taaagtgctc agatttcaac tgtgtaagcc    780

attgatataa cgctgtaatt aaaaatgttt atatgaaaaa aaaaaaaaaa aaaaaa        836
```

<210> SEQ ID NO 71
<211> LENGTH: 618
<212> TYPE: DNA
<213> ORGANISM: Homo sapien

<400> SEQUENCE: 71

```
gttgcagtga gctcaagtgt tgggtgtatc agctcaaaac accatgtgat gccaatcatc     60

tccacaggag caatttgttt accttttttt tctgatgctt tactaacttc atcttttaga    120

tttaaatcat tagtagatcc tagaggagcc agtttcagaa aatatagatt ctagttcagc    180

accacccgta gttgtgcatt gaaataatta tcattatgat tatgtatcag agcttctggt    240

tttctcattc tttattcatt tattcaacaa ccacgtgaca aacactggaa ttacaggatg    300

aagatgagat aatccgctcc ttggcagtgt tatactatta tataacctga aaaaacaaac    360

aggtaatttt cacacaaagt aatagatatc atgacacatt taaaataggg cactactgga    420

acacacagat aggacatcca ggttttgggt caatattgta gactttttgg tggatgagat    480

atgcaggttg atrccagaag gacaacaaaa acatatgtca gatagaaggg aggagcaaat    540

gccaagagct ggagctgagg aagatcactg tgaaattcta tgtagtctag ttggctggat    600

gctagagcaa agaggtgg                                                  618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctcccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                         806
```

<210> SEQ ID NO 73
<211> LENGTH: 301
<212> TYPE: DNA
<213> ORGANISM: Homo sapien
<220> FEATURE:
<221> NAME/KEY: misc_feature -continued
<222> LOCATION: (1)...(301)
<223> OTHER INFORMATION: n = A,T,C or G

<400> SEQUENCE: 73
actctggtaa gcttgttgtt gtccaagtga agctccctca gatgaggcgt gttggccana 60
gagccattgt caacagcaga gatgctgttg aaactcaatc ccaacttagc caaattattc 120
agtcctttca ggctagctgc atcaactctg ctgattttgt tgccatcaag atgtaattcc 180
gtaagggaag gaggaagacc ttgaggaatg ctggygatat tggyatcagc aatgcggatg 240
tasgaagagc ttcttcmttc cctggaaagc cccattttca atyccttgag ctcttcakcg 300
g 301

<210> SEQ ID NO 74
<211> LENGTH: 401
<212> TYPE: DNA
<213> ORGANISM: Homo sapien

<400> SEQUENCE: 74
agtttacatg atccctgtaa cagccatggt ctcaaactca gatgcttcct ccatctgcca 60
agtgtgttct ggatacagag cacatcgtgg cttctggggt cacactcagc ttaggctgtg 120
ggtccacaga gcactcatct ggctgggcta tggtggtggt ggctctactc aagaagcaaa 180
gcagttacca gcacattcaa acagtgtatt gaacatcttt taaatatcaa agtgagaaac 240
aagaaggcaa cataataatg ttatcagaaa gatgttagga agtaaggaca gctgtgtaaa 300
gcttgaggct gaaaagtagc ttgccagctt catttctttg gtttcttggg tagtgggccg 360
ccggaacagc aagatgtgag gttctggttc atggatcata t 401

<210> SEQ ID NO 75
<211> LENGTH: 612
<212> TYPE: DNA
<213> ORGANISM: Homo sapien

<400> SEQUENCE: 75
ttatttttca atttttattt tggttttctt acaaaggttg acattttcca taacaggtgt 60
aagagtgttg aaaaaaaaat tcaaattttt ggggagcgag ggaaggagtt aatgaaactg 120
tattgcacaa tgctctgatc aatccttctt tttctctttt gcccacaatt taagcaagta 180
gatgtgcaga agaaatggaa ggattcagct ttcagttaaa aaagaagaag aagaaatggc 240
aaagagaaag ttttttcaaa tttctttctt ttttaattta gattgagttc atttatttga 300
aacagactgg gccaatgtcc acaaagaatt cctggtcagc accaccgatg tccaaaggtg 360
caatatcaag gaagggcagg cgtgatggct tatttgtttt gtattcaatg attgtctttc 420
cccattcatt tgtcttttta gagcagccat ctacaagaac agtgtaagtg aacctgctgt 480
tgccctcagc aacaagttca acatcattag agccctgtag aatgacagcc tttttcaggt 540
tgccagtctc ctcatccatg tatgcaatgc tgttcttgca gtggtaggtg atgttctgag 600
aggcatagtt gg 612

<210> SEQ ID NO 76
<211> LENGTH: 844
<212> TYPE: DNA
<213> ORGANISM: Homo sapien

<400> SEQUENCE: 76
ggctttcgag cggccgcccg ggcaggtctg atggttctcg taaaaacccc gctagaaact 60

-continued

```
gcagagacct gaaattctgc catcctgaac tcaagagtgg agaatactgg gttgacccta    120

accaaggatg caaattggat gctatcaagg tattctgtaa tatggaaact ggggaaacat    180

gcataagtgc caatcctttg aatgttccac ggaaacactg gtggacagat tctagtgctg    240

agaagaaaca cgtttggttt ggagagtcca tggatggtgg ttttcagttt agctacggca    300

atcctgaact tcctgaagat gtccttgatg tgcagcykgc attccttcga cttctctcca    360

gccgagcttc ccagaacatc acatatcact gcaaaaatag cattgcatac atggatcagg    420

ccagtggaaa tgtaaagaag gccctgaagc tgatggggtc aaatgaaggt gaattcaagg    480

ctgaaggaaa tagcaaattc acctacacag ttctggagga tggttgcacg aaacacactg    540

gggaatggag caaaacagtc tttgaatatc gaacacgcaa tgctgttcct tgacattgca    600

ccaccaatgt ccagaggtgc aatgtcaagg aacggcaggc gagatggctt atttgttttg    660

tattcaatga ttgtcttgcc ccattcattt gtctttttgg agcagccatc gactaggaca    720

gagtaggtga acctgctgtt gccctcagca acaagttcca catcgttgga accctgcaga    780

agcacagcct tgttcaarct gcccgtctcc tcatccagat acctcggccg cgaccacgct    840

aatc                                                                  844
```

<210> SEQ ID NO 77
<211> LENGTH: 314
<212> TYPE: DNA
<213> ORGANISM: Homo sapien

<400> SEQUENCE: 77

```
ccagtcctcc acttggcctg atgagagtgg ggagtggcaa gggacgtttc tcctgcaata     60

gacacttaga tttctctctt gtgggaagaa accacctgtc catccactga ctcttctaca    120

ttgatgtgga aattgctgct gctaccacca cctcctgaag aggcttccct gatgccaatg    180

ccagccatcc tggcatcctg gccctcgagc aggctgcggt aagtagcgat ctcctgctcc    240

agccgtgtct ttatgtcaag cagcatcttg tactcctggt tctgagcctc catctcgcat    300

cggagctcac tcag                                                       314
```

<210> SEQ ID NO 78
<211> LENGTH: 548
<212> TYPE: DNA
<213> ORGANISM: Homo sapien

<400> SEQUENCE: 78

```
accaagagcc aagtgttaca caggatattt taaaaataaa atgtttttgg aatcctcacc     60

tcccatgcta tcttctaaga taactacaaa tattcttcaa agatttaact gagttctgcc    120

aaggacctcc caggactcta tccagaatga ttattgtaaa gctttacaaa tcccaccttg    180

gccctagcga taattaggaa atcacaggca aacctcctct ctcggagacc aatgaccagg    240

ccaatcagtc tgcacattgg ttttgttaga tactttgtgg agaaaaacaa aggctcgtga    300

tagtgcagct ctgtgcctac agagagcctc ccttttggtt ctgaaattgc tgatgtgaca    360

gagacaaagc tgctatgggt ctaaaacctt caataaagta actaatgaca ctcaaggtcc    420

tgggactctg agacagacgg tggtaaaacc cacagctgcg attcacattt ccaatttatt    480

ttgagctctt tctgaagctg ttgcttccta cctgagaatt cccatttaga gagctgcaca    540

gcacagtc                                                              548
```

<210> SEQ ID NO 79
<211> LENGTH: 646

-continued

<212> TYPE: DNA
<213> ORGANISM: Homo sapien

<400> SEQUENCE: 79
accccgtcac tatgtgaata aaggcagcta gaaaatggac tcaattctgc aagccttcat 60
ggcaacagcc catattaaga cttctagaac aagttaaaaa aaatcttcca tttccatcca 120
tgcatgggaa aagggcttta gtatagttta ggatggatgt gtgtataata ataaaatgat 180
aagatatgca tagtggggga ataaagcctc agagtccttc cagtatgggg aatccattgt 240
atcttagaac cgagggattt gtttagattg ttgatctact aattttttc ttcacttata 300
tttgaatttt caatgatagg acttattgga aattggggat aattctgttg tggtattaaa 360
taatattcat tttttaaaaa ctcatcttgg tattgagtta gtgcattgac ttccaatgaa 420
ttgacataag cccatatttc attttaacca gaaacaaaaa ctagaaaatg ttactcccta 480
aataggcaac aatgtatttt ataagcactg cagagattta gtaaaaaaca tgtatagtta 540
ctttagaaac aacttctgac acttgagggt tacccaatgg tctccttccc attctttata 600
tgaggtaaat gcaaaccagg gagccaccga ataaacagcc ctgagt 646

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80
gtctgaatga gcttcnctgc gagatggganc ancataaccc agaantccaa aancntanng 60
aacgnnaaaa cccgntngaa caagnaaacn gcaactnacg gccgcctgnt gnagggcgag 120
gacgcccacc tctcctcctc ccagttctcc tctggatcgc agncatccan agatgtgacc 180
tcttccagcc gccaaatccg caccaaggtc atggatgtgc acgatggcaa ggtgggtgtc 240
cacccacgaa caggtccttc gcaccaagaa ctgagg 276

<210> SEQ ID NO 81
<211> LENGTH: 647
<212> TYPE: DNA
<213> ORGANISM: Homo sapien

<400> SEQUENCE: 81
gtcctgcctt tcatcttttc tttaaaaaaa ataaatgttt acaaaacatt tccctcagat 60
tttaaaattc atggaagtaa taaacagtaa taaaatatgg atactatgaa aactgacaca 120
cagaaaaaca taaccataaa atattgttcc aggatacaga tattaattaa gagtgacttc 180
gttagcaaca cgtagacatt catacatatc cggtggaaga ctggtttctg agatgcgatt 240
gccatccaaa cgcaaatgct tgatcttgga gtaggrtaat ggccccagga tcttgcagaa 300
gctctttatg tcaaacttct caagttgatt gacctccagg taatagtttt caaggttttc 360
attgacagtt ggtatgtttt taagcttgtt ataggacaga tccagctcaa ccagggatga 420
cacattgaaa gaatttccag gtattccact atcagccagt tcgttgtgag ataaacgcag 480
atactgcaat gcattaaaac gcttgaaata ctcatcaggg atgttgctga tcttattgtt 540
gtctaagtag agagttagaa gagagacagg gagaccagaa ggcagtctgg ctatctgatt 600
gaagctcaag tcaaggtatt cgagtgattt aagaccttta aaagcag 647

-continued

<210> SEQ ID NO 82
<211> LENGTH: 878
<212> TYPE: DNA
<213> ORGANISM: Homo sapien

<400> SEQUENCE: 82
ccttctttcc ccactcaatt cttcctgccc tgttattaat taagatatct tcagcttgta 60
gtcagacaca atcagaatya cagaaaaatc ctgcctaagg caaagaaata taagacaaga 120
ctatgatatc aatgaatgtg ggttaagtaa tagatttcca gctaaattgg tctaaaaaag 180
aatattaagt gtggacagac ctatttcaaa ggagcttaat tgatctcact tgttttagtt 240
ctgatccagg gagatcaccc ctctaattat ttctgaactt ggttaataaa agtttataag 300
atttttatga agcagccact gtatgatatt ttaagcaaat atgttattta aaatattgat 360
ccttcccttg gaccaccttc atgttagttg ggtattataa ataagagata caaccatgaa 420
tatattatgt ttatacaaaa tcaatctgaa cacaattcat aaagatttct cttttatacc 480
ttcctcactg gccccctcca cctgcccata gtcaccaaat tctgttttaa atcaatgacc 540
taagatcaac aatgaagtat tttataaatg tatttatgct gctagactgt gggtcaaatg 600
tttccatttt caaattattt agaattctta tgagtttaaa atttgtaaat ttctaaatcc 660
aatcatgtaa aatgaaactg ttgctccatt ggagtagtct cccacctaaa tatcaagatg 720
gctatatgct aaaaagagaa aatatggtca agtctaaaat ggctaattgt cctatgatgc 780
tattatcata gactaatgac atttatcttc aaaacaccaa attgtcttta gaaaaattaa 840
tgtgattaca ggtagagaac ctcggccgcg accacgct 878

<210> SEQ ID NO 83
<211> LENGTH: 645
<212> TYPE: DNA
<213> ORGANISM: Homo sapien

<400> SEQUENCE: 83
acaaacattt tacaaaaaag aacattacca atatcagtgg cagtaagggc aagctgaaga 60
ataaatagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacgct atttcccatc 300
taaactcatt taagccttca caatgtcgca atggattcag ttacttgcaa acgatcccgg 360
gttgtcatac agatacttgt ttttacacat aacgctgtgc catcccttcc ttcactgccc 420
cagtcaggtt tcctgttgtt ggaccgaaag gggatacatt ttagaaatgc ttccctcaag 480
acagaagtga gaaagaaagg agaccctgag gccaggatct attaaacctg gtgtgtgcgc 540
aaaagggagg gggaaggcag gaatttgaaa ggataaacgt ctcctttgcg ccgaggaatc 600
aggaagcgtg actcacttgg gtctgggacg ataccgaaat ccggt 645

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

-continued

```
tctgatgtca atcacaactt gaaggatgcc aatgatgtac caatccaatg tgaaatctct     60

cctcttatct cctatgctgg agaaggatta gaaggttatg tggcagataa agaattccat    120

gcacctctaa tcatcgatga gaatggagtt catgggctgg tgaaaaatgg tatttgaacc    180

agataccaag ttttgtttgc cacgatagga atagctttta tttttgatag accaactgtg    240

aacctacaag acgtcttgga caactgaagn ttaaatatcc acangggttt attttgcttg    300

g                                                                    301
```

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

```
agcgtgggtc gcggcncgan gtagagaacc gactgaaacg tttgagatga agaaagttct     60

cctcctgatc acagccatct tggcagtggc tgttggtttc ccagtctctc aagaccagga    120

acgagaaaaa agaagtatca gtgacagcga tgaattagct tcagggtttt ttgtgttccc    180

ttacccatat ccatttcgcc cacttccacc aattccattt ccaagatttc catggtttan    240

acgtaatttt cctattccaa tacctgaatc tgcccctaca actccccttc ctagcg        296
```

<210> SEQ ID NO 86
<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctcccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                         806
```

<210> SEQ ID NO 87
<211> LENGTH: 620
<212> TYPE: DNA
<213> ORGANISM: Homo sapien

<400> SEQUENCE: 87

-continued

```
tttttgcatc agatctgaaa tgtctgagag taatagtttc tgttgaattt ttttttgttc     60

atttttctgc acagtccatt ctgtttttat tactatctag gcttgaaata tatagtttga    120

aattatgaca tccttcctct ttgttatttt cctcatgatt gctttggcta ttcaaagttt    180

attttagttt catgtaaatt tttgaattgt attttccatt attgtgaaaa tagtaccact    240

gcaattttaa taggaagttt attgaatcta tagattactt tggataatat ggcacttcaa    300

taatattcat gttttcaatt catagacaaa atattttaaa atttatttgt atcttttcta    360

atttttcctt tttttattgt aaagatttac ctccttggtt aatattttcc tcagaaattt    420

attatttaag gtatagtcaa taaaattttc ttcctctatt ttgtcagata gtttaagtgt    480

atgaaaccat agatatactt gtatgttaat tttatatttt gctaatttac tgagtgtatt    540

tattagttta gagaggtttt aatgtactgt ttatggtttt ttaaatataa gattacttat    600

tttttaaaaa aaaaaaaaaa                                                620
```

```
<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

tagctgtgnt cagcaggccg aggttttttt tttttttgag atggagtctc gccctgtcac     60

ccaggctgga gtgcagtggc ctgatctcag ctcactgcaa gctccacctc ctggattcac    120

gctattctcc tgcctcagcc tcccaagtag ctgggactac aggcgcccgc caccacgccc    180

agctaattnt ttgnattttt agtacnagat gcggtttcat cgtgttagcc agcatggnct    240

cgatctcctg acctcgtgaa ctgcccgcct cggcctccca aagacctgcc cgggcnggcc    300

gctcgaaa                                                             308
```

```
<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89

agcggccgcc cgggcaggtc tgttaagtaa catacatatc accttaataa aaatcaagat     60

gaaatgtttt agaaactatt ttatcaaaag tggctctgat acaaagactt gtacatgatt    120

gttcacagca gcactattaa tgccaaaaag tagacaaaac ctaaatgtcc attaactgat    180

aagcaaaatg tggtatatcc atacaatgga atattatgta gcccacaaca tggcatggag    240

tactacaaca tggatgagcc tcaaaaacgt tatgctaaat gaaaaaagtc agatatagga    300

aaccacatgt catatgatcc catttatatg aaatagccag aaaaggcaag tcatagaaac    360

aagatagatc ggaaaatggg ttggaggact acaaatggca ccagggatct ttgaagttga    420

tggaaatggt ctaaaatcag actgtggntg tggttgaaca agtctgtaaa tttaccaaaa    480

tgcgttaata ca                                                        492
```

```
<210> SEQ ID NO 90
<211> LENGTH: 390
```

-continued

<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90
tcgagcggcc gcccgggcag gtacaagctt tttttttttt tttttttttt ttttctaaca 60
gttctctgtt ttattgcaat acagcaaagt ctggttaata ttaagngata tcaacataaa 120
gtattggtga ggagtctttt gtgacatttt ttaccatccc accttaaata tttctgtgca 180
aaanaatcca catcattgtt tggtancana ggatctctta aaaagttccc taanacactg 240
agggcataaa accaaacaaa ataaaataag gagtgatagg ctaaagcagt atcttcccct 300
ccatccacat ttgncaagca ttatattcta accaaaaaat gatcacacca ggccatgcaa 360
aactgtccaa tattaccgag aaaaaaccct 390

<210> SEQ ID NO 91
<211> LENGTH: 192
<212> TYPE: DNA
<213> ORGANISM: Homo sapien

<400> SEQUENCE: 91
agcgtggtcg cggccgaggt ctgtcaatta atgctagtcc tcaggattta aaaaataatc 60
ttaactcaaa gtccaatgca aaaacattaa gttggtaatt actcttgatc ttgaattact 120
tccgttacga aagtccttca catttttcaa actaagctac tatatttaag gcctgcccgg 180
gcggccgctc ga 192

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92
agcgtggtcg cggccgaggt ctgacaacta acaaagaagc aaaaactggc atcttggaca 60
tcctagtatt acacttgcaa gcaattagaa cacaaggagg gccaaggaaa aagtttagct 120
ttgaatcact tccaaatcta ctgattttga ggttccgcag tagttctaac aaaacttttc 180
agacaatgtt aactttcgat taagaaagaa aaaaaacccca aacatcttca ggaattccat 240
gccaggttca gtctcttcca gtgagcccgc ttgctaaaag tccacgtgca ccattaatta 300
gctgggctgg cagcaccatg taaaaagaag cctattcacc accaaccaca cagactagac 360
atgtaaagta ggatcaagta atggatgaca accatggtcg tggaatatgg tcaatgagag 420
tcagaaaagt acaggcacca gtacaagcag cagataacag aattgacggg ccaaaggata 480
aaaataggct tatttaaata ggatgctaca gaacacatnc acttctaatt ggaagctgct 540
ttacactggg tggcattgna ccatatgcat 570

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)

-continued

<223> OTHER INFORMATION: n = A,T,C or G

<400> SEQUENCE: 93
tcgagcggcc gcccgggcag gtccaggttt ttatttagtt gtgtaatctt ggacaagtta 60
cctaactttt ttgagtctga atatatttaa tctgcaaaat gagaatcatg ataatacgtc 120
ataggcttaa ttaggaggat taaatgaaat aatttatagg tggtgccatg gttacataca 180
agtattagta gttaattctt ttcctttgtt tacttttata gtataggttg gatgaaggtt 240
ccagtatagg caaaaatact acttggggggt aaagtagagt gtgatacttt atttgaaatg 300
ttccctgaat ctgatcttta ctttttgnta ctgctgcact acccaaatcc aaattttcat 360
cccaacattc ttggatttgt gggacagcng tagcagcttt tccaatataa tctatactac 420
atcttttctt actttggtgc tttttg 446

<210> SEQ ID NO 94
<211> LENGTH: 409
<212> TYPE: DNA
<213> ORGANISM: Homo sapien

<400> SEQUENCE: 94
cgagcggccg cccgggcagg tccatcagct cttctgctta gaatacgagg cagacagtgg 60
agaggtcaca tcagttatcg tctatcaggg tgatgaccca agaaaggtga gtgagaaggt 120
gtcggcacac acgcctctgg atccacccat gcgagaagcc ctcaagttgc gtatccagga 180
ggagattgca aagcgccaga gccaacactg accatgttga aggcgttctc tccaggctgg 240
attcactgca ctcggaagaa ttctgcccag ggaatttagt gtgggggtac caggaccagt 300
ttgtcttgat cttgagaccc ccagagctgc tgcatccata gggtgttgca ggactacacc 360
tggcctgcct tgcagtcatt ctttcttata tgttgaccca tttgcccaa 409

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95
tcgagcggcc gcccgggcag gtcctacttg tttgcagctt ccacacactg cacctaccta 60
ctacctctct tccatgctta actgggttta gaaaggtgag ctatgcgtag aagaactact 120
tgggatattc aagtgctgta tttgaacgat aagcctatag ataacagtct gaagctgcaa 180
gggagacttt gttagtacac tactataaac aggtaaacta cctgtttgta cttgatatag 240
tgcatatgaa atgactgatt taatacaaaa ctacagaaca tgcaaaattt tttctgagat 300
gttaagtatt acttcagtgg agaacaaaac ttacttaacc tttcgctaat gcatgtagta 360
ccagaaagca aacatggttt tagcttcctt tactcaaaat atgaacatta agtggttgtg 420
aattttgtct gccaagtggt tcagaaaata cattataaat aacctaagtt aaaaaaaaga 480 aactgngaac 490

<210> SEQ ID NO 96
<211> LENGTH: 223
<212> TYPE: DNA
<213> ORGANISM: Homo sapien

<400> SEQUENCE: 96

-continued agcgtggtcg cggccgaggt ctggaagccc accctaggac ttgaatggca ccttgtcctt 60
tctctgccag taatgcaatc caacacaata tgctacaggg aaaacagaat ttccacggtg 120
ccgccctctg gtacaaggga aacagcacgc aaagcaaaag gccacagagg gctccctgag 180
aatccagtac aactaagcga ggacctgccc gggcggccgc tcg 223

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97
tcgagcggcc gcccgggcag gtctgtgcag gagacactga agtgggtagt gtccataatc 60
tttttagcct gttgctgaaa ttccagttgt actccttcaa accaaaatgc ttacaggatc 120
atgggaaagc ctcggttgca gaaatcaaga caggcaagtg ggaagataac tcggctttga 180
ggttaaacag atctgggttc aaagcatagt ttcactctct gtcttgtgaa gtgtcctggg 240
tgaagtcatt tcctctcttg aatttcagag aggatgaaaa tataaaaagt ataataacta 300
tcttcataat ctttgtgagg attaaagaag acgaagtgtg tgaaaagcta agcacagagc 360
aggcattcta caataagtag ttattatttt tggaaccatc ccgnccctag ccccagccca 420
attaccttct cttagnctct tcatatcgaa ngccgtaatc ttgaccttct cttgcnactg 480
gattggtgct ggttgatgcc caaacttccc gagatgctgt ctgggaa 527

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98
tcgagcggcc gcccgggcag gtctggctcc catggccctt ggggtggcct gactctgtca 60
ctattcctaa aaccttctag gacatctgct ccaggaagaa ctttcaacac caaaattcat 120
ctcaatttta cagatgggaa aagtgattct gagaccagac cagggtcagg ccaaggtcat 180
ccagcatcag tggctgggct gagactgggc ccagggaacc ctgtctgctc ctctttttcc 240
cagagctgtg agttctctag ccaaggctgc actcttgagg gagagccagg aagcatagct 300
gaggccatga caacctcact cttcacctga aaatttaacc cgtggcagag gatccaggca 360
catataggct tcggagccaa acaggacctc ggccgcgacc acgctaagcc gaattccagc 420
acactggcgg ccgttactag tggatcccga gcttnggtac caagcttggc gtaatcatgg 480
gcatagctgg ttcctggggt gaaaatggta tccg 514

<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G -continued

<400> SEQUENCE: 99
tcgagcggcc gcccgggcag gtctgaagaa acaggtataa atttggcagc cagtaatttt 60
gacagggaag ttacagcttg catgacttta aatatgtaaa tttgaaaata ctgaatttcg 120
agtaatcatt gtgctttgtg ttgatctgaa aaatataaca ctggctgtcg aagaagcatg 180
ttcaaaaata tttaattcac ttcaaaatgt catacaaatt atggtggttt ctatgcaccc 240
ctaaagcttc aagtcattta gctcaggtac atactaaagt aatatattaa ttcttccagt 300
acagtggtgt ttcataccat tgacatttgc ataccctaga ataatttaag aaagacatgt 360
gtaatattca caatgttcag aaaagcaagc aaaaggtcaa ggaacctgct ttggttcttc 420
tggagatggn ctcatatcag cttcataaac attcattcta caaaatagta agctaaccat 480
ttgaacccca atttccagat taagcatatt ttctcataaa tnatgaagcc 530

<210> SEQ ID NO 100
<211> LENGTH: 529
<212> TYPE: DNA
<213> ORGANISM: Homo sapien

<400> SEQUENCE: 100
agcgtggtcg cggccgaggt ccaggcacgg tggcttatgt gtgtaatccc agcacttggg 60
gaggctgagg gaggtggatc acttgagtcc aggagtttga gaccagtctg ggcaacatgg 120
cgaaacttca tcactaccaa agaagaaaaa aattagccag gtgtggtggt gtatgcctgt 180
agtcccagat actctggtgg ctgaggtgag aggatagctt gagcccagga aattgaggct 240
gcagtgaact atgattgcac tactgtgctc cagcttgggc aacagagtga gatcttgtct 300
ccaaaagtcc ttgaaggatt ttaggaagtt gttaaaagtc ttgaaacgat gtttgggggc 360
atgttagggt tcttgaatgt ttaattcctc taataactgc ttattcaaga gaagcatttc 420
tgactgggtg cggggcagtg gcttcatgcc ccataatccc agtactttgg gaggctgaag 480
caggaacatt gcttgagccc aggacttcaa gaacagcctg ggtaacata 529

<210> SEQ ID NO 101
<211> LENGTH: 277
<212> TYPE: DNA
<213> ORGANISM: Homo sapien

<400> SEQUENCE: 101
tcgagcggcc gcccgggcag gtcgcaggaa gaggatggaa actgaggagt ccaggaagaa 60
gagggaacga gatcttgagc tggaaatggg agatgattat attttggatc ttcagaagta 120
ctgggattta atgaatttgt ctgaaaaaca tgataagata ccagaaatct gggaaggcca 180
taatatagct gattatattg atccagccat catgaagaaa ttggaagaat tagaaaaaga 240
agaagagctg agaacagacc tcggccgcga ccacgct 277

<210> SEQ ID NO 102
<211> LENGTH: 490
<212> TYPE: DNA
<213> ORGANISM: Homo sapien

<400> SEQUENCE: 102
gcgtggtcgc ggccgaggtc tgacggcttt gctgtcccag agccgcctaa acgcaagaaa 60
agtcgatggg acagttagag gggatgtgct aaagcgtgaa atcagttgtc cttaattttt 120
agaaagattt tggtaactag gtgtctcagg gctgggttgg ggtccaaagt gtaaggaccc 180
cctgccctta gtggagagct ggagcttgga gacattaccc cttcatcaga aggaattttc 240

-continued ggatgttttc ttgggaagct gttttggtcc ttggaagcag tgagagctgg gaagcttctt 300
ttggctctag gtgagttgtc atgtgggtaa gttgaggtta tcttgggata aagggtcttc 360
tagggcacaa aactcactct aggtttatat tgtatgtagc ttatattttt tactaaggtg 420
tcaccttata agcatctata aattgacttc tttttcttag ttgtatgacc tgccccgggc 480
ggccgctcga 490

<210> SEQ ID NO 103
<211> LENGTH: 490
<212> TYPE: DNA
<213> ORGANISM: Homo sapien

<400> SEQUENCE: 103
gagcggccgc ccgggcaggt ccaaaccagc ttgctcataa gtcattaacc aaatccatta 60
taggtaattt gttcagttca atgtttacaa ttcttatgga aaaaattagc aacacacaca 120
tttaaaacgt gtgcatttac ctttgcgtga gtgcttaaaa tacatatttc tatttcaaga 180
tgacatttaa aaattattct aatatatcag cagcaaaaat ataatttgca attacaaaaa 240
actaaactag aatccttaag ttattctcat gtttacagtt gtgattcttt aataaatact 300
attatgcagc tctattgttt aagctttctg gatttggttt aaacacatgc atatatattg 360
tcaattgtgg gaagctttac aagttatatt ccatgcactt tttggacaga gttctaacag 420
agccagccag tccacaaaac aggcaagaca aaagttgaat taactggggc aaaataggac 480
tcttatgcaa 490

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct 60
cggcctccca aagtgttggg attacaggca tgagccactg cgcccgaccg agttgaacat 120
ttaatgtcag actaggccag agtttctcaa tctttttatt ctcacttccc aaaggagccg 180
ttggagattt tcccctcaat ctctctcctt catgaaattt cataccacaa atatagtatg 240
ttttatttat gtactgtgac cctttgaagg atcacaaacc aatataatag tttttctttt 300
taacccgtca aggaccaagt ttttgcccct gttggaaatg cataaactgg actgatgaat 360
tggtatagat ggcttttatc atgaggatca gaaaaacttg aaattccttg gctacgacac 420
tccatattta tcaccgtata gggaggacct tggtatgggg aagtagaaac acttctacac 480
tttacagca 489

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105
gcgtggtcgc ggccgaggtc tgactggctt cagccccaga agttgagctg gcctttagac 60
aaaataattg cacctccctc tgctgcttat tcccttccgt ttttcatttg agtgtgaaca 120

-continued gttagataaa atctgtggct gnctcttcca ccttgctcta gtttccattg ctgtgagcag 180
gccctcctat gccccgcatt tagctacaat gctgtggact cacttgattc tttttctccg 240
agctttgtct agaaatatgt gaaggtgagg ttaagtgctt ctctgtgtag atccacttag 300
ccctgtctgc tgtctcgatg ggcgttgctt cgtctctcct ctcttccatc ctttccattt 360
gcttctcacc accttctggc ttcttttctt aatgcaataa aggcagtttc taacaaagaa 420
agaatgtggg ctttggagtt agacagacct ggntttaaat tctgcttctg gctctccaa 479

<210> SEQ ID NO 106
<211> LENGTH: 511
<212> TYPE: DNA
<213> ORGANISM: Homo sapien

<400> SEQUENCE: 106
tcgcggccga ggtccaaaac gtggattcca atgacctgcc ttgagcccgc ggttgccagg 60
agttggacct gcagtagtat gggaagctca cggcctaaat accgactgcc ctctgacccc 120
accgtccagc gattctagaa catttctagt aggaaagaca tagcaaggga ttttcatgat 180
tgggaaatac tgggagacaa gctgaagatt tgttaagggc tatgcttctg tcatctttta 240
ggtatttaag gctactcctt tagctagcta ctttgagctg tttaaagtga ctatctccct 300
acacagagtt acacaatgag catctctgaa agagaatatt accctggatt tccaaagatg 360
tactctaaca ggatgaccag gcaaaaggtg acccggggga ggagtctgtt ataacactcg 420
gacccacatg ttctcaaggc acttcagaac tttgggaaat cattttgtac cggatcctca 480
gaaagcattt atggaaatac acatccttta g 511

<210> SEQ ID NO 107
<211> LENGTH: 451
<212> TYPE: DNA
<213> ORGANISM: Homo sapien

<400> SEQUENCE: 107
ggccgcccgg gcaggtccag aatatcaaat caaaaggtca caaatgttca cttcctcctc 60
caccctctta catattggat cttcaattgc aatagggagt gtaagatggg cattttagag 120
acgtagttgc atcagcagaa gcaaacccat cttatacaaa tgggttttgg ggataggaaa 180
aggctgctaa aaattcacaa gtcaccattc cccagaagca atgaatagcc gtagaagacc 240
aaggaagatc aacaagtttc caaagtgcta aagccagaga tttggccctt ccaaaatacc 300
accaggacgc ctggacccgt gggctctccg catgtcacca ctgactgcca ggatgctgct 360
gcacctccct tccttgagac acaacagaga gacagtgaag tcacccaaga ctgggatcat 420
cagaggctcc tcatgcttgc tacagagaag c 451

<210> SEQ ID NO 108
<211> LENGTH: 461
<212> TYPE: DNA
<213> ORGANISM: Homo sapien

<400> SEQUENCE: 108
ccgcccgggc aggtcctgaa aacattcaga ctaatcaaaa tggtactact gtaacttctt 60
ataatacata atataaaagt ttttgaaaga tatagacaca attaacccct aaacaacaca 120
ctatctgatt ctcaaaagca atggctattt aacaagatgt aaaaggacaa taacatatca 180
aagaactttc acacacctaa agatagcatt tagcagcaag ttagtcagac aaaacaaaca 240
caaatatttt cacatttcct atgtttgttt ttaactttac ttcataaagc cactgataat 300

-continued tgaggtttct ttcaagtata agatttctaa aattaaaaac tgtttttgac atatttttat 360
aaagaaataa aaagcaaaac gcaatccaac tatttatatg agtccctctt ctccaacagc 420
tttagatggt tttctgagta cttttttaca cagaatattt t 461

<210> SEQ ID NO 109
<211> LENGTH: 441
<212> TYPE: DNA
<213> ORGANISM: Homo sapien

<400> SEQUENCE: 109
ggccgcccgg gcaggtctga ttataagaga aagaaatcca gtgacacgag ggcaggcagg 60
ccccgctctg ctctgatcga gaaaagcttc ctgatgtcag ggagatggaa ctgccaccat 120
cagaaccatg gcactttggg tgaaggtgtg tcagcgacca agggggcagg aaatgggcag 180
tgactaaggg ggcaggaaac aggcaggcac atggcaaggt tctcccagcc catcagccca 240
gtgatggcct cgattttgaa gctgcactac tgtctgaaaa gcacaattac tggtgactct 300
taacaaactt cagcatactg gggaaggaga ctgtcaagta actgaattgg aaagatgaaa 360
aagaaccatc tctaaaagtt gatgcttgtc agaagaataa cctcctttgt gcaagtcttg 420
caacatcttc attcaaccac a 441

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110
ggtcgcggcc gaggtctggg gaaggggtga gaatccctgg gccttgccca gtcctgagct 60
ctgggtgtct gcagggaagc acagtggtga gttagtgtta aagaaagcat ccagagaggt 120
aagaggggct tgggtagcac cctttgcctc tgtcacttcc gcaaaaactt cttgttgagg 180
aggaagatga gaaggttgac attgactttg gccttgttga agagtttcat gacagccaca 240
ccctcatact ggagctgcan gagatcctga tagtgaagct tgaaatcgct ccatgtccac 300
acccaggaac ttggcattta cttcaaactt tcctgcctca tctcccggcg tgatgtcaaa 360
natgacgttt cttgaagtga gaggcgggaa agatcttcaa tttccaccaa agacaccctt 420
tttccaggaa gcttgagcaa caagtgtaat g 451

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111
ggccgacgtt cgacctgact tctttngagc agntgncact acccgtcttg aggaatgccg 60
actgcagaca gtggcccang gcaaagagtg tgcgtcatcg atganattgg naagatggag 120
ctcttcagtc agnttttcat tcaagctgnt cgtcagacgc tgtctacccc agggactata 180
atcctnggca caatcccagt tcctanagga aagccactgn ctcttgtaga agaaatcana 240

-continued

```
cacanaaagg atgtgaacng tgtttaatgt caccaaggga aaacatgaaa ccaccttctg    300

ccagatatcg ggacgttgcg tgcagatcaa gcacgnaagt gaagacgcgt gcattccttg    360

ccttccgtga acgantgccc agntcaagaa gancctgatg gaaccct                  407
```

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

```
tcgcggccga ggtcggccga ggtctgacat ctgttgtctg tgataaccac ttctgtattg     60

cgtcttaacc acttctgtat tgtgtggttt taactgccta aggcggcaat gggcagtggg    120

cccctttccc ttaggatggg tatcaattca acaatattta taaggcattt actgtgtgct    180

aagcatttgg aagacccagg ctacaaaata agacatagtt cctgccctcc aggccagcag    240

agggaggcac aaatacccag gaatctctga tgggtgtgaa gtgcggtcgt gggccacaga    300

aaatgaccgt catggagacc ctgctaaagg tcggaccctg agcccaaagg ggtattcaga    360

agnggagatg attttggccc cactcataga tgggtggcaa a                        401
```

<210> SEQ ID NO 113
<211> LENGTH: 451
<212> TYPE: DNA
<213> ORGANISM: Homo sapien

<400> SEQUENCE: 113

```
gtcgcggccg aggtccatat taaaaagtcc atcataaaca aagactcctc ctcatggtat     60

gaatatgctc catatgccca taatggtgca taacggactt agaaattcca atgagtctta    120

gggttgaaat ttccaatgac ctgagcaagg cagctcccta tagcttctgg ataacatttt    180

acacccagag ttcaggctta aacagaccta tcaacacaat tattttcgga ttgtctgtct    240

agaaaacggc aatgctcaaa ggaatataaa taagggtggg gggacatatg cttccagcct    300

ggcctttctc catgtggtaa aaaacaatgg aatggctgtg ttaatttttt tttaatcttt    360

tctgaccttt actatgtttg gtaatggaaa taagtcaggg aaaacaaaat gaacaggtct    420

catcacttaa ttaatactgg gttttcttct t                                   451
```

<210> SEQ ID NO 114
<211> LENGTH: 441
<212> TYPE: DNA
<213> ORGANISM: Homo sapien

<400> SEQUENCE: 114

```
ggccgcccgg gcaggtccat cctgtcagag atgggagaag tcacagacgg aatgatggat     60

acaaagatgg ttcactttct tacacactat gctgacaaga ttgaatctgt tcatttttca    120

gaccagttct ctggtccaaa aattatgcaa gaggaaggtc agcctttaaa gctacctgac    180

actaagagga cactgttgtt tacatttaat gtgcctggct caggtaacac ttacccaaag    240

gatatggagg cactgctacc cctgatgaac atggtgattt attctattga taaagccaaa    300

aagttccgac tcaacagaga aggcaaacaa aaagcagata agaaccgtgc ccgagtagaa    360

gagaacttct tgaaacttga cacatgtgca aagacaggaa gcagcacagt ctcggcggga    420

ggaagaaaaa aagaacagag a                                              441
```

-continued

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaaggaaaag aagcaaagag actcagtcca 60
taatgctgat tagttagaag aaagggctag gattgagaaa gtaccaggaa cttttaatta 120
tttaaaagag aatgctgact gttaatgttt taaatcttac tgttcaaatg tactaatatg 180
aatttttacc ctttgtgcat gaatattcta aacaactaga agacctccac aatttagcag 240
ttatgaaagt taaacttttt attataaaaa ttctaaacct tactgctcct ttaccaggaa 300
catgacacac tatttancat cagttgcata cctcgccaat agtataattc aactgtcttg 360
cccgaacaat catctccatc tggaagacgt aagcctttag aaacacattt ttctattaat 420
ttctctagaa c 431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca aagaagacga 60
aggcagagtg gtgtcaaatc tttgacggca cagatgcctg tgtgactccg gttctgactt 120
ttgaggaggt tgttcatcat gatcacaaca aggaaccggg gctcgtttat caccagtgag 180
gagcaggacg tgagccccccg ccctgcacct ctgctgttaa acaccccagc catcccttct 240
ttcaaaaggg atcctttcat aggagaacac actgaggaga tacttgaaga atttggattc 300
agcccgcgaa gagatttatc aagcttaact cagataaaat cattgaaagt aataaggtaa 360
aagctaagtc tctaacttcc aggcccacgg ctcaagtgaa tttcgaatac tgcatttaca 420
g 421

<210> SEQ ID NO 117
<211> LENGTH: 489
<212> TYPE: DNA
<213> ORGANISM: Homo sapien

<400> SEQUENCE: 117
agcgtggtcg cggccgaggt aaggctgcga ggttgtggtg tctgggaaac tccgaggaca 60
gagggctaaa tccatgaagt ttgtggatgg cctgatgatc cacagcggag accctgttaa 120
ctactacgtt gacactgctg tgcgccacgt gttgctcaga cagggtgtgc tgggcatcaa 180
ggtgaagatc atgctgccct gggacccaac tggtaagatt ggccctaaga agcccctgcc 240
tgaccacgtg agcattgtgg aacccaaaga tgagatactg cccaccaccc ccatctcaga 300
acagaagggt gggaagccag agccgcctgc catgccccag ccagtcccca cagcataaca 360
gggtctcctt ggcagacctg cccgggcggc cgctcgaaag cccgaattcc agcacactgg 420
cggccgttac tagtggatcc cagctcggta ccaagcttgg cgtaatcatg gtcatagctg 480
gtttcctgt 489

-continued

<210> SEQ ID NO 118
<211> LENGTH: 489
<212> TYPE: DNA
<213> ORGANISM: Homo sapien

<400> SEQUENCE: 118
tcgagcggcc gcccgggcag gtattgaata cagcaaaatt ctatatacaa agtgacctgg 60
acctgctgct tcaaaacatg atcctttctt actaatatct tgatagtcgg tccatagagc 120
attagaaagc aattgactct taaataaaca gaaaagtgcc taatgcacat taaatgaatg 180
gcctaactac tggaacttta gtagttctat aaggtgatta acataggtag gatccagttc 240
ctatgacagg ctgctgaaga acagatatga gcatcaagag gccattttgt gcactgccac 300
cgtgatgcca tcgtgtttct ggatcataat gttcccatta tctgattcta gacacaccac 360
aggaatatca gtggggtcag aggttagctt agctgcttgc tgggctagaa cagatatcac 420
tccagcatgc tcatctgaca gggtcccgcg gcaacccaga ttaagtcctt gtgaatctgt 480
gcacaggga 489

<210> SEQ ID NO 119
<211> LENGTH: 181
<212> TYPE: DNA
<213> ORGANISM: Homo sapien

<400> SEQUENCE: 119
taggttccag agacttttgg cccaggagga atatttactt ttagctctgg acatcattac 60
aaaaaggaat atttcccaaa cctcttcaga ccgagaatac atgggtaaaa ttattaaata 120
gttgtataat aaaaataatt ttttccttaa aaaaaaaaaa aacctcggcc gcgaccacgc 180
t 181

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120
gcgtggtcgc ggccgaggtc catttaaaac aaagaaaaat actaaagcca ctagtaaaca 60
tctgatgtgc aaaatacaac atcctctagt tggctttatg ccattattac ataagctcca 120
aatagctcat cttaaattaa aaagaaaaag tggctgtccc atctctgctg cataaatcag 180
attttttttt aaaggtttag agtactttaa ggaagggaag ttcaaaactg ccagtgaaat 240
tcacagagaa tacaaattta gcaatttaat ttcccaaagc tctttgaaga agcaagagag 300
tctctcttct taatgcagtg ttctcccaag aggaactgta attttgcttg gtacttatgc 360
tgggagatat gcaaaatgtg tttttcaatg tttgctagaa tataatggtt cctcttcagt 420
gnctggttca tcctggaact catgggttaa gaaggacttc ttggagccga actgcccggg 480 cgggccntt 489

<210> SEQ ID NO 121
<211> LENGTH: 531
<212> TYPE: DNA
<213> ORGANISM: Homo sapien

<400> SEQUENCE: 121

-continued

```
cgagcggccg cccgggcagg tggccagcgc tggtcccgca gacgccgaga tggaggaaat     60
atttgatgat gcgtcacctg gaaagcaaaa ggaaatccaa gaaccagatc ctacctatga    120
agaaaaaatg caaactgacc gggcaaatag attcgagtat ttattaaagc agacagaact    180
ttttgcacat ttcattcaac ctgctgctca gaagactcca acttcacctt tgaagatgaa    240
accagggcgc ccacgaataa aaaaagatga gaagcagaac ttactatccg ttggcgatta    300
ccgacaccgt agaacagagc aagaggagga tgaagagcta ttaacagaaa gctccaaagc    360
aaccaatgtt tgcactcgat ttgaagactc tccatcgtat gtaaaatggg gtaaactgag    420
agattatcag gtcccgagga ttaaactggc tcatttcttt gtatgagaat ggcatcaatg    480
gtatccttgc agatgaaatg ggcctaggaa agactcttca acaatttctc t             531
```

<210> SEQ ID NO 122
<211> LENGTH: 174
<212> TYPE: DNA
<213> ORGANISM: Homo sapien

<400> SEQUENCE: 122

```
tcgagcggcc gcccgggcag gtctgccaac agcagaggcg gggcctccgg catcttcaaa     60
gcacctctga gcaggctcca gccctctggc tgcgggaggg gtctggggtc tcctctgagc    120
tcggcagcaa agcagatgtt atttctctcc cgcgacctcg gccgcgacca cgct          174
```

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

```
agcgtggtcg cggccgaggt cctcaaccaa gagggttgat ggcctccagt caagaaactg     60
tggctcatgc cagcagagct ctctcctcgt ccagcaggcg ccatgcaagg gcaggctaaa    120
agacctccag tgcatcaaca tccatctagc anagagaaaa ggggcactga agcagctatg    180
tctgccaggg gctaggggct cccttgcaga cagcaatgct acaataaagg acacagaaat    240
gggggaggtg ggggaagccc tatttttata acaaagtcaa acagatctgt gccgttcatt    300
cccccagaca cacaagtaga aaaaaaccaa tgcttgtggt ttctgccaag atggaatatt    360
cctccttcct aanttccaca catggccgtt tgcaatgctc gacagcattg cactgggctg    420
cttgtctctg tggtctgggc accagtagct tgggccccat atacacttct cagttcccac    480
anggcttatg gccnangggc angctccaat tttcaagcac cacgaaggaa g             531
```

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc     60
acttaccaag cccaggaata atgactttta aagccttgaa tatcaactaa gacaaattat    120
gccaattctg atttctcaca tatacttaga ttacacaaag ataaagcttt agatgtgatc    180
attgtttaat gtagacttat ctttaaagtt tttaattaaa aactacagaa gggagtaaac    240
```

-continued

```
agcaagccaa atgatttaac caaatgattt aagagtaaaa ctcactcaga aagcattata    300

cgtaactaaa tatacatgag catgattata tacatacatg aaactgcaat tttatggcat    360

tctaagtaac tcatttaagt acatttttgg catttaaaca aagatcaaat caagct        416
```

```
<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

agcgtggtcg cggccgaggt gcttttttttt ttttttttt ttttttttt gctattctaa      60

aggggaaggc cccttttttat taaacttgta cattttactt tccttctttc anaatgctaa   120

taaaaaactt ttgtttatac ttaaaaaaac cataaatcan acaaacaaaa gaaacgattc    180

caacatcact tctgngatg                                                 199
```

```
<210> SEQ ID NO 126
<211> LENGTH: 490
<212> TYPE: DNA
<213> ORGANISM: Homo sapien

<400> SEQUENCE: 126

cgtggtcgcg gccgaggtcc agttgctcta agtggattgg atatggttgg agtggcacag     60

actggatctg ggaaaacatt gtcttatttg cttcctgcca ttgtccacat caatcatcag    120

ccattcctag agagaggcga tgggcctatt tgtttggtgc tggcaccaac tcgggaactg    180

gcccaacagg tgcagcaagt agctgctgaa tattgtagag catgtcgctt gaagtctact    240

tgtatctacg gtggtgctcc taagggacca caaatacgtg atttggagag aggtgtggaa    300

atctgtattg caacacctgg aagactgatt gactttttag agtgtggaaa aaccaatctg    360

agaagaacaa cctaccttgt ccttgatgaa gcagatagaa tgcttgatat gggctttgaa    420

ccccaaataa ggaagattgt ggatcaaata agacctgata ggcaaactct aatgtggagt    480

gcgacttggc                                                           490
```

```
<210> SEQ ID NO 127
<211> LENGTH: 490
<212> TYPE: DNA
<213> ORGANISM: Homo sapien

<400> SEQUENCE: 127

cgtggtcgcg gccgaggtcg gccgaggtct ggagatctga gaacgggcag actgcctcct     60

caagtgggtc cctgacccct gacccccgag cagcctaact gggaggcacc ccccagcagg    120

ggcacactga cacctcacac ggcagggtat tccaacagac ctgaagctga gggtcctgtc    180

tgttagaagg aaaactaaca agcagaaagg acagccacat caaaaaccca tctgtacatc    240

accatcatca aagaccaaaa gtaaataaaa ccacaaagat gggaaaaaaa cagaacagaa    300

aaactggaaa ctctaaaaag cagagcacct ctcctcttcc aaaggaacgc agttcctcac    360

cagcaatgga acaaagctgg atggagaatg actttgacga gctgagaaaa gaacgcttca    420

gacgatcaaa ttactctgag ctacgggagg acattcaaac caaaggcaaa gaagttgaaa    480

actttgaaaa                                                           490
```

-continued

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128
cgtggtcgcg gccgaggtgc tttttttttt tttttttttt tttttttttt tgctgattta 60 tttttctnt ttattgttac atacaatgta taaacacata aaacanaaaa cagtagggat 120
cctctaggat ctctagggan acagtaaagt anaaagaggt ctcanaaaca tttttttaaa 180
gtacaagaca ttcagngctc ggcccaaagg cgtaaaaggt ttanagccag canatagctg 240
nactaaaggc tccgtctntn tccccanagc caggacaacc ccagggagct ntccattagc 300
agccagtcca cgcaggcagg atgctgcgga aaaagctcta tgctganaac attcccettg 360 atggaaagaa gggcaacaca aaaggggtaa ctaanagctc cttcctctcg tgagggcgac 420
aactgaggaa cagaaaagga gtgtcccatg tcacttttga ccccctccc 469

<210> SEQ ID NO 129
<211> LENGTH: 419
<212> TYPE: DNA
<213> ORGANISM: Homo sapien

<400> SEQUENCE: 129
gcgtggtcgc ggccgaggtc tgattttcat ttaaatattt cagagctata gcatttgcct 60
ccatgctcaa atccacacca ttggggctta agccgctcat gccaacatta gcaaatgaca 120
tgcagtttaa tccagagatc actgcttctg ggctgatgca tgccaacaca ctggcgtgat 180
ccacgttatg tgcatttttc ttcactttag tgggagaatc aatttttact ccaaggcttc 240
ttagttgctt aagagttgca ttaaggacac aatctttgtc caccagtctt gaatgatgtg 300 ttttttctt tgtatggtaa acgttttggg ttctggtgca ttcatgactg ataattactg 360
ctttggtaga cggctgctca agtttccttg gaggaactat ttaataggtg ggttacttg 419

<210> SEQ ID NO 130
<211> LENGTH: 354
<212> TYPE: DNA
<213> ORGANISM: Homo sapien

<400> SEQUENCE: 130
agcgtggtcg cggccgaggt ccatctgagg agataaccac atcactaaca aagtgggagt 60
gaccccgcag agcacgctgt ggaattccat agttggtctc atccctggtc agtttccaca 120
tgatgatggt cttatctcga gaggcggaga ggatcatgtc cgggaactgc ggggtagtag 180
cgatctgggt tacccagccg ttgtggccct tgagggtgcc acgaagggtc atctgctcag 240
tcatggcggc ggcgagagcg tgtgtcgctg cagcgacgag gatggcactg gatggcttag 300
agaaactagc accacaacct ctcctgccgc acctgcccgg gcggcccgct cgaa 354

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G -continued

<400> SEQUENCE: 131
cgagcggccg cccgggcagg tctggcagca gcttcctctg gaataattga cagctttgtg 60
ctgcctgact aaaatttgaa atgacaaccg ctgaatgtaa aatgatgtac ctacaatgag 120
agagatttag gaatactatc tgtcaatcca tagatgtaga aacaaaacaa actacagaat 180
gaaaacaaac ttattttaaa ccaaagaaac aaatgtatcc aaaatatagt ccatgatata 240
tttgattact agtataacca cagttgaaaa cttaaaaaaa aaaattgaca ttttttgtaa 300
tgggtactaa tggatttata aaaggtttct gtttccaaag atgttattgg ggtccacata 360
ttccttgaag acttcagcat cccaaagccc gacatcagag atactttcct ttagccattg 420
nttcccgtaa cttgcccact ccatggtgat gtgacaggct tcccttcatt agca 474

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132
ggccgaggtg gggaattcat gtggaggtca gagtggaagc aggtgtgaga gggtccagca 60
gaaggaaaca tggctgccaa agtgtttgag tccattggca agtttggcct ggccttagct 120
gttgcaggag gcgtggtgaa ctctgcctta tataatgtgg atgctgggca cagagctgtc 180
atctttgacc gattccgtgg agtgcaggac attgtggtag gggaagggac tcattttctc 240
atcccgtggg tacagaaacc aattatcttt gactgccgtt ctcgaccacg taatgtgcca 300
gtcatcactg gtagcaaaga tttacagaat gtcaacatca cactgcgcat cctcttccgg 360
cctgtcgcca gccagcttcc tcgcatcttc accagcatcg ganaggacta tgatgaaccg 420
tgtgctgccg tccatcacaa ctgagatcct caagtcagtg gtggctcgct ttga 474

<210> SEQ ID NO 133
<211> LENGTH: 387
<212> TYPE: DNA
<213> ORGANISM: Homo sapien

<400> SEQUENCE: 133
tgctcgagcg gccgccagtg tgatggatat ctgcagaatt cggcttagcg tggtcgcggc 60
cgaggtctgc gggcccctta gcctgccctg cttccaagcg acggccatcc cagtagggga 120
ctttcccaca ctgtgccttt acgatcagcg tgacagagta gaagctggag tgcctcacca 180
cacggcccgg aaacagcggg aagtaactgg aaagagcttt aggacagctt agatgccgag 240
tgggcgaatg ccagaccaat gatacccaga gctacctgcc gccaacttgt tgagatgtgt 300
gtttgactgt gagagagtgt gtgtttgtgt gtgtgttttg ccatgaactg tggccccagt 360
gtatagtgtt tcagtggggg agaactg 387

<210> SEQ ID NO 134
<211> LENGTH: 401
<212> TYPE: DNA
<213> ORGANISM: Homo sapien

<400> SEQUENCE: 134
ggccgcccgg gcaggtctga tgaagaacac gggtgtgatc cttgccaatg acgccaatgc 60
tgagcggctc aagagtgttg tgggcaactt gcatcggctg ggagtcacca acaccattat 120

-continued

```
cagccactat gatgggcgcc agttccccaa ggtggtgggg ggctttgacc gagtactgct    180

ggatgctccc tgcagtggca ctggggtcat ctccaaggat ccagccgtga agactaacaa    240

ggatgagaag gacatcctgc gcttgtgctc acctccagaa ggaagttgct cctgagtgct    300

attgactctt gtcaatgcga ccttcaagac aggaggctac ctggtttact gcacctgttc    360

tatcacagtg agacctctgc catggcagaa caggggaagc t                        401
```

<210> SEQ ID NO 135
<211> LENGTH: 451
<212> TYPE: DNA
<213> ORGANISM: Homo sapien

<400> SEQUENCE: 135

```
ggtcgcggcc gaggtctgtt cctgagaaca gcctgcattg gaatctacag agaggacaac     60

taatgtgagt gaggaagtga ctgtatgtgg actgtggaga aagtaagtca cgtgggccct    120

tgaggacctg gactgggtta ggaacagttg tactttcaga ggtgaggtgt cgagaaggga    180

aagtgaatgt ggtctggagt gtgtccttgg ccttggctcc acagggtgtg ctttcctctg    240

gggccgtcag ggagctcatc ccttgtgttc tgccagggtg gggtaccggg gtttgacact    300

gaggagggta acctgctggc tggagcggca gaacagtggc cttgatttgt cttttggaag    360

attttaaaaa ccaaaaagca taaacattct ggtccttcac aatgctttct ctgaagaaat    420

acttaacgga aggacttctc cattcaccat t                                   451
```

<210> SEQ ID NO 136
<211> LENGTH: 411
<212> TYPE: DNA
<213> ORGANISM: Homo sapien

<400> SEQUENCE: 136

```
ggccgcccgg gcaggtctga atcacgtaga atttgaagat caagatgatg aagccagagt     60

tcagtatgag ggttttcgac ctgggatgta tgtccgcgtt gagattgaaa atgttccctg    120

tgaatttgtg cagaactttg accccctta ccccattatc ctgggtggct tgggcaacag    180

tgagggaaat gttggacatg tgcaggtggg tccctttgct gcgtatttgg tgcctgaggc    240

tctgtggatt tcccctccat caatcatctt accctctcat ccccctcaga tgcgtctgaa    300

gaaacatctc tggtataaga aaatcctcaa gtcccaagat ccaatcatat tttctgtagg    360

gtggaggaag tttcagacca tcctgctcta ttatatccga agaccacaat g             411
```

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

```
cggccgcccg ggcaggtcgg ttggtgcggc ctccattgtt cgtgttttaa ggcgccatga     60

ggggtgacag aggccgtggt cgtggtgggc gctttggttc cagaggaggc ccaggaggag    120

ggttcaggcc ctttgcacca catatcccat ttgacttcta tttgtgtgaa atggcctttc    180

cccggntcaa gccagcacct cgatgaaact t                                   211
```

<210> SEQ ID NO 138

-continued

<211> LENGTH: 471
<212> TYPE: DNA
<213> ORGANISM: Homo sapien

<400> SEQUENCE: 138
gccgcccggg caggtctggg ctggcgactg gcatccaggc cgtaactgca aatctatgct 60
aggcggggtc tcccttctgt gtgttcaagt gttctcgact tggattctta actattttaa 120
aaaatgcact gagtttgggt taaaaaccaa ccaccaaaat ggatttcaac acagctctaa 180
agccaagggc gtggccggct ctcccaacac agcgactcct ggaggccagg tgcccatggg 240
cctacatccc ctctcagcac tgaacagtga gttgattttt ctttttacaa taaaaaaagc 300
tgagtaatat tgcataggag taccaagaaa ctgcctcatt ggaaacaaaa actatttaca 360
ttaaataaaa agcctggccg caggctgcgt ctgccacatt tacagcacgg tgcgatgcac 420
acggtgacca aaccacggag gcaagcttct ggcactcaca ccacgacccg c 471

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139
gtcgcggccg aggtctgttc tttagctcag atttaaacct gctgtctctt ctttatttgc 60
agaatgaatt cccagttcct gagcagttca agaccctatg gaacgggcag aagttggtca 120
ccacagtgac agaaattgct ggataagcga agtgccactg ggttctttgc cctcccttca 180
caccatggga taaatctgta tcaagacggt tcttttctag atttcctcta cctttttgct 240
cttaaaactg cttctctgct ctgagaagca cagctacctg ccttcactga aatatacctc 300
aggctgaaat ttggggtggg atagcaggtc agttgatctt ctgcaggaag gtgcagcttt 360
tccatatcag ctcaaccacg ccgncagtcc attcttaagg aactgccgac taggactgat 420
gatgcatttt agcttttgag cttttggggg gtattctacc aaccaacagt ccatttggaa 480
a 481

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140
gtcgcggccg aggtttccca tttaagaaaa atagatcttg agattctgat tcttttccaa 60
acagtcccct gctttcatgt acagcttttt ctttacctta cccaaaattc tggccttgaa 120
gcagttttcc tctatggctt tgcctttctg attttctcag aggctcgagt ctttaatata 180
accccaaatg aaagaaccaa ggggaggggt gggatggcac tttttttgt tggtcttgtt 240 ttgttttgtt ttttggttgg ttgggttccg ttattttta agattagcca ttctctgctg 300
ctatttccct acataatgtc aatttttaac cataattttg acatgattga gatgtacttg 360 aggcttttt gntttaattg agaaaagact ttgcaatttt ttttttagga tgagcctctc 420
c 421

-continued

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141
cgantngccc gcccgggcan gtctgtctaa ntttntcang gaccacgaac agaaactcgt 60
gcttcaccga anaacaatat cttaaacatc gaanaattta aatattatga aaaaaaacat 120
tgcaaaatat aaaataaata nnaaaaggaa aggaaacttt gaaccttatg taccgagcaa 180
atccaggtct agcaaacagt gctagtccta nattacttga tntacaacaa cacatgaata 240
ca 242

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142
agcgtggtcg cggcncgang tccacagggc anatattctt ttagtgtctg gaattaaaat 60
gtttgaggtt tangtttgcc attgtctttc caaaaggcca aataattcan atgtaaccac 120
accaagtgca aacctgtgct ttctatttca cgtactgttg tccatacagt tctaaataca 180
tgtgcagggg attgtagcta atgcattaca cagtcgttca gtcttctctg cagacacact 240
aagtgatcat accaacgtgt tatacactca actagaanat aataagcttt aatctgaggg 300
caagtacagt cctgacaaaa gggcaagttt gcataataga tcttcgatca attctctctc 360
caaggggccc gcaactaggc tattattcat aaaacacaac tgaanagggg attggtttta 420
ctggtaaatc atgtgntgct aaatcatttt ctgaacagtg gggtctaaat cantcattga 480
tttagtggca gccacctgcc cggcggccgn tcgaagccca attctgcaga tatccatcac 540
actggcggcc g 551

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143
cgagnggccc gcccgggcag gtatcttcac aaactcaaca aaggcactac atgagacttc 60
acattcccct agtccaatag ctgacaaatt tttgcaacgt tctgcaatgc gaattaactc 120
ttcatcaagt ggccgtaatc catttgcaca cactactagt tcaaccagtc tagggcatgt 180
cattcccaca cggccaagca catctttgct tactgatctc ccaaagtaca gatgggtggc 240
aggtatttca tagcgaaaga aggggtcaaa ttcttcttca tataanaaaa aatacatcac 300
taagttcact ttgggtgaat gtctgatgaa agcatcccag ctactcttct gaatagtatg 360

-continued

```
gaagtgtgtc tgtccaggat tctcactgac tacatcaatg cgcaaatgtt ctaatcgaac    420

atgtttttca gaagacaatg caagtaacaa ctcatcactc aataagtggt aagttcaggg    480

ctagttctct taagccgnga cactgatcag cacac                               515


<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144

tgcattctct ntggatgcan acctgcccgt tggtagggac tntgctcaca cggaacatgg     60

acggttacac ctgtgccgtg ggtgacgtcc accagcttct ggatcatctc ggcgngggtg    120

ttgtggaagg gcagactatc cacctccatg cncacgatgc ccganacgcc actccggact    180

ntgtgctgca ccaanatgcc cagcattnta tcttcaagca nagcacttat cagggtcctt    240

ggcacac                                                              247


<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145

cgtgggtcgc ggcccgangt ctgctgtaac aaaacaccat agtctgggca gctcatagac     60

aatggaattt tatttctcac gcttctggag gctggattcc aagatcaagg ttccaggaga    120

ctcagtgtct ggcaaggtct cggtttctgc ctcanagatg gtgccatctg gctgtgtcct    180

cacaagtagg aaggtgcaag aagctcccct caggctctgt ctgtaagaca ctgatcccat    240

tcatganggg gaaacgtaat gacctaatca gcccccagag accccacttc taacaccatc    300

accttgggg                                                            309


<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146

agcgtgggtc gcggcncgac gtcctgtcca tatttcacag cccgagaact aatacaagat     60

gctgacatca tattttgtcc ctacaactat cttctanatg cacaaataag ggaaagtatg    120

gatttaaatc tgaaagaaca ggttgtcatt ttanatgaag ctcataacat cgaggactgt    180

gctcgggaat cagcaagtta cagtgtaaca gaagttcagc ttcggtttgc tcgggatgaa    240

ctanatagta tggtcaacaa taatataagg aaganagatc atgaacccct acgagctgtg    300

tgctgtagcc tcattaattg gntagaagca aacgctgaat atcttgnana angagantat    360

gaatcagctt gtaaaatatg gagtggaaat gaaatgctct taactttaca caaaatgggt    420

atcaccactg ctacttttcc cattttgcng gtaagatatn ttttctacct gngaaacgta    480
```

-continued tttaag 486

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147
gccgcccggg cangttcgac attacntnga gttccatgat gtacaattct ttcacgaaaa 60
acaatgaatg caagaatttg aggatctcct tactcctccc ttttacagat ggtctctcaa 120
tcccttcttc ttcctcttca tcttcatctt cttctgaacg cgctgccggg taccacggct 180
ttctttgtct ttatcgtgag atgaaggtga tgcttctgtt tcttctacca taactgaaga 240
aatttcgctg caagtctctt gactggctgt ttctccgact tcgcctttnt gtcaaacgng 300
agtcttttta cctcatgccc ctcagcttca cagcatcttc atctggatgt tnatttctca 360
aagggctcac tgaggaaact tctgattcan atgtcgaana gcactgtgaa gttttctctt 420
cattttgctg 430

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148
cccgggcagg tctgtgttgn tttncaaccg gtgtcctccc cagcgtccag aananggaaa 60
tgtggagcgg gtgatgatga cccctcgctg tcctgtcacc tcctgcacag cttcgtatgt 120
gggtctggtc tgggaccacc cgtacaggtt gtgcacgttg tagtgctcca cgggggagct 180
gtccggcagg atctgctgac tctccatgca cagagtcttg ctgctcaggc ccttgtccct 240
agattccaaa tatggcatat agggtggggt tatttagcat ttcattgctg cagcccctga 300
cagatccatc cacaaaattt gatggctcat tcatatcaat ccacaatcca tcaaacttca 360
agctcttctc tggntctcga nggtttgcat agaactcttc tatctctttc ttccaccacg 420
canacctcgg ncgcgaccac gctaagccga attctgcana tatccatcac actggcggcc 480
gct 483

<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149
ctttcacgaa nacaatgaat gcaagaattt gaggatctcc ttactcctcc cttttacaga 60
tggtctctca atcccttctt cttcctcttc atcttcatct tcttctgaac gcgctgccgg 120
gtaccacggc tttctttgtc tttatcgtga gatgaaggtg atgcttctgt ttcttctacc 180

-continued

```
ataactgaag aaatttcgct gcaagtctct tgactggctg tttctccgac ttcgcctttt    240

tgcaaacgtg agtcttttta cctcatgccc ctcagcttcc acagcatctt catctggatg    300

ttcatttctc aaagggctca ctgaggaaac ttctgactca catgtcgaag aagcactgng    360

agtttctctt catttgctgc aaanttgctc tttgctggct gngctctcag accacccatt    420

tggctgcatg ggggctgac                                                 439
```

```
<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

ggcncgcccg ggcangtcca ctccactttt gagctctgag ggaatacctt caggagggac     60

agggtcaggg agtcctggca gctccgcagc agagattcac attcattcag agacttgttg    120

tccagtgcaa tgccattgat cgcaacgatc ctgtctccca cagcaaggga cccttcttta    180

gcggcagggc ttccaggcag cacagcggca gcatacactc cattctccag actgatgcca    240

ctgtctttct gtccactgan gttgatgtgc agcggcgtga ccaccttccc acccagggac    300

ttcctccgcc gcacgaccat gttgatgggc cccctnccca ttgaggagcg ccttgatggc    360

ctgcttcttg nccttggtga tgaagtccac atcggtgatt ctcacagcca gtcattgacc    420

cttaagcggn catcagcaat gcttcctttg gccactttag ngacaaatat gccacagtcc    480

ccgggaaaca agggtcattc acaccttctg gcatatcaaa cacctcggcc gggancacta    540

agccgaattc tgcagatatc catcacactg gngggccg                            578
```

```
<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

cgagcggccc gcccgggcag gtctgggaga tcagcgactg ctgccacgtg cccagaaatg     60

gctcgtcctt tcactacagc ggaatgcaat gagggtgggt gagaagatga tgggtcggtt    120

atttcattcc ttttcttttt acaacttcac tttcagagac ttcagcgttc catgtctgct    180

gtgctgtgga acccagagtg ctcttgcctg gatggctgag aatcccttgg accctggaag    240

cacctactcc atgatggccc ggtatagtgc aggctcaata taatcttccc ggtatcttga    300

gttgataact cgttgccgtt tcttttcttg cttaacctct ttctctgtga aaatctcatt    360

gaagcgcatg tctgaagcta ctgacagtct anatttgact ctcttgggaa gctcttcatc    420

cagtgtgtat acatcatctc tcttaaccac aagttggagc catncttaaa cttcacctgg    480

tacatttgga tagggtggga ggc                                            503
```

```
<210> SEQ ID NO 152
<211> LENGTH: 553
<212> TYPE: DNA
<213> ORGANISM: Homo sapien
<220> FEATURE:
<221> NAME/KEY: misc_feature
```

-continued

<222> LOCATION: (1)...(553)
<223> OTHER INFORMATION: n = A,T,C or G

<400> SEQUENCE: 152
agcgtggtcg cggcccgagg tccactgagc tccgccttcc ccgggctccc tgaggaagca 60
gagtcctgac ttccaggaag gacaggacac agaggcaaga actcagcctg tgaggctctg 120
ggtggctcct gaggccagag gacgccttcc gcgatccatg gctcagcatc gtccttctgg 180
cttcccagcc ccgggccgaa cgttcgggtt aataagcaga gcagttattc ggctcctggc 240
aggagctccc ccgttagttt ccacgttgtg agcacattca tacttaagac tgnttctctt 300
tgtgttttaa gcgtctgtct ctgtagtaaa ctgaaatgtt aacagaaatg cagacctgcc 360
cgggcggccg ctcgaaagcc gaattctgca gatatccatc acactggcgg ccgctcgagc 420
atgcatctag anggcccaat tcgccctata gtgagtcgna ttacaattca ctgggccgcg 480
ntttacaacg tcgtgactgg gaaaaccctg cggtacccac ttaatcgcct tgcagnacat 540
ccccctttcg cca 553

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153
tcgagcggct cgcccgggca ggtccaccta gcatggctcc tctaaacacg caactcagcg 60
aggggacccc cttcacctct ggcaagagag ctgggtagat cagaaacttg gtgacacctg 120
gctagcacag agcaggctca cttgtcttgg tcccactacc cagattcctg cagacattgc 180
aaaccaaatg aaggttgntg aatgacccct gtccccagcc acttgttttg gtatcatctg 240
ctctgcagtg gaatgcctgt gtgtttgagt tcactctgca tctgtatatt tgagtataga 300
aaccgantca agtgatctgt gcatncagac acactggggc acctgancac agaacaaatc 360
accttaacga tctggaatga aactgnganc antgcccgcc tgggtgggtc tgganaaact 420
gccgncttct tgttggacct tggccgcacc acct 454

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154
agcgtggtcg cggcccgang gcggcctcct gantganggg aagggacgtg ggggcggcca 60
cggcaggatt aacctccatt tcagctaatc atgggagaga ttaaagtctc tcctgattat 120
aactggttta naggtacagt tccccttaaa aagattattg tggatgatga tgacagtaag 180
atatggtcgc tctatgacgc gggcccccga agtatcaggt gtcctctcat attcctgccc 240
cctgtcagtg gaactgcaga tgtctttttc cggcagattt tggctctgac tggatggggt 300
taccgggtta tcgctttgca gtatccagtt tattgggacc atctcgagtt cttgtgatgg 360
attcacaaaa cttttanacc atttacaatt ggataaagtt catctttttg gcgcttcttt 420

-continued gggangcttt ttggcccana aatttgctga atacactcac aaatctccta gaagccattc 480
cctaatcctc tgcaattcct tcagngacac ctctatcttc aaccaacttg gactggaaac 540
agctttggct gatgcctgca tttatgctca aaaaatagtt cttggaaatt ttcatc 596

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155
ctcganttgg cncgcccggg cangtctgcc tggtttttga ccgngcgagc tatttagnct 60
ctggctctgt ttccggagct caaggnaaaa atcttgaana actcgagcag cttctgtgga 120
tagccttggg tacacatact gccgagcata gccaatgtac tttctcaata gctggtgggg 180
aatgggatct attgtttctc caggaaccac ctttagtctt tctgataatg gcttctcaga 240
aactacttca agtacggaag tatttgaatc ttgactatnc atacgagcta ctgtggcact 300
gctaatgggn tctctgctnt ccagctctta ttgcaatcac atg 343

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156
tcgagcggcc cgcccgggca ggtctggcac cacncagatc gattaactgg ctcatctgat 60
ctcgtggccc ccaccctgga actgacttag cacaaaagga cacctcaatt ccttatgatt 120
tcatctccga cccaaccaat caacaccctt gactcactgg ccttccccct cccaccaaat 180
tatccttaaa aactctgatc cccgaatgct cagggagatc gatttgagta ctaataagac 240
tccagtctcc tgcacaagca gctctgtgta ctcttcctct attgcaattc ctgtcttgat 300
aaatcggctc tgtgtaggcg gcggaagaag tgaacctgtt gggcggttac cacctctgtc 360
gtgtgtgaca gttgntttga atctctaatt gctcagtaca gatccacatg caggttaagt 420
aagaagcttt tgaagaaaat ggaaagtctt aagtgatggc ttccaagaaa tcaaacctac 480
attaattagg gaacaacgga ctttacgtat cacaaatgaa gagactgacn aagtaaatca 540
acttggcctt ttctta 556

<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157
ggtccacaaa aatatatnaa ataagctgga tatataaaan caaacactta acatngncan 60
cattccttca gttattcaaa ctcactgata nctaacnggg agnagttggn attctggaag 120
acttcctaag ctaaaagtat atttacatat ttacaacaca ngtaaatata acngaagaac 180

-continued

```
tacttcaaat aangnngaaa ttccagaatt ctanagattt atagctatag ntnacaanta    240

tcaccaattg gtttgcaatc aanngnccag cactacttat gannaangtt taactannaa    300

accaaaaggg gagaaaacct ggnagggaaa nat                                 333
```

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

```
tcgagcggcc gcccgggcag gtctggtaca tttgtgcgag gtccggcact ctgttctcat     60

ccagtaagtg gtcgagccct ttctgcagaa ttgctgttaa atgttctcct aatagctgtt    120

tctccacaca agcaatcagt ggtttctgtg tgctgtggtc caagtaagtg attactctgt    180

ctccctcttc ttctaagcgt ttacttacat ggttaagata ttctggaacc tctctttcct    240

gcattaacct ttggccttcg gcagcatata agcaattagt ctcttccaaa aatttcagtt    300

caaatgaatc tttatacacc tgcaggtcag acagcatgcc caggnaggct ccgcaacagg    360

ctccggtcca cggcctcgcc gctcctctcg cgctcgatca gcagtaggat tccatcaatg    420

gttttactct gaaccatttt atcactaata atatgggttc taaacagttc taatcccata    480

tcccagatgg agggcagcgt ggagttctgc agcacatagg tgcggtccaa gaacaggaag    540

atgcttctga tcatgaatca tttgnctggc aatggtcctg ccagcacgtg gtaatctttc    600

ttttaaaaat aaacccttat ctaaacgtc                                      629
```

<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

```
tcgagcggcc gcccgggcag gttctagagg ganaatctgg ctgatttggg aataaaaatat    60

aatcgaatat tcaacaccat gaagataaat cttattttgg aaatctactg accttaatac    120

cccaagcttg ccctgaatac tttgattgga attggaatat atcaaaaaag gttagtattt    180

ttgttgtagt taggatacta aaaggatatt agttacccaa gagatccaat ttgtttttct    240

gatgaatagt gttcagtaaa atgaagcagt cttaagagtg actaataatt tcaaagtgat    300

ttttcgtcta ttcttaatat tttttaatta tttattttta agagttttat accttgagca    360

gatacaatga tccgctttag tgagaggaca atttctgatt gattgttttc tcttcaggcc    420

atctcacctc ttcattctct tgttacattt gaagcagttg atataatggg tttatacttt    480

aaaagataga catggtgcca tgaagtttgg ggaagttggg tgaattatcc cattctagtt    540

acagangagc tttccttaaa tgccctttac ttctangttt ggtcaagaag tcattttctg    600

agtaaaagtt attttcatat atgttgggg                                      629
```

<210> SEQ ID NO 160
<211> LENGTH: 519
<212> TYPE: DNA

-continued

<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160
tcgagcggcg cgcccgggca ggtctgctgg gattaatgcc aagttnttca gccataaggt 60
agcgaaatct agcagaatcc agattacatc cacttccaat cacgcggtgt ttgggtaatc 120
cacttagttt ccagataaca tacgtaagaa tgtccactgg gttggaaacc acaattatga 180
tgcaatcagg actgtacttg acgatctgag gaataatgaa tttgaagaca ttaacatttc 240
tctgcaccag attgagccga ctctcccctt cttgctgacg gactcctgca gttaccacta 300
caatcttana attgggcggg tcacagaata atctttatct gccacaattt taggtgctga 360
agaaataagc tcccatgctg cagatccatc atttctnctt taagcttatc ttccaaaaca 420
tccacaagan caangttcat cagccagaga ctttcccaga atgctgatag nacacgccat 480
accaacttgt ccaacancca ctacagcgat cttattggt 519

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161
cgagnggccc gcccgggcag gtccagtaag cntttnacga tgatgggaaa ggttatgcaa 60
ggtcccagcg gtacaacgag ctgtttctac atcatttgta ttctgcatgg tacgtacaat 120
agcagacacc atctgaggag aacgcatgat agcgtgtctg gaagcttcct ttttagaaag 180
ctgatggacc ataactgcag ccttattaac caccacctgg tcctcgtcat ttagcagttt 240
tgtcagttca gggattgcac gtgtggcang ttctgcatca tcttgatagt taatcaagtt 300
tacaactggc atgtttcagc atctgcgatg ggctcagcaa acgctggaca ttantgggat 360
gagcagcatc aaactgtgta natgggatct gcatgccctc atctaatgtc tcagggaaca 420
tagcagctcg taccctctga gctcga 446

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162
agcgtngtcg cggcccgang tcctgggaag cctttnttgc tgagcctcac agcctctgtc 60
aggcggctgc ggatccagcg gtccaccagg ctctcatggc ctccgggctg ggaggngggt 120
gagggcacaa aacccttccc aaggccacga anggcaaact tggtggcatt ccanagcttg 180
ttgcanaagt ggcggnaacc cagtatccgg ttcacatcca ggntgatgtc acgaccctgg 240
gacatgtang cacataatcc aaaccggaga gcatcggtgc cacattcacg aatccccgct 300
gggaagtcag ctttctgccc ttctttggcc ttctccacct cgctgggatc cagg 354

-continued

<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163
tttttcncca agtcctcttg ccgngggatc tngactgcaa tttaagacac ttctaattag 60
ttatacccag gccctgcaaa attgctgggt ttatataata tattcttgct gcacgaagat 120
ttattattct gttggatgat tctattttaa ttntatttat tctggccaaa aaagaacctt 180
ctccgctcgt caagagangc caatntgtct tgaaggacaa gagaaagatg ctaacacaca 240
ctttcttctt cttgagga 258

<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164
ggaacatatt acttttaaat tacttgggtc aatgaaacat ttaataaaaa catttgcttc 60
tctatataat acgtatgtat aaaataagcc ttttcanaaa ctctggttct cataatcctc 120
tataaatcan atgatctgac ttctaagagg aacaaattac agnaaggggt atacattnat 180
gaatactggt agtactagag ganngacgct aaaccactct actaccactt gcggaactct 240
cacagggtaa atgacaaagc caatgactga ctctaaaaac aa 282

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165
gcccgggcan gtcctgtaat cccagctact cangangctg agtcatgana atcgcctgaa 60
tccgggaggt agaggccgca gcgagcaaag attaagccac tgcactccag tctgggtgac 120
agagtgagaa tctgtctgtt gctcctctgg cattggtctg aaatgggttt gtagaacatg 180
ccacagaagg accagcanca gcaacaaatg gatttgtgga angcgtagct ccaaatggag 240
cangcacact tgatgaagca cgctgtgtct gtgcagangc aaccactggc actgttccaa 300
aaacattgct gctagcatta cttgtggaag tatacgcatt actggaggtg gctgcanaac 360
tgaaaacgct gtctagttct gccanagctg catacttgnc tgaanatgca cttgactgac 420
tgggaactga accacanaac caacaggacc tttacctgtg ga 462

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)

-continued

<223> OTHER INFORMATION: n = A,T,C or G

<400> SEQUENCE: 166
cgtgggtcgc ggcncgangt ctgaaaccaa tccagaacta aacatcagca cacaaaaaat 60
accaggatag atggaatcaa aagactctga agccaaaagg aggctaggga gagcaactga 120
acttagcaag ctgaggactt cagtgtccat catccgatcc tgccctgtaa caacaggtct 180
atatgataga gatattccat ctgagctgga ggccattatc cttagcaaac taacacagaa 240
cagaaaacca aatacatgtt ctcatttaga agtaggagct aaatgatgag aactcaagga 300
cacaaagaaa ggaacaacag acactggggc ctacttgagg gtggagggtg ggaggaggga 360
gaaga 365

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167
agcgtggtcg cggcgcgang tccagcccta gcttgcctgt gactccgcct tcactgggtg 60
ctctctctaa aagttgctga ctctttactg tatctcccaa ttcccactcc attggttcca 120
taaggggagg ggtgtctcac tcaacatggt gttcctggta ccaagaactg gctgacgaag 180
ctgggtgccg tggctcatgc ctgtaatccc agcacttttg ggaggccaag aagggcggat 240
cacctgaggt ctggagttca agatcagcct gaccaacatg atgaaaccaa gtctccacta 300
aaaatataaa acaattagcc aggcatggtg gtgggtgcct gnaatcccag ctactgggga 360 ngct 364

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168
cccgggcagg tcaaaaccca aaacctttca ttttagccca aaccagctca tgattaggta 60
tacaaggata acagaaccag ttgtcaggac gagcatttga caagtaaaag caattcttgc 120
aaagctgcag ttcatccagc tcatggcatg tgtctttata tagcatcctc gcaatgtcag 180
cttgctcact gtctgctcca tagaaaatca cggtattgtg gagaagcaat tgggcatcag 240
ctttgaactc ttcataactt cggtatttcc cttcattcac tttctcttga atggtgggaa 300
cgtccacaga cctcggccgc gaccacgcta agcccgaatt ctgcagatat ccatcacact 360
ggcggccgtt cgagcatggc atctagaagg cccaattcgc ctatagngag tcgnattacc 420
aattcactgg ccgtcgnttt acaacgc 447

<210> SEQ ID NO 169
<211> LENGTH: 524
<212> TYPE: DNA
<213> ORGANISM: Homo sapien
<220> FEATURE:
<221> NAME/KEY: misc_feature -continued
<222> LOCATION: (1)...(524)
<223> OTHER INFORMATION: n = A,T,C or G

<400> SEQUENCE: 169
cgantngcgc gcccgggcag gtctgagcag cctttctgnn tgctggacta ttgggattgg 60
gttcatccaa cagagactgt atggatgtta gaatggaaga cacatcatag gttggactcc 120
aacggttctg aagtatgtcc agacatatac taccatctgc atagactaag aacaaagaag 180
taggtacatt aaacgtaaca agaccactaa ggttttaaca ttatagacaa aacanaaata 240
gtcaaganta ctttgctttt gaagtttaaa gattcctatg ttgcttccca gttaactgcc 300
taaaaagata agncataacc accactagtg aaataatcan gatgatcaga gaatgtcana 360
tgtgatcagt ataaaactgg angatattna gtgtcatcct ttggaaaagg ctgccctatn 420
atccaggaaa tcanaaacat tnttgaacag ggnccctagc tatccacaga catgtgggaa 480
attcattccc caaatngtag gctggatccc ctatctgaaa taac 524

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgancggcn cgcccgggca ggtgacaaac ctgttattga agatgttggt tctgatgagg 60
aanaanatca gaagggatgg tgacaagaan aanaanaaga agattaagga aaagtacatc 120
gatcaagaag agctcaacaa aacaaagccc atctggacca gaaatcccga cgatattact 180
aatgangagt acggagaatt ctataanagc ttgaccaatg actgggaaga tcacttggca 240
gtgaagcatt tttcagttga nggacagttg gaattcagag cccttctatn tgtcccacga 300
cgtgctcctt ttgatctgtt tganancaga aa 332

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171
cgagnggcnc gcccgggcag gtctgttgat agcgacttaa cagaaaagtc tagacaaaca 60
taagcataaa aaattacagt ctttctaccc ttgggaatgg ggagaaaaag gaatctctac 120
cccaagacca gaaataataa gtcctgtttc tggtcctgaa catccagaat tatggaggct 180
ttggcctgac accacattan aatttggtct ggaaatcaaa ctttaganac angagatcgt 240
aagccatttt atactatcga cctaaattcc agtctaacgg ttcctttaca aagttgcgga 300
aagccctctt atatgctagc tgtaggaaat atag 334

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)

-continued

<223> OTHER INFORMATION: n = A,T,C or G

<400> SEQUENCE: 172
agcgtggtcg cggcccgang tctgcctata aaactagact tctgacgctg ggctccagct 60
tcattctcac aggtcatcat cctcatccgg gagagcagtt gtctgagcaa cctctaagtc 120
gtgctcatac tgtgctgcca aagctgggtc catgacaact tctggtgggg cgagagcagg 180
catggcaaca aattccaagt tagggtctcc aatgagcttc ctagcaagcc agaggaaggg 240
cttttcaaag ttgtagttac ttttggcaga aatgtcgtag tactgaagat tcttctttcg 300
gtggaagaca atggatttcg ccttcacttt ctgccttaat atccactttg gtgccacaca 360
acacaatggg gatgntttca cacacttngn accanatctc tatgccagnt aggccatttt 420
ggaagnactt cganggtac 439

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173
cgatnggccg cccgggcagg tcctgtaaaa naggaaattc agacatcgta cgactcgtaa 60
ttgaatgtgg agctgactgc aatattttgt caaagcacca gaatagtgcc ctgcactttg 120
cgaagcagtc taacaatgtg cttgtgtacg acttgctgaa gaaccattta gagacacttt 180
caagagtagc agaagagaca ataaaggatt actttgaagc tcgccttgct ctgctagaac 240
cagtttttcc aatcgcatgt catcgactct gtgagggtcc agatttttca acagatttca 300
attaccaacc cccacagaac ataccagaag gctctggcat cctgctgttt atcttccatg 360
caaacttttt gggtaaagaa gttattgctc ggctctgtgg accgtgtagt gtacaagctg 420
tagttctgaa tgataaattt cagcttcctg tttttctggg tctcgctctg ttgtccaggc 480
tggagtgcag tggcgcggat tacagctcac tggagtcttg acttcccagg cacaagcaat 540
cctcccacct cagcctccta actacctggg actaaaaatg caccgccacc acattccgg 599

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174
tcgatttggc cgcccgggca ggtccatgcn gnttntgccc attcccatgg ngcccgacaa 60
ncccatcccc gaggccgaca tccccatgtt catgttcatg cccaccatgc cctggctcat 120
ccctgcgctg ttccccagag gggccattcc catggtgccc gtcattacac cgggcatgtt 180
cataggcatg ggtcccccca ggagagggtt agnttgaggc cggacaggaa gcatgtttga 240
tggagaactg aggttcacag nctccaaaac tttgagtcat cacattcata ggctgctgca 300
tattctgtct gctgaatcca ttgtatncag tgatggcctg ctggggnttt ggaaggctng 360
cataccaggt agtaagntcg tctaggctga tgtttacacc tggggtcaga ccaagtanga 420
gggcaaggtt ttgctgactg atttctggga cccatatc 458

-continued

<210> SEQ ID NO 175
<211> LENGTH: 1206
<212> TYPE: DNA
<213> ORGANISM: Homo sapien

<400> SEQUENCE: 175
ggcacgagga agttttgtgt actgaaaaag aaactgtcag aagcaaaaga aataaaatca 60
cagttagaga accaaaaagt taaatgggaa caagagctct gcagtgtgag gtttctcaca 120
ctcatgaaaa tgaaaattat ctcttacatg aaaattgcat gttgaaaaag gaaattgcca 180
tgctaaaact ggaaatagcc acactgaaac accaatacca ggaaaaggaa aataaatact 240
ttgaggacat taagatttta aaagaaaaga atgctgaact tcagatgacc ctaaaactga 300
aagaggaatc attaactaaa agggcatctc aatatagtgg gcagcttaaa gttctgatag 360
ctgagaacac aatgctcact tctaaattga aggaaaaaca agacaaagaa atactagagg 420
cagaaattga atcacaccat cctagactgg cttctgctgt acaagaccat gatcaaattg 480
tgacatcaag aaaaagtcaa gaacctgctt tccacattgc aggagatgct tgtttgcaaa 540
gaaaaatgaa tgttgatgtg agtagtacga tatataacaa tgaggtgctc catcaaccac 600
tttctgaagc tcaaaggaaa tccaaaagcc taaaaattaa tctcaattat gccggagatg 660
ctctaagaga aaatacattg gtttcagaac atgcacaaag agaccaacgt gaaacacagt 720
gtcaaatgaa ggaagctgaa cacatgtatc aaaacgaaca agataatgtg aacaaacaca 780
ctgaacagca ggagtctcta gatcagaaat tatttcaact acaaagcaaa aatatgtggc 840
ttcaacagca attagttcat gcacataaga aagctgacaa caaaagcaag ataacaattg 900
atattcattt tcttgagagg aaaatgcaac atcatctcct aaaagagaaa aatgaggaga 960
tatttaatta caataaccat ttaaaaaacc gtatatatca atatgaaaaa gagaaagcag 1020
aaacagaagt tatataatag tataacactg ccaaggagcg gattatctca tcttcatcct 1080
gtaattccag tgtttgtcac gtggttgttg aataaatgaa taaagaatga gaaaaccaga 1140
agctctgata cataatcata atgataatta tttcaatgca caactacggg tggtgctgct 1200
cgtgcc 1206

<210> SEQ ID NO 176
<211> LENGTH: 317
<212> TYPE: PRT
<213> ORGANISM: Homo sapien

<400> SEQUENCE: 176

Met Gly Thr Arg Ala Leu Gln Cys Glu Val Ser His Thr His Glu Asn
1 5 10 15

Glu Asn Tyr Leu Leu His Glu Asn Cys Met Leu Lys Lys Glu Ile Ala
20 25 30

Met Leu Lys Leu Glu Ile Ala Thr Leu Lys His Gln Tyr Gln Glu Lys
35 40 45

Glu Asn Lys Tyr Phe Glu Asp Ile Lys Ile Leu Lys Glu Lys Asn Ala
50 55 60

Glu Leu Gln Met Thr Leu Lys Leu Lys Glu Glu Ser Leu Thr Lys Arg
65 70 75 80

Ala Ser Gln Tyr Ser Gly Gln Leu Lys Val Leu Ile Ala Glu Asn Thr
85 90 95

Met Leu Thr Ser Lys Leu Lys Glu Lys Gln Asp Lys Glu Ile Leu Glu
100 105 110

-continued

```
Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile
305                 310                 315
```

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177
ccaatcatct ccacaggagc 20

<210> SEQ ID NO 178
<211> LENGTH: 1665
<212> TYPE: DNA
<213> ORGANISM: Homo sapien

<400> SEQUENCE: 178
gcaaactttc aagcagagcc tcccgagaag ccatctgcct tcgagcctgc cattgaaatg 60
caaaagtctg ttccaaataa agccttggaa ttgaagaatg aacaaacatt gagagcagat 120
cagatgttcc cttcagaatc aaaacaaaag aaggttgaag aaaattcttg ggattctgag 180
agtctccgtg agactgtttc acagaaggat gtgtgtgtac ccaaggctac acatcaaaaa 240
gaaatggata aaataagtgg aaaattagaa gattcaacta gcctatcaaa aatcttggat 300
acagttcatt cttgtgaaag agcaagggaa cttcaaaaag atcactgtga acaacgtaca 360
ggaaaaatgg aacaaatgaa aaagaagttt tgtgtactga aaaagaaact gtcagaagca 420
aaagaaataa aatcacagtt agagaaccaa aaagttaaat gggaacaaga gctctgcagt 480
gtgaggtttc tcacactcat gaaaatgaaa attatctctt acatgaaaat tgcatgttga 540
aaaaggaaat tgccatgcta aaactggaaa tagccacact gaaacaccaa taccaggaaa 600

-continued

```
aggaaaataa atactttgag gacattaaga ttttaaaaga aaagaatgct gaacttcaga    660
tgaccctaaa actgaaagag gaatcattaa ctaaaagggc atctcaatat agtgggcagc    720
ttaaagttct gatagctgag aacacaatgc tcacttctaa attgaaggaa aaacaagaca    780
aagaaatact agaggcagaa attgaatcac accatcctag actggcttct gctgtacaag    840
accatgatca aattgtgaca tcaagaaaaa gtcaagaacc tgctttccac attgcaggag    900
atgcttgttt gcaaagaaaa atgaatgttg atgtgagtag tacgatatat aacaatgagg    960
tgctccatca accactttct gaagctcaaa ggaaatccaa aagcctaaaa attaatctca   1020
attatgccgg agatgctcta agagaaaata cattggtttc agaacatgca caaagagacc   1080
aacgtgaaac acagtgtcaa atgaaggaag ctgaacacat gtatcaaaac gaacaagata   1140
atgtgaacaa acacactgaa cagcaggagt ctctagatca gaaattattt caactacaaa   1200
gcaaaaatat gtggcttcaa cagcaattag ttcatgcaca taagaaagct gacaacaaaa   1260
gcaagataac aattgatatt cattttcttg agaggaaaat gcaacatcat ctcctaaaag   1320
agaaaaatga ggagatattt aattacaata accatttaaa aaaccgtata tatcaatatg   1380
aaaaagagaa agcagaaaca gaaaactcat gagagacaag cagtaagaaa cttcttttgg   1440
agaaacaaca gaccagatct ttactcacaa ctcatgctag gaggccagtc ctagcattac   1500
cttatgttga aaatcttacc aatagtctgt gtcaacagaa tacttatttt agaagaaaaa   1560
ttcatgattt cttcctgaag cctgggcgac agagcgagac tctgtctcaa aaaaaaaaaa   1620
aaaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
1               5                   10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys
```

-continued

<210> SEQ ID NO 180
<211> LENGTH: 1681
<212> TYPE: DNA
<213> ORGANISM: Homo sapien

<400> SEQUENCE: 180
gatacagtca ttcttgtgaa agagcaaggg aacttcaaaa agatcactgt gaacaacgta 60
caggaaaaat ggaacaaatg aaaaagaagt tttgtgtact gaaaaagaaa ctgtcagaag 120
caaaagaaat aaaatcacag ttagagaacc aaaaagttaa atgggaacaa gagctctgca 180
gtgtgagatt gactttaaac caagaagaag agaagagaag aaatgccgat atattaaatg 240
aaaaaattag ggaagaatta ggaagaatcg aagagcagca taggaaagag ttagaagtga 300
aacaacaact tgaacaggct ctcagaatac aagatataga attgaagagt gtagaaagta 360
atttgaatca ggtttctcac actcatgaaa atgaaaatta tctcttacat gaaaattgca 420
tgttgaaaaa ggaaattgcc atgctaaaac tggaaatagc cacactgaaa caccaatacc 480
aggaaaagga aaataaatac tttgaggaca ttaagatttt aaaagaaaag aatgctgaac 540
ttcagatgac cctaaaactg aaagaggaat cattaactaa aagggcatct caatatagtg 600
ggcagcttaa agttctgata gctgagaaca caatgctcac ttctaaattg aaggaaaaac 660
aagacaaaga aatactagag gcagaaattg aatcacacca tcctagactg gcttctgctg 720
tacaagacca tgatcaaatt gtgacatcaa gaaaaagtca agaacctgct ttccacattg 780
caggagatgc ttgtttgcaa agaaaaatga atgttgatgt gagtagtacg atatataaca 840
atgaggtgct ccatcaacca ctttctgaag ctcaaaggaa atccaaaagc ctaaaaatta 900
atctcaatta tgccggagat gctctaagag aaaatacatt ggtttcagaa catgcacaaa 960
gagaccaacg tgaaacacag tgtcaaatga aggaagctga acacatgtat caaaacgaac 1020
aagataatgt gaacaaacac actgaacagc aggagtctct agatcagaaa ttatttcaac 1080
tacaaagcaa aaatatgtgg cttcaacagc aattagttca tgcacataag aaagctgaca 1140
acaaaagcaa gataacaatt gatattcatt ttcttgagag gaaaatgcaa catcatctcc 1200
taaaagagaa aaatgaggag atatttaatt acaataacca tttaaaaaac cgtatatatc 1260
aatatgaaaa agagaaagca gaaacagaaa actcatgaga gacaagcagt aagaaacttc 1320
ttttggagaa acaacagacc agatctttac tcacaactca tgctaggagg ccagtcctag 1380
cattacctta tgttgaaaaa tcttaccaat agtctgtgtc aacagaatac ttattttaga 1440
agaaaaattc atgatttctt cctgaagcct acagacataa aataacagtg tgaagaatta 1500
cttgttcacg aattgcataa aagctgccca ggatttccat ctaccctgga tgatgccgga 1560
gacatcattc aatccaacca gaatctcgct ctgtcactca ggctggagtg cagtgggcgc 1620
aatctcggct cactgcaact ctgcctccca ggttcacgcc attctctggc acagcctccc 1680
g 1681

<210> SEQ ID NO 181
<211> LENGTH: 432
<212> TYPE: PRT
<213> ORGANISM: Homo sapien

<400> SEQUENCE: 181

Asp Thr Val His Ser Cys Glu Arg Ala Arg Glu Leu Gln Lys Asp His
1 5 10 15

Cys Glu Gln Arg Thr Gly Lys Met Glu Gln Met Lys Lys Lys Phe Cys

-continued

```
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
            420                 425                 430

<210> SEQ ID NO 182
```

-continued

<211> LENGTH: 511
<212> TYPE: DNA
<213> ORGANISM: Homo sapiens

<400> SEQUENCE: 182
gaagtttcat gaggtttagc ttttctgggc tggggagtgg agagaaagaa gttgcagggc 60
ttacaggaaa tcccagagcc tgaggttttc tcccagattt gagaactcta gattctgcat 120
cattatcttt gagtctatat tctcttgggc tgtaagaaga tgaggaatgt aataggtctg 180
ccccaagcct ttcatgcctt ctgtaccaag cttgtttcct tgtgcatcct tcccaggctc 240
tggctgcccc ttattggaga atgtgatttc caagacaatc aatccacaag tgtctaagac 300
tgaatacaaa gaacttcttc aagagttcat agacgacaat gccactacaa atgccataga 360
tgaattgaag gaatgttttc ttaaccaaac ggatgaaact ctgagcaatg ttgaggtgtt 420
tatgcaatta atatatgaca gcagtctttg tgatttattt taactttctg caagaccttt 480
ggctcacaga actgcagggt atggtgagaa a 511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt 60
cttctctgcc atcttctcat actggtcacg catctcgttc agaatgcggc tcaggtccac 120
gccaggtgca gcgtccatct ccacattgac atctccaccc acctggcctc tcagggcatt 180
catctcctcc tcgtggttct tcttcaggta ggccagctcc tccttcaggc tctcaatctg 240
catctccagg tcagctctgg 260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag 60
agggcctttt ctagctgtat gactgttact tgaccttctt tgaaaagcat tcccaaaatg 120
ctctatttta gatagattaa cattaaccaa cataattttt tttagatcga gtcagcataa 180
atttctaagt cagcctctag tcgtggttca tctctttcac ctgcatttta tttggtgttt 240
gtctgaagaa aggaaagagg aaagcaaata cgaattgtac tatttgtacc aaatctttgg 300
gattcattgg caaataattt cagtgtggtg tattattaaa tagaaaaaaa aaattttgtt 360
tcctaggttg aaggtctaat tgataccgtt tgacttatga tgaccattta tgcactttca 420
aatgaatttg ctttcaaaat aaatgaagag cagacctcgg c 461

<210> SEQ ID NO 185
<211> LENGTH: 531
<212> TYPE: DNA
<213> ORGANISM: Homo sapiens

<400> SEQUENCE: 185
tctgatttta tttccttctc aaaaaaagtt atttacagaa ggtatatatc aacaatctga 60
caggcagtga acttgacatg attagctggc atgatttttt cttttttttc ccccaaacat 120
tgtttttgtg gccttgaatt ttaagacaaa tattctacac ggcatattgc acaggatgga 180

-continued tggcaaaaaa aagtttaaaa acaaaaaccc ttaacggaac tgccttaaaa aggcagacgt 240
cctagtgcct gtcatgttat attaaacata catacacaca atctttttgc ttattataat 300
acagacttaa atgtacaaag atgttttcca ctttttttcaa tttttaaaca caacagctat 360
aaacctgaac acatatgcta tcatcatgcc ataagactaa aacaattata tttagcgaca 420
agtagaaagg attaaatagt caaatacaag aatgaaaaac gcagtacata gtgtcgcgaa 480
ctcaaatcgg catttagata gatccagtgg tttaaacggc acgtttttgc t 531

<210> SEQ ID NO 186
<211> LENGTH: 441
<212> TYPE: DNA
<213> ORGANISM: Homo sapiens

<400> SEQUENCE: 186
cattcctttc ctcgcgttgg ggtttctctg tgtcagcgag cctcggtaca ctgatttccg 60
atcaaaagaa tcatcatctt taccttgact tttcagggaa ttactgaact ttcttctcag 120
aagatagggc acagccattg ccttggcctc acttgaaggg tctgcatttg ggtcctctgg 180
tctcttgcca agtttcccaa ccactcgagg gagaaatatc gggaggtttg acttcctccg 240
gggctttccc gagggcttca ccgtgagccc tgcggccctc agggctgcaa tcctggattc 300
aatgtctgaa acctcgctct ctgcctgctg gacttctgag gccgtcactg ccactctgtc 360
ctccagctct gacagctcct catctgtggt cctgttgtac tggacggggt ccccagggtc 420
ctgggggctt ttttcctgtc t 441

<210> SEQ ID NO 187
<211> LENGTH: 371
<212> TYPE: DNA
<213> ORGANISM: Homo sapiens

<400> SEQUENCE: 187
aaaagtgaat gagtaactat tatattgttg gcaataataa gttgcaaaat catcaggctg 60
caggctgctg atggtgagag tgaactctgt cccagatcca ctgccgctga accttgatgg 120
gaccccagat tctaaactag acgccttatg gatcaggagc tttggggctt tccctggttt 180
ctgttgatac caggccaacc aactactaac actctgactg gcccggcaag tgatggtgac 240
tctgtctcct acagttgcag acagggtgga aggagactgg gtcatctgga tgtcacattt 300
ggcacctggg agccagagca gcaggagccc caggagctga gcggggaccc tcatgtccat 360
gctgagtcct g 371

<210> SEQ ID NO 188
<211> LENGTH: 226
<212> TYPE: DNA
<213> ORGANISM: Homo sapiens

<400> SEQUENCE: 188
ggtatataaa ttgagatgcc cccccaggcc agcaaatgtt cctttttgtt caaagtctat 60
ttttattcct tgatattttt cttttttttt tttttgtgga tggggacttg tgaatttttc 120
taaaggtgct atttaacatg ggaggagagc gtgtgcggct ccagcccagc ccgctgctca 180
ctttccaccc tctctccacc tgcctctggc ttctcaggac ctgccc 226

<210> SEQ ID NO 189
<211> LENGTH: 391
<212> TYPE: DNA

-continued

<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189
tgggtgaagt ttattctgtt ttcacatcta ggttgttggg ganagtgata gacaaagttc 60
tggattctgg gcatcgtcgg cgcatgcttg taatcctact tgggaggttg anacaggaga 120
cctcggccgc naccacgcta agggcgaatt ctgcanatat ccatcacact ggcggccgct 180
cgagcatgca tctanagggc ccaattcncc ctatagtgag ncgtattaca attcactggc 240
cgtcgtttta caacgtcgtg actgggaaaa ccctggcgtt acccaactta atcgccttgc 300
agcacatccc cctttcncca gctggcttaa tancgaagag gcccgcaccg atcgcccttc 360
ccaacanttg cgcagcctga atggcgaatg g 391

<210> SEQ ID NO 190
<211> LENGTH: 501
<212> TYPE: DNA
<213> ORGANISM: Homo sapiens

<400> SEQUENCE: 190
catcttggcc tttttgagct gtttccgctt cttctcatcc cggtcactgt caccctcatt 60
actggaggag ctggcagagg cgttgctgtc aaactcctct gccacatctt cctcctcttc 120
acctgggttg aatgactcat cggtttcttc tcctgagtca tcgctgctgt cattggcatt 180
ctcctcccgg atcttgcctt cctccttcat cctctccaag taggcatcat gctggtcctc 240
atcagagtca gcatattcat cgtagcttgg gttcatgccc tctttcaatc ctcggttttt 300
gatgttgagc tttttcgcgt tgacaaaatc aaacagtttc ccgtactcct ccctctcaat 360
gctgctgaag gtatactgag tgccctgctt ggtctcaatt tcaaagtcaa aggaacgagt 420
agtagtggta ccacgagcaa agttgacaaa ggagatctca tcgaagcgga tgtgcacagg 480
tggcttgtgg acgtagatga a 501

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191
ggaaaaactg tgaaaaatat atctgaattt attaagtaca gtataaaana gggttgtggc 60
aacagaaagt aaaaactaac atggattgct ataaatatgc tgaagcctag ttgttcaaat 120
gatacaattc tctcatgcta ctctaaagtt tataaagaaa aaggatttac actttacaca 180
ctgtacacaa aaggaatacc ttctgagagc cagggagtgg ggaaagggga aggagacttg 240
a 241

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G -continued

<400> SEQUENCE: 192
tggtcntgga ttcacanata aantanatcg actaaaactg gcagaaattg tgaagcaggt 60
gatagaagan caaaccacgt cccacgaatc ccaataatga cagcttcaga ctttgctttt 120
ttaacaattt gaaaaattat tctttaatgt ataaagtaat tttatgtaaa ttaataaatc 180
ataatttcat ttccacattg attaaagctg ctgtatagat ttagggngca ggacttaata 240
atagnggaaa tgaaattatg atttattaat c 271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc 60
taacttcctg tgcctttcct atcacctcga gaagtaatta tcagttggtt tggatttttg 120
gaccaccgtt cagtcatttt gggttgccgt gctcccaaaa cattttaaat gaaagtattg 180
gcattcaaaa agacagcaga caaaatgaaa gaaaatgaga gcagaaagta agcatttcca 240
gcctatctaa tttctttagt tttctatttg cctccagtgc agtccatttc ctaatgtata 300
ccagcctact gtactattta aaatgctcaa tttcagcacc gatggacctg c 351

<210> SEQ ID NO 194
<211> LENGTH: 311
<212> TYPE: DNA
<213> ORGANISM: Homo sapiens

<400> SEQUENCE: 194
ctgagacaca gaggcccact gcgaggggga cagtggcggt gggactgacc tgctgacagt 60
caccctccct ctgctgggat gaggtccagg agccaactaa aacaatggca gaggagacat 120
ctctggtgtt cccaccaccc tagatgaaaa tccacagcac agacctctac cgtgtttctc 180
ttccatccct aaaccacttc cttaaaatgt ttggatttgc aaagccaatt tggggcctgt 240
ggagcctggg gttggatagg gccatggctg gtcccccacc atacctcccc tccacatcac 300
tgacacagac c 311

<210> SEQ ID NO 195
<211> LENGTH: 381
<212> TYPE: DNA
<213> ORGANISM: Homo sapiens

<400> SEQUENCE: 195
tgtcagagtg gcactggtag aagttccagg aaccctgaac tgtaagggtt cttcatcagt 60
gccaacagga tgacatgaaa tgatgtactc agaagtgtcc tggaatgggg cccatgagat 120
ggttgtctga gagagagctt cttgtcctgt ctttttcctt ccaatcaggg gctcgctctt 180
ctgattattc ttcagggcaa tgacataaat tgtatattcg gttcccggtt ccaggccagt 240
aatagtagcc tctgtgacac cagggcgggg ccgagggacc acttctctgg gaggagaccc 300
aggcttctca tacttgatga tgtagccggt aatcctggca cgtggcggct gccatgatac 360
cagcagggaa ttgggtgtgg t 381

<210> SEQ ID NO 196
<211> LENGTH: 401
<212> TYPE: DNA

-continued

<213> ORGANISM: Homo sapiens

<400> SEQUENCE: 196
cacaaacaag aggagcacca gacctcctct tggcttcgag atggcttcgc cacaccaaga 60
gcccaaacct ggagacctga ttgagatttt ccgccttggc tatgagcact gggccctgta 120
tataggagat ggctacgtga tccatctggc tcctccaagt gagtaccccg gggctggctc 180
ctccagtgtc ttctcagtcc tgagcaacag tgcagaggtg aaacgggagc gcctggaaga 240
tgtggtggga ggctgttgct atcgggtcaa caacagcttg gaccatgagt accaaccacg 300
gcccgtggag gtgatcacca gttctgcgaa ggagatggtt ggtcagaaga tgaagtacag 360
tattgtgagc aggaactgtg agcactttgt cacccagacc t 401

<210> SEQ ID NO 197
<211> LENGTH: 471
<212> TYPE: DNA
<213> ORGANISM: Homo sapiens

<400> SEQUENCE: 197
ctgtaatgat gtgagcaggg agccttcctc cctgggccac ctgcagagag ctttcccacc 60
aactttgtac cttgattgcc ttacaaagtt atttgtttac aaacagcgac catataaaag 120
cctcctgccc caaagcttgt gggcacatgg gcacatacag actcacatac agacacacac 180
atatatgtac agacatgtac tctcacacac acaggcacca gcatacacac gtttttctag 240
gtacagctcc caggaacagc taggtgggaa agtcccatca ctgagggagc ctaaccatgt 300
ccctgaacaa aaattgggca ctcatctatt cctttctct tgtgtcccta ctcattgaaa 360
ccaaactctg gaaaggaccc aatgtaccag tatttatacc tctagtgaag cacagagaga 420
ggaagagagc tgcttaaact cacacaacaa tgaactgcag acacagacct g 471

<210> SEQ ID NO 198
<211> LENGTH: 201
<212> TYPE: DNA
<213> ORGANISM: Homo sapiens

<400> SEQUENCE: 198
ggtccattga ggctctgtcg gccatgccca cagttcgaag ctttgccaac gaggagggcg 60
aagcccagaa gtttagggaa aagctgcaag aaataaagac actcaaccag aaggaggctg 120
tggcctatgc agtcaactcc tggaccacta gtatttcagg tatgctgctg aaagtgggaa 180
tcctctacat tggtgggcag a 201

<210> SEQ ID NO 199
<211> LENGTH: 551
<212> TYPE: DNA
<213> ORGANISM: Homo sapiens

<400> SEQUENCE: 199
tctggcacag atcttcaccc acacggcggt ccacgtgctg atcatcttcc gggtctcacc 60
gggcctggaa cacaccatct tccccatgag cccggtgccc agtctggtga cttccatctt 120
ggcccctggc cttatgtccc agttatgacc cctgacttca actctggctc ttaccctgta 180
actccagtcc atctctgaca tttttaacac ccggccttgt gaccgtggac atagctcctg 240
acctcgattc ccatcttgag cccagtgtta gtccatgaga tcatgacctg actcctggtc 300
tccaaccttg tgatcctaat tctgggacct caatcctagc ctctgaactt gggaccctgg 360
agctcctgac cttagtcctg accgctaccc ttgattctga cctttgatcc tgtaacttag 420

-continued

```
gggtggcccc tgaccttatt actgtcattt agctccttga ccttgccact tcaatcctgg    480

ctttatgacc tcctactctc aattttaact ttaaccaaat gaccaaattt gtgacactaa    540

atgaccacaa t                                                          551
```

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200

```
cagctcancg ggcgacatgc ccctacaagt tggcanaagn ggctgccact gctgggtttg     60

tgtaagagag gctgctgnca ccattacctg cagaaacctt ctcatagggg ctacgatcgg    120

tactgctagg gggcacatag cgcccatggg tgtggtaggt ggggnactcn ntnataggat    180

ggtaggtatc ccgggctgga aanatgnnca g                                    211
```

<210> SEQ ID NO 201
<211> LENGTH: 111
<212> TYPE: DNA
<213> ORGANISM: Homo sapiens

<400> SEQUENCE: 201

```
ccagtgaaag gaaacaaaac tggcagtttg tccatttgaa tatcagacct agtttcttct     60

taatttccac actatttctc ccatattcct taaacttctt ggcatccacc t              111
```

<210> SEQ ID NO 202
<211> LENGTH: 331
<212> TYPE: DNA
<213> ORGANISM: Homo sapiens

<400> SEQUENCE: 202

```
tgaaaataca gaataccagg tggtcccaaa tgtttgaagt tctttgaaca gaaagagaga     60

ggagagagag agagaggaaa attccctaac ccttggttta aagacaatat tcatttattg    120

ctcaaatgat gcttttaagg gaggacagtg gaataaaata aacttttttt ttctccctac    180

aatacataga agggttatca aaccactcaa gtttcaaaat ctttccaggg tccaatatca    240

cttttttttct ttcggttcaa tgaaaagcta aatgtaataa tactaattat agataaaatt    300

ttattttact ttttaaaaat ttgtccagac c                                    331
```

<210> SEQ ID NO 203
<211> LENGTH: 491
<212> TYPE: DNA
<213> ORGANISM: Homo sapiens

<400> SEQUENCE: 203

```
agtcacccag tctacttagt acctggttgc tgcctctgac cttttcagct tgataccctg     60

ggctttagtg taaccaataa atctgtagtg accttacctg tattccctgt gctatcctgt    120

gggaaggtag gaatgggcta agtatgatga atgtataggt tagggatctt ttggttttaa    180

atcacagaaa acctaattca aactggctta aaataaaaag gatttattgg ttcatgtaac    240

tagaaagtcc ataggtagtg ctggctccag gtgaagactt gacccagtag ttcagtatgt    300

ctctaaatac cggactgact tttttctcac tgttgcatct tctgtaggac catttaagtc    360
```

-continued

```
tgggccactt aatggctgcc agcattccta agattacact tttccccatt tatgtccaat    420

cagaaaaaga aggcatcttt gtaccagaaa tctcagcaaa agccctaata ttcacactga    480

ttaggacctg c                                                         491


<210> SEQ ID NO 204
<211> LENGTH: 361
<212> TYPE: DNA
<213> ORGANISM: Homo sapiens

<400> SEQUENCE: 204

tcccttcctc ccccatgtga taaatgggtc cagggctgat caaagaactc tgactgcaga     60

actgccgctc tcagtggaca gggcatctgt tatcctgaga cctgtggcag acacgtcttg    120

ttttcatttg atttttgtta agagtgcagt attgcagagt ctagaggaat ttttgtttcc    180

ttgattaaca tgattttcct ggttgttaca tccagggcat ggcagtggcc tcagccttaa    240

acttttgttc ctactcccac cctcagcgaa ctgggcagca cggggagggt ttggctaccc    300

ctgcccatcc ctgagccagg taccaccatt gtaaggaaac actttcagaa attcagacct    360

c                                                                    361


<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<221> NAME/KEY: misc_feature
<222> LOCATION: (3)
<223> OTHER INFORMATION: n=A,T,C or G

<400> SEQUENCE: 205

cnngtacagt tcttcctgga tggccgacac agatcctggg gaaaggcaat cctggcactg     60

ctctgaaacc agagctcctc ctccctcccc gggcagggtg gagctgagaa gggctgctct    120

agcgttggga ctccacctcc atacacctga tattttgata gggcaggtcc ctgctatggg    180

ccactgttct gggcagtata gtatgcttga cagcatcctt ggcatctatc caccagatcc    240

cagagcaccc gctactagct gtgacaacat cctccaaaca ttgcaaaatt tcccctggga    300

ggcaagattg cctcagatgg gagaatcacg ctctagggaa atctgctggt atgagaaccc    360

caactcccca ctccactgag cctccagatg gcgagcaggc tgcagctcca gcacagacac    420

gaagctccct ccagccactg acggtccatg gctggggtta cccaggacct c             471


<210> SEQ ID NO 206
<211> LENGTH: 261
<212> TYPE: DNA
<213> ORGANISM: Homo sapiens

<400> SEQUENCE: 206

tagagtattt agagtcctga gataacaagg aatccaggca tcctttagac agtcttctgt     60

tgtcctttct tcccaatcag agatttgtgg atgtgtggaa tgacaccacc accagcaatt    120

gtagccttga tgagagaatc caattcttca tctccacgaa tagcaagttg caagtgacga    180

ggggtaatac gctttacctt taagtctttt gatgcatttc ctgccagttc aagtacctct    240

gcggtgaggt actccaggat g                                              261


<210> SEQ ID NO 207
```

-continued

<211> LENGTH: 361
<212> TYPE: DNA
<213> ORGANISM: Homo sapiens

<400> SEQUENCE: 207

```
gctctccggg agcttgaaga agaaactggc tacaaagggg acattgccga atgttctcca     60

gcggtctgta tggacccagg cttgtcaaac tgtactatac acatcgtgac agtcaccatt    120

aacggagatg atgccgaaaa cgcaaggccg aagccaaagc caggggatgg agagtttgtg    180

gaagtcattt ctttacccaa gaatgacctg ctgcagagac ttgatgctct ggtagctgaa    240

gaacatctca cagtggacgc cagggtctat tcctacgctc tagcactgaa acatgcaaat    300

gcaaagccat ttgaagtgcc cttcttgaaa ttttaagccc aaatatgaca ctggacctgc    360

c                                                                    361
```

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

```
agaggagatn tttgccatgc ctgaatnctt tcctatncca ccctancact taacatatta     60

cttagtctgc tttgntaaaa gcaagtatta ccttnaactt gnctcttact ctttgccctt    120

tagctaacta ataaagnttg atntaggcat tattatataa ttctgagtca ttcatggtat    180

ctctcatgtt tgatgtattt tncaaactaa gatctatgat agtttttttt ccanagttcc    240

attaaatcat ttatttcctt tactttctca cctctgtnga aacatttaga aactggattt    300

gggaacccan ttttggaaaa ccagattcat agtcatgaaa atggaaactt ncatattctg    360

tttttgaaaa gatgtggacc t                                              381
```

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209

```
gtggagagca agtgatttat taaagcaaga cgttgaaacc tttacattct gcagtgaaga     60

tcagggtgtc attgaaagac agnggaaacc aggatgaaag tttttacatg tcacacacta    120

catttcttca atattttcac caggacttcc gcaatgaggc ttcgtttctg aagggacatc    180

tgatccgtgc atctcttcac tcctaacttg gctgcaacag cttccacctg c             231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc     60

atgtcagtta tctccactaa catatccaag aatctttgta ggacaatttc tccacctgca    120

aggtttttta ggtagaactc ttcttttaag gcaattagcc cattgccaaa aggttttact    180
```

-continued

```
gtcttaaagc tgtctttctg agatctaatt ccaaggactt ctccacagct aagtgagatg    240
cctcacacca ttaggtgatg ctttggacag aacagagtat tttcatcttg tgtttaaagc    300
aattccttgg cttcggctcc tcaccacttt ctatgccagt ctcccattta tgtccctagt    360
aatgcctatg c                                                         371
```

<210> SEQ ID NO 211
<211> LENGTH: 471
<212> TYPE: DNA
<213> ORGANISM: Homo sapiens

<400> SEQUENCE: 211

```
tttattttaa aagaaaaaaa ttaaaataga gccaacaaat gcaattaaga aaaaaaaagt     60
attgagacac aaggggacct acatgttctg gtctaagaag catgcaagta ttacaaagca    120
ttccagatac agtatgacag aggaacagtg aacaagcatt ggaacgatgc tctttctttc    180
agaaacggga agtctaacag ttatgttttc acaatggtag tgattaaacc atctttattt    240
ttaaggaatt ttataggaag aattttagca ccatcattaa aggaaaaata ataatacctt    300
tttagccctg cctatctcca gtcttggaat aataacagaa gcatagcacc tttcagtatc    360
taaaatataa acaagaatag taagtccatc ccagcttcta gagatgaggt agctcatgct    420
aagaaatgtt gggtcatttt tcctatgaaa gttcaaaggc caaatggtca c             471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat     60
atattttggg ttcaaaaaaa gtaaaaagat aatgtagctg catttctttg gttattttgg    120
gccccaaata tttcctcatc tttttgttgt tgtcatggat ggtggtgaca tggacttgtt    180
tatagaggac aggtcagctc tctggctcgg tgatctacat tctgaagttg tctgaaaatg    240
tcttcatgat taaattcagc ctaaacgttt tgccgggaac actgcagaga caatgctgtg    300
agtttccaac ctcagcccat ctgcgggcag agaaggtcta gtttgtccat caccattatg    360
atatcaggac tggttacttg gttaaggagg ggtctacctc g                        401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213

```
tgtgaagcat acataaataa atgaagtaag ccatactgat ttaatttatt ggatgttatt     60
ttccctaaga cctgaaaatg aacatagtat gctagttatt tttcagtgtt agccttttac    120
tttcctcaca caatttggaa tcatataata taggtacttt gtccctgatt aaataatgtg    180
acggatagaa tgcatcaagt gtttattatg aaaagagtgg aaaagtatat agcttttanc    240
aaaaggtgtt tgcccattct aagaaatgag cgaatatata gaaatagtgn gggcatttct    300
tcctgttagg tggagtgtat gtgttgacat ttctccccat ctcttcccac tctgtttnnt    360
```

-continued

```
ccccattatt tgaataaagt gactgctgaa nangactttg aatccttatc cacttaattt    420

aatgtttaaa gaaaaaccta taatggaaag tgagactcct t                        461


<210> SEQ ID NO 214
<211> LENGTH: 181
<212> TYPE: DNA
<213> ORGANISM: Homo sapiens

<400> SEQUENCE: 214

cctgagcttc tactcctttc ccttaagatt cctccaaagc accagctcca taaaatcctt     60

cagctcccca gacccacacc aagaacccca catgttaatt ggatcagcca aatctacaag    120

cagataagtc ctaaggagaa tgccgaagcg tttttcttct tcctcaagcc tagcatgaga    180

c                                                                    181


<210> SEQ ID NO 215
<211> LENGTH: 581
<212> TYPE: DNA
<213> ORGANISM: Homo sapiens

<400> SEQUENCE: 215

ctgctttaag aatggttttc caccttttcc ccctaatctc taccaatcag acacatttta     60

ttatttaaat ctgcacctct ctctatttta tttgccaggg gcacgatgtg acatatctgc    120

agtcccagca cagtgggaca aaaagaattt agaccccaaa agtgtcctcg gcatggatct    180

tgaacagaac cagtatctgt catggaactg aacattcatc gatggtctcc atgtattcat    240

ttattcactt gttcattcaa gtatttattg aatacctgcc tcaagctaga gagaaaagag    300

agtgcgcttt ggaaatttat tccagttttc agcctacagc agattatcag ctcggtgact    360

tttctttctg ccaccattta ggtgatggtg tttgattcag agatggctga atttctattc    420

ttagcttatt gtgactgttt cagatctagt ttgggaacag attagaggcc attgtcctct    480

gtcctgatca ggtggcctgg ctgtttcttt ggatccctct gtcccagagc cacccagaac    540

cctgactctt gagaatcaag aaaacaccca gaaaggacct c                        581


<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216

ccgatgtcct gcttctgtgg accaggggct cctctgnngg tggcctcaac cacggctgag     60

atccctagaa gtccaggagc tgtggggaag agaagcactt agggccagcc agccgggcac    120

ccccacttgc gccccgaccc acgctcacgc accagacctg cccnggcggt cgctcnaaag    180

ggcgaattct gcagatatcc atcacactgg cggacgctcg agcatgcatc tagagggccc    240

aattcaccct atantgagtc gtattacaat tcactggccg t                        281


<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G
```

-continued

<400> SEQUENCE: 217
atagcaggtt tcaacaattg tcttgtagtt tgnagtaaaa agacataaga aagagaaggt 60
gtggtttgca gcaatccgta gttggtttct caccataccc tgcagttctg tgagccaaag 120
gtcttgcaga aagttaaaat aaatcacaaa gactgctgtc atatattaat tgcataaaca 180
cctcaacatt gctcagagtt tcatccgttt ggttaagaaa acattccttc aattcatcta 240
tggcatttgt agtggcattg tcgtctatga actcttgaag aagttctttg tattcagtct 300
tagacacttg tggattgatt gncttggaaa tcacattctc caataaggga cctcgg 356

<210> SEQ ID NO 218
<211> LENGTH: 321
<212> TYPE: DNA
<213> ORGANISM: Homo sapiens

<400> SEQUENCE: 218
ttgtccatcg ggagaaaggt gtttgtcagt tgtttcataa accagattga ggaggacaaa 60
ctgctctgcc aatttctgga tttctttatt ttcagcaaac actttcttta aagcttgact 120
gtgtgggcac tcatccaagt gatgaataat catcaagggt ttgttgcttg tcttggattt 180
atatagagct tcttcatatg tctgagtcca gatgagttgg tcaccccaac ctctggagag 240
ggtctggggc agtttgggtc gagagtcctt tgtgtccttt ttggctccag gtttgactgt 300
ggtatctctg gacctgcctg g 321

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219
ccggttaggt ccacgcgggg gcagtggagg cacaggctca nggtggccgg gctacctggc 60
accctatggc ttacaaagta gagttggccc agtttccttc cacctgaggg gagcactctg 120
actcctaaca gtcttccttg ccctgccatc atctggggtg gctggctgtc aagaaaggcc 180
gggcatgctt tctaaacaca gccacaggag gcttgtaggg catcttccag gtggggaaac 240
agtcttagat aagtaaggtg acttgtctaa g 271

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220
gtcctacgac gaggaccagc ttttcttctt cnacttttcc canaacactc gggtgcctcg 60
cctgcccgaa tttgctgact gggctcagga acagggagat gctcctgcca ttttatttga 120
caaagagttc tgcgagtgga tgatccagca aataggccca aaacttgatg ggaaaatccc 180
ggtgtccaga gggtttccta tcgctgaagt gttcacgctg aagcccctgg agtttggcaa 240
gcccaacact ttggtctgtt ttgtcagtaa tctcttccca cccatgctga cagtgaactg 300

-continued gtagcatcat tccgtccctg tggaaggatt tgggcctact tttgtctcag a 351

<210> SEQ ID NO 221
<211> LENGTH: 371
<212> TYPE: DNA
<213> ORGANISM: Homo sapiens

<400> SEQUENCE: 221
gtctgcagaa gcgtgtctga ggtgtccggt ggaggtggca gccgagctct gggactaatc 60
accgtgctgg ggacggcacc gcgtcaggat gcaggcagat ccctgcagaa gtgtctaaaa 120
ttcacactcc tcttctggag ggacgtcgat ggtattagga tagaagcacc aggggacccc 180
acgaacggtg tcgtcgaaac agcagccctt atttgcacac tgggagggcg tgacaccagg 240
aaaaccacaa ttctgtcttt cacggggggc cactgtacac gtctctgtct gggcctcggc 300
cagggtgccg agggccagca tggacaccag gaccagggcg cagatcacct tgttctccat 360
ggtggacctc g 371

<210> SEQ ID NO 222
<211> LENGTH: 471
<212> TYPE: DNA
<213> ORGANISM: Homo sapiens

<400> SEQUENCE: 222
gtccatgttc catcattaat gttccaacat caccagggac acaaagctgc aaaaatgaga 60
agggaaataa ggttagagaa aggatccggg caatcttaag gactgaggaa gacatgttcc 120
ccaacccttg aactcacaaa ccctgaagct caaggattgc atccttcctc caaatctcac 180
tcaacataat aagtgcagaa caacatgcca aagcactgta tgaagcacta gggacaaaga 240
caaggtcaaa atccttgtaa ccaaatttaa tggtattgta atgcagtgtt aacacaggac 300
agtaacagaa cacccaagaa ccaaacagaa gagggtaggg ataagcataa atgaagtaac 360
atgaaataaa cttccaaatg gaaaacttgt ccataccccc agggcaagtc aactacagtc 420
tcccaaagga cataaattcc acttagggca cactagacag aaaacaatat t 471

<210> SEQ ID NO 223
<211> LENGTH: 411
<212> TYPE: DNA
<213> ORGANISM: Homo sapiens

<400> SEQUENCE: 223
agttgctcta caatgacaca caaatcccgt taaataaatt ataaacaagg gtcaattcaa 60
atttgaagta atgttttagt aaggagagat tagaagacaa caggcatagc aaatgacata 120
agctaccgat taactaatcg gaacatgtaa aacagttaca aaaataaacg aactctcctc 180
ttgtcctaca atgaaagccc tcatgtgcag tagagatgca gtttcatcaa agaacaaaca 240
tccttgcaaa tgggtgtgac gcggttccag atgtggattt ggcaaaacct catttaagta 300
aaaggttagc agagcaaagt gcggtgcttt agctgctgct tgtgccgctg tggcgtcggg 360
gaggctcctg cctgagcttc cttccccagc tttgctgcct gagaggaacc a 411

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G -continued

<400> SEQUENCE: 224
ggtctgaagt ttgataacaa agaaatatat ntaagacaaa aatagacaag agttaacaat 60
aaaaacacaa ctatctgttg acataacata tggaaacttt ttgtcagaaa gctacatctt 120
cttaatctga ttgtccaaat cattaaaata tggatgattc agtgccattt tgccagaaat 180
tcgtttggct ggatcataga ttaacatttt cgagagcaaa tccaagccat tttcatccaa 240
gtttttgaca tgggatgcta ggcttcctgg tttccatttg ggaaatgtat tcttatagtc 300
ctgtaaagat tccacttctg g 321

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225
atgtctgggg aaagagttca ttggcaaaag tgtnctccca agaatggttt acaccaagca 60
gagaggacat gtcactgaat ggggaaaggg aaccccccgta tccacagtca ctgtaagcat 120
ccagtaggca ggaagatggc tttgggcagt ggctggatga aagcagattt gagataccca 180
gctccggaac gaggtcatct tctacaggtt cttccttcac tgagacaatg aattcagggt 240
gatcattctc t 251

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226
gttaggtccc aggccccccg ccaagnggtt accnnnntna ccactcctga cccaaaaatc 60
aggcatggca ttaaaacgtt gcaaattcct ttactgttat cccccccacc accaggacca 120
tgtagggtgc agtctttact ccctaacccg tttcccgaaa aaggtgctac ctcctttcca 180
gacagatgag agagggcagg acttcaggct ggatccacca ctgggctctc cctccccccag 240 cctggagcac gggaggggag gtgacggctg gtgactgatg gatgggtagt gggctgagaa 300
gaggggacta ggaagggcta ttccaggctc a 331

<210> SEQ ID NO 227
<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg 60
gctgaagcta gaagtgcaac cccctcctga tttctgcagc aagatgaact gccttatccc 120
cagcccgcag gaatgttcat atctgagcaa tcaatgggca ctgtgttcaa ccacgccatt 180
ttcaagattg gctccttaaa ccacccacaa ggcaccagct ctgggagaag ctgcagggag 240
aagagaacaa agccctcgct gtgatcagga tgggtgtctc atacctttttc tctggggtca 300

-continued ttccaggtat gagacagagt tgaacctgcg catgagcgtg gaggccgaca tcaacggcct 360
gcgcagggtg ctggatgagc tgaccctgga c 391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228
gttgtccata gccacctcct gggatagaag ctttntagtt catagttcga ttagtgtgtc 60
cttaggacat aggtccagcc ctacagatta gctgggtgaa gaaggcaagt gtctcgacag 120
ggcttagtct ccaccctcag gcatggaacc attcagggtg aagcctggga tgtgggcaca 180
ggagactcag gctgatataa aaataacaaa atcagtaata aaaaaattat aaaacctgtt 240
gcttgtctga atagatttga gcaacagtct tgcttttgtt aaaatcctgg agccgttaag 300
tcctgaatat tcttctggac atcattgctg gctggagaaa ggagccccag gcccggctcg 360
gctgacatct gtcaggtttg gaagtctcat c 391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229
gtccatggct tctcacccag acagtctttc tgggcaactt ggggaagccc ctgttctgct 60
caagtctcac cccatggaag aggtggggga agggggcctt ggtttttcag gaagacgggt 120
tggagagcac gagtcactac aaagcagtaa aagtgaatgg tgtctccagg ggctgggtcc 180
agaacaccgc ggagagcccc anccataaag gtgtgttccg cctctggcct gcaggaatct 240
ctttgaatct ctttgattgg tggctccaag agcaatggga agtcaacagc caggaggctg 300
gactgggttc cctgggaccc cgaggtccca gaggctgctg g 341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg 60
gggctaaagg aaatggacaa tgcaggacag ctagtgtttc tggctacaga aggggaccat 120
cttcagttgt ctgaagaatg gttttatgcc cacatcatac cattccttgg atgaaacccg 180
tatagttcac aatagagctc agggagcccc taactcttcc aaaccacatg ggagacagtt 240
tccttcatgc ccaagcctga gctcagatcc agcttgcaac taatccttct atcatctaac 300
atgccctact tggaaagatc taagatctga atcttatcct ttgccatctt ctgttaccat 360
atggtgttga atgcaagttt aattaccatg gagattgttt tacaaacttt tgatgtggtc 420
aagttcagtt ttagaaaagg gagtctgttc cagatcagtg ccagaactgt gcccaggccc 480
aaaggagaca actaactaaa gtagtgagat a 511

-continued

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct 60
cccctcgtgt cagctcaggc agctcgaggc ccccgaccaa cacttgcagg ggtccctgct 120
agttagcgcc ccaccgccgt ggagttcgta ccgcttcctt agaacttcta cagaagccaa 180
gctccctgga gccctgttgg cagctctagc tttgcagtcg tgtaattggc ccaagtcatt 240
gtttttctcg cctcactttc caccaagtgt ctagagtcat gtgagcctcg tgtcatctcc 300
ggggtggacc t 311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt 60
ctaaaaagcg gttctgtaac tctcaatcca gagatgttaa aaatgtttct aggcacggta 120
ttagtaaatc aagtaaattt catgtcctct taaaggacaa acttccagag atttgaatat 180
aaatttttat atgtgttatt gattgtcgtg taacaaatgg cccccacaaa ttagtagctt 240
aaaatagcat ttatgatgtc actgttttct ttgccttttc attaatgttc tgtacagacc 300
tatgtaaaca acttttgtat atgcatatag gatagctttt ttgagggtat a 351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc 60
acagccaccc ccagtatgcc gctccaggac tctgggacta gggcgccaaa gtgtgcaaat 120
gaaaatacag gatacccagg gaactttgaa tttcagattg tgaaaagaaa acaaatcttg 180
agactccaca atcaccaagc taaaggaaaa agtcaagctg ggaactgctt agggcaaagc 240
tgcctcccat tctattcaca gtcatccccc tgaggctcac ctgcatagct gattgcttcc 300
tttcccctat cgcttctgta aaaatgcaga ctcactgagc cagactaaat tgtgtgttca 360
gtggaaggct gatcaagaac tcaaaagaat gcaacctttt gtctcttatc tactacaacc 420
aggaagcccc cacttaaggg ttgtcccacc ttactggact gaaccaaggt acatcttaca 480
cctactgatt gatgtctcat gtccccctaa g 511

<210> SEQ ID NO 234
<211> LENGTH: 221
<212> TYPE: DNA
<213> ORGANISM: Homo sapiens

<400> SEQUENCE: 234
caggtccagc gaaggggctt cataggctac accaagcatg tccacataac cgaggaagct 60
ctctccatca gcatagcctc cgatgaccat ggtgttccac aaagggttca tcttcgagcg 120

-continued

```
ccggctgtac atggccctgg tcagccatga atgaatagct ctaggactat agctgtgtcc    180

atctcccaga agctcctcat caatcaccat ctggccgaga c                        221
```

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

```
ggtccaagaa agggacatct atgtgaaagt ganactgaga cagtgctggt cacaggtcat     60

gctgcagaat aatacattcc caggcactgt cacgtggggg acccaagagg ccccaggagt    120

gacctataac ctctccagaa agaccactct gtgtggcatc acagtccaca cagtttaagg    180

aaatatttag acttaacaat cagacaccag ctcttactca cacttacact cacagcccac    240

acacaagtgt gcaaacatac acacacatat atatttcctg atacattcat ggaatatcag    300

agccctgccc tgaagtcgtt agtgtctctg ctccccaaac cgctgctccc acattggcta    360

agctccctca agagacctca g                                              381
```

<210> SEQ ID NO 236
<211> LENGTH: 441
<212> TYPE: DNA
<213> ORGANISM: Homo sapiens

<400> SEQUENCE: 236

```
aggtcctgtt gccccttctt tttgcccaac ttcgccattt gggaattgga atatttaccc     60

aacacctgta ctgcattgaa tattggaagc aaataacttg gctttgatct tataggctca    120

cagatggagg aacgtacctt gaagttcaga tgagatttcg gacttttgag ttgatgctga    180

aacagcttga gatttttggg gactactgag agatgataat tgtattgtgc aatatgagaa    240

ggacatgaga tttggtgggc ataggtgtga aatgacattg tttggatgtg tttaccctcc    300

aaatctcttg ttgaatgtga tcttaaacgt tggtggtggg cctagtggaa ggtgttgaat    360

catgggggtg gactcttcat aatttgctta gctccatccc cttggtgatg agcaagtcct    420

tgctctgttg tgtcacatga g                                              441
```

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237

```
tcctaaaaaa ttagctgacc ttgttaaaaa tgttggcgtg agcagtatat tattacctat     60

cttttttat tgtgtgtgtg ngtgtgtgtn ttaaactaat tggctgaaat atctgcctgt    120

ttccctcttt acatttttct tgtttctttc cttatttatc tttgtccatc ttgagatcta    180

ctgtaaagtg aatnttttaa tgaaaacann nccaagttnt actctcactg ggnttgggac    240

atcagatgta attgagaggc caacaggtaa gtcttcatgt c                        281
```

<210> SEQ ID NO 238
<211> LENGTH: 141

-continued

<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238
gtctgcctcc tcctactgtt tccctctatn aaaaagcctc cttggcgcag gttccctgag 60
ctgtgggatt ctgcactggt gcttnggatt ccctgatatg ttccttcaaa tccactgaga 120
attaaataaa catcgctaaa g 141

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239
aacaatctaa acaaatccct cggttctann atacaatgga ttccccatat tggaaggact 60
ctgangcttt attcccccac tatgcntatc ttatcatttt attattatac acacatccat 120
cctaaactat actaaagccc ttttcccatg catggatgga aatggaagat tttttttaa 180 cttgttctag aagtcttaat atgggctgtt gccatgaagg cttgcagaat tgagtccatt 240
ttctagctgc ctttattcac atagtgatgg ggtactaaaa gtactgggtt gactcagaga 300
gtcgctgtca ttctgtcatt gctgctactc taacactgag caacactctc ccagtggcag 360
atcccctgta tcattccaag aggagcattc atccctttgc tctaatgatc aggaatgatg 420
cttattagaa aacaaactgc ttgacccagg aacaagtggc ttagcttaag naaacttggc 480
tttgctcana tccctgatcc t 501

<210> SEQ ID NO 240
<211> LENGTH: 451
<212> TYPE: DNA
<213> ORGANISM: Homo sapiens

<400> SEQUENCE: 240
tgtcctgaaa ggccattact aatagaaaca cagcctttcc aatcctctgg aacatattct 60
gtctgggttt ttaatgtctg tggaaaaaaa ctaaacaagt ctctgtctca gttaagagaa 120
atctattggt ctgaaggttt ctgaacctct ttctggttct cagcagaagt aactgaagta 180
gatcaggaag ggctgcctc aggaaaattc ctagatccta ggaattcagt gagaccctgg 240
gaaggaccag catgctaatc agtgtcagtg aatccacagt ctttacttcc tgcctcataa 300
agggccaggt ctccccagta ccaagtcctt tcctcatgaa gttgtgttgc ctcaggctgt 360
ttagggacca ttgcctgtct tggtcacatg agtctgtctc cttactttag tccctgggca 420
atccttgctt aatgcttttg ttgactcaac g 451

<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G -continued

<400> SEQUENCE: 241

```
aatctccagt gtgatggtat cggggttaga gcttcaatct ccagtgtgat ggtactgcag     60
cnagagcttc aatctccagt gngatggtat tagggttaga tcttcaatct ccagtgtgat    120
ggtatcaggg ttagagcttc agcctccagt gtgatggtat cagggttaga gcttcagcct    180
ccagtgtgat ggtatcgggg ttagatcttc aatccccagt ggtggtggtt agagcttcaa    240
tctccagtgt gatggtattg gggttagagc ttcaatctcc agtctgatgg tgtttcggga    300
tggggctttt aagatgtaat tagggtttaa gatcataagg gacctggtct gatggggatt    360
agtncgcttn tatgaagaga cacangaggg cttgctctat ctctgactct c             411
```

<210> SEQ ID NO 242
<211> LENGTH: 351
<212> TYPE: DNA
<213> ORGANISM: Homo sapiens

<400> SEQUENCE: 242

```
ttccccttca caacagtaga gacctacaca gtgaactttg gggacttctg agatcagcgt     60
cctaccaaga ccccagccca actcaagcta cagcagcagc acttcccaag cctgctgacc    120
acagtcacat cacccatcag cacatggaag gcccctggta tggacactga aaggaagggc    180
tggtcctgcc cctttgaggg ggtgcaaaca tgactgggac ctaagagcca gaggctgtgt    240
agaggctcct gctccacctg ccagtctcgt aagaaatggg gttgctgcag tgttggagta    300
ggggcagagg gagggagcca aggtcactcc aataaaacaa gctcatggca c             351
```

<210> SEQ ID NO 243
<211> LENGTH: 241
<212> TYPE: DNA
<213> ORGANISM: Homo sapiens

<400> SEQUENCE: 243

```
gtctgtgctt tatcaggaaa agcacaagaa tatgtttttc tacctaaaac cctcttctac     60
tttaaaaatg gtttgctgaa tttttctatg tttttaaaat gtttttatgc tttttttaa    120
acacgtaaag gatggaacct aatcctctcc cgagacgcct cctttgtgtt aatgcctatt    180
cttacaacag agaaacaagt acattaatat aaaaacgagt tgattattgg ggtataaaat    240
a                                                                    241
```

<210> SEQ ID NO 244
<211> LENGTH: 301
<212> TYPE: DNA
<213> ORGANISM: Homo sapiens

<400> SEQUENCE: 244

```
ggtccagagc aatagcgtct gtggtgaagc gcctgcactc ctcgggagac atgcctggct     60
tatatgctgc atccacataa ccatagataa aggtgctgcc ggagccacca atggcaaaag    120
gctgtcgagt cagcattcct cccagggttc catatacctg acctccttca cgttggtccc    180
agccagctac catgagatgt gcagacaagt cctctcgata tttatagctg atatttctca    240
ccacatttgc agcagccaaa acaagtggag gttcctccag ttctatccca tggagctcca    300
g                                                                    301
```

<210> SEQ ID NO 245
<211> LENGTH: 391
<212> TYPE: DNA
<213> ORGANISM: Homo sapiens

<400> SEQUENCE: 245
ctgacactgc tgatgtgggc cggggggcgc cgaggcacaa ctggtggccg gaccattgag 60
gcacctggag ggtaggcagc ttgtggtgca gacaccacag agagagaaaa gttggatgga 120
gtggtgggaa taatcagggt ggcacactgt gcctagaagc ttccagggcc accaagagaa 180
tgggaaggga aactacaaca ttcacaacag aaataggagt caattcactt agacccagaa 240
ctccagaaag ggggagtgta ggaatctaca atttcaaagc cagctcgtgt ctacctagag 300
ccccaaactg cataagcacc aggattgtac accttagtcc ctcaagatag tttcaagtga 360
gcgtgcaatt cactcttaca gaggagggcc t 391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246
tcctccacag gggaagcagg aagttngacc agcttcaggc tggaacgtgc ccagggcaca 60
gagctggcaa ggtgcaaagn cntctgcaga atattcacca ggttgacaca gacctccaca 120
ttcagacata ttccaagctt ctggggtctt cagggcccca gaatttcctg gtcttgggca 180
tggtncacaa gtcatttgtc cttcctcatt ttggaaggtt ccatttggac ataaaatgca 240
agcgttctcg tgctncatna taataggtcc cagcctgcac tgacacattt g 291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
cactgagtga atgagtatat aatttatgaa aacagaaaag tgctttggaa aaaaaaaaag 60
acaacaggag tacatacagn gaaccaaaaa gagtgtacca ggaggagcan accctgaaca 120
gttanaacta tggaaatcgc tatgctttgt gttgtcacag gagttaaaat aggaataccc 180
tgcatacaat aaatatttat tggataaata actaagcctg ataccctttt caatgcgtta 240
tacanactnt atcatcacac cactaatcta agttctcana agttaaacat tacaagactt 300
cagaacaaca taggcgtntt tggctccatt taacanaana aggaccatag tgatcattta 360
atctctatga gtctgtctta tcttctggaa aaggggccta acaccatttc cttttgcaaa 420
aaggtagctg ccttgcttcc agttctacca tcctntagca acccatcttt n 471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca 60
aatgtcccca tcccacccac tcacatgaca tggctcccga gccctgagat ctgtatccca 120
agaacctcag ttgagaaata tttatggcag cttcactgtt gctcaagagc ctgggtattg 180
tagcagcctg ggggcaggtt gtccctaatg ttctccaagt tcttcacatc agccagaatc 240
ccatctatgc ttgtctccag caaatggagg tggcccctct gctgacgtgc cctctcttcc 300
agctctgaca tcatgggccg cagttggctg ttgatctggg tcttggctcg ggaaagcttc 360
tgctccagta agaccagccc ctcttcatct acactgagag gctggtccat cagatgcagg 420
aggccgtcta atgtgttgag tgtgtcttgg attgtaaccc cagcgttctt ggctctggta 480
tcaaccttct gggcttctgt aatcaccatc tgtactgcat ccatattcgt gtcgaactcc 540
agctccttcc t 551

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249
atntccagag ggaccgtaag actggtacaa gtttacacca taagaggcga cgtggtcagc 60
cacaatgtct tcacctccac aggggctcat cacggnggtc agggcaaggg cccccagcat 120
cagagctttg tttaggatca tcctcttccc aaggcagcct tagcagttgc tgacctgccc 180
g 181

<210> SEQ ID NO 250
<211> LENGTH: 551
<212> TYPE: DNA
<213> ORGANISM: Homo sapiens

<400> SEQUENCE: 250
tctgtagcta ggatgagctg gctctcaagc aaaagtttgt cttcctgggt ccatttgtgg 60
ttatcacttg ttattgaatg tacatcacaa attaaagtct gcattgttgg acgtaagaga 120
atgtgccgac tttggtaacc aggagatttc atgttactgg actgcctgta gtcacgtatt 180
tctgctatga cacatccgca atgaaaaata ttaacctgag atttttctag gagatcaacc 240
aaaataggag gtaattcttc tgcatccaaa tattcaagca actctccttc ttcatagggc 300
agtcgaatgg tctcggaatc tgatccgttt tttcccctga gcatcagaga atatccctca 360
tttcctgggt atagattgac cactaaacat gacaaagtct cttgcataac aagcttctct 420
aacaagttca catttcttct taatttctta acttcaggtt ctttttcaca ttcttcaata 480
tacaagtcat aaagtttttg aaatacagat tttcttccac ttgataggta tttcctttta 540
ggaggtctct g 551

<210> SEQ ID NO 251
<211> LENGTH: 441
<212> TYPE: DNA
<213> ORGANISM: Homo sapiens

<400> SEQUENCE: 251
tgtctgctct cccatcctgg ttactatgag tcgctcttgg cagaaaggac cacagatgga 60
gagcttggca ctcgctccaa ctttgccgaa aagaggacaa ccaccaaagt agtaggtaaa 120
aacacaattt tagcagcagt gaaataaaaa gaggaagtga ggatggggcc aggccgcaac 180
tataattaaa ctgtctgttt aggagaagct gaatccagaa gaaacacaag ctgtaaagtg 240

-continued agagaggaca gggagcaggg cctttggaga gcaggagagg acaggctgtc accaagcgct 300
gctcggactc tgccctgaaa gatttgaatt ggacactgtc cagtcacgtg tgtggcaaac 360
cgtactccaa gcacttttct cacggcagag gaaggagctg ccatggctgt acccctgaac 420
gtttgtgggg ccagcgatgt g 441

<210> SEQ ID NO 252
<211> LENGTH: 406
<212> TYPE: DNA
<213> ORGANISM: Homo sapiens

<400> SEQUENCE: 252 ttttttttg aacaagtaaa aatttcttta tttgctgaca ataagataac ctacagggaa 60
aacctgatga aatctattaa aaagttacta aaactaataa aagaatttag gaaggttata 120
gaatgtaaga ccaagacaca aaaatcaatt acatttctat ataatagcaa tgaacagata 180
ctgaaatttt aaaaactaaa tcattttaca aaagtatcac aatatgaaac actccgggat 240
aaattggata aaagatgtgc aagactgtac aaaagctaca aaacatttat gaaggaaatt 300
ggaagataga aacaagatag aaaatgaaaa tattgtcaag agtttcagat agaaaatgaa 360
aaacaagcta agacaagtat tggagaagta tagaagatag aaaaat 406

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253
gaaggagttc agtagcaaag tcacacctgt ccaattccct gagctttgct cactcagcta 60
atgggatggc aaaggtggtg gtgctttcat cttcaggcag aagcctctgc ccatccccct 120
caagggctgc aggcccagtt ctcatgctgc ccttgggtgg gcatctgtta acagaggaga 180
acgtctgggt ggcggcagca gctttgctct gagtgcctac aaanctaatg cttggtgcta 240
gaaacatcat cattattaaa cttcagaaaa gcagcagcca tgttcagtca ggctcatgct 300
gcctcactgc ttaagtgcct gcaggagccg cctgccaagc tccccttcct acacctggca 360
cactggggtc tgcacaaggc tttgtcaacc aaagacagct tccccctttt gattgcctgt 420
agactttgga gccaagaaac actctgtgtg actctacaca cacttcaggt ggtttgtgct 480
tcaaagtcat tgatgcaact tgaaaggaaa cagtttaatg gtggaaatga actaccattt 540
ataa 544

<210> SEQ ID NO 254
<211> LENGTH: 339
<212> TYPE: DNA
<213> ORGANISM: Homo sapiens

<400> SEQUENCE: 254
tggcattcag ggcagtgtct tctgcatctc ctaggaacct cgggagcggc agctccggcg 60
cctggtagcg agaggcgggt tccggagatc ccggcctcac ttcgtcccac tgtggttagg 120
ggtgagtcct gcaaatgtta agtgatttgc tcaaggtgcc catttcgcag gaattggagc 180
ccaggccagt tctctgagcc tatcattagg gctaaaggag tgcgtgatca gaatggtgtc 240

-continued

```
tggacggttc tacttgtcct gcctgctgct ggggtccctg ggctctatgt gcatcctctt    300

cactatctac tggatgcagt actggcgtgg tggctttgc                           339


<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255

gaggtttttt nttttttttt tttttttttt caattaaana tttgatttat tcaagtatgt     60

gaaaacattn tacaatggaa acttttntta aatgctgcat gtnctgtgct atggaccacn    120

cacatacagc catgctgttt caaaaaactt gaaatgccat tgatagttta aaaactntac    180

ncccgatgga aaatcgagga aaacaattta atgtttcatn tgaatccana ggngcatcaa    240

attaaatgac agctccactt ggcaaataat agctgttact tgatggtatc caaaaaaaaa    300

tggttgggga tggataaatt caaaaatgct tccccaaagg ngggnggttt ttaaaaagtt    360

tcaggncaca acccttgcan aaaacactga tgcccaacac antga                    405


<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256

gggcangtct ggtcctctcc ccacatgtca cactctcctc agcctctccc ccaaccctgc     60

tctccctcct cccctgccct agcccaggga cagagtctag gaggagcctg gggcagagct    120

ggaggcagga agagagcact ggacagacag ctatggtttg gattggggaa gaggttagga    180

agtaggttct taaagaccct tttttagta                                      209


<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257

tctggacacc ataatccctt ttaagtggct ggatggtcac acctctccca ttgacaagct     60

gggttaagtc aataggttga ctaggatcaa cacgacccaa atcaataaga tactgcagtc    120

tattgagact caaaggctta tactggcgtc tgaaactatg tccttcgtta aacccgtatt    180

ttgggattcg gatgtaaaat ggagtctggc ctccctcaaa gcccaagcgg ggccgggttc    240

ctctttgcct ttctccttta tggcctctgc cacattttct acctcttctc cgacctcttg    300

gtcttntctc nggtttcttg gagccgggat tcggctttaa gtn                      343


<210> SEQ ID NO 258
<211> LENGTH: 519
<212> TYPE: DNA
<213> ORGANISM: Homo sapiens
```

-continued

<400> SEQUENCE: 258
gcggcttctg acttctagaa gactaaggct ggtctgtgtt tgcttgtttg cccacctttg 60
gctgataccc agagaacctg ggcacttgct gcctgatgcc cacccctgcc agtcattcct 120
ccattcaccc agcgggaggt gggatgtgag acagcccaca ttggaaaatc cagaaaaccg 180
ggaacaggga tttgcccttc acaattctac tccccagatc ctctcccctg gacacaggag 240
acccacaggg caggacccta agatctgggg aaaggaggtc ctgagaacct tgaggtaccc 300
ttagatcctt ttctacccac tttcctatgg aggattccaa gtcaccactt ctctcaccgg 360
cttctaccag ggtccaggac taaggcgttt tctccatagc ctcaacattt tgggaatctt 420
cccttaatca cccttgctcc tcctgggtgc ctggaagatg gactggcaga gacctctttg 480
ttgcgttttg tgctttgatg ccaggaatgc cgcctagtt 519

<210> SEQ ID NO 259
<211> LENGTH: 371
<212> TYPE: DNA
<213> ORGANISM: Homo sapiens

<400> SEQUENCE: 259
attgtcaact atatacacag tagtgaggaa taaaatgcac acaaaacaat ggatagaata 60
tgaaaatgtc ttctaaatat gaccagtcta gcatagaacc ttcttctctt ccttctcagg 120
tcttccagct ccatgtcatc taacccactt aacaaacgtg gacgtatcgc ttccagaggc 180
cgtcttaaca actccatttc caaaagtcat ctccagaaga catgtatttt ctatgatttc 240
ttttaaacaa atgagaattt acaagatgtg taactttcta actctatttt atcatacgtc 300
ggcaacctct ttccatctag aagggctaga tgtgacaaat gttttctatt aaaaggttgg 360
ggtggagttg a 371

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G

<400> SEQUENCE: 260
ttggattttt tgacttgcga tttcagtttt tttacttttt tttttttttt ttttganaaa 60
tactatattt attgtcaaag agtggtacat aggtgagtgt tcatcttccc tctcatgccg 120
gtatactctg cttcgctgtt tcagtaaaag ttttccgtag ttctgaacgt cccttgacca 180
caccataana caagcgcaag tcactcanaa ttgccactgg aaaactggct caactatcat 240
ttgaggaaag actganaaag cctatcccaa agtaatggac atgcaccaac atcgcggtac 300
ctacatgttc ccgtttttct gccaatctac ctgtgtttcc aagataaatt accacccagg 360
gagtcacttc ctgctatgtg aacaaaaacc cggtttcttt ctggaggtgc ttgactactc 420 tctcgngagc 430

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)

-continued

<223> OTHER INFORMATION: n=A,T,C or G

<400> SEQUENCE: 261
tcctgacgat agccatggct gtaccactta actatgattc tattccaact gttcagaatc 60
atatcacaaa atgacttgta cacagtagtt tacaacgact cccaagagag gaaaaaaaaa 120
aaaaaagacg cctcaaaatt cactcaactt ttgagacagc aatggcaata ggcagcanag 180
aagctatgct gcaactgagg gcacatatca ttgaagatgt cacaggagtt taagagacag 240
gctggaaaaa atctcatact aagcaaacag tagtatctca taccaagcaa aaccaagtag 300
tatctgctca gcctgccgct aacagatctc acaatcacca actgtgcttt aggactgtca 360
ccaaa 365

<210> SEQ ID NO 262
<211> LENGTH: 500
<212> TYPE: DNA
<213> ORGANISM: Homo sapiens

<400> SEQUENCE: 262
cctagatgtc atttgggacc cttcacaacc attttgaagc cctgtttgag tccctgggat 60
atgtgagctg tttctatgca taatggatat tcggggttaa caacagtccc ctgcttggct 120
tctattctga atccttttct ttcaccatgg ggtgcctgaa gggtggctga tgcatatggt 180
acaatggcac ccagtgtaaa gcagctacaa ttaggagtgg atgtgttctg tagcatccta 240
tttaaataag cctattttat cctttggccc gtcaactctg ttatctgctg cttgtactgg 300
tgcctgtact tttctgactc tcattgacca tattccacga ccatggttgt catccattac 360
ttgatcctac tttacatgtc tagtctgtgt ggttggtggt gaataggctt ctttttacat 420
ggtgctgcca gcccagctaa ttaatggtgc acgtggactt ttagcaagcg ggctcactgg 480
aagagactga acctggcatg 500

<210> SEQ ID NO 263
<211> LENGTH: 413
<212> TYPE: DNA
<213> ORGANISM: Homo sapiens

<400> SEQUENCE: 263
ctcagagagg ttgaaagatt tgcctacgaa agggacagtg atgaagctaa gctctagatc 60
caggatgtct gacttcaaat tgaaactccc aaagtaatga gtttggaagg gtggggtgtg 120
gcctttccag gatgggggtc ttttctgctc ccagcggata gtgaaacccc tgtctgcacc 180
tggttgggcg tgttgctttc ccaaaggttt tttttttagg tccgtcgctg tcttgtggat 240
taggcattat tatctttact ttgtctccaa ataacctgga gaatggagag agtagtgacc 300
agctcagggc cacagtgcga tgaggaccat cttctcacct ctctaaatgc aggaagaaac 360
gcagagtaac gtggaagtgg tccacaccta ccgccagcac attgtgaatg aca 413

<210> SEQ ID NO 264
<211> LENGTH: 524
<212> TYPE: DNA
<213> ORGANISM: Homo sapiens

<400> SEQUENCE: 264
tccaatgggg ccctgagagc tgtgacagga actcacactc tggcactggc agcaaaacac 60
cattccaccc cactcatcgt ctgtgcacct atgttcaaac tttctccaca gttccccaat 120
gaagaagact catttcataa gtttgtggct cctgaagaag tcctgccatt cacagaaggg 180

-continued

```
gacattctgg agaaggtcag cgtgcattgc cctgtgtttg actacgttcc cccagagctc    240

attaccctct ttatctccaa cattggtggg aatgcacctt cctacatcta ccgcctgatg    300

agtgaactct accatcctga tgatcatgtt ttatgaccga ccacacgtgt cctaagcaga    360

ttgcttaggc agatacagaa tgaagaggag acttgagtgt tgctgctgaa gcacatcctt    420

gcaatgtggg agtgcacagg agtccaccta aaaaaaaaaa tccttgatac tgttgcctgc    480

ctttttagtc accccgtaac aagggcacac atccaggact gtgt                     524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg     60

aagacaaatg agacaggatt tggcctgcgg gttcttcaga cttctctacc acctccatta    120

actcttcatc ttggcttgac gtaggcaatg cactattttg ctcttttgtt tctggagatg    180

acccagcacc acttctttct cttggcgggg ttctaagtgt gtctttgaat accagtgaag    240

actcaggcct atcctgtact ggaaagggac taaatttgtc tttctgtcta ggaggtgatg    300

cagtagcatc ctcctgaggg ggtaaggcca ttttctcttt ttga                     344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

```
ccacaatgtc cataacttga gcaggctttg gcatcccacc accccccttca gaccaataca     60

cactatgttg gaggaacnac tttaaaatgt aaaatgagaa atgggcactg aacactccat    120

cctcactccc aacagcccac ccacacacct cttcaactgc tatccaaaca tggaggagct    180

cttgtggaag agaggctcaa caccaaataa                                     210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n = A,T,C or G

<400> SEQUENCE: 267

```
tcggncctcc caccctctna ctgaaattct ntgaaattct cccctttggg atgaggatgg     60

caaccccagg catgtaccct cccaacctgg gacccgacct aataccctaa catcctgctg    120

acagtggctg ttctcgctgg gcaggcgtcc caaagcacat cgagccagat tcaggcagag    180

tggaactggc ccctcagcca tcagtggagg tggcctggga ggctctaccc tgaacggg      238
```

<210> SEQ ID NO 268
<211> LENGTH: 461
<212> TYPE: DNA
<213> ORGANISM: Homo sapiens
<220> FEATURE:

-continued

<221> NAME/KEY: misc_feature
<222> LOCATION: (459)
<223> OTHER INFORMATION: n=A,T,C or G

<400> SEQUENCE: 268
tcctcaagga catgcccctt gatagaaact cagttcctgt ctccagttcc ctcctggacc 60
tgatccccca aatgcagggc ctgggactat atccagttcc ttattttcag aggcccatgc 120
acaagatgca cagcaaataa gtgctgaata aagacccagc tactgctagc ttaccctgct 180
ccaaacattc accaagtcct cagcaaagag ggccatccat tcacctcttc taaaaacaca 240
ctgagctccc cagtctatac cccaagatat gcttggctcc caactatccc tcctctctca 300
tctccaagcc agtttcccct ttctaagtat actgatatta ccaaagacac tgacaatctt 360
cttttcctac ctctccccag tgactaggtt tgcagcagga gctctataag tcctagtata 420
cagcagaagc tccataaatg tgtgctgacc taacattang c 461

<210> SEQ ID NO 269
<211> LENGTH: 434
<212> TYPE: DNA
<213> ORGANISM: Homo sapiens

<400> SEQUENCE: 269
ctgtgttggt gagcaccgat tcccactcaa tatggcgtgg cttacagtct tcattaggtt 60
cccgctccca accagaatga ggaatgatca cttcatctgt caaggcatgc agtgcatggt 120
ccacaatctc cattttgatt gagtcatggg atgaaagatt ccacagggtt ccggtaataa 180
cttcagtaag gtccatatca cgagcctttc gaagcaatcg cacaagggca ggcacaccat 240
cacagttttt tatggcaatc ttgttatcct ggtcacgtcc aaaagagata ttcttgagag 300
ctccacaggc tccaaggtgc acttcctttt tgggatggtc taacaatccc accagtactg 360
ggatgccctt gagcttccgc acgtcagtct tcaccttgtc attgcggtag cataagtgtt 420
gcaggtatgc aaga 434

<210> SEQ ID NO 270
<211> LENGTH: 156
<212> TYPE: DNA
<213> ORGANISM: Homo sapiens

<400> SEQUENCE: 270
ctgcaccagc gattaccagt ggcattcaaa tactgtgtga ctaaggattt tgtatgctcc 60
ccagtagaac cagaatcaga caggtatgag ctagtcaaca gcaagtcttt gttggattcg 120
agtaggctca ggatctgctg aaggtcggag gagtta 156

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271
ccactgtcac ggtctgtctg acacttactg ccaaacgcat ggcaaggaaa aactgcttag 60
tgaagaactt agaagctgtg gagaccttgg ggtccacgtn caccatctgc tctgataaaa 120
ctggaactct gactcanaac cggatgacag tggcccacat gtggtttgac aatcaaatcc 180
atgaagctga tacgacagag aatcagagtg gtgtctcttt tgacaagact tcagctacct 240

-continued

```
ggcttgctct gtccagaatt gcaggtcttt gtaacagggc agtgtttcag gctaaccagg    300

aaaacctacc tattcttaag cgggcagttg caggagatgc ctctgagtca gcactcttaa    360

agtgcataga gctgtgctgt ggntncgtga aggagatgag agaaagatac nccaaaatcg    420

tcgagatacc cttcaactcc accaacaagt accagttgtc tattcataag aaccccaaca    480

catcggagcc ccaacacctg ttggtgatga agggcgcccc agaaaggatc cta           533
```

<210> SEQ ID NO 272
<211> LENGTH: 630
<212> TYPE: DNA
<213> ORGANISM: Homo sapiens

<400> SEQUENCE: 272

```
tggtattttt ctttttcttt tggatgtttt atactttttt ttcttttttc ttctctattc     60

ttttcttcgc cttcccgtac ttctgtcttc cagttttcca cttcaaactt ctatcttctc    120

caaattgttt catcctacca ctcccaatta atctttccat tttcgtctgc gtttagtaaa    180

tgcgttaact aggctttaaa tgacgcaatt ctccctgcgt catggatttc aaggtctttt    240

aatcaccttc ggtttaatct ctttttaaaa gatcgccttc aaattatttt aatcacctac    300

aacttttaaa ctaaacttta agctgtttaa gtcaccttca ttttaatcta aaagcattgc    360

ccttctattg gtattaattc ggggctctgt agtcctttct ctcaattttc ttttaaatac    420

atttttttact ccatgaagaa gcttcatctc aacctccgtc atgttttaga aaccttttat    480

cttttccttc ctcatgctac tcttctaagt cttcatattt tctcttaaaa tcttaagcta    540

ttaaaattac gttaaaaact taacgctaag caatatctta gtaacctatt gactatattt    600

tttaagtagt tgtattaatc tctatctttc                                     630
```

<210> SEQ ID NO 273
<211> LENGTH: 400
<212> TYPE: DNA
<213> ORGANISM: Homo sapiens

<400> SEQUENCE: 273

```
tctggtttgc cctccagttc attctgaatc tagacttgct cagcctaatc aagttcctgt     60

acaaccagaa gcgacacagg ttcctttggt atcatccaca agtgaggggt acacagcatc    120

tcaacccttg taccagcctt ctcatgctac agagcaacga ccacagaagg aaccaattga    180

tcagattcag gcaacaatct ctttaaatac agaccagact acagcatcat catcccttcc    240

tgctgcgtct cagcctcaag tatttcaggc tgggacaagc aaacctttac atagcagtgg    300

aatcaatgta aatgcagctc cattccaatc catgcaaacg gtgttcaata tgaatgcccc    360

agttcctcct gttaatgaac cagaaacttt aaaacagcaa                          400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274

```
tntgagtatg tcccagagaa ggtgaagaaa gcggaaaaga aattagaaga gaatccatat     60

gaccttgatg cttggagcat tctcattcga gaggcacaga atcaacctat agacaaagca    120
```

-continued

```
cggaagactt atgaacgcct tgttgcccag ttccccagtt ctggcagatt ctggaaactg    180

tacattgaag cagaggttac tattttattt tattttttct tatatcagta ttgcagcatt    240

cactgtagtg atagaaaaca agttaggaac atagccaatt aggacaagga ggatttaaat    300

gtgtcttacc tttattttgt aaaataggta taaaggagta attaaaatga a             351
```

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

```
gcgnggtcgc nnncgaggtc tgagaagccc ataccactat ttgttgagaa atgtgtggaa     60

tttattgaag atacagggtt atgtaccgaa ggactctacc gtgtcagcgg gaataaaact    120

gaccaagaca atattcaaaa gcagtttgat caagatcata atatcaatct agtgtcaatg    180

gaagtaacag taaatgctgt agctggagcc cttaaagctt tctttgcaga tctgccagat    240

cctttaattc catattctct tcatccagaa ctattggaag cagcaaaaat cccggataaa    300

acagaacgtc ttcatgcctt gaaagaaatt gttaagaaat ttcatcctgt aaactatgat    360

gtattcagat acgtgataac a                                              381
```

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

```
gctcngactc cggcgggacc tgctcggagg aatggcgccg ccgggttcaa gcactgtctt     60

cctgttggcc ctgacaatca tagccagcac ctgggctctg acgcccactc actacctcac    120

caagcatgac gtggagagac taaaagcctc gctggatcgc cctttcacaa atttggaatc    180

tgccttctac tccatcgtgg gactcagcag ccttggtgct caggtgccag atgcaaagaa    240

agcatgtacc tacatcagat ctaaccttga tcccagcaat gtggattccc tcttctacgc    300

tgcccaggcc agccaggccc tctcaggatg tgagatctct atttcaaatg agaccaaaga    360

tctgcttctg gcagacctcg gccgcgacca                                     390
```

<210> SEQ ID NO 277
<211> LENGTH: 378
<212> TYPE: DNA
<213> ORGANISM: Homo sapiens

<400> SEQUENCE: 277

```
tgggaacttc tggggtagga cgttgtctgc tatctccagt tccacagacc caaccagtta     60

cgatggtttt ggaccattta tgccgggatt cgacatcatt ccctataatg atctgcccgc    120

actggagcgt gctcttcagg atccaaatgt ggctgcgttc atggtagaac caattcaggg    180

tgaagcaggc gttgttgttc cggatccagg ttacctaatg ggagtgcgag agctctgcac    240

caggcaccag gttctcttta ttgctgatga aatacagaca ggattggcca gaactggtag    300

atggctggct gttgattatg aaaatgtcag acctgatata gtcctccttg gaaaggccct    360
```

-continued ttctgggggc ttataccc 378

<210> SEQ ID NO 278
<211> LENGTH: 366
<212> TYPE: DNA
<213> ORGANISM: Homo sapiens

<400> SEQUENCE: 278
ggagggcaca ttccttttca cctcagagtc ggtcggggaa ggccacccag ataagatttg 60
tgaccaaacc agtgatgctg tccttgatgc ccaccttcag caggatcctg atgccaaagt 120
agcttgtgaa actgttgcta aaactggaat gatccttctt gctggggaaa ttacatccag 180
agctgctgtt gactaccaga aagtggttcg tgaagctgtt aaacacattg gatatgatga 240
ttcttccaaa ggttttgact acaagacttg taacgtgctg gtagccttgg agcaacagtc 300
accagatatt gctcaaggtg ttcatcttga cagaaatgaa gaagacattg gtgctggaga 360
ccaggg 366

<210> SEQ ID NO 279
<211> LENGTH: 435
<212> TYPE: DNA
<213> ORGANISM: Homo sapiens

<400> SEQUENCE: 279
cctaagaact gagacttgtg acacaaggcc aacgacctaa gattagccca gggttgtagc 60
tggaagacct acaacccaag gatggaaggc ccctgtcaca aagcctacct agatggatag 120
aggacccaag cgaaaaagat atctcaagac taacggccgg aatctggagg cccatgaccc 180
agaacccagg aaggatagaa gcttgaagac ctggggaaat cccaagatga gaaccctaaa 240
ccctacctct tttctattgt ttacacttct tactcttaga tatttccagt tctcctgttt 300
atctttaagc ctgattcttt tgagatgtac tttttgatgt tgccggttac ctttagattg 360
acaagtatta tgcctggcca gtcttgagcc agctttaaat cacagctttt acctatttgt 420
taggctatag tgttt 435

<210> SEQ ID NO 280
<211> LENGTH: 435
<212> TYPE: DNA
<213> ORGANISM: Homo sapiens

<400> SEQUENCE: 280
tctggatgag ctgctaactg agcacaggat gacctgggac ccagcccagc caccccgaga 60
cctgactgag gccttcctgg caaagaagga gaaggccaag gggagccctg agagcagctt 120
caatgatgag aacctgcgca tagtggtggg taacctgttc cttgccggga tggtgaccac 180
ctcgaccacg ctggcctggg gcctcctgct catgatccta cacctggatg tgcagcgtga 240
gcccagacct gtccgggcgg ccgctcgaaa ttccagcaca ctggcggccg ttactagtgg 300
atccgagctc ggtaccaagc ttggcgtaat catggtcata gctgtttcct gtgtgaaatt 360
gttatccgct cacaattcca cacaacatac gagccggaag cataaagtgt aaagcctggg 420
gtgcctaatg agtga 435

<210> SEQ ID NO 281
<211> LENGTH: 440
<212> TYPE: DNA
<213> ORGANISM: Homo sapiens -continued

<400> SEQUENCE: 281
catctgatct ataaatgcgg tggcatcgac aaaagaacca ttgaaaaatt tgagaaggag 60
gctgctgaga tgggaaaggg ctccttcaag tatgcctggg tcttggataa actgaaagct 120
gagcgtgaac gtggtatcac cattgatatc tccttgtgga aatttgagac cagcaagtac 180
tatgtgacta tcattgatgc cccaggacac agagacttta tcaaaaacat gattacaggg 240
acatctcagg ctgactgtgc tgtcctgatt gttgctgctg gtgttggtga atttgaagct 300
ggtatctcca agaatgggca gacccgagag catgcccttc tggcttacac actgggtgtg 360
aaacaactaa ttgtcggtgt taacaaaatg gattccactg agccccctac agccagaaga 420
gatatgagga aattgttaag 440

<210> SEQ ID NO 282
<211> LENGTH: 502
<212> TYPE: DNA
<213> ORGANISM: Homo sapiens

<400> SEQUENCE: 282
tctgtggcgc aggagccccc tcccccggca gctctgacgt ctccaccgca gggactggtg 60
cttctcggag ctcccactcc tcagactccg gtggaagtga cgtggacctg gatcccactg 120
atggcaagct cttccccagc gatggttttc gtgactgcaa gaagggggat cccaagcacg 180
ggaagcggaa acgaggccgg ccccgaaagc tgagcaaaga gtactgggac tgtctcgagg 240
gcaagaagag caagcacgcg cccagaggca cccacctgtg ggagttcatc cgggacatcc 300
tcatccaccc ggagctcaac gagggcctca tgaagtggga gaatcggcat gaaggcgtct 360
tcaagttcct gcgctccgag gctgtggccc aactatgggg ccaaaagaaa aagaacagca 420
acatgaccta cgagaagctg agccgggcca tgaggtacta ctacaaacgg gagatcctgg 480
aacgggtgga tggccggcga ct 502

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283
ccatattaga ttactggaac atctaagcat cagtgtgtga ccatgcgaac aaaagacttc 60
ggggagtgtc tatttttaaa aaggtttatg tgtgtcgagg cagttgtaaa agatttactg 120
cagaatcaan cccactttta ggcttangac caggttctaa ctatctaaaa atattgactg 180
ataacaaaaa gtgttctaaa tgtggctatt ctgatccata nttgnttttt aaagaaaaaa 240
antgtntata cagaaagagt ntaaaagttc tgtgaattna atgcaaatta gncnccantc 300
ttgacttccc aaanacttga ttnatacctt tnactcctnt cnnttcctgn ncttcnttaa 360
nntcaatnat tnggnagtnn anggccntcn gnanaacacc nttncncgnt ccncgcaatc 420
canccgcctt nan 433

<210> SEQ ID NO 284
<211> LENGTH: 479
<212> TYPE: DNA
<213> ORGANISM: Homo sapiens

<400> SEQUENCE: 284

-continued tctggaagga tcagggatct gagcaaagcc aagtttactt aagctaagcc acttgttcct 60
gggtcaagca gtttgttttc taataagcat cattcctgat cattagagca aagggatgaa 120
tgctcctctt ggaatgatac aggggatctg ccactgggag agtgttgctc agtgttagag 180
tagcagcaat gacagaatga cagcgactct ctgagtcaac ccagtacttt tagtaccccg 240
tcactatgtg aataaaggca gctagaaaat ggactcaatt ctgcaagcct tcatggcaac 300
agcccatatt aagacttcta gaacaagtta aaaaaaaatc ttccatttcc atccatgcat 360
gggaaaaggg ctttagtata gtttaggatg gatgtgtgta taataataaa atgataagat 420
atgcatagtg ggggaataaa gcctcagagt ccttccagta tggggaatcc attgtatct 479

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285 ttttttttt ttttttttt tcaatanaaa tgccataatt tattccattg tataaaaaag 60
tcatccttat gtaacaaaat gtnttcttan aanaanaaat atattatttc aggtcataaa 120
taatcagcaa acatacaact gttggcaact aaaaaaaaac ccaacactgg tattttccat 180
cagngctgaa aacaaacctg cttaaanata tatttacagg gatagtncag tnctcaaaaa 240
caaaaattga ggtattttgg ttcttctagg agtagacaat gacattttgg gangggcaga 300
cccctnnccc aaaaaataaa ataagggnat nttcttcant atngaanann gggggcgccc 360
cggggaaaan naaaccttgg gnngggggtt tggcccaagc ccttgaaaaa aaantttntt 420
tcccaaaaaa aacng 435

<210> SEQ ID NO 286
<211> LENGTH: 301
<212> TYPE: DNA
<213> ORGANISM: Homo sapiens

<400> SEQUENCE: 286
cctggtttct ggtggcctct atgaatccca tgtagggtgc agaccgtact ccatccctcc 60
ctgtgagcac cacgtcaacg gctcccggcc cccatgcacg ggggagggag atacccccaa 120
gtgtagcaag atctgtgagc ctggctacag cccgacctac aaacaggaca agcactacgg 180
atacaattcc tacagcgtct ccaatagcga gaaggacatc atggccgaga tctacaaaaa 240
cggccccgtg gagggagctt tctctgtgta ttcggacttc ctgctctaca agtcaggagt 300
g 301

<210> SEQ ID NO 287
<211> LENGTH: 432
<212> TYPE: DNA
<213> ORGANISM: Homo sapiens

<400> SEQUENCE: 287
tccagcttgt tgccagcatg agaaccgcca ttgatgacat tgaacgccgg gactggcagg 60
atgacttcag agttgccagc caagtcagcg atgtggcggt acagggggac ccccttctca 120
acggcaccag ctttgcagac ggcaagggac acccccagaa tggcgttcgc accaaactta 180

-continued

```
gatttatttt ctgttccatc catctcgatc atcagtttgt caatcttctc ttgttctgtg    240

acgttcagtt tcttgctaac cagggcaggc gcaatagttt tattgatgtg ctcaacagcc    300

tttgagacac ccttccccat atagcgagtc ttatcattgt cccggagctc tagggcctca    360

tagataccag ttgaagcacc actgggcaca gcagctctga agagaccttt tgaggtgaag    420

agatcaacct ca                                                         432
```

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

```
tctggctcaa gtcaaagtcc tggtcctctt ctccgcctcc ttcttcatca tagtaataaa     60

cgttgtcccg ggtgtcatcc tctgggggca gtaagggctc tttgaccacc gctctcctcc    120

gaagaaacag caagagcagc agaatcagaa ttagcaaagc aagaattcct ccaagaatcc    180

ccagaatggc aggaatttgc aatcctgctt cgacaggctg tgccttccta cagacgccgg    240

cggccccttc acantcacac acgctgacct ctaaggtggt cacttggtct ttattctggt    300

tatccatgag cttgagattg attttg                                          326
```

<210> SEQ ID NO 289
<211> LENGTH: 451
<212> TYPE: DNA
<213> ORGANISM: Homo sapiens

<400> SEQUENCE: 289

```
gtcccggtgt ggctgtgccg ttggtcctgt gcggtcactt agccaagatg cctgaggaaa     60

cccagaccca agaccaaccg atggaggagg aggaggttga gacgttcgcc tttcaggcag    120

aaattgccca gttgatgtca ttgatcatca atactttcta ctcgaacaaa gagatctttc    180

tgagagagct catttcaaat tcatcagatg cattggacaa aatccggtat gaaagcttga    240

cagatcccag taaattagac tctgggaaag agctgcatat taaccttata ccgaacaaac    300

aagatcgaac tctcactatt gtggatactg gaattggaat gaccaaggct gacttgatca    360

ataaccttgg tactatcgcc aagtctggga ccaaagcgtt catggaagct ttgcaggctg    420

gtgcagatat ctctatgatt ggacctcggc c                                    451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

```
tttttttttt tcaaaacagt atattttatt ttacaatagc aaccaactcc ccagtttgtt     60

tcaattgtga catctagatg gcttaagatt actttctggt ggtcacccat gctgaacaat    120

atttttcaat cttccaaaca gcaaagactc aaaagagatt ctgcatttca catcagttca    180

caagttcaag agtcttccat ttatcttagc ttttggaata aattatcttt gaggtagaag    240

gacaatgacg aagccactta attccttgtg tctgcataaa agcagattta ttcatcacaa    300
```

-continued

```
cttcatttat gtgaataaag cagatgatga taaaatgttc tcttattctt gtttaatcag    360

tagtggtagt gatgccagaa acttgtaaat gcacttcaaa ccaattgtgg ctcaagtgta    420

ngtggttccc caaggctggt accaatgaga ctggggtttg ggaattagtt ggtcatcatc    480

cctcctgctg ccca                                                      494
```

<210> SEQ ID NO 291
<211> LENGTH: 535
<212> TYPE: DNA
<213> ORGANISM: Homo sapiens

<400> SEQUENCE: 291

```
tcgcgtgctt aacatgaaaa caaactttgt gctgtttggt tcattgtatg cattgatgga     60

gtcttgtctc tcatcatggg gtgtctgacc atccaacctg cagtactcat aatttctcca    120

catgcaataa tcttccaaaa tgtccaatac ccttgtcatt tgactgaaga ttagtactcg    180

tgaaccttgt tcttttaact tagggagcag cttgtctaaa accaccattt tgccactgtt    240

ggttactaga tgcatatctg ttgtataagg tggaccaggt tctgctccat caaagagata    300

tggatgatta caacattttc tcaactgcat taggatgttc aataacctca ttttgtccat    360

cttgcctgct gagttgagta tatctatatc cttcattaat atccgagtat accattccct    420

ttgcattttg ctgaggccca catagatttt tacttccttc tttggaggca aactcttttc    480

aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

```
tacnagcccg tgctgatcga gatcctggtg gaggtgatgg atccttcctt cgtgtgcttg     60

aaaattggag cctgcccctc ggcccataag cccttgttgg gaactgagaa gtgtatatgg    120

ggcccaagct actggtgcca gaacacagag acagcagccc agtgcaatgc tgtcgagcat    180

tgcaaacgcc atgtgtggaa ctaggaggag gaatattcca tcttggcaga aaccacagca    240

ttggtttttt tctacttgtg tgtctggggg aatgaacgca cagatctgtt tgactttgtt    300

ataaaaatag ggctccccca cctcccccat ttttgtgtcc tttattgnag cattgctgtc    360

tgcaagggag ccccta                                                    376
```

<210> SEQ ID NO 293
<211> LENGTH: 320
<212> TYPE: DNA
<213> ORGANISM: Homo sapiens

<400> SEQUENCE: 293

```
tcggctgctt cctggtctgg cggggatggg tttgctttgg aaatcctcta ggaggctcct     60

cctcgcatgg cctgcagtct ggcagcagcc ccgagttgtt tcctcgctga tcgatttctt    120

tcctccaggt agagttttct ttgcttatgt tgaattccat tgcctctttt ctcatcacag    180

aagtgatgtt ggaatcgttt cttttgtttg tctgatttat ggttttttta agtataaaca    240

aaagtttttt attagcattc tgaaagaagg aaagtaaaat gtacaagttt aataaaaagg    300
```

-continued ggccttcccc tttagaatag 320

<210> SEQ ID NO 294
<211> LENGTH: 359
<212> TYPE: DNA
<213> ORGANISM: Homo sapiens

<400> SEQUENCE: 294
ctgtcataaa ctggtctgga gtttctgacg actccttgtt caccaaatgc accatttcct 60
gagacttgct ggcctctccg ttgagtccac ttggctttct gtcctccaca gctccattgc 120
cactgttgat cactagcttt ttcttctgcc cacaccttct tcgactgttg actgcaatgc 180
aaactgcaag aatcaaagcc aaggccaaga gggatgccaa gatgatcagc cattctggaa 240
tttggggtgt ccttatagga ccagaggttg tgtttgctcc accttcttga ctcccatgtg 300
agtgtccatc tgattcagat ccatgagtgg tatgggaccc cccactgggg tggaatgtg 359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295
cctgagttgg gctgactgcc agagacagac ccctctgggt ctcggtgaac cagccaggca 60
tttacctcag tggttggcac ctggaacctg tccagggccc tcacctgact gaggagccgc 120
cgggcagtga agtaattgtc caggtctatg ctcttggggt ggataccata gccatccaag 180
gtattcctca ggttgtggaa ctgggtctga gtataggcag aactgggccc caggatgatc 240
tcccggagtg ggggaagctg tgaggtcagg taagtatcca cgtccacccg taccccaatc 300
aaactcagca gaatggtgaa ctggagaagt ccttccgtta agtatttctt cagagaaagc 360
attgctgaag gaccagaatg tttatgcttt ttggttttta aaatcttcca aaagacaaat 420
caaggccact gctctgccgc tccagccagc aggttaccct cctcagtgtc aaaccccgta 480
ccccaccctg gcagaacaca agggatgagc tccctgacgg ccccagagga aagcacaccc 540
tgtggagcca aggccaanga cacactccag accacattca cttt 584

<210> SEQ ID NO 296
<211> LENGTH: 287
<212> TYPE: DNA
<213> ORGANISM: Homo sapiens

<400> SEQUENCE: 296
ccttatcatt cattcttagc tcttaattgt tcattttgag ctgaaatgct gcattttaat 60
tttaaccaaa acatgtctcc tatcctggtt tttgtagcct tcctccacat cctttctaaa 120
caagatttta aagacatgta ggtgtttgtt catctgtaac tctaaaagat cctttttaaa 180
ttcagtccta agaaagagga gtgcttgtcc cctaagagtg tttaatggca aggcagccct 240
gtctgaagga cacttcctgc ctaagggaga gtggtatttg cagacta 287

<210> SEQ ID NO 297
<211> LENGTH: 457
<212> TYPE: DNA
<213> ORGANISM: Homo sapiens

<400> SEQUENCE: 297

-continued

```
ccaattgaaa caaacagttc tgagaccgtt cttccaccac tgattaagag tggggtggca     60

ggtattaggg ataatattca tttagccttc tgagctttct gggcagactt ggtgaccttg    120

ccagctccag cagccttctt gtccactgct ttgatgacac ccaccgcaac tgtctgtctc    180

atatcacgaa cagcaaagcg acccaaaggt ggatagtctg agaagctctc aacacacatg    240

ggcttgccag gaaccatatc aacaatggca gcatcaccag acttcaagaa tttagggcca    300

tcttccagct tttaccaga acggcgatca atcttttcct tcagctcagc aaacttgcat    360

gcaatgtgag ccgtgtggca atccaataca ggggcatagc cggcgcttat ttggcctgga    420

tggttcagga taatcacctg agcagtgaag ccagacc                             457
```

<210> SEQ ID NO 298
<211> LENGTH: 469
<212> TYPE: DNA
<213> ORGANISM: Homo sapiens

<400> SEQUENCE: 298

```
tctttgactt tccttgtcta cctcctctgg agatctcaaa ttctccaggt tccatgctcc     60

cagagatctc aatgattcct gattctcctc ttccaggagt ctgaatgtct cttggttcac    120

ttccacagac tccagtggtt cttgaatttc cttttctaga ggattcattg ccccctgatt    180

tatttcttct ggagtccaca gtggtgcttg agtttctgga gatttcagtg tttccaggtt    240

ctcttgtccc gcagacttca gtgattctag gatctctgtt tctaaagatt ttactgcctc    300

tatgctctct tctttgagtg actttaagaa ctcttgattc tcattttcaa gaggtctagc    360

tatctcctgg tcaagagact tcagtggttc tagatccact ttttctgggg gtcttaatgt    420

catctgatcc tgttccccta gagacctccg tcgctgttga gtctctttt                469
```

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299

```
tctgtggaga ggatgaggtt gagggaggtg gggtatntcg ctgctctgac cttaggtaga     60

gtcctccaca gaagcatcaa antggactgg cacatatgga ctcccttcac aggccacaat    120

gatgtgtctc tccttcgggc tggnccggta tgcacagttg gggta                    165
```

<210> SEQ ID NO 300
<211> LENGTH: 506
<212> TYPE: DNA
<213> ORGANISM: Homo sapiens

<400> SEQUENCE: 300

```
tctgaggaaa gtttgggctt attagtattt gctccagcga acctccaagt tttctccatt     60

gcggacaacg taactaccag ctccttggct cagtggttcg cctccactca gaagttccca    120

gtaggttctg tcattattgt tggcacatag gccctgaata caggtgatat agggccccca    180

tgagcgctcc tccattgtga aaccaaatat agtatcattc attttctggg ctttctccat    240

cacactgagg aagacagaac catttagcac agtgacattg gtgaaatatg tttcattgat    300

tctcacagag taattgacgg agatatatga ttgtgagtca ggaggtgtca cagttatagg    360
```

-continued ctcatcagcg gagatgttga agttacctga agcagagacg caagaagagt ctttgttaat 420
atccaagaag gtctttccca tcagggcagg taagacctgg gctgcagcgt ttggattgct 480
gaatgctcct tgagaaattt ccgtga 506

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301
tcctaaggca gagcccccat cacctcaggc ttctcagttc ccttagccgt cttactcaac 60
tgcccctttc ctctccctca gaatttgtgt ttgctgcctc tatcttgttt tttgtttttt 120
cttctggggg gggtctagaa cagtgcctgg cacatagtag gcgctcaata aatacttgtt 180
tgttgaatgt ctcctctctc tttccactct gggaaaccta ngnttctgcc attctgggtg 240
accctgtatt tntttctggt gcccattcca tttgnccagn taatacttcc tcttaaaaat 300
ctcc 304

<210> SEQ ID NO 302
<211> LENGTH: 492
<212> TYPE: DNA
<213> ORGANISM: Homo sapiens

<400> SEQUENCE: 302
ttttcagtaa gcaacttttc catgctctta atgtattcct ttttagtagg aatccggaag 60
tattagattg aatggaaaag cacttgccat ctctgtctag gggtcacaaa ttgaaatggc 120
tcctgtatca catacggagg tcttgtgtat ctgtggcaac agggagtttc cttattcact 180
ctttatttgc tgctgtttaa gttgccaacc tcccctccca ataaaaattc acttacacct 240
cctgcctttg tagttctggt attcacttta ctatgtgata gaagtagcat gttgctgcca 300
gaatacaagc attgcttttg gcaaattaaa gtgcatgtca tttcttaata cactagaaag 360
gggaaataaa ttaaagtaca caagtccaag tctaaaactt tagtactttt ccatgcagat 420
ttgtgcacat gtgagagggt gtccagtttg tctagtgatt gttatttaga gagttggacc 480
actattgtgt gt 492

<210> SEQ ID NO 303
<211> LENGTH: 470
<212> TYPE: DNA
<213> ORGANISM: Homo sapiens

<400> SEQUENCE: 303
tctggggcag caggtactcc ctacggcact agtctacagg gggaaggacg ctctgtgctg 60
gcagcggtgg ctcacatggc ctgtctgcac tgtaaccaca ggctgggatg tagccaggac 120
ttggtctcct tggaagacag gtctgatgtt tggccaatcc agtccttcag accctgcctg 180
aaacttgtat cttacgtgaa cttaaagaat aaaatgcatt tctaccccga tctcgccccc 240
aggactggca cgacaggccc acggcagatt agatcttttc ccagtactga tcggtgcgtg 300
gaattccagc caccacttct gattcgattc cacagtgatc ctgtcctctg agtattttaa 360
agaagccatt gtcaccccag tcagtgttcc aggagttggc aaccagccag tagggtgtgc 420
cattctccac tccccagccc aggatgcgga tggcatggac ctcggccgcg 470

-continued

<210> SEQ ID NO 304
<211> LENGTH: 79
<212> TYPE: DNA
<213> ORGANISM: Homo sapiens

<400> SEQUENCE: 304
tgtcccattg ttaactcagc ctcaaatctc aactgtcagg ccctacaaag aaaatggaga 60
gcctcttctg gtggatgcg 79

<210> SEQ ID NO 305
<211> LENGTH: 476
<212> TYPE: DNA
<213> ORGANISM: Homo sapiens

<400> SEQUENCE: 305
tcactgagcc accctacagc cagaagagat atgaggaaat tgttaaggaa gtcagcactt 60
acattaagaa aattggctac aaccccgaca cagtagcatt tgtgccaatt tctggttgga 120
atggtgacaa catgctggag ccaagtgcta acgtaagtgg ctttcaagac cattgttaaa 180
aagctctggg aatggcgatt tcatgcttac acaaattggc atgcttgtgt ttcagatgcc 240
ttggttcaag ggatggaaag tcacccgtaa ggatggcaat gccagtggaa ccacgctgct 300
tgaggctctg gactgcatcc taccaccaac tcgtccaact gacaagccct tgcgcctgcc 360
tctccaggat gtctacaaaa ttggtggtaa gttggctgta aacaaagttg aatttgagtt 420
gatagagtac tgtctgcctt cataggtatt tagtatgctg taaatatttt taggta 476

<210> SEQ ID NO 306
<211> LENGTH: 404
<212> TYPE: DNA
<213> ORGANISM: Homo sapiens

<400> SEQUENCE: 306
tctgtctcgg agctcagggc gcagccagca cacacaggag cccacaggac agccacgtct 60
tcacagaaac tacagaagtc aggacccagg cgaggacctc aggaacaagt gccccctgca 120
gacagagaga cgcagtagca acagcttctg aacaactaca taataatgcg gggagaatcc 180
tgaagaccac tgcatcccac aagcactgac aaccacttca ggattttatt tcctccactc 240
taacccccag atccatttat gagaagtgag tgaggatggc aggggcatgg agggtgaagg 300
gacagcaagg atggtctgag ggcctggaaa caatagaaaa tcttcgtcct ttagcatatc 360
ctggactaga aaacaagagt tggagaagag gggggttgat acta 404

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307
tcctgcctan acatctgtga gggcctcaag ggctgctgcc tcgactttct ccctagctaa 60
gtccacccgt ccagggacac agccagggca ctgctctgtg ctgacttcca ctgcagccaa 120
gggtcaaaat gaagcatctg cggaggccag gactccttgg catcggacac agtcagggga 180
aaagccaccc tgactctgca ggacagaggg tctagggtca tttggcagga gaacactggt 240

-continued

```
gtgccaaggg aagcnancat                                                260

<210> SEQ ID NO 308
<211> LENGTH: 449
<212> TYPE: DNA
<213> ORGANISM: Homo sapiens

<400> SEQUENCE: 308

tctgtgctcc cgactcctcc atctcaggta ccaccgactg cactgggcgg ggccctctgg     60

ggggaaaggc tccacggggc agggatacat ctcgaggcca gtcatcctct ggaggcagcc    120

caatcaggtc aaagattttg cccaactggt cggcttcaga gtttccacag aagagaggct    180

ttcgacgaaa catctctgca aagatacagc caacactcca catgtccaca ggtgttgcat    240

atgtggactg cagaagaact tcgggagctc ggtaccagag tgtaacaacc ttgatcgttt    300

cggctggcaa gcctggtggg ggtgccttgt ccagatatgt ccttaggtcc tggtctacat    360

gctcaaacac cagggttacc ttgatctccc ggtcagttcg ggatgtggca cagacgtcca    420

tcagccggac aacattggga tgctcaaaa                                      449

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309

ctgtggaaac ctggggtgcc gggtaaatgg agaactccag cttggatttc ttgccataat     60

caactgagag acgttccatg agcagggagg tgaacccaga accagttccc ccaccaaagc    120

tgtggaaaac caagaagccc tgaagaccgg tgcactggtc agccagcttg cgaattcggt    180

ccaacacaag gtcaatgatc tccttgccaa tggtgtagtg ccctcgggca tagttattgg    240

cagcatcttc cttgcctgtg atgagctgct cagggtggaa gagctggcgg taggtgccag    300

tgcgaacttc atcaatgact gtgggttcca agtctacaaa cacagcccgg ggcacgtgct    360

tgccagcgcc cgtctcactt gaanaagggt gtttgaagga agtcatctcc t             411

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310

tcctcgtcca gcttgactcg attagtcctc ataaggtaag caaggcagat ggtggctgac     60

cgggaaatgc ctgcctggca gtggacaaac acccttcctc cagcattctt gatggagtct    120

atgaagtcaa tggcctcgtt gaaccaggag ctgatgtctg ccttgtggtt gtcctccaca    180

gggatgctct tgtactggta gtgaccctca aaatggttgg gacaattggc tgagacgttg    240

atcaaggcan ttatgcccaa ggcatccagc atgtccttgc gggaagcgtg atacgcactg    300

cccaggtaca gaaagggcag                                                320

<210> SEQ ID NO 311
<211> LENGTH: 539
```

-continued

<212> TYPE: DNA
<213> ORGANISM: Homo sapiens

<400> SEQUENCE: 311
tctggcccat gaagctgaag ttgggagaga tgatgcttcg cctctgcttc acaaactcaa 60
aggcctcgtc cagcttgact cgattagtcc tcataaggta agcaaggcag atggtggctg 120
accgggaaat gcctgcctgg cagtggacaa acacccttcc tccagcattc ttgatggagt 180
ctatgaagtc aatggcctcg ttgaaccagg agctgatgtc tgccttgtgg ttgtcctcca 240
cagggatgct cttgtactgg tagtgaccct caaaatggtt gggacaattg gctgagacgt 300
tgatcaaggc agttatgccc aaggcatcca gcatgtcctt gcgggaagcg tgatacgcac 360
tgcccaggta cagaaagggc aggatttcca ccgggccacc ctgaaatcca gaaatatcca 420
acattcatca agcttgctca aagccaaggc cagtgcccat acccacaaaa actttctgct 480
ggaaaagtca atttcagata ccgagtgaac tcagttctgt tgctggagga taaataaat 539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg 60
cagaccatgt cctgctgttc tagggtcatg actgtgtgta ctctaaagtt gccactctca 120
caggggtcag tgatacccac tgaacctggc aggaacagtc ctgcagccag aatctgcaag 180
cagcgcctgt atgcaacgtt tagggccaaa ggctgtctgg tggggttgtt catcacagca 240
taatggccta gtaggtcaag gatccagggt gtgaggggct caaagccagg aaaacgaatc 300
ctcaagtcct tcagtagtct gatgagaact ttaactgtgg actgagaagc attttcctcg 360
aaccagcggg catgtcggat ggctgctaag gcactctgca atactttgat atccaaatgg 420
agttctggat ccagttttcg aagattgggt ggcactgttg taatgagaat cttca 475

<210> SEQ ID NO 313
<211> LENGTH: 456
<212> TYPE: DNA
<213> ORGANISM: Homo sapiens

<400> SEQUENCE: 313
tccacttaaa gggtgcctct gccaactggt ggaatcatcg ccacttccag caccacgcca 60
agcctaacat cttccacaag gatcccgatg tgaacatgct gcacgtgttt gttctgggcg 120
aatggcagcc catcgagtac ggcaagaaga agctgaaata cctgccctac aatcaccagc 180
acgaatactt cttcctgatt gggccgccgc tgctcatccc catgtatttc cagtaccaga 240
tcatcatgac catgatcgtc cataagaact gggtggacct ggcctgggcc gtcagctact 300
acatccggtt cttcatcacc tacatccctt tctacggcat cctgggagcc ctccttttcc 360
tcaacttcat caggttcctg gagagccact ggtttgtgtg ggtcacacag atgaatcaca 420
tcgtcatgga gattgaccag gaggacctcg gcccgc 456

<210> SEQ ID NO 314
<211> LENGTH: 477
<212> TYPE: DNA
<213> ORGANISM: Homo sapiens

<400> SEQUENCE: 314

-continued tgcgtgggct tctggaagcc tggatctgga atcattcacc agattattct ggaaaactat 60
gcgtaccctg gtgttcttct gattggcact gactcccaca cccccaatgg tggcggcctt 120
gggggcatct gcattggagt tgggggtgcc gatgctgtgg atgtcatggc tgggatcccc 180
tgggagctga agtgccccaa ggtgattggc gtgaagctga cgggctctct ctccggttgg 240
tcctcaccca aagatgtgat cctgaaggtg gcaggcatcc tcacggtgaa aggtggcaca 300
ggtgcaatcg tggaatacca cgggcctggt gtagactcca tctcctgcac tggcatggcg 360
acaatctgca acatgggtgc agaaattggg gccaccactt ccgtgttccc ttacaaccac 420
aggatgaaga agtatctgag caagaccggc cgggaagaca ttgccaatct agctgat 477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315
caggtactgg atgtcaggtc tgcgaaactt cttanatttt gacctcagtc cataaaccac 60
actatcacct cggccatcat atgtgtctac tgtggggaca actggagtga aaacttcggt 120
tgctgcaggt ccgtgggaaa atcagtgacc agttcatcag attcatcaga atggtgagac 180
tcatcagact ggtgagaatc atcagtgtca tctacatcat cagagtcgtt cgagtcaatg 240
g 241

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316
nttntgtgat agtgtggttt atggactgag gncaaaatnt aagaagtttc gcagacctga 60
catccaancc tgcccgngcg gncgctcgaa aggncgaatt ctgcagatat ccatcacact 120
ggcggccgct cgagcatgca tctagagggc ccaattcgcc ctatantgag tnatattaca 180
attcactggc cgtcnnttta caacgtcgtg actgggaaaa ccctggcgtt acccaactta 240
a 241

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317
aggtaccctg ctcancagcc tgggngcctg ggttgtctcc ttgtccatcc actggtccat 60
tctgctctgc atttttttgt tcctcttttg gaggttccac tttgggtttg ggctttgaaa 120
ttatagggct acaantacct cggccgaaac cacnctaagg gcgaattctg cagatatcca 180
tcacactggc ggncgctcga gcatgcatct agagggccca attcgcccta tagtgagtcg 240

-continued t 241

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318
cgngnacaan ntacattgat gganggtntg nggntctgan tntttantta cantggagca 60
ttaatatttt cttnaacgtn cctcacttc ctgaantaaa nactctgggt tgtagcgctc 120
tgtgctnana accacntnaa ctttacatcc ctcttttgga ttaatccact gcgcggccac 180
ctctgccgcg accacgctaa gggcnaattc tgcagatatc catcacactg gcggccgctc 240 n 241

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319
caggtactga tcggtgcgtg gaantccagc caccanttnt gattcgattc cacagtgatc 60
ctgtcctctg agtattttaa agaagccatt gtcaccccag tcagtgttcc aggagttggc 120
aaccagccag tagggtgtgc cattctccac tccccagccc aggatgcgga tggcatggcc 180
acccatcatc tctccggtga cgtgttggta cctcggccgc gaccacgcta agggcgaatt 240
c 241

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc 60
taaacaagtg actatactag cataaatcat tctagtaaaa cagctaaggt atagacattc 120
taataatttg ggaaaaccta tgattacaag tgaaaactca gaaatgcaaa gatgttggtt 180
ttttgtttct cagtctgctt tagcttttaa ctctnnnaan cncatgcaca cttgnaactc 240
t 241

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G -continued

<400> SEQUENCE: 321
angtaccaac agagcttagt aattnntaaa aagaaaaaat gatctttttc cgacttctaa 60
acaagtgact atactagcat aaatcattct agtaaaacag ctaaggtata gacattctaa 120
taatttggga aaacctatga ttacaagtga aaactcagaa atgcaaagat gttggttttt 180
tgtttctcag tctgctttag cttttaactc tggaagcgca tgcacacntg aactctgctc 240
a 241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atctttttcc gacttctaaa 60
caagtgacta tactagcata aatcattctt ctagtaaaac agctaaggta tagacattct 120
aataatttgg gaaaacctat gattacaagt aaaaactcag aaatgcaaag atgttggttt 180
tttgtttctc agtctgcttt agcttttaac tctggaagcg catgcacact gaactctgct 240
c 241

<210> SEQ ID NO 323
<211> LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta 60
ggtctcaagt tatgagaatc tccatggctt tcaggggcta aacttttctg ccattctttt 120
gctcttaccg ggctcagaag gacatgtcag gtgggatacg tgtttctctt tcagagctga 180
agaaagggtc tgagctgcgg aatcagtaga gaaagccttg gtctcagtga ctccttggct 240
t 241

<210> SEQ ID NO 324
<211> LENGTH: 241
<212> TYPE: DNA
<213> ORGANISM: Homo sapiens

<400> SEQUENCE: 324
aggtactgtc gtatcctcag ccttgttcta tttctttatt ttagctttac agagattagg 60
tctcaagtta tgagaatctc catggctttc aggggctaaa cttttctgcc attcttttgc 120
tcttaccggg ctcagaagga catgtcaggt gggatacgtg tttctctttc agagctgaag 180
aaagggtctg agctgcggaa tcagtagaga aagccttggt ctcagtgact ccttggcttt 240
c 241

<210> SEQ ID NO 325
<211> LENGTH: 241
<212> TYPE: DNA
<213> ORGANISM: Homo sapiens

<400> SEQUENCE: 325
ggcaggtaca tttgttttgc ccagccatca ctcttttttg tgaggagcct aaatacattc 60
ttcctggggt ccagagtccc cattcaaggc agtcaagtta agacactaac ttggcccttt 120
cctgatggaa atatttcctc catagcagaa gttgtgttct gacaagactg agagagttac 180

-continued atgttgggaa aaaaaaagaa gcattaactt agtagaactg aaccaggagc attaagttct 240
g 241

<210> SEQ ID NO 326
<211> LENGTH: 241
<212> TYPE: DNA
<213> ORGANISM: Homo sapiens

<400> SEQUENCE: 326
gcaggtacat ttgttttgcc cagccatcac tcttttttgt gaggagccta aatacattct 60
tcctggggtc cagagtcccc attcaaggca gtcaagttaa gacactaact tggccctttc 120
ctgatggaaa tatttcctcc atagcagaag ttgtgttctg acaagactga gagagttaca 180
tgttgggaaa aaaaagaagc attaacttag tagaactgat ccaggagcat taagttctga 240
a 241

<210> SEQ ID NO 327
<211> LENGTH: 241
<212> TYPE: DNA
<213> ORGANISM: Homo sapiens

<400> SEQUENCE: 327
ggtaccagac caagtgaatg cgacagggaa ttatttcctg tgttgataat tcatgaagta 60
gaacagtata atcaaaatca attgtatcat cattagtttt ccactgcctc acactagtga 120
gctgtgccaa gtagtagtgt gacacctgtg ttgtcatttc ccacatcacg taagagcttc 180
caaggaaagc caaatcccag atgagtctca gagagggatc aatatgtcca tgattatcag 240
g 241

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 328
ggtacnagac caaatgaang ccacagggaa ttatttcctg tgttgataat tcatgaagta 60
gaacantata atcaaaatca attgtatcat cattagtttt ccactgcctc acactagtga 120
gctgtgccaa gtagtagtgt gacacctgtg ttgtcatttc ccacatcacg taagagcttc 180
caaggaaagc caaatcccag atgagtctca gagagggatc aatatgtcca tnatcatcan 240
g 241

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329
ttcaggtcga gttggctgca gatttgtggt gcnttctgag ccgtctgtcc tgcgccaaaa 60
ngcttcaaag tattattaaa aacatatgga tccccatgaa gccctactac accaaagttt 120

-continued

```
accaggagat ttggatagga atggggctga tgggcttcat cgtttataaa atccgggctg    180

ctgataagaa gtaaggcttt gaaagcttca gcgcctgctn ctggtcanna ctaaccatan    240

n                                                                    241


<210> SEQ ID NO 330
<211> LENGTH: 241
<212> TYPE: DNA
<213> ORGANISM: Homo sapiens

<400> SEQUENCE: 330

ttttgtgcag atttgtggtg cgttctgagc cgtctgtcct gcgccaagat gcttcaaagt     60

attattaaaa acatatggat ccccatgaag ccctactaca ccaaagttta ccaggagatt    120

tggataggaa tggggctgat gggcttcatc gtttataaaa tccgggctgc tgataaaaga    180

agtaaggctt tgaaagcttc agcgcctgct cctggtcatc actaaccaga tttacttgga    240

g                                                                    241


<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331

nttttaggna ctttgggctc cagacttcac tggtcttagg nattgaaacc atcacctggn     60

ntgcattcct catgactgag gttaacttaa aacaaaaatg gtaggaaagc tttcctatnc    120

ttcnggtaag anacaaatnt nctttaaaaa aangtggaag gcatgacnta cgtgagaact    180

gcacaaactg gccactgaca aaaatgaccc ccatttgtgt gacttcattg agacacatta    240

c                                                                    241


<210> SEQ ID NO 332
<211> LENGTH: 241
<212> TYPE: DNA
<213> ORGANISM: Homo sapiens

<400> SEQUENCE: 332

tgtgaggaga gggaacatgc tgagaaactg atgaagctgc agaaccaacg aggtggccga     60

atcttccttc aggatatcaa gaaaccagac tgtgatgact gggagagcgg gctgaatgca    120

atggagtgtg cattacattt ggaaaaaaat gtgaatcagt cactactgga actgcacaaa    180

ctggccactg acaaaaatga cccccatttg tgtgacttca ttgagacaca ttacctgaat    240

g                                                                    241


<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 333

caggtacaag cttttttttt tttttttttt tttttttttt ttgnaaatac tntttattgn     60

aaatattcta tcctaaattc catatagcca attaattntt acanaatntt ttgttaattt    120
```

-continued ttgngngtat aaattttaca aaaataaagg gtatgtttgt tgcacacaac ttacaaataa 180
taataaactn tttattgnaa atattnttta ttgnaaatat tctttatcct aaattccata 240
t 241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334
tacctgctgn aggggntgaa gncntctctg ctgccccagg catctgcanc ccctgctgct 60
ggttctgccc ctgctgcagc agaggagaag aaagatgaga agaaggagga gtctgaagag 120
tcagatgatg acatgggatt tggccttttt gattaaannc ctgctcccct gcaaataaag 180
cctttttaca caaaaaaaaa aaaaaaaaaa aaaaaaaaaa aagcttgtac ctgcccnggc 240
g 241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335
ctatgtgctg ggatgactat ggagacccaa atgtctcana atgtatgtcc cagaaacctg 60
tggctgcttc aaccattgac agttttgctg ctgctggctt ctgcagacag tcaagctgca 120
gctcccccaa aggctgtgct gaaacttgag cccccgtgga tcaacgtgct ccaggaggac 180
tctgtgactc tgacatgcca gggggctcgc agccctgaga gcgactccat tcagtggttc 240
c 241

<210> SEQ ID NO 336
<211> LENGTH: 241
<212> TYPE: DNA
<213> ORGANISM: Homo sapiens

<400> SEQUENCE: 336
taccaaccta tgcagccaag caacctcagc agttcccatc aaggccacct ccaccacaac 60
cgaaagtatc atctcaggga aacttaattc ctgcccgtcc tgctcctgca cctcctttat 120
atagttccct cacttgattt ttttaacctt ctttttgcaa atgtcttcag ggaactgagc 180
taatactttt ttttttcttg atgttttctt gaaaagcctt tctgttgcaa ctatgaatga 240
a 241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G -continued

<400> SEQUENCE: 337
ggtactgtat gtagctgcac tacaacagat tcttaccgtc tccacanagg tcatanattg 60
taaatggtna atactgactt ttttttatt cccttgactc aagacagcta acttcatttt 120
cagaactgtt ttaaaccttt gtgtgctggt ttataaaata atgtgtgtaa tccttgttgc 180
tttcctgata ccagactgtt tcccgtggtt ggttagaata tattttgntt tgatgcttat 240
a 241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt 60
ctcaaatgga gttttccact ttcctttgaa gtagacagca ttcaccagga tcatcctggt 120
atccccatct acagaacctt caggtaacaa gtttgggatt ttgcctttgg tttgagtctt 180
gacccaggaa ttaatctttt ttctagcttc ttctgcacat tctaggaagt ctactgcctg 240
g 241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg 60
aaagtgtctg caactccaaa gatcaaggcc ataacccagg agaccatcaa cggaagatta 120
gttctttgtc aagtgaatga aatccaaaag cacgcatgag accaatgaaa gtttccgcct 180
gttgtaaaat ctattttccc ccaaggaaag tccttgcaca gacaccagtg agtgagttct 240
a 241

<210> SEQ ID NO 340
<211> LENGTH: 241
<212> TYPE: DNA
<213> ORGANISM: Homo sapiens

<400> SEQUENCE: 340
gtagccctca cacacacatg cccgtaacag gatttatcac aagacacgcc tgcatgtaga 60
ccagacacag ggcgtatgga aagcacgtcc tcaagactgt agtattccag atgagctgca 120
gatgcttacc taccacggcc gtctccacca gaaaaccatc gccaactcct gcgatcagct 180
tgtgacttac aaaccttgtt taaaagctgc ttacatggac ttctgtcctt taaaagcttc 240
c 241

<210> SEQ ID NO 341
<211> LENGTH: 241
<212> TYPE: DNA
<213> ORGANISM: Homo sapiens

<400> SEQUENCE: 341
gtaccgccta ctttcgtctc atgtctccga acttcttgct gatggccgtt ccaacgttgc 60
tgaaagctgc agttgccttt tgccctgcgt gactcagggt ttcatgtgtt ttcttgtagg 120
cagtggtagt ctgcatgtca tgccagcttt tgctgaagtt ctgttttaat tcattcatca 180

-continued ggttcatgcc gagttttgtt ttatctcaac tagatgcctt tctttcgctg acaaaacttg 240
t 241

<210> SEQ ID NO 342
<211> LENGTH: 241
<212> TYPE: DNA
<213> ORGANISM: Homo sapiens

<400> SEQUENCE: 342
gtacattggt gctataaata taaatgctac ttatgaagca tgaaattaag cttctttttt 60
cttcaagttt tttctcttgt ctagcaatct gttaggcttc tgaaccaaga ccaaatgttt 120
acgttcctct gctgcatacc aacgttactc caaacaataa aaatctatca tttctgctct 180
gtgctgagga atggaaaatg aaaccccccac cccctgaccc ctaggactat acagtggaaa 240
c 241

<210> SEQ ID NO 343
<211> LENGTH: 241
<212> TYPE: DNA
<213> ORGANISM: Homo sapiens

<400> SEQUENCE: 343
gtacatgtgg tagcagtaat ttttttgaag caactgcact gacattcatt tgagttttct 60
ctcattatca gattctgttc caaacaagta ttctgtagat ccaaatggat taccagtgtg 120
ctacagactt cttattatag aacagcattc tattctacat caaaaatagt ttgtgtaagt 180
tagttttggt taccatctaa aatattttta aatgttcttt acataaaaat ttatgttgtg 240
t 241

<210> SEQ ID NO 344
<211> LENGTH: 241
<212> TYPE: DNA
<213> ORGANISM: Homo sapiens

<400> SEQUENCE: 344
ggtacaaaat tgttggaatt tagctaatag aaaaacatag taaatattta caaaaacgtt 60
gataacatta ctcaagtcac acacatataa caatgtagac aggtcttaac aaagtttaca 120
aattgaaatt atggagattt cccaaaatga atctaatagc tcattgctga gcatggttat 180
caatataaca tttaagatct tggatcaaat gttgtccccg agtcttctgc aatccagtcc 240
t 241

<210> SEQ ID NO 345
<211> LENGTH: 241
<212> TYPE: DNA
<213> ORGANISM: Homo sapiens

<400> SEQUENCE: 345
ggtacgaagc tgagcgcacg ggggttgccc cagcgtggag cctggacctc aaacttcacg 60
gaaaatgctc tctctctttg acaggcttcc agctgtctcc taatttcctg gatgaactct 120
ccccggcgat ttaactgatc ctgaaaagtg gtgagaggac tgaggaagac aaccaggtca 180
gcgttagatc ggcctctgag ggtggtgccc ttgcctgagg agccaccctt taccaccttg 240
g 241

<210> SEQ ID NO 346

-continued

<211> LENGTH: 241
<212> TYPE: DNA
<213> ORGANISM: Homo sapiens

<400> SEQUENCE: 346
caggtaccac tgagcctgag atggggatga gggcagagag aggggagccc cctcttccac 60
tcagttgttc ctactcagac tgttgcactc taaacctagg gaggttgaag aatgagaccc 120
ttaggtttta acacgaatcc tgacaccacc atctataggg tcccaacttg gttattgtag 180
gcaaccttcc ctctctcctt ggtgaagaac atcccaagcc agaaagaagt taactacagt 240
g 241

<210> SEQ ID NO 347
<211> LENGTH: 241
<212> TYPE: DNA
<213> ORGANISM: Homo sapiens

<400> SEQUENCE: 347
aggtacatct aaaggcatga agcactcaat tgggcaatta acattagtgt ttgttctctg 60
atggtatctc tgagaatact ggttgtagga ctggccagta gtgccttcgg gactgggttc 120
acccccaggt ctgcggcagt tgtcacagcg ccagccccgc tggcctccaa agcatgtgca 180
ggagcaaatg gcaccgagat attccttctg ccactgttct cctacgtggt atgtcttccc 240
a 241

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348
angtacttgg caagattnga tgctcttgng ctcantgaca tcattcataa cttgtnngtg 60
tgancagagg aggagnncat catcntgtcc tcattcgtca gnnncctctc ctctctgaat 120
ctcaaacaag ttgataatgg agaaaaattt gaattctcag gattgaggct ggactggttc 180
cgcctacang catacactag cgtggctaag gcccctctgc accctgcatg anaaccctga 240
c 241

<210> SEQ ID NO 349
<211> LENGTH: 241
<212> TYPE: DNA
<213> ORGANISM: Homo sapiens

<400> SEQUENCE: 349
gcaggtacca tttgtctgac ctctgtaaaa aatgtgatcc tacagaagtg gagctggata 60
atcagatagt tactgctacc cagagcaata tctgtgatga agacagtgct acagagacct 120
gctacactta tgacagaaac aagtgctaca cagctgtggt cccactcgta tatggtggtg 180
agaccaaaat ggtggaaaca gccttaaccc cagatgcctg ctatcctgac taatttaagt 240
c 241

<210> SEQ ID NO 350
<211> LENGTH: 241
<212> TYPE: DNA
<213> ORGANISM: Homo sapiens -continued

<400> SEQUENCE: 350
aggtactgtg gatatttaaa atatcacagt aacaagatca tgcttgttcc tacagtattg 60
cgggccagac acttaagtga aagcagaagt gtttgggtga ctttcctact taaaattttg 120
gtcatatcat ttcaaaacat ttgcatcttg gttggctgca tatgctttcc tattgatccc 180
aaaccaaatc ttagaatcac ttcatttaaa atactgagcg gtattgaata cttcgaagca 240
g 241

<210> SEQ ID NO 351
<211> LENGTH: 241
<212> TYPE: DNA
<213> ORGANISM: Homo sapiens

<400> SEQUENCE: 351
tacagaaatc atttggagcc gttttgagac agaagtagag gctctgtcaa gtcaatactg 60
cattgcagct tggtccactg aagaagccac gcctgagata caaaagatgc actacacttg 120
acccgcttta tgttcgcttc ctctcccctt ctctctcatc aactttatta ggttaaaaca 180
ccacatacag gctttctcca aatgactccc tatgtctggg gtttggttag aattttatgc 240
c 241

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352
gtaccctgtn gagctgcacc aagattannt ggggccatca tgactgcanc cacnacgang 60
acgcaggcgt gnagtgcatc gtctgacccg gaaacccttt cacttctctg ctcccgaggt 120
gtcctcnggc tcatatgtgg gaaggcanan gatctctgan gagttncctg gggacaactg 180
ancagcctct ggagaggggc cattaataaa gctcaacatc attggcaaaa aaaaaaaaaa 240
a 241

<210> SEQ ID NO 353
<211> LENGTH: 241
<212> TYPE: DNA
<213> ORGANISM: Homo sapiens

<400> SEQUENCE: 353
aggtaccagt gcattaattt gggcaaggaa agtgtcataa tttgatactg tatctgtttt 60
ccttcaaagt atagagcttt tggggaagga aagtattgaa ctgggggttg gtctggccta 120
ctgggctgac attaactaca attatgggaa atgcaaaagt tgtttggata tggtagtgtg 180
tggttctctt ttggaatttt tttcaggtga tttaataata atttaaaact actataaaaa 240
c 241

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: (1)...(241)

-continued

<223> OTHER INFORMATION: n = A,T,C or G

<400> SEQUENCE: 354
ngcaggtccg ggcaggtacc aagattcatt ctcatcaaaa actagaaaca gaagggcaaa 60
ttccagtttc cttctgggat tgaatacttt caagtaaggt cttcgacaaa caatcagggg 120
gccaattaat ccactgtaga ggtccttaac ttgatccaca gttgaataat aagcccatgg 180
aatacaagca gaatcctctg ttccagctcc agatctttct gggattttcc atacgtaagt 240
g 241

<210> SEQ ID NO 355
<211> LENGTH: 241
<212> TYPE: DNA
<213> ORGANISM: Homo sapiens

<400> SEQUENCE: 355
ggtacccacc ctaaatttga actcttatca agaggctgat gaatctgacc atcaaatagg 60
ataggatgga ccttttttttg agttcattgt ataaacaaat tttctgattt ggacttaatt 120
cccaaaggat taggtctact cctgctcatt cactctttca aagctctgtc cactctaact 180
tttctccagt gtcatagata gggaattgct cactgcgtgc ctagtctttc ttcacttacc 240
t 241

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356
aggtactgta attgagcatc cggaatntgg agaagtaatt tagctacagg gtgaccaacg 60
caagaacata tgccagttcc tcgtagagat tggactggct aaggacgatc agctgaaggt 120
tcatgggttt taagtgcttg tggctcactg aagcttaagt gaggatttcc ttgcaatgag 180
tagaatttcc cttctctccc ttgtcacagg tttaaaaacc tcacagcttg tataatgtaa 240
c 241

<210> SEQ ID NO 357
<211> LENGTH: 241
<212> TYPE: DNA
<213> ORGANISM: Homo sapiens

<400> SEQUENCE: 357
ttttgtacca ccgatatgat caaggaaaat tctgcccatt tttatggctg aagttctaaa 60
aacctaattc aaagttcttc catgatccta cactgcctcc aagatggtcc aggctggcat 120
aaggcctgag cggcggtgag atccgcggct gccagcagct tgtcgctctt cagctggtat 180
gaagcccctc ggccacccga gtctccagga cctgcccggg cgccgctcga aagggcgaat 240
t 241

<210> SEQ ID NO 358
<211> LENGTH: 241
<212> TYPE: DNA
<213> ORGANISM: Homo sapiens
<220> FEATURE:
<221> NAME/KEY: misc_feature -continued
<222> LOCATION: (1)...(241)
<223> OTHER INFORMATION: n = A,T,C or G

<400> SEQUENCE: 358
aggtacgggg agtgggggtg aagcntgttc tctacatagg caacacagcc gcctaantca 60
caaagtcagt ggtcggccgc ttcgaccaac atgtggtgag cattccacgg gcgcatgaag 120
tctgggtgct gtgctcgagt ctctgaatat tttgatagga agcgacaaga aaattcaaac 180
tgctctttgc tgactactgg aaagtgaaaa gatgctcaag tttaccattc aaagaaacca 240
t 241

<210> SEQ ID NO 359
<211> LENGTH: 241
<212> TYPE: DNA
<213> ORGANISM: Homo sapiens

<400> SEQUENCE: 359
gaggtacaca aaaggaatac cttctgagag ccagggagtg aggaaagggg aaggagactt 60
gacgtcaagg gtgcttttga ggaacatgac gggccagcca gcctgcccca actttgaggc 120
cctgctgggc tcttgtgact ataaatatac tgtctatttc taatgcaatc cgtctttcct 180
gaaagatctt gttatctttt actattgaga catgctttca tttttgtggt cctgtttcca 240
a 241

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360
ngtactctat actaattctg ccttttata cttaattcta aatttctccc ctctaattta 60
caacaaattt tgtgattttt ataagaatct atgcctcccc aattctcaga ttcttctctt 120
ttctccttta tttctttgct taaattcagt ataagctttc ttggtatttt aggcttcatg 180
cacattctta ttcctaaaca ccagcagttc ttcagagacc taaaatccag tataggaata 240
a 241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc 60
ccactttgta cttttcttac tatcctgtct agaatcatgt cttatgattt taacagatat 120
agaaccactc ctagaaaatg ttctttcact ttctcgtttc ctttttaatc tatcatcctg 180
actactgaac ttaaaatctt tttcttccct tttttgtttc tcttttcttt tatcctgttc 240
a 241

<210> SEQ ID NO 362
<211> LENGTH: 241
<212> TYPE: DNA
<213> ORGANISM: Homo sapiens
<220> FEATURE:

-continued

<221> NAME/KEY: misc_feature
<222> LOCATION: (1)...(241)
<223> OTHER INFORMATION: n = A,T,C or G

<400> SEQUENCE: 362
aggtactttt atacctngct tangtcagtg acagatttac caatgacaac acaattttaa 60
aattccaaca catatattac tttgtcctat gaagggcaaa aagtcaatat attttaaatt 120
ttaaaaacag aatggatata atgacctttt tacacatcag tgatatttaa aagacttaaa 180
gagacaatac tatggttgag acactggctt cctattccag ccctaattaa agaaaaaata 240
g 241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363
ttangtacta aaaacaaaat cctaattctg ttttaaagag ctgggagatg ttaatcatat 60
gctcagtttt tccacgttat aatttcctaa atgcaaactt ttcaatcagg gcagttcaaa 120
ttcattacat cacagtaaat aacagtagcc aactttgatt ttatgcttat aggaaaaaaa 180
atcctgtaga tataaaaaca gcaaattttg acaaataaaa ctcaaaccat tcatccctaa 240
a 241

<210> SEQ ID NO 364
<211> LENGTH: 241
<212> TYPE: DNA
<213> ORGANISM: Homo sapiens

<400> SEQUENCE: 364
ggtacaagca gttagtcctg aaggcccctg ataagaatgt catcttctcc ccactgagca 60
tctccaccgc cttggccttc ctgtctctgg gggcccataa taccaccctg acagagattc 120
tcaaaggcct caagttcaac ctcacggaga cttctgaggc agaaattcac cagagcttcc 180
agcacctcct gcgcaccctc aatcagtcca gcgatgagct gcagctgagt atgggaaatg 240
c 241

<210> SEQ ID NO 365
<211> LENGTH: 241
<212> TYPE: DNA
<213> ORGANISM: Homo sapiens

<400> SEQUENCE: 365
cgaggtactg agattacagg catgagccac cacgcccggc caaaaacatt taaaaaatga 60
ctgtccctgc tcaaatactg cagtaggaaa tgtaatttga catatatcac ttccagaaaa 120
aaactttaaa tctttctata aaatgaattt gatacatcat cagcatgaag tgaagttaaa 180
atctcttaca aagtaaattc aggtatatca acaatgagat ccaaaagtat cggttcaaga 240
t 241

<210> SEQ ID NO 366
<211> LENGTH: 241
<212> TYPE: DNA
<213> ORGANISM: Homo sapiens -continued

<400> SEQUENCE: 366
ggcaggtaca catcaaacac ttcattgcct aaatgcaggg acatgcttcc atctgaccac 60
ttgactatcc gagcattgct ttctttaatt tcatttcctt cttcatctcg gcgtatcctc 120
catcttatag tattttctac ctttaatttt aacctggttc taccttcttc atccagcatt 180
tcttcatctt caaattcatc ttcataatac tgggctctac acttgagaaa gttgggcagt 240
t 241

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367
gcaggtacaa ataattcctg ttgtnacatt tagtggacgc gattatctgt atacctcaaa 60
ttttaattta agaaagtatc acttaaagag catctcattt tctatagatt gaggcttaat 120
tactgaaaag tgactcaacc aaaaagcaca taacctttta aaggagctac acctaccgca 180
gaaagtcaga tgccctgtaa ataactttgg tctttcaaaa tagtggcaat gcttaagata 240
c 241

<210> SEQ ID NO 368
<211> LENGTH: 241
<212> TYPE: DNA
<213> ORGANISM: Homo sapiens

<400> SEQUENCE: 368
tttgtacatt gttaatagtg accctcggag gaaatggatt tctcttctat taaaaactct 60
atggtatata agcattacat aataatgcta cttaaccacc ttttgtctca agaattatca 120
ccaaagtttt ctggaaataa gtccacataa gaattaaata tttaaaaggt gaaatgttcc 180
ttattttaac tttagcaaga tcttttcttt ttcattaaga aacactttaa taattttaaa 240
g 241

<210> SEQ ID NO 369
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat 60
aaacaaaaca ccaaccagcc acagcagttg tgtcaagcat gacaattggt ctagtcttca 120
cattttatta gtaagtctat caagtaagag atgaagggtc tagaaaacta gacacaaagc 180
aaccagggtc caaatcacca aggtagatct gtgcttagct aaagggaaac acccgaagat 240
t 241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: (1)...(241)

-continued

<223> OTHER INFORMATION: n = A,T,C or G

<400> SEQUENCE: 370
ngttcacagt gcccctccgg cctcgccatg aggctcttcc tgtcgctccc ggtcctggtg 60
gtggttctgt cgatcgtctt ggaaggccca gccccagccc aggggacccc agacgtctcc 120
agtgccttgg ataagctgaa ggagtttgga aacacactgg aggacaaggc tcgggaactc 180
atcagccgca tcaaacagag tgaactttct gccaagatgc gggagtggtt ttcagaagac 240
a 241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 371
ggcaggtcat cttgagcctt gcacatgata ctcagattcc tcacccttgc ttaggagtaa 60
aacaatatac tttacagggt gataataatc tccatagtta tttgaagtgg cttgaaaaag 120
gcaagattga cttttatgac attggataaa atctacaaat cagccctcga gttattcaat 180
gataactgac aaactaaatt atttccctag aaaggaagat gaaaggnagt ggagtgtggt 240
t 241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 372
aggtacagca aagcgaccct tggtgnnata gatcagacgg aaattctctc ccgtcttgnc 60
aatgctgatg acatccatga atccagcagg gtaggttata tcagttcgga ccttgccatc 120
gattttaatg aaccgctgca tgcaaatctt ctttacttca tctcctgtca gggcatactt 180
aagtctgttc ctcaggaaaa tgatgagggg gagacactct ctcaacttgt ggggaccggt 240
g 241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca 60
gaagcagtag aaaatcttag cattccaatg gaaggcatgt atttgtaaaa tattctaaaa 120
tcagctctat agtttccttg tcctctttga taagggatca gacagagggt gtgtcccccct 180 tcagcagcta cccttcttga caaactggtc tccaataata cctttcagaa acttacaaga 240
c 241

<210> SEQ ID NO 374
<211> LENGTH: 241

-continued

<212> TYPE: DNA
<213> ORGANISM: Homo sapiens

<400> SEQUENCE: 374
caggtactaa aacttacaat aaatatcaga gaagccgtta gtttttacag catcgtctgc 60
ttaaaagcta agttgaccag gtgcataatt tcccatcagt ctgtccttgt agtaggcagg 120
gcaatttctg ttttcatgat cggaatactc aaatatatcc aaacatcttt ttaaaacttt 180
gatttatagc tcctagaaag ttatgttttt taatagtcac tctactctaa tcaggcctag 240
c 241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt 60
gaagaccatc acctccgtgg ccatgaccag tgctctgccc atcatccaga agctagagcc 120
gcaaattgca gttgccaata cctatgcctg taaggggcta gacaggattg aggagagact 180
gcctattctg aatcagccat caactcagat tgttgccaat gccaaaggcg ctgtgactgg 240
g 241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa acttttgttt atacttaaaa 60
aaaccataaa tcagacaaac aaaagaaacg attccaacat cacttctgtg atgagaaaag 120
aggcaatgga attcaacata agcaaagaaa actctacctg gaggaaagaa atcgatcagc 180
gaagaaacaa ctcggggctg ctgccagact gcaggccatg cgaggaggag cctcctagag 240
g 241

<210> SEQ ID NO 377
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377
tcctttctgt ccaggtgatt cacagactag acctttctta tcctcctcct agagttttga 60
cttgggactc tagtgttaag atgatgagcc cgtgcatcag gtccttctgc actttggtgg 120
aagtctccca gggtaggttt cctatttgaa acagtggaat catgtttcca gtgataaagt 180
ttaatgacct catccttttt tttttttttc tcatctgcca tttgtgtgtc ttanatgggt 240
t 241

<210> SEQ ID NO 378
<211> LENGTH: 241
<212> TYPE: DNA
<213> ORGANISM: Homo sapiens -continued

<400> SEQUENCE: 378
aggtcagcga tcaggtcctt tatgggcagc tgctgggcag ccccacaagc ccagggccag 60
ggcactatct ccgctgcgac tccactcagc ccctcttggc gggcctcacc cccagcccca 120
agtcctatga gaacctctgg ttccaggcca gcccccttggg gaccctggta accccagccc 180
caagccagga ggacgactgt gtctttgggc cactgctcaa cttccccctc ctgcagggga 240
t 241

<210> SEQ ID NO 379
<211> LENGTH: 241
<212> TYPE: DNA
<213> ORGANISM: Homo sapiens

<400> SEQUENCE: 379
tacggagcaa tcgaagaggc atatccacac ttggggtggc tatagggctg gaaaatgctg 60
aagatgactg ctttcactga ggtcaaggat tgtaatattg ccagctttgt aaagccatta 120
aagcagaagt ttcttcagtg atcttctctc taagaaacac catcacctcc atgtgcctta 180
cagaggcccc ctgcgttctg ctgcattgct tttgcgcaat cccttgatga tgaagatggt 240
c 241

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380
acgtacacgc agaccgacat gggnnnttca ggcntnagat caaactcaaa acctgnaatg 60
atatccactc tctttttctt aagctcaggg aaatattcca agtagaagtc canaaagtca 120
tcggctaana tgcttcngaa tttgaattca tgcacatagg ccttgaaaaa actgtcaaac 180
tgannctgat cacccaccaa gtgggccntn tatgacacaa agcagaaacc tttctcntan 240
g 241

<210> SEQ ID NO 381
<211> LENGTH: 241
<212> TYPE: DNA
<213> ORGANISM: Homo sapiens

<400> SEQUENCE: 381
aggtacaact taatggatta gcttttgggt ttaactgaat atatgaagaa attgggtctg 60
tctaaagaga gggtatttca tatggctttt agttcacttg tttgtatttc atcttgattt 120
ttttctttgg aaaataaagc attctatttg gttcagattt ctcagatttg aaaaaggctc 180
tatctcagat gtagtaaatt atttcctttc agtttgtgaa agcaggattt gactctgaaa 240
g 241

<210> SEQ ID NO 382
<211> LENGTH: 241
<212> TYPE: DNA
<213> ORGANISM: Homo sapiens

<400> SEQUENCE: 382
gtactgctat aatcaatacg tctgatagac aggtttatcc actatattga ccctacctct 60

-continued

```
aaaaggattg tcataattta tatgctttat gtttacacct atgatacagt tgccttggaa    120

cacaaaattt ttcattgtaa ttaaaaaaag aagagttgtg cagacagaag aaatcaaatc    180

taagaaaatc acaggagtag ataaatactc tagaattcat atacccttgg aagatgggtt    240

t                                                                    241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact     60

gtatttaagt ctgtgcaaat aatccttcag aagaaatatc caagattctg tttgcagagg    120

tcattttgtc tctcaaagat gattaaatga gtttgtcttc agataaagtg ctcctgtcca    180

gcagaactca aaaggccttc aagctgttca gtaagtgtag ttcagataag actccgtcat    240

a                                                                    241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag     60

attctataaa atcagttata tcaacatata aaggagtgtg attttcagtt tgttttttta    120

agtaaatatg accaaactga ctaaataaga aggcaaaaca aaaaattatg cttccttgac    180

aaggcctttg gagtaaacaa aatgctttaa ggctcctggt gaatggggtt gcaaggatga    240

a                                                                    241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc     60

tggtccctga ccccacagtg agctgtttag atgatccttc acatcttcct gatcaactgg    120

aagacactcc aatcctcagt gaagactctc tggagccctt caactctctg gcaccaggta    180

ggtttggagg ctatgtccct ttaacttatc catgcagagt agccaaactt tacctgaaag    240

a                                                                    241
```

<210> SEQ ID NO 386
<211> LENGTH: 241
<212> TYPE: DNA
<213> ORGANISM: Homo sapiens

<400> SEQUENCE: 386

```
aggtaccttt ttcctctcca aaggaacagt ttctaaagtt ttctgggggg aaaaaaaact     60

tacatcaaat ttaaaccata tgttaaactg catattagtt gtgttacacc aaaaaattgc    120

ctcagctgat ctacacaagt ttcaaagtca ttaatgcttg atataaattt actcaacatt    180

aaattatctt aaattattaa ttaaaaaaaa aactttctaa gggaaaaata aacaaatgta    240
```

-continued

```
g                                                                  241


<210> SEQ ID NO 387
<211> LENGTH: 241
<212> TYPE: DNA
<213> ORGANISM: Homo sapiens

<400> SEQUENCE: 387

accccactgg ccgctgtgga gtatctccac tctcccctcg tgagggccgc tcccaccgac     60

cagtcgaact ttcgtaaatg gagttaatgt gtttccactc ccttttccc ctttctggcc    120

ttttggtcca gaatttcctg gccttccggc atatcctggg agtcctcgac ttccaggaaa    180

gccaattgct ccccgatcac ctttaagacc cggaggacct attggacctg gaaatcctcg    240

t                                                                  241


<210> SEQ ID NO 388
<211> LENGTH: 241
<212> TYPE: DNA
<213> ORGANISM: Homo sapiens

<400> SEQUENCE: 388

tttgtactct tgtccacagc agagacattg agtataccat tggcatcaat gtcaaaagtg     60

acttcaatct gaggaacacc tcggggtgca ggaggtatgc ctgtgagttc aaacttgcca    120

agcaggttgt tatcctttgt catggcacgc tcgccttcat aaacctgaat aagtacacca    180

ggctggttgt cagaataggt agtgaaggtc tgtgtctgct tggtaggaat ggtggtatta    240

c                                                                  241


<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389

tacctntgtt agtgagcacc ttgtcttntg tgcttatntc ttnaagataa atacatggaa     60

ggatgtgaaa atcggaacac caactatgtg tctcactgca tctaagtgaa gcagccacag    120

ctgtgagagt tttcaaagca gaaagatgct gatgtgacct ctggaattca gacatactga    180

gctatgggtc agaagtgttt tacttaaaaa gcaaacaatc cccaggaaat actgaatagg    240

a                                                                  241


<210> SEQ ID NO 390
<211> LENGTH: 241
<212> TYPE: DNA
<213> ORGANISM: Homo sapiens

<400> SEQUENCE: 390

gcaggtacat ccacatgttc ctccaaatga cgtttggggt cctgcttgcc aacattcttt     60

attgccagct gttcaggtgt catcttatct tcttcttcta cagccttatt gtaattcttg    120

gctaattcca acatctcttt taccactgat tcattgcgtt tacaatgttc actgtagtcc    180

tgaagtgtca aaccttccat ccaactcttc ttatgcaaat ttagcaacat cttctgttcc    240

a                                                                  241
```

-continued

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391
cnggcacaan cttntgtttt tnntnttttt ttttttttn tctttatttn tttttantnt 60
taaanaaaaa nnntannnaa annngggttt aaatnctntn nncagancat taaaactgaa 120
ggggaaaaaa aaaccaaaaa cgagcttntt anttnacntg ggnttgggnn gntgctgatn 180
tnaagaagca anntttanan cnngcnnnat ganngagngn tcannttgaa atttnnaccc 240
t 241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gttttttcta 60
cattagaaat aagatgccac acaaggaact acattccaga tttaaagaaa tgaaaggata 120
ccattagtgt gtataacaga ttattgttca tacttgtaaa gcatcttatg tcattgagaa 180
tataaagaac agtgccttag aagacagtga aaggtaagct ctagcttaat gtctatgatt 240
t 241

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
ggcaggtaca taagcataat cagttatgga cagcttcttg tataaattgc tattcancaa 60
tacataaact gcctnaaaga tttatgctta caggtagaca ttcaatttac caataaaaca 120
gcatgttctg aaaatatggg cacattttaa aacatattaa gacagttctg ttaaccataa 180
tagtcccaca gtatgactga gtaataagaa tctacttcaa aagnaaaaaa aaaattaatc 240
a 241

<210> SEQ ID NO 394
<211> LENGTH: 241
<212> TYPE: DNA
<213> ORGANISM: Homo sapiens

<400> SEQUENCE: 394
aggtacagca gcagtagatg gctgcaacaa ccttcctcct accccagccc agaaaatatt 60
tctgccccac cccaggatcc gggaccaaaa taaagagcaa gcaggccccc ttcactgagg 120
tgctgggtag ggctcagtgc cacattactg tgctttgaga aagaggaagg ggatttgttt 180
ggcactttaa aaatagagga gtaagcagga ctggagaggc cagagaagat accaaaattg 240
g 241

-continued

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395
nggcnggnnc caanatatga aatntnanta tnatacatga tnaaaagctt tatntatttt 60
agtgagtaat taagtttaca ctgtgaataa ggattaattc ccagatgacc atctacagtt 120
actaccacat agagggtata cacggatgga tcgattacaa gaatataaaa cttattttcc 180
ttcctgtatc cacatttctt tgcaatgtga atttgcaggc cctctcaaga agtggagtct 240
a 241

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396
gaggtacacc ttgaatgaca atgctnggag cccccctgtg gtcatcgacg cctccactgc 60
cattgatgca ccatccaacc tgcgtttcct ggccaccaca cccaattcct tgctggtatc 120
atggcagccg ccacgtgcca ggattaccgg ctacatcatc aagtatgaga agcctgggtc 180
tcctcccaga gaagtggtcc ctcggccccg ccctggtgtc acagaggcta ctattactgg 240
c 241

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 397
ggcaggtacc agcaggggga tgtgtttctg gggaattgtg gctctggaag cttcacggtt 60
tcccagaatg tggaaaatat atctgtgcan gatagaaatc ctgcccagag gctgtttctg 120
tctcatttga gctctccttc atgtggcaga gctgactgtg gcggtttagg agcctacatt 180
ttagaaaagc ttacctcaaa gttctgcatt gagcctgagc actggaaagg agataaaata 240
a 241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 398
gangtgacca ngacatcacc tnacacntgg aaagcganga nttgaatggt gcntacaang 60

-continued

```
ccntacccnt tgcccannac ctgaacgcgc cttntgattg ggacagccgt gggaaggaca    120

gttatgaaac nantcanctg gatgaccana gtgntgaaac cnacanncac angcnntcna    180

cattatataa ncggaaagct aatgatgaga gcaatgatca ttccgatgtn attgatagtc    240

a                                                                    241


<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399

cagagtgaga tgggagtggg agggccaatc tgatacagaa gggggtgaag ggtagggccc     60

ctgagcagcc cacccettac cctgacgaag gcaatcctcc tctggaatgt ctcttccctc    120

ttcagtctgg gttctgcctc agccacgaac tgggaaggag tgaggaacat cccaacggca    180

atgagagtat cccagtgact ccaaacagga angaatcagt gttcanaaag tcagggccct    240

t                                                                    241


<210> SEQ ID NO 400
<211> LENGTH: 241
<212> TYPE: DNA
<213> ORGANISM: Homo sapiens

<400> SEQUENCE: 400

ggtactcttg ctcttttagc tagagtgtat gtgaaaataa agaaatacat cattgtattc     60

acaaccatgt gtcttcattt ataacttttt gtttaaaaaa tttttagttc aagtttagtt    120

cattgatatt atcctctgaa tgcagttaag gctgggcaga aattctactc atgtgacatc    180

tgccacaggt ctattttgaa gcttttcttc taatgggcaa tgtttgtcct taccaggatt    240

t                                                                    241


<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401

nncaggtact ttgtagagca gagagaggct ttggttcctc ctttcttcaa tcacgtggag     60

atgtgtcatc acctgggatt tcatctgggc cgccttttct gggtcaacag ccaacacatg    120

ctggtaatga cggatggtat gtaagcgatc tttgttctca gcacggacat aacgccgtaa    180

ggcctggaga atgcgatgag gccgtggcgg gtcagactgc aaggcagcca ggtagttctc    240

c                                                                    241


<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: (1)...(241)
```

-continued

<223> OTHER INFORMATION: n = A,T,C or G

<400> SEQUENCE: 402
ggcaggtcca aaaaaaacct aaaaanngtt tcaggaatgt agagaaatat ccaacttaaa 60
tagcgaaaaa gtgcaccata attactgctg cactgcagtc atttctgcaa ttcccatgtt 120
tcttaaataa ctatcttgtc agataacaca caatataaag agcaattatg aaaaacagac 180
atttacatat acttctaaag tcttattggg aatatcctgt ttggccattg ggataaccaa 240
t 241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403
aggtgttaac tacccgctcc gagacgggat tgatgacgag tcctatgang ccattttcaa 60
gccggtcatg tccaaagtaa tggagatgtt ccagcctagt gcggtggtct tacagtgtgg 120
ctcagactcc ctatctgggg atcggttagg ttgcttcaat ctaactatca aaggacacgc 180
caagtgtgtg gaatttgtca agagctttaa cctgcctatg ctgatgctgg gaggcggtgg 240
t 241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt 60
ttctgtcttc ttttcacggc attcaaagta ggaataaact ttgcttgtgt tgggtggata 120
ttgtttatag tgagtaacct tgtaggagtc ggtggccagg aggatgttga actcggcttc 180
tgccgcagga ttcatctcgg gccggaggac aaggggcccg cgcgccgcga gctccctgac 240
c 241

<210> SEQ ID NO 405
<211> LENGTH: 266
<212> TYPE: DNA
<213> ORGANISM: Homo sapiens

<400> SEQUENCE: 405
ttctgggctg gggagtggag agaaagaagt tgcagggctt acaggaaatc ccagagcctg 60
aggttttctc ccagatttga gaactctaga ttctgcatca ttatctttga gtctatattc 120
tcttgggctg taagaagatg aggaatgtaa taggtctgcc ccaagccttt catgccttct 180
gtaccaagct tgtttccttg tgcatccttc ccaggctctg gctgcccctt attggagaat 240
gtgatttcca agacaatcaa tccaca 266

<210> SEQ ID NO 406
<211> LENGTH: 231
<212> TYPE: DNA
<213> ORGANISM: Homo sapiens

<400> SEQUENCE: 406

-continued ttggtgaaga accattcctc ggcatccttg cggttcttct ctgccatctt ctcatactgg 60
tcacgcatct cgttcagaat gcggctcagg tccacgccag gtgcagcgtc catctccaca 120
ttgacatctc cacccacctg gcctctcagg gcattcatct cctcctcgtg gttcttcttc 180
aggtaggcca gctcctcctt caggctctca atctgcatct ccaggtcagc t 231

<210> SEQ ID NO 407
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt 60
ttgtgccata atgcagcagt atggagggag gattttatgg agaaatgggg atagtcttca 120
tgaccacaaa taaataaagg aaaactaagc tgcattgtgg gttttgaaaa ggttattata 180
cttcttaaca attctttttt tcagggactt ttctagctgt atgactgtta cttgaccttc 240
tttgaaaagc attcccaaaa tgctct 266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg 60
acttttcagg gaattactga actttcttct cagaagatag ggcacagcca ttgccttggc 120
ctcacttgaa gggtctgcat ttgggtcctc tggtctcttg ccaagtttcc cagccactcg 180
agggagtaat atctggaggg caaagaagag acttatgtta ttgttgaacc tccagccaca 240
gggaggagca tgggcatggg t 261

<210> SEQ ID NO 409
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat 60
ctgtcccaga cccgctgcca ctgaatcggt cagggatccc ggattcccgg gtagatgccc 120
agtaaatgag cagtttagga ggctgtcctg gtttctgctg gtaccaagct aagtagttct 180
tattgttgga gctgtctaaa acactctggc tggtcttgca gttgatggtg gccctctcgc 240
ccagagacac agccagggag tgtgga 266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410
caaaaggtnc tttttgntca aaancnattt ttattccttg atatttttct tttttttttt 60
tttgnggatg gggacttgtg aatttttcta aaggggnnnn ttnannnngg aagaaaaccn 120

-continued

```
ngntccggtt ccagccaaac cngtngctna ctttccacct tntttccacc tccctcnggt    180

t                                                                    181


<210> SEQ ID NO 411
<211> LENGTH: 261
<212> TYPE: DNA
<213> ORGANISM: Homo sapiens

<400> SEQUENCE: 411

gcccctgcag tacttggccg atgtggacac ctctgatgag gaaagcatcc gggctcacgt     60

gatggcctcc caccattcca agcggagagg ccgggcgtct tctgagagtc agggtctagg    120

tgctggagtg cgcacggagg ccgatgtaga ggaggaggcc ctgaggagga agctggagga    180

gctggccagc aacgtcagtg accaggagac ctcgtccgag gaggaggaag ccaaggacga    240

aaaggcagag cccaacaggg a                                              261


<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

nttttntctt tacaattcag tcttcaacaa cttgagagct ttcttcatgt tgncaagcaa     60

cagagctgta tctgcaggnt cgtaagcata nagacngttt gaatatcttc cagngatatc    120

ggctctaact gncagagatg ggtcaacaaa cataatcctg gggacatact g             171


<210> SEQ ID NO 413
<211> LENGTH: 266
<212> TYPE: DNA
<213> ORGANISM: Homo sapiens

<400> SEQUENCE: 413

ttaggaccaa agatagcatc aactgtattt gaaggaactg tagtttgcgc attttatgac     60

atttttataa agtactgtaa ttctttcatt gaggggctat gtgatggaga cagactaact    120

cattttgtta tttgcattaa aattattttg ggtctctgtt caaatgagtt tggagaatgc    180

ttgacttgtt ggtctgtgta aatgtgtata tatatatacc tgaatacagg aacatcggag    240

acctattcac tcccacacac tctgct                                         266


<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 414

tttgccataa ttgagtgaaa agtggcagat ggcattaact ctgctccgct tcaagctggc     60

tccatgacca ctcaaggcct ccccancctg ttcgtcaagt tgtcctcaag tccaagcaat    120

ggaatccatg tgtttgcaaa aaaagtgtgc tanttttaag gnctttcgta taagaatnaa    180

tganacaatt ttcctaccaa aggangaaca aaaggataaa tataatacaa aatatatgta    240

tatggttgtt tgacaaatta tataac                                         266
```

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415
cctccatcca gtctattaat tgttgccggg aagctanagt aagtagttcg ccagttaata 60
gtttgcgcaa cgttgttgcc attgctacag gcatcgtggt gtnacgctcg tcgattggta 120
tggcttcatt cagctccggt tcccaacgat caaggcgagt tacatgatcc cccatgttgt 180
gcaaaaaagc ggttagctcc ttcggtcctc cgatcgttgt canaagtaag ttggccgcag 240
tgttatcact catggttatg gcagca 266

<210> SEQ ID NO 416
<211> LENGTH: 878
<212> TYPE: DNA
<213> ORGANISM: Homo sapiens

<400> SEQUENCE: 416
cctgacgata gccatggctg taccacttaa ctatgattct attccaactg ttcagaatca 60
tatcacaaaa tgacttgtac acagtagttt acaacgactc ccaagagagg aaaaaaaaaa 120
aaaaagacgc ctcaaaattc actcaacttt tgagacagca atggcaatag gcagcagaga 180
agctatgctg caactgaggg cacatatcat tgaagatgtc acaggagttt aagagacagg 240
ctggaaaaaa tctcatacta agcaaacagt agtatctcat accaagcaaa accaagtagt 300
atctgctcag cctgccgcta acagatctca caatcaccaa ctgtgcttta ggactgtcac 360
caaagtcaga ttcggtgcta accaggtggc atctatgatc aacgtcgccc ctcttattta 420
acaaagggct ctgaaggagg tgttctccaa gcaacaagga gactgcttca gtacaagact 480
ttgcaccttg aattcaattg catcaagtgt ggatagcaaa ataagtatct taccattgaa 540
atatgtgttc agcctaagat tttacccacc agcagaacaa aagtgagggt gagagggatg 600
ggccagtgag gggatggggg agaaaaaaaa atcacaggat taccaccaaa gccttgtttt 660
aaaagggctc ccttcactat tcaggaaggg aagtggaagg agaaattaac caattcctgc 720
cacagcagcc ctttttggct gcttccacaa tagatacttt atggagtggc acagccaacc 780
ctatctgtga cctgccctgc ggataaacac agccaagcag gtttaattag atcaaagaca 840
caaagggcta ttccctcctt tcataacaac gcagacct 878

<210> SEQ ID NO 417
<211> LENGTH: 514
<212> TYPE: DNA
<213> ORGANISM: Homo sapiens

<400> SEQUENCE: 417
ttctgacttc tagaagacta aggctggtct gtgtttgctt gtttgcccac ctttggctga 60
tacccagaga acctgggcac ttgctgcctg atgcccaccc ctgccagtca ttcctccatt 120
cacccagcgg gaggtgggat gtgagacagc ccacattgga aaatccagaa aaccgggaac 180
agggatttgc ccttcacaat tctactcccc agatcctctc ccctggacac aggagaccca 240
cagggcagga ccctaagatc tggggaaagg aggtcctgag aaccttgagg taccettaga 300

-continued

```
tccttttcta cccactttcc tatggaggat tccaagtcac cacttctctc accggcttct    360

accagggtcc aggactaagg cgttttctcc atagcctcaa cattttggga atcttccctt    420

aatcaccctt gctcctcctg ggtgcctgga agatggactg gcagagacct ctttgttgcg    480

ttttgtgctt tgatgccagg aatgccgcct agtt                                514
```

<210> SEQ ID NO 418
<211> LENGTH: 352
<212> TYPE: DNA
<213> ORGANISM: Homo sapiens

<400> SEQUENCE: 418

```
ctgcaccagc gattaccagt ggcattcaaa tactgtgtga ctaaggattt tgtatgctcc     60

ccagtagaac cagaatcaga caggtatgag ctagtcaaca gcaagtcttt gttggattcg    120

agtaggctca ggatctgctg aaggtcggag gagttagtcc ccgcaatcaa gagcctgtct    180

tcctgaagcc cttggtgata ttttgccact cagccaagaa tgaggatgca tccttcagat    240

tctctatgtc ccgaacctgg aacccatcca cgccagcttg cagccaaaac tccagagcat    300

ccttcacctt ggtggaaaaa aaaaaaaaaa aaaaaaaaaa aaaaaaaaaa aa            352
```

<210> SEQ ID NO 419
<211> LENGTH: 344
<212> TYPE: DNA
<213> ORGANISM: Homo sapiens

<400> SEQUENCE: 419

```
ctggacacca taatcccttt taagtggctg gatggtcaca cctctcccat tgacaagctg     60

ggttaagtca ataggttgac taggatcaac acgacccaaa tcaataagat actgcagtct    120

attgagactc aaaggcttat actggcgtct gaaactatgt ccttcgttaa acccgtattt    180

tgggattcgg atgtaaaatg gagtctggcc tccctcaaag cccaagcggg gccgggttcc    240

tctttgcctt tctcctttat ggcctctgcc acattttcta cctcttctcc gacctcttgg    300

tcttctctcc ggtttcttgg agccgggatt cggctttaag ttgg                     344
```

<210> SEQ ID NO 420
<211> LENGTH: 935
<212> TYPE: DNA
<213> ORGANISM: Homo sapiens

<400> SEQUENCE: 420

```
cgaaagtcaa cgttaagggg ctcaggtgaa ccatgatgat gaccttctgt tgactttgaa     60

atattggctc ttgtgggtga caaaagccag acaagctgtg gctgtggtcc gattttaaga    120

cgaggttctc aaagatccaa aggagggaaa gggtattgga aacactgtgt atcatctgag    180

acacacgtgt cctcatgatc ttaaatgcct actttaaagc cacctaatac tgcccttcat    240

tgtggtcaga agagatttct acaaaagcac tcagaattct ggaggcagtt gtgattttgc    300

catgtggcag ttggtttgtg gagttgggca ggtgtgaaag ggtaaaactc cacttctgaa    360

tgctgcttct gccccctggg acccagcaca ttgttagacc atcttcttga ctgaaaattc    420

tctcctgatg ctgagccctg caccaccacc ttccttttcc taactatgaa ttgatggcaa    480

agtccactca aaacaaccag ttaagtgctc acgagagagt agtcaagcac ctccagaaag    540

aaaccgggtt tttgttcaca tagcaggaag tgactccctg ggtggtaatt tatcttggaa    600

acacaggtag attggcagaa aaacgggaac atgtaggtac cgcgatgttg gtgcatgtcc    660

attactttgg gataggcttt ctcagtcttt cctcaaatga tagttgagcc agttttccag    720
```

-continued

```
tggcaattct gagtgacttg cgcttgtctt atggtgtggt caagggacgt tcagaactac    780

ggaaaacttt tactgaaaca gcgaagcaga gtataccggc atgagaggga agatgaacac    840

tcacctatgt accactcttt gacaataaat atagtatttc tcaaaaaaaa aaaaaaaaaa    900

agtaaaaaaa ctgaaatcgc aagtcaaaaa atcca                               935
```

<210> SEQ ID NO 421
<211> LENGTH: 745
<212> TYPE: DNA
<213> ORGANISM: Homo sapiens

<400> SEQUENCE: 421

```
ggcttcgagc ggccgcccgg gcaggtccta gatgtcattt gggacccttc acaaccattt     60

tgaagccctg tttgagtccc tgggatatgt gagctgtttc tatgcataat ggatattcgg    120

ggttaacaac agtcccctgc ttggcttcta ttctgaatcc ttttctttca ccatggggtg    180

cctgaagggt ggctgatgca tatggtacaa tggcacccag tgtaaagcag ctacaattag    240

gagtggatgt gttctgtagc atcctattta aataagccta ttttatcctt tggcccgtca    300

actctgttat ctgctgcttg tactggtgcc tgtacttttc tgactctcat tgaccatatt    360

ccacgaccat ggttgtcatc cattacttga tcctacttta catgtctagt ctgtgtggtt    420

ggtggtgaat aggcttcttt ttacatggtg ctgccagccc agctaattaa tggtgcacgt    480

ggacttttag caagcgggct cactggaaga gactgaacct ggcatggaat tcctgaagat    540

gtttggggtt tttttctttc ttaatcgaaa gttaacattg tctgaaaagt tttgttagaa    600

ctactgcgga acctcaaaat cagtagattt ggaagtgatt caaagctaaa ctttttcctt    660

ggccctcctt gtgttctaat tgcttgcaag tgtaatacta ggatgtccaa gatgccagtt    720

tttgcttctt tgttagttgt cagac                                          745
```

<210> SEQ ID NO 422
<211> LENGTH: 764
<212> TYPE: DNA
<213> ORGANISM: Homo sapiens

<400> SEQUENCE: 422

```
gagttcagta gcaaagtcac acctgtccaa ttccctgagc tttgctcact cagctaatgg     60

gatggcaaag gtggtggtgc tttcatcttc aggcagaagc ctctgcccat ccccctcaag    120

ggctgcaggc ccagttctca tgctgccctt gggtgggcat ctgttaacag aggagaacgt    180

ctgggtggcg gcagcagctt tgctctgagt gcctacaaag ctaatgcttg gtgctagaaa    240

catcatcatt attaaacttc agaaaagcag cagccatgtt cagtcaggct catgctgcct    300

cactgcttaa gtgcctgcag gagccgcctg ccaagctccc cttcctacac ctggcacact    360

ggggtctgca caaggctttg tcaaccaaag acagcttccc ccttttgatt gcctgtagac    420

tttggagcca agaaacactc tgtgtgactc tacacacact tcaggtggtt tgtgcttcaa    480

agtcattgat gcaacttgaa aggaaacagt ttaatggtgg aaatgaacta ccatttataa    540

cttctgtttt tttattgaga aaatgattca cgaattccaa atcagattgc caggaagaaa    600

taggacgtga cggtactggg ccctgtgatt ctcccagccc ttgcagtccg ctaggtgaga    660

ggaaaagctc tttacttccg cccctggcag ggacttctgg gttatgggag aaaccagaga    720

tgggaatgag gaaaatatga actacagcag aagcccctgg gcag                     764
```

<210> SEQ ID NO 423

-continued

<211> LENGTH: 1041
<212> TYPE: DNA
<213> ORGANISM: Homo sapiens

<400> SEQUENCE: 423

```
ctcagagagg ttgaaagatt tgcctacgaa agggacagtg atgaagctaa gctctagatc     60
caggatgtct gacttcaaat tgaaactccc aaagtaatga gtttggaagg gtggggtgtg    120
gcctttccag gatgggggtc ttttctgctc ccagcggata gtgaaacccc tgtctgcacc    180
tggttgggcg tgttgctttc ccaaaggttt ttttttagg tccgtcgctg tcttgtggat     240
taggcattat tatctttact ttgtctccaa ataacctgga gaatggagag agtagtgacc    300
agctcagggc cacagtgcga tgaggaccat cttctcacct ctctaaatgc aggaagaaac    360
gcagagtaac gtggaagtgg tccacaccta ccgccagcac attgtgaatg acatgaaccc    420
cggcaacctg cacctgttca tcaatgccta caacaggtat tgggatgtag ttcagccaca    480
tcattgctat ttatgaggtg tcttctgtag atccgaaatg tgggacagat gagagggaga    540
gtataaaatg agcggaagag gcaggctctg agtttgagca aatagattaa taggacaggt    600
gtccccagga aggacacctg gcctgtaagc tggttcctgg cattcagctc gccttgcagg    660
gatctgaaca aacactccag accactgggg gtgcagacgt gagagggacg cagtcgcaca    720
ctcagagggt tgagagtaaa tatgtgtgcc cgctgctgac cttcacgaaa ggccaaatgt    780
aagaagagct aagtgagaga gcagcaaagc actcctggag gccggggata atccaggcag    840
gcttctggga gtttgtcatt ccaaggataa ggaggacctg aacatggcct ttgcctaagg    900
cgtggccctc tcaaccagca ctaggtgctt atctggagct cagctagggg aggagacagc    960
tcagggccat tggtgtcagc cagagactct gtaatcttcc agggagctcg ctcaacctgc   1020
tgagctcgct ctgccacgca c                                             1041
```

<210> SEQ ID NO 424
<211> LENGTH: 1288
<212> TYPE: DNA
<213> ORGANISM: Homo sapiens

<400> SEQUENCE: 424

```
ctaagaactg agacttgtga cacaaggcca acgacctaag attagcccag ggttgtagct     60
ggaagaccta caacccaagg atggaaggcc cctgtcacaa agcctaccta gatggataga    120
ggacccaagc gaaaaaggta tctcaagact aacggccgga atctggaggc ccatgaccca    180
gaacccagga aggatagaag cttgaagacc tggggaaatc ccaagatgag aaccctaaac    240
cctacctctt ttctattgtt tacacttctt actcttagat atttccagtt ctcctgttta    300
tctttaagcc tgattctttt gagatgtact ttttgatgtt gccggttacc tttagattga    360
cagtattatg cctgggccag tcttgagcca gctttaaatc acagctttta cctatttgtt    420
aggctatagt gttttgtaaa cttctgtttc tattcacatc ttctccactt gagagagaca    480
ccaaaatcca gtcagtatct aatctggctt ttgttaactt ccctcaggag cagacattca    540
tataggtgat actgtatttc agtcctttct tttgacccca gaagccctag actgagaaga    600
taaaatggtc aggttgttgg ggaaaaaaaa gtgccaggct ctctagagaa aaatgtgaag    660
agatgctcca ggccaatgag aagaattaga caagaaatac acagatgtgc cagacttctg    720
agaagcacct gccagcaaca gcttccttct ttgagcttag tccatccctc atgaaaaatg    780
actgaccact gctgggcagc aggagggatg atgaccaact aattcccaaa ccccagtctc    840
attggtacca gccttgggga accacctaca cttgagccac aattggtttt gaagtgcatt    900
```

-continued tacaagtttc tggcatcact accactactg attaaacaag aataagagaa cattttatca 960
tcatctgctt tattcacata aatgaagttg tgatgaataa atctgctttt atgcagacac 1020
aaggaattaa gtggcttcgt cattgtcctt ctacctcaaa gataatttat tccaaaagct 1080
aagataaatg gaagactctt gaacttgtga actgatgtga aatgcagaat ctcttttgag 1140
tctttgctgt ttggaagatt gaaaaatatt gttcagcatg ggtgaccacc agaaagtaat 1200
cttaagccat ctagatgtca caattgaaac aaactgggga gttggttgct attgtaaaat 1260
aaaatatact gttttgaaaa aaaaaaac 1288

<210> SEQ ID NO 425
<211> LENGTH: 446
<212> TYPE: DNA
<213> ORGANISM: Homo sapiens

<400> SEQUENCE: 425
ccacttaaag ggtgcctctg ccaactggtg gaatcatcgc cacttccagc accacgccaa 60
gcctaacatc ttccacaagg atcccgatgt gaacatgctg cacgtgtttg ttctgggcga 120
atggcagccc atcgagtacg gcaagaagaa gctgaaatac ctgccctaca atcaccagca 180
cgaatacttc ttcctgattg ggccgccgct gctcatcccc atgtatttcc agtaccagat 240
catcatgacc atgatcgtcc ataagaactg ggtggacctg gcctgggccg tcagctacta 300
catccggttc ttcatcacct acatcccttt ctacggcatc ctgggagccc tccttttcct 360
caacttcatc aggttcctgg agagccactg gtttgtgtgg gtcacacaga tgaatcacat 420
cgtcatggag attgaccagg aggacc 446

<210> SEQ ID NO 426
<211> LENGTH: 874
<212> TYPE: DNA
<213> ORGANISM: Homo sapiens

<400> SEQUENCE: 426
tttttttttt tttttttttt ttttttcaat taaagatttg atttattcaa gtatgtgaaa 60
acattctaca atggaaactt ttattaaatg ctgcatgtac tgtgctatgg accacgcaca 120
tacagccatg ctgtttcaga agacttgaaa tgccattgat agtttaaaaa ctctacaccc 180
gatggagaat cgaggaagac aatttaatgt ttcatctgaa tccagaggtg catcaaatta 240
aatgacagct ccacttggca aataatagct gttacttgat ggtatccaag aagaaatggt 300
tggtgatgga taaattcaga aatgcttccc caaaggtggg tggtttttaa aaagttttca 360
ggtcacaacc cttgcagaaa acactgatgc ccaacacact gattcgcggt ccaggaaaca 420
cgggtcttcc aagttccaag ggctggggt tccccaacga tcaagttcct gtgctgtaat 480
caagagggtc ctttggactg gatagggagc acttgggagc tgtacaccat cagtcataat 540
ggatggcagt gtaaaagatg atccaaatga cctgagatgc tcctgaggag tggtgcacca 600
gacccaggag tgccactgta gggctgcttc tttgctttag tcatcacaca cacacacagc 660
tccagagcag caatggcctt tcctgtaaca ggaaaaaagc ctcctgctat tcccaagaac 720
cctcgtaatg gcaaaactcc ccaaatgaca cccaggacca cagcaatgat ctgtcggaac 780
cagtagatca catctaaaaa ttcatcctta tcctcccagg ccgcgtcgct ccgcagcacc 840
ttactccaga cggagacttt gagggccccg ttgg 874

<210> SEQ ID NO 427

-continued

<211> LENGTH: 638
<212> TYPE: DNA
<213> ORGANISM: Homo sapiens

<400> SEQUENCE: 427
acttgtaatt agcacttggt gaaagctgga aggaagataa ataacactaa actatgctat 60
ttgatttttc ttcttgaaag agtaaggttt acctgttaca ttttcaagtt aattcatgta 120
aaaaatgata gtgattttga tgtaatttat ctcttgtttg aatctgtcat tcaaaggcca 180
ataatttaag ttgctatcag ctgatattag tagctttgca accctgatag agtaaataaa 240
ttttatgggc gggtgccaaa tactgctgtg aatctatttg tatagtatcc atgaatgaat 300
ttatggaaat agatatttgt gcagctcaat ttatgcagag attaaatgac atcataatac 360
tggatgaaaa cttgcataga attctgatta aatagtgggt ctgtttcaca tgtgcagttt 420
gaagtattta aataaccact cctttcacag tttattttct tctcaagcgt tttcaagatc 480
tagcatgtgg attttaaaag atttgccctc attaacaaga ataacattta aaggagattg 540
tttcaaaata tttttgcaaa ttgagataag gacagaaaga ttgagaaaca ttgtatattt 600
tgcaaaaaca agatgtttgt agctgtttca gagagagt 638

<210> SEQ ID NO 428
<211> LENGTH: 535
<212> TYPE: DNA
<213> ORGANISM: Homo sapiens

<400> SEQUENCE: 428
acaagatgat tcttcctcct caatttgaca gatcaaagaa gtatcccttg ctaattcaag 60
tgtatggtgg tccctgcagt cagagtgtaa ggtctgtatt tgctgttaat tggatatctt 120
atcttgcaag taaggaaggg atggtcattg ccttggtgga tggtcgagga acagctttcc 180
aaggtgacaa actcctctat gcagtgtatc gaaagctggg tgtttatgaa gttgaagacc 240
agattacagc tgtcagaaaa ttcatagaaa tgggtttcat tgatgaaaaa agaatagcca 300
tatggggctg gtcctatgga ggatacgttt catcactggc ccttgcatct ggaactggtc 360
ttttcaaatg tggtatagca gtggctccag tctccagctg ggaatattac gcgtctgtct 420
acacagagag attcatgggt ctcccaacaa aggatgataa tcttgagcac tataagaatt 480
caactgtgat ggcaagagca gaatatttca gaaatgtaga ctatcttctc atcca 535

<210> SEQ ID NO 429
<211> LENGTH: 675
<212> TYPE: DNA
<213> ORGANISM: Homo sapiens

<400> SEQUENCE: 429
actattttca accctgagca ttaacactgc ataccaaggg ggggtgggtc aagaagctgg 60
ttagatcgaa gcacaagcac aagccactga tattctctat gtgatcaggt ttttacaaaa 120
aaatacatag ttttcaataa ataatgctta attttacaac tttgatacag caatgtcata 180
caccgtttca acacactaca ctctgcatgc tagatagtct acgagaagac gaaactttgc 240
catgcatttt ctttcccccc tagtgctatc aaacacttca tcctccagcg cactgcctca 300
ggtagcttta ccttctctct gtttcacagc aataggccgt gcgctggcat gcaaactcta 360
aaaaaggtcc cccccacaaa ccactcagac ttctacacaa aagggttttt cagcttttct 420
gctcccaaac ctggagtggc taagaaagta agtttcatgt ggccttggaa aatacacact 480
tgttaacagt gtcatgctga aaactgctct aaaacatcag gtggttctgt cctggtggcc 540
gtcacgaagc attatgggat gccataacca ctaggagtcc caaaccggaa aaaataggcc 600
tccgttttaa aacagtcaat tcaaaaaagg tgtcacagaa caaatgcaaa agactcttaa 660
acccacaaca tatgt 675

<210> SEQ ID NO 430
<211> LENGTH: 434
<212> TYPE: DNA
<213> ORGANISM: Homo sapiens

<400> SEQUENCE: 430
acctctgcca gaagtccagc gagaggacct cacagtagag cacaggccac tccgggagtg 60
catcagaaga ttcatcctca tggaggaaga aggcttcaaa cgtgaatggg taggagaagt 120
gagccacctt gtccattgcc agggacttgg tggtgcaggt ctgtgttact cctgagagct 180
gctggaatgc tgggcttgac cagtgagcag ttggcaattc tacaaagaag tggacgtaga 240
gattgtcata ctcatagcct tgggctgaaa cgacctctcc atttacaaag agccggaggg 300
cacctgggac agtcatctca aagtcggtgc ctacgaggct gctgagatac tccttgtgcc 360
ggccataaag atccttgaac actcgccgtt cccgctcctc ctcctccggc tgtgcgtggg 420
gggaaacatt gtcg 434

<210> SEQ ID NO 431
<211> LENGTH: 581
<212> TYPE: DNA
<213> ORGANISM: Homo sapiens

<400> SEQUENCE: 431
acacaagcct ccagcccgac ccagcggcct aatgaaactc tggcaaccta tcctgggcgt 60
ggccacgagt atccagctcc aagcccaagt gaggcgggga gtcaacttcc ccatgattgc 120
caagtgacca agaccagaag cagggacgat taggctagtt ctgcggcaag gtgaactgga 180
gaccctgtct ctgccctcct tccctggcct gtcccacaga catcccgttg tttaacccac 240
tgcctttgca aggacctgct ctgtccactc caaatcaaag gatacttgca tccttcttac 300
acagactccc atctctctgc tcatagtggt cccaggctgc ccgagaaaaa gaaacttggg 360
tcagtagaag gctcattagt gtgaaggagt gagaggccag gccttcctgt gacataatgc 420
ttctatgctt gtttcctaaa cacttggtcc acacacaata cctgggcagg aagagagaac 480
caagcaccac tggatggctc tggagccagg ggacttctat gcacatacaa ccaacatcac 540
cccactctgc tcatctgtgc ctccaccctg aacagcagag t 581

<210> SEQ ID NO 432
<211> LENGTH: 532
<212> TYPE: DNA
<213> ORGANISM: Homo sapiens

<400> SEQUENCE: 432
actccaactc aagtttacaa gttacacctt tgccacagcc ttggctaaat cttgaactag 60
tgcagaattc agctgtggta gagtgctgat cttagcatgc ttcgatgtgg catacttgtt 120
cttgacagtc atgtgctttg taagtccttg atttaccatg actacattct tagccaggtg 180
ctgcataact ggaagaagag attcttcagt atatgacagg taatgttgta gagttggtgt 240
ccattcacca ttatccagaa ttttcagtgc taagcaaaaa gctcctgctg caatttgaga 300
aggaggaaag tgcaccatgt catagtccaa catagttagt tccatcaggt atttggccaa 360

-continued

```
agtatgttgc tcgacatcaa cctctccaat cttagatgct ctccgaagga agtgcaaagg    420

tagaggccga cccagaccaa agtttaaagc tcttagaatc ttcatttcca tctgtctgat    480

ttggtgctta gtataagtgt tgtcagtcac aaaagcaaag tcaccaattt ct           532
```

<210> SEQ ID NO 433
<211> LENGTH: 531
<212> TYPE: DNA
<213> ORGANISM: Homo sapiens

<400> SEQUENCE: 433

```
acttggtttt acagctcctt tgaaaactct gtgtttggaa tatctctaaa aacatagaaa     60

acactacagt ggtttagaaa ttactaattt tacttctaag tcattcataa accttgtcta    120

tgaaatgact tcttaaatat ttagttgata gactgctaca ggtaataggg acttagcaag    180

ctcttttata tgctaaagga gcatctatca gattaagtta gaacatttgc tgtcagccac    240

atattgagat gacactaggt gcaatagcag ggatagattt tgttggtgag tagtctcatg    300

ccttgagatc tgtggtggtc ttcaaaatgg tggccagcca gatcaaggat gtagtatctc    360

atagttccca ggtgatattt ttcttattag aaaaatatta taactcattt gttgtttgac    420

acttatagat tgaaatttcc taatttattc taaattttaa gtggttcttt ggttccagtg    480

ctttatgttg ttgttgtttt tggatggtgt tacatattat atgttctaga a             531
```

<210> SEQ ID NO 434
<211> LENGTH: 530
<212> TYPE: DNA
<213> ORGANISM: Homo sapiens

<400> SEQUENCE: 434

```
acaagagaaa acccctaaaa aaaggatggc tttagatgac aagctctacc agagagactt     60

agaagttgca ctagctttat cagtgaagga acttccaaca gtcaccacta atgtgcagaa    120

ctctcaagat aaaagcattg aaaaacatgg cagtagtaaa atagaaacaa tgaataagtc    180

tcctcatatc tctaattgca gtgtagccag tgattattta gatttggata agattactgt    240

ggaagatgat gttggtggtg ttcaagggaa aagaaaagca gcatctaaag ctgcagcaca    300

gcagaggaag attcttctgg aaggcagtga tggtgatagt gctaatgaca ctgaaccaga    360

ctttgcacct ggtgaagatt ctgaggatga ttctgatttt tgtgagagtg aggataatga    420

cgaagacttc tctatgagaa aaagtaaagt taaagaaatt aaaaagaaag aagtgaaggt    480

aaaatcccca gtagaaaaga aagagaagaa atctaaatcc aaatgtaatg               530
```

<210> SEQ ID NO 435
<211> LENGTH: 677
<212> TYPE: DNA
<213> ORGANISM: Homo sapiens

<400> SEQUENCE: 435

```
accttatgat ctaattaata gatattagaa acagtagaaa gacaagttac acgtcaatgc     60

ccaatgacta gagtcaacat taaagagttg taatttaagt aatccaaact gacatctaat    120

tccaaaatca tttataaaat gtatttggct ttggaatcca caggacttca aacaagcaaa    180

gtttcactgc agatagtcac aaagatgcag atacactgaa atacttaaga gccttattaa    240

tgatttttgt tattttggat cttctgtttt tttcttatta tggtccgaag cctccttaat    300

accaatttat cagacagaag catgtcatct tgttgttcaa gataatccag taaattttca    360

gtccattcaa gtgccgcttt atggctaata cgcttctctg gattcagttc tgtttttcta    420
```

-continued

```
ctcttactgg aaggcttttg ctcagcagcc ttggtctggt cctcagcact ttcactgtca    480

gtcagcacct gacagcttga gtcactgctc cgagagtcga accactgatc aatattctca    540

atgtcaacat gttcacattc ttctgtgttc tgtaaaactg ttgctaaatt agctgctaaa    600

atggctcctt catcaatgtt catacctgaa ttctcttcat tgccagggaa aagtttttc     660

catgctttgg ttatggt                                                   677
```

<210> SEQ ID NO 436
<211> LENGTH: 573
<212> TYPE: DNA
<213> ORGANISM: Homo sapiens

<400> SEQUENCE: 436

```
acctcttagg gtgggagaaa tggtgaagag ttgttcctac aacttgctaa cctagtggac     60

agggtagtag attagcatca tccggataga tgtgaagagg acggctgttt ggataataat    120

taaggataaa atttggccag ttgacagatt ctgtttccag cagtttttac agcaacagtg    180

gagtgcttca gtattgtgtt cctgtaaatt taattttgat ccgcaatcat ttggtataca    240

atgctgtttg aagttttgtc ctattggaaa agtcttgtgt tgcaggggtg cagttaagat    300

ctttgtgatg aggaatggga tgggctaatt ttttgccgtt ttcttggaat tgggggcatg    360

gcaaatacag tagggtagtt tagttcttta cacagaacat gataaactac acctgttgat    420

gtcaccgtct gtcaatgaat attatagaag gtatgaaggt gtaattacca taataacaaa    480

acaccctgtc tttagggctg acctttcgtc ctttgacctc ctcagcctcc attcccatct    540

tcgctcagac tgcaagtatg tttgtattaa tgt                                 573
```

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 437

```
acaattggta tccatatctt gttgaaattg taatgggaaa acaatatatt tcaatctcta     60

tgtagatagt gggtttttgt tttcataata tattctttta gtttactgta tgagttttgc    120

aggactgcat aatagatcac cacaatcata acatcttagg accacagaca tttatgagat    180

catggcttct gtgggttaga agtatgctca tgtcttaact gggtcctctg ctcagtctta    240

tctggctgca atcaaggtgt cagctgggct gaattttcat ttggaatctt gactgggaaa    300

gagtctgctt ccaaggtcat gaagtttgct ggcaaaatgt atgtttttat gacagtatga    360

ctgaaatccc aagctatctc ctgactttta gctgggtaat ctcaggccct aaatgttgcc    420

tacagttcct agaggctggt cacagttctt agccatgtgg atttcctcaa catggctgct    480

tgcttcatca agtcagcaag aatagcctgt catatcagtg tatatcaggc tcactcagga    540

taatttccct actgatgagc caaacactaa ctgattttag agcttaacta catctgcaaa    600

attcngttca ccagaggcaa gtcatattca gggaaggaga agtgt                    645
```

<210> SEQ ID NO 438
<211> LENGTH: 485
<212> TYPE: DNA
<213> ORGANISM: Homo sapiens -continued

<400> SEQUENCE: 438
acagaattga gagacaagat tgcttgtaat ggagatgctt ctagctctca gataatacat 60
atttctgatg aaaatgaagg aaaagaaatg tgtgttctgc gaatgactcg agctagacgt 120
tcccaggtag aacagcagca gctcatcact gttgaaaagg ctttggcaat tctttctcag 180
cctacaccct cacttgttgt ggatcatgag cgattaaaaa atcttttgaa gactgttgtt 240
aaaaaaagtc aaaactacaa catatttcag ttggaaaatt tgtatgcagt aatcagccaa 300
tgtatttatc ggcatcgcaa ggaccatgat aaaacatcac ttattcagaa aatggagcaa 360
gaggtagaaa acttcagttg ttccagatga tgatgtcatg gtatcgagta ttctttatat 420
tcagttccta tttaagtcat ttttgtcatg tccgcctaat tgatgtagta tgaaaccctg 480
catct 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc 60
aggttcaaca gtatggctcc aaatgatgaa atttcattct gattttctgg ctgaagacta 120
ttctgtttgt gtatgtccac cacagttact ttatcccttc atctgtggat gggcagaatg 180
aaacatatat ggaaatgttc tgtgcaataa aaacagcagt ggtaacacag atgtaggctc 240
tgagtgtctc actggagact gaagtccaca gatatgcaac aaagcctttg tctccctgat 300
gtttttgcct cctgctggtc atgtgctttc acacatcaag agaggacatt taacatttga 360
gccacagtgt catttgctgt tgtctgatgg ttggttggca gagaatttga actggagatg 420
aactttatta tccaggacgc tgagagtata acatgcatga cagagctttt agagcactgt 480
gatgtaacat gtcaagcaga aatagggagc atgtttacag ccattctatg aaa 533

<210> SEQ ID NO 440
<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca 60
cactctcaca ctcgcaccca gaattgtcaa agatacagat tgtaaaaatc tacgatccct 120
cagtctcact cacaaaaaat aaaatctcat gtccccaacg aacccagagt cagacgacag 180
ctggagcatt ggcagggaca gtcagaaagg agacaagtga aaacggtcag atggacacag 240
gcggaggaga aaagacagag ggagagagac catcgggaac aatcagaggg gccgagacga 300
tcagaaaagg gtcagcccga gacaggctga gccagagttt c 341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441
aagtttgggg ataatttatt atgcagcaag agataataca caggacttct canagcactt 60

-continued

```
aatatgttaa tataaatctc caanaaaaaa gatatacaat gaaacattcc tcttagttat    120

ctggccaagg anactttntt tttttganaa tattcttcaa aaagctgatc taatgatatg    180

gctctggtcc tacaattcca tgtaacttct aaccttgatt ttatctcatg agcaaatcat    240

ttatccttcc agaacctcaa cttttccctt ttacaaagta gaaataaacc atctgccttt    300

acataaatca ttaatacagc cctggatggg cagattctga gctatttttg gctgggggt    360

gggaaatagc ctgtggaggt cctaaaaaga tctacggggc tcgagatggt tctctgcaag    420

gtagcaggtg ggctcagggc ccatttcagt ctttgttccc caggccattt ccacaaaatg    480

gtgagaaata gtgtcttctt ttagcttgct cataactcaa agatgggggg catggacctg    540

ggcctttcta ggctagggca tgaacctcct cc                                  572
```

```
<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442

tcccagctgc actgcttaca cgtcttcctt cgtnttcacc taccccgagg ctgactcctt     60

ccccagntgt gcagctgccc accgcaaggg cagcagcagc aatgagcctt cctctgactc    120

gctcagctca cccacgctgc tggccctgtg agggggcagg gaaggggagg cagccggcac    180

ccacaagtgc cactgcccga gctggtgcat tacagagagg agaaacacat cttccctaga    240

gggttcctgt agacctaggg aggaccttat ctgtgcgtga aacacaccag gctgtgggcc    300

tcaaggactt gaaagcatcc atgtgtggac tcaagtcctt acctcttccg gagatgtagc    360

aaaacgcatg gagtgtgta                                                 379
```

```
<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n = A,T,C or G

<400> SEQUENCE: 443

acatgccccc aaaggctcgc ttcattgcta cgattctcta cttaaatcca cattcacagc     60

tattgcctca gaccctctgg aggaggggcc aggggttagc tggctttgaa tagcatgtag    120

agcacaggca gtgtggccac aaatgtcaca caggtgacca gggtgctata gatggtgttc    180

ctgttgactt gggcttctag tctctgctcc gtgtctgaca gtgccaagat catgctcccc    240

tgctccagca agaagctggg catagccccg tctgctggtt ccaccaggcc tgggtgtgct    300

gcagacttta caagctgaac caccccagcc atttggctac aagtcttttc taggccatca    360

agctgctctc gtaagccttc tagacatgaa tggacttgcc tggaatgact aagctgctct    420

ttcaaggcag ctgaaaggac atcnacatct ctgtctctgg tcgggggact acctgcctgt    480

gacccagagt cctgccctgg cccagcagca t                                   511
```

```
<210> SEQ ID NO 444
<211> LENGTH: 612
<212> TYPE: DNA
```

-continued

<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 444
acaggaagaa ttctacagtt aatctatcac agtgttccag caaagcatat gttgaaaact 60
acagttttca atctaacatc taaattttaa aaagtagcat ttcagcaaca aacaagctca 120
gagaggctca tggcaaaagt gaaataacag aactattgct cagatgtctg caaagtcaag 180
ctgctgccct cagctccgcc cacttgaagg cttaggcaga cacgtaaggt ggcggtggct 240
ccttggcagc accattcaca gtggcatcat catacggagg tagcagcacc gtagtgtcat 300
tgctggtaac ataaaccagg acatcagagg agttcctacc attgatgtat cggtagcagt 360
tccaaacaca gctaatcaag taacccttaa aagtcaagat aatgctaata aacagaagaa 420
taataaggac caaacaggta ggattcactg acatgacatc atctctgtag ggaaaattag 480
gaggcagttg ccgtatgtat tcctgaatgg agtttggata aataagcaca gtgattgcaa 540
ccaacanctt cagggcaaag tcaaagatct ggtaacagaa gaatgggatg atccaggctg 600
cgcgttgctt gt 612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445
accatcctgt tccaacagag ccattgccta ttcctaaatt gaatctgact gggtgtgccc 60
ctcctcggaa cacaacagta gaccttaata gtggaaacat cgatgtgcct cccaacatga 120
caagctgggc cagctttcat aatggtgtgg ctgctggcct gaagatagct cctgcctccc 180
agatcgactc agcttggatt gtttacaata agcccaagca tgctgagttg gccaatgagt 240
atgctggctt tctcatggct ctgggtttga atgggcacct taccaagctg gcgactctca 300
atatccatga ctacttgacc aagggccatg aaatgacaag cattggactg ctacttggtg 360
tttctgctgc aaaactaggc accatggata tgtctattac tcggcttgtt agcattcgca 420
ttcctgctct cttacccccca acgtccacag agttggatgt tcctcacaat gtccaagtgg 480
ctgcagtggt tggcattggc cttgtatatc aagggacagc tcacagacat actgcagaag 540
tcctgttggc tgagatagga cggcctcctg gtcctgaaat ggaatactgc actgacagag 600
agtcatactc cttagctgct ggcttggccc tgggcatggt ctncttgggg catggcagca 660
atttgatagg tatgtntgat ctcaatgtgc ctgagcagct ctatcagt 708

<210> SEQ ID NO 446
<211> LENGTH: 612
<212> TYPE: DNA
<213> ORGANISM: Homo sapiens

<400> SEQUENCE: 446
acaagcaacg cgcagcctgg atcatcccat tcttctgtta ccagatcttt gactttgccc 60
tgaacatgtt ggttgcaatc actgtgctta tttatccaaa ctccattcag gaatacatac 120
ggcaactgcc tcctaatttt ccctacagag atgatgtcat gtcagtgaat cctacctgtt 180

-continued

```
tggtccttat tattcttctg tttattagca ttatcttgac ttttaagggt tacttgatta    240

gctgtgtttg gaactgctac cgatacatca atggtaggaa ctcctctgat gtcctggttt    300

atgttaccag caatgacact acggtgctgc tacccccgta tgatgatgcc actgtgaatg    360

gtgctgccaa ggagccaccg ccaccttacg tgtctgccta agccttcaag tgggcggagc    420

tgagggcagc agcttgactt tgcagacatc tgagcaatag ttctgttatt tcacttttgc    480

catgagcctc tctgagcttg tttgttgctg aaatgctact ttttaaaatt tagatgttag    540

attgaaaact gtagttttca acatatgctt tgctggaaca ctgtgataga ttaactgtag    600

aattcttcct gt                                                        612
```

<210> SEQ ID NO 447
<211> LENGTH: 642
<212> TYPE: DNA
<213> ORGANISM: Homo sapiens

<400> SEQUENCE: 447

```
actgaaagaa ttaaagtcag aagtcttccc aaaacaaaaa gaactgccca cagagaaaat     60

cctttctgat acttttcatt gctaaaataa aacaggcggg aaatgtggaa aagaaattca    120

acaaaataat gtagcaccag aagaacaagt cctagatgat tcaagttcaa aaggtaagct    180

ccagcaatgt ggaagaggta aagaccaatg tagacaagct gacgaggaat atcttctttt    240

ttggttttct ggaagtagag ttcaggaaaa gcatgaagcc agtaagccag ctgtgatatg    300

tagaaaaact tcatttgaaa tgtcatcagg ttatggggat aagccctcca taagatagtt    360

gggtctgaga tgtagttttc agagatgaga atgaatgtgc cccaaacaca ggcaaaaagg    420

tagaacgcac taagctgacc agattcatta aacttgctgt gttttgtttt ggagaagtgc    480

attcgcctgt taattttatc caacatatac tcttgaatta cggcatgaat aattatcgcc    540

actagcatgt agaagaaaac agtagccaaa tctttgatgc catagtaata aagggacact    600

gattcagtag cttgttcttc tgttgctggg agggtgacat tg                       642
```

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 448

```
accagaagac cttagaaaaa ggaggaaagg aggagaggca gataatttgg atgaattcct     60

caaagngttt gaaaatccag aggttcctag agaggaccag caacagcagc atcagcagcg    120

tgatgttatc gatgagccca ttattgaaga gccaagccgc ctccaggagt cagtgatgga    180

ggccagcaga acaaacatag atgagtcagc tatgcctcca ccaccacctc agggagttaa    240

gcgaaaagct ggacaaattg acccagagcc tgtgatgcct cctcagcagg tagagcagat    300

ggaaatacca cctgtagagc ttcccccaga agaacctcca aatatctgtc agctaatacc    360

agagttagaa cttctgccag aaaaagagaa ggag                                394
```

<210> SEQ ID NO 449
<211> LENGTH: 494
<212> TYPE: DNA
<213> ORGANISM: Homo sapiens
<220> FEATURE:

-continued

<221> NAME/KEY: misc_feature
<222> LOCATION: (1)...(494)
<223> OTHER INFORMATION: n = A,T,C or G

<400> SEQUENCE: 449
acaaaaaaca caaggaatac aacccaatag aaaatagtcc tgggaatgtg gtcagaagca 60
aaggcntgag tgtctttctc aaccgtgcaa aagccgtgtt cttcccggga aaccaggaaa 120
aggatccgct actcaaaaac caagaattta aaggagtttc ttaaatttcg accttgtttc 180
tgaagctcac ttttcagtgc cattgatgtg agatgtgctg gagtggctat taaccttttt 240
ttcctaaaga ttattgttaa atagatattg tggtttgggg aagttgaatt ttttataggt 300
taaatgtcat tttagagatg gggagaggga ttatactgca ggcagcttca gccatgttgt 360
gaaactgata aaagcaactt agcaaggctt cttttcatta ttttttatgt ttcacttata 420
aagtcttagg taactagtag gatagaaaca ctgtgtcccg agagtaagga gagaagctac 480
tattgattag agcc 494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct 60
tcatgactga ggttaactta aaacaaaaat ggtaggaaag ctttcctatg cttcgggtaa 120
gagacaaatt tgcttttgta gaattggtgg ctgagaaagg cagacagggc ctgattaaag 180
aagacatttg tcaccactag ccaccaagtt aagttgtgga acccaaaggt gacggccatg 240
gaaacgtaga tcatcagctc tgctaagtag ttaggggaag aaacatattc aaaccagtct 300
ccaaatggga tcctgtggtt acagtgaatg gccactcctg ctttattttt cctgagattg 360
ccgagaataa catggcactt atactgatgg gcagatgacc agatgaacat catcatccca 420
agaatatgga accaccgtgc ttgcatcaat agatttttcc ctgttatgta ggcattcctg 480
ccatccattg gcacttggct cagcacagtt aggccaacaa ggacataata gacaagtcca 540
aaacagt 547

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451
actacttnnt ggttaaaang ccactggtag agtcatctga ntgtaaacaa tgtccctgca 60
ctgctggaaa aatccactgg ctcccaagaa aagaaaatgg tctgaagcct ctgttgtggc 120
tctcacaact catctttccc taagtcatca agctccacat cactgaggtc aatgtcatcc 180
tccacgggaa gctcgccatc cctgccgtcc caaggctctc tctcaacgat ggtagggaaa 240
gccccgcctc ctacaggtgc cgtggagcca cgcccaaaag agagctccct gagaaactcg 300
ttgatgcctt gctcactgaa ggagcctttt agcagagcaa atttcatctt gcgtgcattg 360
atggcggcca tggcggggta ccca 384

-continued

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452
actctaaagt tgccactctc acaggggtca gtgataccca ctgaacctgg caggaacagt 60
cctgcagcca gaatctgcaa gcagcgcctg tatgcaacgt ttagggccaa aggctgtctg 120
gtggggttgt tcatcacagc ataatggcct agtaggtcaa ggatccaggg tgtgaggggc 180
tcaaagccag gaaaacgaat cctcaagtcc ttcagtagtc tgatgagaac tttaactgtg 240
gactgagaag cattttcctc gaaccagcgg gcatgtcgga tggctgctaa ngcactctgc 300
aatactttga tatccaaatg gagttctgga tccagttttc naagattggg tggcactgtt 360
gtaatganaa tcttcactgt a 381

<210> SEQ ID NO 453
<211> LENGTH: 455
<212> TYPE: DNA
<213> ORGANISM: Homo sapiens

<400> SEQUENCE: 453
actgtgctaa acagcctata gccaagtttt aaagagttac aggaacaact gctacacatt 60
caaagaacag gcattcactg cagcctcctg atttgacctg atgggaggga caggagaatg 120
agtcactctg ccaccacttt tcctgccttg gatttgtaga ggatttgttt tgctctaatt 180
tgtttttcct atatctgccc tactaaggta cacagtctgg gcactttgaa aatgttaaag 240
tttttaacgt ttgactgaca gaagcagcac ttaaaggctt catgaatcta ttttccaaaa 300
aaagtatgct ttcagtaaaa cattttacca ttttatctaa ctatgcactg acatttttgt 360
tcttcctgaa aaggggattt atgctaacac tgtattttta atgtaaaaat atacgtgtag 420
agatatttta acttcctgag tgacttatac ctcaa 455

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454
acagagcanc tttacaagtt gtcacatttc tttataaatt tttttaaagc tacagtttaa 60
tacaaaatga attgcggttt tattacatta ataacctttc acctcagggt tttatgaaga 120
ggaaagggtt ttatgcaaaa gaaagtgcta caattcctaa tcattttaga cactttagga 180
gggggtgaag ttgtatgata aagcagatat tttaattatt tgttatcttt ttgtattgca 240
agaaatttct tgctagtgaa tcaagaaaac atccagattg acagtctaaa atggctactg 300
gtattttagt taattcaaaa atgaaacttt tcagtgattc actttactaa cattctattt 360
gagaaggctt attggtaaag ttt 383

<210> SEQ ID NO 455
<211> LENGTH: 383
<212> TYPE: DNA

-continued

<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 455
actcctttan gacaaggaaa caggtatcag catgatggta gcagaaacct tatcaccaag 60
gtgcaggagc tgacttcttc caaagagttg tggttccggg cagcggtcat tgccgtgccc 120
attgctggag ggctgatttt agtgttgctt attatgttgg ccctgaggat gcttcgaagt 180
gaaaataaga ggctgcagga tcagcggcaa cagatgctct cccgtttgca ctacagcttt 240
cacggacacc attccaaaaa ggggcaggtt gcaaagttag acttggaatg catggtgccg 300
gtcagtgggc acgagaactg ctgtctgacc tgtgataaaa tgagacaagc agacctcagc 360
aacgataaga tcctctcgct tgt 383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456
acaaacattt tacaaaaaag aacattacca atatcagtgg cagtaagggc aagctgaaga 60
atangtagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacact atttcccatc 300
taaactcatt taagccttca caatgtcgca atggattcag ttacttgcaa acgatcccgg 360
gttgtcatac agatacttgt tttttacaca taacgctgtg ccatcccttc cttcactgcc 420
ccagtcaggt ttcctgttgt tggaccgaaa ggggatacat tttagaaatg cttccctcaa 480
gacagaagtg agaaagaaag gagaccctga ggccaggatc tattaaacct ggtgtgtgcg 540
caa 543

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 457
actggtgcca atattgncat ggtgagctcc tctctaatgt cttccagggc accaatatct 60
gcccatgtca cattagggac agtgacaaag ccttcccttt tggcagaggg ttggactgag 120
gatagagcaa caatgaaatc attcagttca atgcacagtc cttgcatctg ctcctctgag 180
aggggatctt ggtctcttag caaccccagc agcctttgta attcatcctg tgtttcagaa 240
gtgggctcag ttcccagcct ttcctcctgg actcctttag atggcaaatc ttccatttca 300
ggatttttct tctgctgttc ctgtagcttc attaagactc tattgactgc acacattgct 360
gcctctcggc acagtgccat gagatcagca ccaacaaagc ctggagttag gtgtgctaag 420

-continued

```
tgacagaaat caaaagcttg aggaagcctc agttttctgc acaatgtttg aagtattctt    480

tccctggatg cttcatctgg gatacctagg catatttctc ggtcgaacct tcccgcacgt    540

ctca                                                                 544
```

```
<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

acctntaggc tcaacggcag aancttcacc acaaaagcga aatgggcaca ccacagggag     60

aaaactggtt gtcctggatg tttgaaaagt tggtcgttgt catggtgtgt tacttcatcc    120

tatctatcat taactccatg gcacaaagtt atgccaaacg aatccagcag cggttgaact    180

cagaggagaa aactaaataa gtagagaaag ttttaaactg cagaaattgg agtggatggg    240

ttctgcctta aattgggagg actccaagcc gggaaggaaa attccctttt ccaacctgta    300

tcaattttta caactttttt cctgaaagca gtttagtcca tactttgcac tgacatactt    360

tttccttctg tgctaaggta ag                                             382
```

```
<210> SEQ ID NO 459
<211> LENGTH: 168
<212> TYPE: DNA
<213> ORGANISM: Homo sapiens

<400> SEQUENCE: 459

ctcgtactct agccaggcac gaaaccatga agtagcctga tccttcttag ccatcctggc     60

cgccttagcg gtagtaactt tgtgttatga atcacatgaa agcatggaat cttatgaact    120

taatcccttc attaacagga gaaatgcaaa taccttcata tcccctca                168
```

```
<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: (1)...(190)
<223> OTHER INFORMATION: n = A,T,C or G

<400> SEQUENCE: 460

acanctgcta ccagggagcc gagagctgac tatcccagcc tcggctaatg tattctacgc     60

catggatgga gcttcacacg atttcctcct gcggcagcgg cgaaggtcct ctactgctac    120

acctggcgtc accagtggcc cgtctgcctc aggaactcct ccgagtgagg gaggaggggg    180

ctcctttccc                                                           190
```

```
<210> SEQ ID NO 461
<211> LENGTH: 495
<212> TYPE: DNA
<213> ORGANISM: Homo sapiens

<400> SEQUENCE: 461

acagacaggc ttctctgcta tcctccaggc agtgtaatag tcaaggaaaa gggcaacagt     60

attggatcat tccttagaca ctaatcagct ggggaaagag ttcattggca aaagtgtcct    120
```

cccaagaatg gtttacacca agcagagagg acatgtcact gaatggggaa agggaacccc 180
cgtatccaca gtcactgtaa gcatccagta ggcaggaaga tggctttggg cagtggctgg 240
atgaaagcag atttgagata cccagctccg gaacgaggtc atcttctaca ggttcttcct 300
tcactgagac aatgaattca gggtgatcat tctctgaggg gctgagaggt gcttcctcga 360
ttttcactac cacattagct tggctctctg tctcagaggg tatctctaag actaggggct 420
tggtatatat gtggtcaaaa cgaattagtt cattaatggc ttccagcttg gctgatgacg 480
tccccactga cagag 495

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462
acactgaaac ataaatccgc aagtcaccac acatacaaca cccggcagga aaaaaacaaa 60
aacagggngt ttacatgatc cctgtaacag ccatggtctc aaactcagat gcttcctcca 120
tctgccaagt gtgttttgga tacagagcac atcgtggctt ctggggtcac actcagctta 180
ggctgtgggt ccacagagca ctcatctggc tgggctatgg tggtggtggc tctactcaag 240
aagcaaagca gttaccagca cattcaaaca gtgtattgaa catcttttaa atatcaaagt 300
gagaaacaag aaggcaacat aataatgtta tcagaaagat gttaggaagt aaggacagct 360
gtgtaaagct tgaggctgaa aagtagcttg ccagcttcat ttctttggtt tcttgggtag 420
tgggcgccgg aacagcaaga tgtgaggttc tggttcatgg atcatataat ggacccatcc 480
ctgactctgc tga 493

<210> SEQ ID NO 463
<211> LENGTH: 3681
<212> TYPE: DNA
<213> ORGANISM: Homo sapiens

<400> SEQUENCE: 463
tccgagctga ttacagacac caaggaagat gctgtaaaga gtcagcagcc acagccctgg 60
ctagctggcc ctgtgggcat ttattagtaa agttttaatg acaaaagctt tgagtcaaca 120
cacccgtggg taattaacct ggtcatcccc accctggaga gccatcctgc ccatgggtga 180
tcaaagaagg aacatctgca ggaacacctg atgaggctgc acccttggcg gaaagaacac 240
ctgacacagc tgaaagcttg gtggaaaaaa cacctgatga ggctgcaccc ttggtggaaa 300
gaacacctga cacggctgaa agcttggtgg aaaaaacacc tgatgaggct gcatccttgg 360
tggagggaac atctgacaaa attcaatgtt tggagaaagc gacatctgga aagttcgaac 420
agtcagcaga agaaacacct agggaaatta cgagtcctgc aaaagaaaca tctgagaaat 480
ttacgtggcc agcaaaagga agacctagga agatcgcatg ggagaaaaaa gaagacacac 540
ctagggaaat tatgagtccc gcaaaagaaa catctgagaa atttacgtgg gcagcaaaag 600
gaagacctag gaagatcgca tgggagaaaa aagaaacacc tgtaaagact ggatgcgtgg 660
caagagtaac atctaataaa actaaagttt tggaaaaagg aagatctaag atgattgcat 720
gtcctacaaa agaatcatct acaaaagcaa gtgccaatga tcagaggttc ccatcagaat 780
ccaaacaaga ggaagatgaa gaatattctt gtgattctcg gagtctcttt gagagttctg 840

-continued

```
caaagattca agtgtgtata cctgagtcta tatatcaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
agttagagaa ccaaaaagtt aaatgggaac aagagctctg cagtgtgagg tttctcacac   2460
tcatgaaaat gaaaattatc tcttacatga aaattgcatg ttgaaaaagg aaattgccat   2520
gctaaaactg gaaatagcca cactgaaaca ccaataccag gaaaaggaaa ataaatactt   2580
tgaggacatt aagattttaa aagaaaagaa tgctgaactt cagatgaccc taaaactgaa   2640
agaggaatca ttaactaaaa gggcatctca atatagtggg cagcttaaag ttctgatagc   2700
tgagaacaca atgctcactt ctaaattgaa ggaaaaacaa gacaaagaaa tactagaggc   2760
agaaattgaa tcacaccatc ctagactggc ttctgctgta caagaccatg atcaaattgt   2820
gacatcaaga aaaagtcaag aacctgcttt ccacattgca ggagatgctt gtttgcaaag   2880
aaaaatgaat gttgatgtga gtagtacgat atataacaat gaggtgctcc atcaaccact   2940
ttctgaagct caaaggaaat ccaaaagcct aaaaattaat ctcaattatg cmggagatgc   3000
tctaagagaa aatacattgg tttcagaaca tgcacaaaga gaccaacgtg aaacacagtg   3060
tcaaatgaag gaagctgaac acatgtatca aaacgaacaa gataatgtga acaaacacac   3120
tgaacagcag gagtctctag atcagaaatt atttcaacta caaagcaaaa atatgtggct   3180
```

-continued

```
tcaacagcaa ttagttcatg cacataagaa agctgacaac aaaagcaaga taacaattga   3240

tattcatttt cttgagagga aaatgcaaca tcatctccta aaagagaaaa atgaggagat   3300

atttaattac aataaccatt taaaaaaccg tatatatcaa tatgaaaaag agaaagcaga   3360

aacagaaaac tcatgagaga caagcagtaa gaaacttctt ttggagaaac aacagaccag   3420

atctttactc acaactcatg ctaggaggcc agtcctagca tcaccttatg ttgaaaatct   3480

taccaatagt ctgtgtcaac agaatactta ttttagaaga aaaattcatg atttcttcct   3540

gaagcctaca gacataaaat aacagtgtga agaattactt gttcacgaat tgcataaagc   3600

tgcacaggat tcccatctac cctgatgatg cagcagacat cattcaatcc aaccagaatc   3660

tcgctctgtc actcaggctg g                                             3681
```

<210> SEQ ID NO 464
<211> LENGTH: 1424
<212> TYPE: DNA
<213> ORGANISM: Homo sapiens

<400> SEQUENCE: 464

```
tccgagctga ttacagacac caaggaagat gctgtaaaga gtcagcagcc acagccctgg     60

ctagctggcc ctgtgggcat ttattagtaa agttttaatg acaaaagctt tgagtcaaca    120

cacccgtggg taattaacct ggtcatcccc accctggaga gccatcctgc ccatgggtga    180

tcaaagaagg aacatctgca ggaacacctg atgaggctgc acccttggcg gaaagaacac    240

ctgacacagc tgaaagcttg gtggaaaaaa cacctgatga ggctgcaccc ttggtggaaa    300

gaacacctga cacggctgaa agcttggtgg aaaaaacacc tgatgaggct gcatccttgg    360

tggagggaac atctgacaaa attcaatgtt tggagaaagc gacatctgga aagttcgaac    420

agtcagcaga agaaacacct agggaaatta cgagtcctgc aaaagaaaca tctgagaaat    480

ttacgtggcc agcaaaagga agacctagga agatcgcatg ggagaaaaaa gaagacacac    540

ctagggaaat tatgagtccc gcaaaagaaa catctgagaa atttacgtgg gcagcaaaag    600

gaagacctag gaagatcgca tgggagaaaa aagaaacacc tgtaaagact ggatgcgtgg    660

caagagtaac atctaataaa actaaagttt tggaaaaagg aagatctaag atgattgcat    720

gtcctacaaa agaatcatct acaaaagcaa gtgccaatga tcagaggttc ccatcagaat    780

ccaaacaaga ggaagatgaa gaatattctt gtgattctcg gagtctcttt gagagttctg    840

caaagattca agtgtgtata cctgagtcta tatatcaaaa agtaatggag ataaatagag    900

aagtagaaga gcctcctaag aagccatctg ccttcaagcc tgccattgaa atgcaaaact    960

ctgttccaaa taaagccttt gaattgaaga atgaacaaac attgagagca gatccgatgt   1020

tcccaccaga atccaaacaa aaggactatg aagaaaattc ttgggattct gagagtctct   1080

gtgagactgt ttcacagaag gatgtgtgtt tacccaaggc tacacatcaa aaagaaatag   1140

ataaaataaa tggaaaatta gaaggtaaga accgtttttt atttaaaaat cagttgaccg   1200

aatatttctc taaactgatg aggagggata tcctctagta gctgaagaaa attacctcct   1260

aaatgcaaac catggaaaaa aagagaagtg caatggtcgt aagttgtatg tctcatcagg   1320

tgttggcaac agactatatt gagagtgctg aaaaggagct gaattattag tttgaattca   1380

agatattgca agacctgaga gaaaaaaaaa aaaaaaaaaa aaaa                    1424
```

<210> SEQ ID NO 465
<211> LENGTH: 674
<212> TYPE: DNA
<213> ORGANISM: Homo sapiens -continued

<400> SEQUENCE: 465
attccgagct gattacagac accaaggaag atgctgtaaa gagtcagcag ccacagccct 60
ggctagctgg ccctgtgggc atttattagt aaagttttaa tgacaaaagc tttgagtcaa 120
cacacccgtg ggtaattaac ctggtcatcc ccaccctgga gagccatcct gcccatgggt 180
gatcaaagaa ggaacatctg caggaacacc tgatgaggct gcacccttgg cggaaagaac 240
acctgacaca gctgaaagct tggtggaaaa aacacctgat gaggctgcac ccttggtgga 300
aagaacacct gacacggctg aaagcttggt ggaaaaaaca cctgatgagg ctgcatcctt 360
ggtggaggga acatctgaca aaattcaatg tttggagaaa gcgacatctg gaaagttcga 420
acagtcagca gaagaaacac ctagggaaat tacgagtcct gcaaaagaaa catctgagaa 480
atttacgtgg ccagcaaaag gaagacctag gaagatcgca tgggagaaaa aagatgactc 540
agttaaggca aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaa 674

<210> SEQ ID NO 466
<211> LENGTH: 1729
<212> TYPE: DNA
<213> ORGANISM: Homo sapiens
<220> FEATURE:
<221> NAME/KEY: unsure
<222> LOCATION: (11)
<223> OTHER INFORMATION: n=A,T,C or G
<221> NAME/KEY: unsure
<222> LOCATION: (1128)
<223> OTHER INFORMATION: n=A,T,C or G

<400> SEQUENCE: 466
gaaagttcga ncagtcagca gaagaaacac ctagggaaat tacgagtcct gcaaaagaaa 60
catctgagaa atttacgtgg ccagcaaaag gaagacctag gaagatcgca tgggagaaaa 120
aagaagacac acctagggaa attatgagtc ccgcaaaaga aacatctgag aaatttacgt 180
gggcagcaaa aggaagacct aggaagatcg catgggagaa aaaagaaaca cctgtaaaga 240
ctggatgcgt ggcaagagta acatctaata aaactaaagt tttggaaaaa ggaagatcta 300
agatgattgc atgtcctaca aaagaatcat ctacaaaagc aagtgccaat gatcagaggt 360
tcccatcaga atccaaacaa gaggaagatg aagaatattc ttgtgattct cggagtctct 420
ttgagagttc tgcaaagatt caagtgtgta tacctgagtc tatatatcaa aaagtaatgg 480
agataaatag agaagtagaa gagcctccta agaagccatc tgccttcaag cctgccattg 540
aaatgcaaaa ctctgttcca aataaagcct ttgaattgaa gaatgaacaa acattgagag 600
cagatccgat gttcccacca gaatccaaac aaaaggacta tgaagaaaat tcttgggatt 660
ctgagagtct ctgtgagact gtttcacaga aggatgtgtg tttacccaag gctacacatc 720
aaaaagaaat agataaaata aatggaaaat tagaagagtc tcctaataaa gatggtcttc 780
tgaaggctac ctgcggaatg aaagtttcta ttccaactaa agccttagaa ttgaaggaca 840
tgcaaacttt caaagcagag cctccgggga agccatctgc cttcgagcct gccactgaaa 900
tgcaaaagtc tgtcccaaat aaagccttgg aattgaaaaa tgaacaaaca ttgagagcag 960
atgagatact cccatcagaa tccaaacaaa aggactatga agaaaattct tgggatactg 1020
agagtctctg tgagactgtt tcacagaagg atgtgtgttt acccaaggct gcgcatcaaa 1080
aagaaataga taaaataaat ggaaaattag aagggtctcc tggtaaanat ggtcttctga 1140

-continued

```
aggctaactg cggaatgaaa gtttctattc caactaaagc cttagaattg atggacatgc   1200

aaactttcaa agcagagcct cccgagaagc catctgcctt cgagcctgcc attgaaatgc   1260

aaaagtctgt tccaaataaa gccttggaat tgaagaatga acaaacattg agagcagatg   1320

agatactccc atcagaatcc aaacaaaagg actatgaaga aagttcttgg gattctgaga   1380

gtctctgtga gactgtttca cagaaggatg tgtgtttacc caaggctgcg catcaaaaag   1440

aaatagataa aataaatgga aaattagaag gtaagaaccg ttttttattt aaaaatcatt   1500

tgaccaaata tttctctaaa ttgatgagga aggatatcct ctagtagctg aagaaaatta   1560

cctcctaaat gcaaaccatg gaaaaaaaga gaagtgcaat ggtcataagc tatgtgtctc   1620

atcaggcatt ggcaacagac tatattgtga gtgctgaaga ggagctgaat tactagttta   1680

aattcaagat attccaagac gtgaggaaaa tgagaaaaaa aaaaaaaaa               1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaaat tagaagggtc tcctgttaaa gatggtcttc     60

tgaaggctaa ctgcggaatg aaagtttcta ttccaactaa agccttagaa ttgatggaca    120

tgcaaacttt caaagcagag cctcccgaga agccatctgc cttcgagcct gccattgaaa    180

tgcaaaagtc tgttccaaat aaagccttgg aattgaagaa tgaacaaaca ttgagagcag    240

atgagatact cccatcagaa tccaaacaaa aggactatga agaaagttct tgggattctg    300

agagtctctg tgagactgtt tcacagaagg atgtgtgttt acccaaggct gcgcatcaaa    360

aagaaataga taaaataaat ggaaaattag aagagtctcc tgataatgat ggtttttctga    420

aggctccctg cagaatgaaa gtttctattc caactaaagc cttagaattg atggacatgc    480

aaactttcaa agcagagcct cccgagaagc catctgcctt cgagcctgcc attgaaatgc    540

aaaagtctgt tccaaataaa gccttggaat tgaagaatga acaaacattg agagcagatc    600

agatgttccc ttcagaatca aaacaaaaga aggttgaaga aaattcttgg gattctgaga    660

gtctccgtga gactgtttca cagaaggatg tgtgtgtacc caaggctaca catcaaaaag    720

aaatggataa aataagtgga aaattagaag attcaactag cctatcaaaa atcttggata    780

cagttcattc ttgtgaaaga gcaagggaac ttcaaaaaga tcactgtgaa caacgtacag    840

gaaaaatgga acaaatgaaa aagaagtttt gtgtactgaa aaagaaactg tcagaagcaa    900

aagaaataaa atcacagtta gagaaccaaa aagttaaatg ggaacaagag ctctgcagtg    960

tgagattgac tttaaaccaa gaagaagaga agagaagaaa tgccgatata ttaaatgaaa   1020

aaattaggga agaattagga agaatcgaag agcagcatag gaaagagtta gaagtgaaac   1080

aacaacttga acaggctctc agaatacaag atatagaatt gaagagtgta gaaagtaatt   1140

tgaatcaggt ttctcacact catgaaaatg aaaattatct cttacatgaa aattgcatgt   1200

tgaaaaagga aattgccatg ctaaaactgg aaatagccac actgaaacac caataccagg   1260

aaaaggaaaa taaatacttt gaggacatta agattttaaa agaaaagaat gctgaacttc   1320

agatgacccc tcgtgcc                                                  1337
```

<210> SEQ ID NO 468
<211> LENGTH: 2307
<212> TYPE: DNA

-continued

<213> ORGANISM: Homo sapiens

<400> SEQUENCE: 468
attgagagca gatgagatac tcccatcaga atccaaacaa aaggactatg aagaaagttc 60
ttgggattct gagagtctct gtgagactgt ttcacagaag gatgtgtgtt tacccaaggc 120
tacacatcaa aaagaaatag ataaaataaa tggaaaatta gaagggtctc ctgttaaaga 180
tggtcttctg aaggctaact gcggaatgaa agtttctatt ccaactaaag ccttagaatt 240
gatggacatg caaactttca aagcagagcc tcccgagaag ccatctgcct tcgagcctgc 300
cattgaaatg caaaagtctg ttccaaataa agccttggaa ttgaagaatg aacaaacatt 360
gagagcagat gagatactcc catcagaatc caaacaaaag gactatgaag aaagttcttg 420
ggattctgag agtctctgtg agactgtttc acagaaggat gtgtgtttac ccaaggctac 480
acatcaaaaa gaaatagata aaataaatgg aaaattagaa gagtctcctg ataatgatgg 540
ttttctgaag tctccctgca gaatgaaagt ttctattcca actaaagcct tagaattgat 600
ggacatgcaa actttcaaag cagagcctcc cgagaagcca tctgccttcg agcctgccat 660
tgaaatgcaa aagtctgttc caaataaagc cttggaattg aagaatgaac aaacattgag 720
agcagatcag atgttccctt cagaatcaaa acaaaagaac gttgaagaaa attcttggga 780
ttctgagagt ctccgtgaga ctgtttcaca gaaggatgtg tgtgtaccca aggctacaca 840
tcaaaaagaa atggataaaa taagtggaaa attagaagat tcaactagcc tatcaaaaat 900
cttggataca gttcattctt gtgaaagagc aagggaactt caaaaagatc actgtgaaca 960
acgtacagga aaaatggaac aaatgaaaaa gaagttttgt gtactgaaaa agaaactgtc 1020
agaagcaaaa gaaataaaat cacagttaga gaaccaaaaa gttaaatggg aacaagagct 1080
ctgcagtgtg aggtttctca cactcatgaa aatgaaaatt atctcttaca tgaaaattgc 1140
atgttgaaaa aggaaattgc catgctaaaa ctggaaatag ccacactgaa acaccaatac 1200
caggaaaagg aaaataaata ctttgaggac attaagattt taaaagaaaa gaatgctgaa 1260
cttcagatga ccctaaaact gaaagaggaa tcattaacta aaagggcatc tcaatatagt 1320
gggcagctta aagttctgat agctgagaac acaatgctca cttctaaatt gaaggaaaaa 1380
caagacaaag aaatactaga ggcagaaatt gaatcacacc atcctagact ggcttctgct 1440
gtacaagacc atgatcaaat tgtgacatca agaaaaagtc aagaacctgc tttccacatt 1500
gcaggagatg cttgtttgca aagaaaaatg aatgttgatg tgagtagtac gatatataac 1560
aatgaggtgc tccatcaacc actttctgaa gctcaaagga aatccaaaag cctaaaaatt 1620
aatctcaatt atgcaggaga tgctctaaga gaaaatacat tggtttcaga acatgcacaa 1680
agagaccaac gtgaaacaca gtgtcaaatg aaggaagctg aacacatgta tcaaaacgaa 1740
caagataatg tgaacaaaca cactgaacag caggagtctc tagatcagaa attatttcaa 1800
ctacaaagca aaaatatgtg gcttcaacag caattagttc atgcacataa gaaagctgac 1860
aacaaaagca agataacaat tgatattcat tttcttgaga ggaaaatgca acatcatctc 1920
ctaaaagaga aaaatgagga gatatttaat tacaataacc atttaaaaaa ccgtatatat 1980
caatatgaaa aagagaaagc agaaacagaa aactcatgag agacaagcag taagaaactt 2040
cttttggaga aacaacagac cagatcttta ctcacaactc atgctaggag gccagtccta 2100
gcatcacctt atgttgaaaa tcttaccaat agtctgtgtc aacagaatac ttattttaga 2160
agaaaaattc atgatttctt cctgaagcct acagacataa aataacagtg tgaagaatta 2220
cttgttcacg aattgcataa agctgcacag gattcccatc taccctgatg atgcagcaga 2280

-continued catcattcaa tccaaccaga atctcgc 2307

<210> SEQ ID NO 469
<211> LENGTH: 650
<212> TYPE: PRT
<213> ORGANISM: Homo sapiens
<220> FEATURE:
<221> NAME/KEY: VARIANT
<222> LOCATION: (1)...(650)
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
                5                   10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
```

-continued

```
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Lys Phe Cys Val Leu Lys Lys Lys Leu
        595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Phe Leu Thr Leu Met Lys Met
625                 630                 635                 640

Lys Ile Ile Ser Tyr Met Lys Ile Ala Cys
                645                 650


<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
                  5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
     50                  55                  60
```

-continued

```
Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Gly Lys Asn Arg
        195                 200                 205

Phe Leu Phe Lys Asn Gln Leu Thr Glu Tyr Phe Ser Lys Leu Met Arg
    210                 215                 220

Arg Asp Ile Leu
225
```

<210> SEQ ID NO 471
<211> LENGTH: 154
<212> TYPE: PRT
<213> ORGANISM: Homo sapiens
<220> FEATURE:
<221> NAME/KEY: unsure
<222> LOCATION: (148)
<223> OTHER INFORMATION: Xaa = Any Amino Acid

<400> SEQUENCE: 471

```
Met Arg Leu His Pro Trp Arg Lys Glu His Leu Thr Gln Leu Lys Ala
                  5                  10                  15

Trp Trp Lys Lys His Leu Met Arg Leu His Pro Trp Trp Lys Glu His
             20                  25                  30

Leu Thr Arg Leu Lys Ala Trp Trp Lys Lys His Leu Met Arg Leu His
         35                  40                  45

Pro Trp Trp Arg Glu His Leu Thr Lys Phe Asn Val Trp Arg Lys Arg
     50                  55                  60

His Leu Glu Ser Ser Asn Ser Gln Gln Lys Lys His Leu Gly Lys Leu
 65                  70                  75                  80

Arg Val Leu Gln Lys Lys His Leu Arg Asn Leu Arg Gly Gln Gln Lys
                 85                  90                  95

Glu Asp Leu Gly Arg Ser His Gly Arg Lys Lys Met Thr Gln Leu Arg
            100                 105                 110

Gln Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
    130                 135                 140

Lys Lys Lys Xaa Lys Lys Lys Lys Lys Lys
145                 150
```

<210> SEQ ID NO 472
<211> LENGTH: 466
<212> TYPE: PRT

-continued

<213> ORGANISM: Homo sapiens
<220> FEATURE:
<221> NAME/KEY: unsure
<222> LOCATION: (329)
<223> OTHER INFORMATION: Xaa = Any Amino Acid

<400> SEQUENCE: 472

```
Met Ser Pro Ala Lys Glu Thr Ser Glu Lys Phe Thr Trp Ala Ala Lys
                5                   10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
        275                 280                 285

Ser Trp Asp Thr Glu Ser Leu Cys Glu Thr Val Ser Gln Lys Asp Val
    290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380
```

-continued

```
Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
        435                 440                 445

Phe Lys Asn His Leu Thr Lys Tyr Phe Ser Lys Leu Met Arg Lys Asp
    450                 455                 460

Ile Leu
465


<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
                5                   10                  15

Asp Gly Leu Leu Lys Ala Asn Cys Gly Met Lys Val Ser Ile Pro Thr
            20                  25                  30

Lys Ala Leu Glu Leu Met Asp Met Gln Thr Phe Lys Ala Glu Pro Pro
        35                  40                  45

Glu Lys Pro Ser Ala Phe Glu Pro Ala Ile Glu Met Gln Lys Ser Val
    50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Lys Gln Lys Asp Tyr Glu Glu Ser Ser
                85                  90                  95

Trp Asp Ser Glu Ser Leu Cys Glu Thr Val Ser Gln Lys Asp Val Cys
            100                 105                 110

Leu Pro Lys Ala Ala His Gln Lys Glu Ile Asp Lys Ile Asn Gly Lys
        115                 120                 125

Leu Glu Glu Ser Pro Asp Asn Asp Gly Phe Leu Lys Ala Pro Cys Arg
    130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175

Ile Glu Met Gln Lys Ser Val Pro Asn Lys Ala Leu Glu Leu Lys Asn
            180                 185                 190

Glu Gln Thr Leu Arg Ala Asp Gln Met Phe Pro Ser Glu Ser Lys Gln
        195                 200                 205

Lys Lys Val Glu Glu Asn Ser Trp Asp Ser Glu Ser Leu Arg Glu Thr
    210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
                245                 250                 255

Ile Leu Asp Thr Val His Ser Cys Glu Arg Ala Arg Glu Leu Gln Lys
            260                 265                 270

Asp His Cys Glu Gln Arg Thr Gly Lys Met Glu Gln Met Lys Lys Lys
```

-continued 275 280 285

Phe Cys Val Leu Lys Lys Lys Leu Ser Glu Ala Lys Glu Ile Lys Ser
290 295 300

Gln Leu Glu Asn Gln Lys Val Lys Trp Glu Gln Glu Leu Cys Ser Val
305 310 315 320

Arg Leu Thr Leu Asn Gln Glu Glu Glu Lys Arg Arg Asn Ala Asp Ile
325 330 335

Leu Asn Glu Lys Ile Arg Glu Glu Leu Gly Arg Ile Glu Glu Gln His
340 345 350

Arg Lys Glu Leu Glu Val Lys Gln Gln Leu Glu Gln Ala Leu Arg Ile
355 360 365

Gln Asp Ile Glu Leu Lys Ser Val Glu Ser Asn Leu Asn Gln Val Ser
370 375 380

His Thr His Glu Asn Glu Asn Tyr Leu Leu His Glu Asn Cys Met Leu
385 390 395 400

Lys Lys Glu Ile Ala Met Leu Lys Leu Glu Ile Ala Thr Leu Lys His
405 410 415

Gln Tyr Gln Glu Lys Glu Asn Lys Tyr Phe Glu Asp Ile Lys Ile Leu
420 425 430

Lys Glu Lys Asn Ala Glu Leu Gln Met Thr Pro Arg Ala
435 440 445

<210> SEQ ID NO 474
<211> LENGTH: 3865
<212> TYPE: DNA
<213> ORGANISM: Homo sapien
<220> FEATURE:
<221> NAME/KEY: misc_feature
<222> LOCATION: (2448)...(2631)
<223> OTHER INFORMATION: 184 bp insert of B726P splice form

<400> SEQUENCE: 474
tccgagctga ttacagacac caaggaagat gctgtaaaga gtcagcagcc acagccctgg 60
ctagctggcc ctgtgggcat ttattagtaa agttttaatg acaaaagctt tgagtcaaca 120
cacccgtggg taattaacct ggtcatcccc accctggaga gccatcctgc ccatgggtga 180
tcaaagaagg aacatctgca ggaacacctg atgaggctgc acccttggcg gaaagaacac 240
ctgacacagc tgaaagcttg gtggaaaaaa cacctgatga ggctgcaccc ttggtggaaa 300
gaacacctga cacggctgaa agcttggtgg aaaaaacacc tgatgaggct gcatccttgg 360
tggagggaac atctgacaaa attcaatgtt tggagaaagc gacatctgga aagttcgaac 420
agtcagcaga agaaacacct agggaaatta cgagtcctgc aaaagaaaca tctgagaaat 480
ttacgtggcc agcaaaagga agacctagga agatcgcatg ggagaaaaaa gaagacacac 540
ctagggaaat tatgagtccc gcaaaagaaa catctgagaa atttacgtgg gcagcaaaag 600
gaagacctag gaagatcgca tgggagaaaa aagaaacacc tgtaaagact ggatgcgtgg 660
caagagtaac atctaataaa actaaagttt tggaaaaagg aagatctaag atgattgcat 720
gtcctacaaa agaatcatct acaaaagcaa gtgccaatga tcagaggttc ccatcagaat 780
ccaaacaaga ggaagatgaa gaatattctt gtgattctcg gagtctcttt gagagttctg 840
caaagattca agtgtgtata cctgagtcta tatatcaaaa agtaatggag ataaatagag 900
aagtagaaga gcctcctaag aagccatctg ccttcaagcc tgccattgaa atgcaaaact 960
ctgttccaaa taaagccttt gaattgaaga atgaacaaac attgagagca gatccgatgt 1020
tcccaccaga atccaaacaa aaggactatg aagaaaattc ttgggattct gagagtctct 1080

-continued

```
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
agttagagaa ccaaaaagtt aaatgggaac aagagctctg cagtgtgaga ttgactttaa   2460
accaagaaga agagaagaga agaaatgccg atatattaaa tgaaaaaatt agggaagaat   2520
taggaagaat cgaagagcag cataggaaag agttagaagt gaaacaacaa cttgaacagg   2580
ctctcagaat acaagatata gaattgaaga gtgtagaaag taatttgaat caggtttctc   2640
acactcatga aaatgaaaat tatctcttac atgaaaattg catgttgaaa aaggaaattg   2700
ccatgctaaa actggaaata gccacactga aacaccaata ccaggaaaag gaaaataaat   2760
actttgagga cattaagatt ttaaaagaaa agaatgctga acttcagatg accctaaaac   2820
tgaaagagga atcattaact aaaagggcat ctcaatatag tgggcagctt aaagttctga   2880
tagctgagaa cacaatgctc acttctaaat tgaaggaaaa acaagacaaa gaaatactag   2940
aggcagaaat tgaatcacac catcctagac tggcttctgc tgtacaagac catgatcaaa   3000
ttgtgacatc aagaaaaagt caagaacctg ctttccacat tgcaggagat gcttgtttgc   3060
aaagaaaaat gaatgttgat gtgagtagta cgatatataa caatgaggtg ctccatcaac   3120
cactttctga agctcaaagg aaatccaaaa gcctaaaaat taatctcaat tatgcmggag   3180
atgctctaag agaaaataca ttggtttcag aacatgcaca aagagaccaa cgtgaaacac   3240
agtgtcaaat gaaggaagct gaacacatgt atcaaaacga acaagataat gtgaacaaac   3300
acactgaaca gcaggagtct ctagatcaga aattatttca actacaaagc aaaaatatgt   3360
ggcttcaaca gcaattagtt catgcacata agaaagctga caacaaaagc aagataacaa   3420
```

-continued

```
ttgatattca ttttcttgag aggaaaatgc aacatcatct cctaaaagag aaaaatgagg   3480

agatatttaa ttacaataac catttaaaaa accgtatata tcaatatgaa aaagagaaag   3540

cagaaacaga aaactcatga gagacaagca gtaagaaact tcttttggag aaacaacaga   3600

ccagatcttt actcacaact catgctagga ggccagtcct agcatcacct tatgttgaaa   3660

atcttaccaa tagtctgtgt caacagaata cttattttag aagaaaaatt catgatttct   3720

tcctgaagcc tacagacata aaataacagt gtgaagaatt acttgttcac gaattgcata   3780

aagctgcaca ggattcccat ctaccctgat gatgcagcag acatcattca atccaaccag   3840

aatctcgctc tgtcactcag gctgg                                         3865
```

```
<210> SEQ ID NO 475
<211> LENGTH: 1002
<212> TYPE: PRT
<213> ORGANISM: Homo sapien
<220> FEATURE:
<221> NAME/KEY: VARIANT
<222> LOCATION: (1)...(1002)
<223> OTHER INFORMATION: Xaa = Any Amino Acid

<400> SEQUENCE: 475

Met Ser Pro Ala Lys Glu Thr Ser Glu Lys Phe Thr Trp Ala Ala Lys
1               5                   10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270
```

-continued

```
Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Lys Phe Cys Val Leu Lys Lys Lys Leu
        595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Leu Thr Leu Asn Gln Glu Glu
625                 630                 635                 640

Glu Lys Arg Arg Asn Ala Asp Ile Leu Asn Glu Lys Ile Arg Glu Glu
                645                 650                 655

Leu Gly Arg Ile Glu Glu Gln His Arg Lys Glu Leu Glu Val Lys Gln
            660                 665                 670

Gln Leu Glu Gln Ala Leu Arg Ile Gln Asp Ile Glu Leu Lys Ser Val
        675                 680                 685

Glu Ser Asn Leu Asn Gln Val Ser His Thr His Glu Asn Glu Asn Tyr
```

-continued

```
    690                 695                 700

Leu Leu His Glu Asn Cys Met Leu Lys Lys Glu Ile Ala Met Leu Lys
705                 710                 715                 720

Leu Glu Ile Ala Thr Leu Lys His Gln Tyr Gln Glu Lys Glu Asn Lys
                725                 730                 735

Tyr Phe Glu Asp Ile Lys Ile Leu Lys Glu Lys Asn Ala Glu Leu Gln
            740                 745                 750

Met Thr Leu Lys Leu Lys Glu Glu Ser Leu Thr Lys Arg Ala Ser Gln
        755                 760                 765

Tyr Ser Gly Gln Leu Lys Val Leu Ile Ala Glu Asn Thr Met Leu Thr
    770                 775                 780

Ser Lys Leu Lys Glu Lys Gln Asp Lys Glu Ile Leu Glu Ala Glu Ile
785                 790                 795                 800

Glu Ser His His Pro Arg Leu Ala Ser Ala Val Gln Asp His Asp Gln
                805                 810                 815

Ile Val Thr Ser Arg Lys Ser Gln Glu Pro Ala Phe His Ile Ala Gly
            820                 825                 830

Asp Ala Cys Leu Gln Arg Lys Met Asn Val Asp Val Ser Ser Thr Ile
        835                 840                 845

Tyr Asn Asn Glu Val Leu His Gln Pro Leu Ser Glu Ala Gln Arg Lys
    850                 855                 860

Ser Lys Ser Leu Lys Ile Asn Leu Asn Tyr Ala Gly Asp Ala Leu Arg
865                 870                 875                 880

Glu Asn Thr Leu Val Ser Glu His Ala Gln Arg Asp Gln Arg Glu Thr
                885                 890                 895

Gln Cys Gln Met Lys Glu Ala Glu His Met Tyr Gln Asn Glu Gln Asp
            900                 905                 910

Asn Val Asn Lys His Thr Glu Gln Gln Glu Ser Leu Asp Gln Lys Leu
        915                 920                 925

Phe Gln Leu Gln Ser Lys Asn Met Trp Leu Gln Gln Gln Leu Val His
    930                 935                 940

Ala His Lys Lys Ala Asp Asn Lys Ser Lys Ile Thr Ile Asp Ile His
945                 950                 955                 960

Phe Leu Glu Arg Lys Met Gln His His Leu Leu Lys Glu Lys Asn Glu
                965                 970                 975

Glu Ile Phe Asn Tyr Asn Asn His Leu Lys Asn Arg Ile Tyr Gln Tyr
            980                 985                 990

Glu Lys Glu Lys Ala Glu Thr Glu Asn Ser
        995                 1000
```

```
<210> SEQ ID NO 476
<211> LENGTH: 356
<212> TYPE: DNA
<213> ORGANISM: Homo sapien

<400> SEQUENCE: 476

aggtctgccg gaaatgttag gcaccccaac tcaagtccca ggccccaggc atctttcctg     60

ccctgccttg cttggcccat ccagtccagg cgcctggagc aagtgctcag ctacttctcc    120

tgcactttga aagacccctc ccactcctgg cctcacattt ctctgtgtga tcccccactt    180

ctgggctctg ccaccccaca gtgggaaagg ccaccctaga aagaagtccg ctggcaccca    240

taggaagggg cctcaggagc aggaagggcc aggaccagaa ccttgcccac ggcaactgcc    300

ttcctgcctc tcccttcct cctctgctct tgatctgtgt ttcaataaat taatgt         356
```

-continued

<210> SEQ ID NO 477
<211> LENGTH: 1876
<212> TYPE: DNA
<213> ORGANISM: Homo sapien

<400> SEQUENCE: 477
atgacctgcg gatcaggatt tggtgggcgc gccttcagct gcatctcggc ctgcgggccg 60
cgccccggcc gctgctgcat caccgccgcc ccctaccgtg gcatctcctg ctaccgcggc 120
ctcaccgggg gcttcggcag ccacagcgtg tgcggaggct ttcgggccgg ctcctgcgga 180
cgcagcttcg gctaccgctc cgggggcgtg tgcgggccca gtcccccatg catcaccacc 240
gtgtcggtca acgagagcct cctcacgccc ctcaacctgg agatcgaccc caacgcgcag 300
tgcgtgaagc aggaggagaa ggagcagatc aagtccctca acagcaggtt cgcggccttc 360
atcgacaagg tgcgcttcct ggagcagcag aacaaactgc tggagacaaa gctgcagttc 420
taccagaacc gcgagtgttg ccagagcaac ctggagcccc tgtttgaggg ctacatcgag 480
actctgcggc gggaggccga gtgcgtggag gccgacagcg ggaggctggc ctcagagctt 540
aaccacgtgc aggaggtgct ggagggctac aagaagaagt atgaggagga ggtttctctg 600
agagcaacag ctgagaacga gtttgtggct ctgaagaagg atgtggactg cgcctacctc 660
cgcaagtcag acctggaggc caacgtggag gccctgatcc aggagatcga cttcctgagg 720
cggctgtatg aggaggagat ccgcattctc cagtcgcaca tctcagacac ctccgtggtt 780
gtcaagctgg acaacagccg ggacctgaac atggactgca tcattgccga gattaaggca 840
cagtatgacg acattgtcac ccgcagccgg gccgaggccg agtcctggta ccgcagcaag 900
tgtgaggaga tgaaggccac ggtgatcagg cacggggaga ccctgcgccg caccaaggag 960
gagatcaatg agctgaaccg catgatccaa aggctgacgg ccgaggtgga gaatgccaag 1020
tgccagaact ccaagctgga ggccgcggtg gctcagtctg agcagcaggg tgaggcagcc 1080
ctcagtgatg cccgctgcaa gctggccgag ctggagggcg ccctgcagaa ggccaagcag 1140
gacatggcct gcctgatcag ggagtaccag gaggtgatga actccaagct gggcctggac 1200
atcgagatcg ccacctacag gcgcctgctg gagggcgagg agcagaggct atgtgaaggc 1260
attggggctg tgaatgtctg tgtcagcagc tcccggggcg gggtcgtgtg cggggacctc 1320
tgcgtgtcag gctcccggcc agtgactggc agtgtctgca gcgctccgtg caacgggaac 1380
gtggcggtga gcaccggcct gtgtgcgccc tgcggccaat tgaacaccac ctgcggaggg 1440
ggttcctgcg gcgtgggctc ctgtggtatc agctccctgg gtgtggggtc ttgcggcagc 1500
agctgccgga aatgttaggc accccaactc aagtcccagg ccccaggcat ctttcctgcc 1560
ctgccttgct tggcccatcc agtccaggcg cctggagcaa gtgctcagct acttctcctg 1620
cactttgaaa gacccctccc actcctggcc tcacatttct ctgtgtgatc ccccacttct 1680
gggctctgcc accccacagt gggaaaggcc accctagaaa gaagtccgct ggcacccata 1740
ggaaggggcc tcaggagcag gaagggccag gaccagaacc ttgcccacgg caactgcctt 1800
cctgcctctc cccttcctcc tctgctcttg atctgtgttt caataaatta atgtagccaa 1860
aaaaaaaaaa aaaaaa 1876

<210> SEQ ID NO 478
<211> LENGTH: 505
<212> TYPE: PRT
<213> ORGANISM: Homo sapien

<400> SEQUENCE: 478

-continued

```
Met Thr Cys Gly Ser Gly Phe Gly Gly Arg Ala Phe Ser Cys Ile Ser
1               5                   10                  15

Ala Cys Gly Pro Arg Pro Gly Arg Cys Cys Ile Thr Ala Ala Pro Tyr
            20                  25                  30

Arg Gly Ile Ser Cys Tyr Arg Gly Leu Thr Gly Gly Phe Gly Ser His
        35                  40                  45

Ser Val Cys Gly Gly Phe Arg Ala Gly Ser Cys Gly Arg Ser Phe Gly
    50                  55                  60

Tyr Arg Ser Gly Gly Val Cys Gly Pro Ser Pro Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
                325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
    370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415
```

-continued

```
Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
            500                 505


<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 479

ggtccattcc tttcctcgcg tnggggtttc tctgtgtcag cgagcctcgg tacactgatt      60

tccgatcaaa agaatcatca tctttacctt gacttttcag ggaattactg aactttcttc     120

tcagaagata gggcacagcc attgccttgg cctcacttga agggtctgca tttgggtcct     180

ctggtctctt gccaagtttc ccagccactc gagggagaaa t                         221
```

COMPOSITIONS AND METHODS FOR THE THERAPY AND DIAGNOSIS OF BREAST CANCER

CROSS-REFERENCE TO RELATED APPLICATIONS

This application is a continuation-in-part of Ser. No. 09/551,621 filed Apr. 17, 2000 which is a continuation-in-part U.S. patent application Ser. No. 09/433,826, filed on Nov. 3, 1999, now U.S. Pat. No. 6,579,973, which is a continuation-in-part of U.S. application Ser. No. 09/389,681, filed on Sep. 2, 1999, now U.S. Pat. No. 6,518,237 which is a continuation-in-part of U.S. application Ser. No. 09/339,338, filed on Jun. 23, 1999, now U.S. Pat. No. 6,573,368, which is a continuation-in-part of U.S. application Ser. No. 09/285,480, filed on Apr. 2, 1999, now U.S. Pat. No. 6,590,076, which is a continuation-in-part of U.S. application Ser. No. 09/222,575, filed Dec. 28, 1998, now U.S. Pat. No. 6,387,697.

TECHNICAL FIELD OF THE INVENTION

The present invention relates generally to therapy and diagnosis of cancer, such as breast cancer. The invention is more specifically related to polypeptides comprising at least a portion of a breast tumor protein, and to polynucleotides encoding such polypeptides. Such polypeptides and polynucleotides may be used in compositions for prevention and treatment of breast cancer, and for the diagnosis and monitoring of such cancers.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

Briefly stated, the present invention provides compositions and methods for the diagnosis and therapy of cancer, such as breast cancer. In one aspect, the present invention provides polypeptides comprising at least a portion of a breast tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NO: 1–175, 178, 180, 182–468, 474, 476, 477, and 479; (b) variants of a sequence recited in SEQ ID NO: 1–175, 178, 180, 182–468, 474, 476, 477 and 479; and (c) complements of a sequence of (a) or (b). In specific embodiments, the polypeptides of the present invention comprise at least a portion of a tumor protein that includes an amino acid sequence selected from the group consisting of sequences recited in SEQ ID NO: 176, 179, 181, 469–473 and 475, and variants thereof.

The present invention further provides polynucleotides that encode a polypeptide as described above, or a portion thereof (such as a portion encoding at least 15 amino acid residues of a breast tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, immunogenic compositions, or vaccines for prophylactic or therapeutic use are provided. Such compositions comprise a polypeptide or polynucleotide as described above and an immunostimulant.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, immunogenic compositions, or vaccines, are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Compositions are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may bc breast cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a breast tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6 (also known as B709P).

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6 (also known as B709P).

SEQ ID NO: 63 is the determined cDNA sequence of B723P.

SEQ ID NO: 64 is the determined cDNA sequence for B7724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051.

SEQ ID NO: 118 is the determined cDNA sequence of 13052.

SEQ ID NO: 119 is the determined cDNA sequence of 13055.

SEQ ID NO: 120 is the determined cDNA sequence of 13058.

SEQ ID NO: 121 is the determined cDNA sequence of 13062.

SEQ ID NO: 122 is the determined cDNA sequence of 13064.

SEQ ID NO: 123 is the determined cDNA sequence of 13080.

SEQ ID NO: 124 is the determined cDNA sequence of 13093.

SEQ ID NO: 125 is the determined cDNA sequence of 13094.

SEQ ID NO: 126 is the determined cDNA sequence of 13095.

SEQ ID NO: 127 is the determined cDNA sequence of 13096.

SEQ ID NO: 128 is the determined cDNA sequence of 13099.

SEQ ID NO: 129 is the determined cDNA sequence of 13100.

SEQ ID NO: 130 is the determined cDNA sequence of 13103.

SEQ ID NO: 131 is the determined cDNA sequence of 13106.

SEQ ID NO: 132 is the determined cDNA sequence of 13107.

SEQ ID NO: 133 is the determined cDNA sequence of 13108.

SEQ ID NO: 134 is the determined cDNA sequence of 13121.

SEQ ID NO: 135 is the determined cDNA sequence of 13126.

SEQ ID NO: 136 is the determined cDNA sequence of 13129.

SEQ ID NO: 137 is the determined cDNA sequence of 13130.

SEQ ID NO: 138 is the determined cDNA sequence of 13134.

SEQ ID NO: 139 is the determined cDNA sequence of 13141.

SEQ ID NO: 140 is the determined cDNA sequence of 13142.

SEQ ID NO: 141 is the determined cDNA sequence of 14376.

SEQ ID NO: 142 is the determined cDNA sequence of 14377.

SEQ ID NO: 143 is the determined cDNA sequence of 14383.

SEQ ID NO: 144 is the determined cDNA sequence of 14384.

SEQ ID NO: 145 is the determined cDNA sequence of 14387.

SEQ ID NO: 146 is the determined cDNA sequence of 14392.

SEQ ID NO: 147 is the determined cDNA sequence of 14398.

SEQ ID NO: 148 is the determined cDNA sequence of 14398.

SEQ ID NO: 149 is the determined cDNA sequence of 14401.

SEQ ID NO: 150 is the determined cDNA sequence of 14402.

SEQ ID NO: 151 is the determined cDNA sequence of 14405.

SEQ ID NO: 152 is the determined cDNA sequence of 14409.

SEQ ID NO: 154 is the determined cDNA sequence of 14412.

SEQ ID NO: 155 is the determined cDNA sequence of 14414.

SEQ ID NO: 156 is the determined cDNA sequence of 14415.

SEQ ID NO: 156 is the determined cDNA sequence of 14416.

SEQ ID NO: 157 is the determined cDNA sequence of 14419.

SEQ ID NO: 158 is the determined cDNA sequence of 14426.

SEQ ID NO: 159 is the determined cDNA sequence of 14427.

SEQ ID NO: 160 is the determined cDNA sequence of 14375.

SEQ ID NO: 161 is the determined cDNA sequence of 14378.

SEQ ID NO: 162 is the determined cDNA sequence of 14379.

SEQ ID NO: 163 is the determined cDNA sequence of 14380.

SEQ ID NO: 164 is the determined cDNA sequence of 14381.

SEQ ID NO: 165 is the determined cDNA sequence of 14382.

SEQ ID NO: 166 is the determined cDNA sequence of 14388.

SEQ ID NO: 167 is the determined cDNA sequence of 14399.

SEQ ID NO: 168 is the determined cDNA sequence of 14406.

SEQ ID NO: 169 is the determined cDNA sequence of 14407.

SEQ ID NO: 170 is the determined cDNA sequence of 14408.

SEQ ID NO: 171 is the determined cDNA sequence of 14417.

SEQ ID NO: 172 is the determined cDNA sequence of 14418.

SEQ ID NO: 173 is the determined cDNA sequence of 14423.

SEQ ID NO: 174 is the determined cDNA sequence of 14424.

SEQ ID NO: 175 is the determined cDNA sequence of B726P-20.

SEQ ID NO: 176 is the predicted amino acid sequence of B726P-20.

SEQ ID NO: 177is a PCR primer.

SEQ ID NO: 178 is the determined cDNA sequence of B726P-74.

SEQ ID NO: 179 is the predicted amino acid sequence of B726P-74.

SEQ ID NO: 180 is the determined cDNA sequence of B726P-79.

SEQ ID NO: 181 is the predicted amino acid sequence of B726P-79.

SEQ ID NO: 182 is the determined cDNA sequence of 19439.1, showing homology to the mammaglobin gene.

SEQ ID NO: 183 is the determined cDNA sequence of 19407.1, showing homology to the human keratin gene.

SEQ ID NO: 184 is the determined cDNA sequence of 19428.1, showing homology to human chromosome 17 clone.

SEQ ID NO: 185 is the determined cDNA sequence of B808P (19408), showing no significant homology to any known gene.

SEQ ID NO: 186 is the determined cDNA sequence of 19460.1, showing no significant homology to any known gene.

SEQ ID NO: 187 is the determined cDNA sequence of 19419.1, showing homology to Ig kappa light chain.

SEQ ID NO: 188 is the determined cDNA sequence of 19411.1, showing homology to human alpha-1 collagen.

SEQ ID NO: 189 is the determined cDNA sequence of 19420.1, showing homology to mus musculus proteinase-3.

SEQ ID NO: 190 is the determined cDNA sequence of 19432.1, showing homology to human high motility group box.

SEQ ID NO: 191 is the determined cDNA sequence of 19412.1, showing homology to the human plasminogen activator gene.

SEQ ID NO: 192 is the determined cDNA sequence of 19415.1, showing homology to mitogen activated protein kinase.

SEQ ID NO: 193 is the determined cDNA sequence of 19409.1, showing homology to the chondroitin sulfate proteoglycan protein.

SEQ ID NO: 194 is the determined cDNA sequence of 19406.1, showing no significant homology to any known gene.

SEQ ID NO: 195 is the determined cDNA sequence of 19421.1, showing homology to human fibronectin.

SEQ ID NO: 196 is the determined cDNA sequence of 19426.1, showing homology to the retinoic acid receptor responder 3.

SEQ ID NO: 197 is the determined cDNA sequence of 19425.1, showing homology to MyD88 mRNA.

SEQ ID NO: 198 is the determined cDNA sequence of 19424.1, showing homology to peptide transporter (TAP-1) mRNA.

SEQ ID NO: 199 is the determined cDNA sequence of 19429.1, showing no significant homology to any known gene.

SEQ ID NO: 200 is the determined cDNA sequence of 19435.1, showing homology to human polymorphic epithelial mucin.

SEQ ID NO: 201 is the determined cDNA sequence of B813P (19434.1), showing homology to human GATA-3 transcription factor.

SEQ ID NO: 202 is the determined cDNA sequence of 19461.1, showing homology to the human AP-2 gene.

SEQ ID NO: 203 is the determined cDNA sequence of 19450.1, showing homology to DNA binding regulatory factor.

SEQ ID NO: 204 is the determined cDNA sequence of 19451.1, showing homology to Na/H exchange regulatory co-factor.

SEQ ID NO: 205 is the determined cDNA sequence of 19462.1, showing no significant homology to any known gene.

SEQ ID NO: 206 is the determined cDNA sequence of 19455.1, showing homology to human mRNA for histone HAS.Z.

SEQ ID NO: 207 is the determined cDNA sequence of 19459.1, showing homology to PAC clone 179N16.

SEQ ID NO: 208 is the determined cDNA sequence of 19464.1, showing no significant homology to any known gene.

SEQ ID NO: 209 is the determined cDNA sequence of 19414.1, showing homology to lipophilin B.

SEQ ID NO: 210 is the determined cDNA sequence of 19413.1, showing homology to chromosome 17 clone hRPK.209_J_20.

SEQ ID NO: 211 is the determined cDNA sequence of 19416.1, showing no significant homology to any known gene.

SEQ ID NO: 212 is the determined cDNA sequence of 19437.1, showing homology to human clone 24976 mRNA.

SEQ ID NO: 213 is the determined cDNA sequence of 19449.1, showing homology to mouse DNA for PG-M core protein.

SEQ ID NO: 214 is the determined cDNA sequence of 19446.1, showing no significant homology to any known gene.

SEQ ID NO: 215 is the determined cDNA sequence of 19452.1, showing no significant homology to any known gene.

SEQ ID NO: 216 is the determined cDNA sequence of 19483.1, showing no significant homology to any known gene.

SEQ ID NO: 217 is the determined cDNA sequence of 19526.1, showing homology to human lipophilin C.

SEQ ID NO: 218 is the determined cDNA sequence of 19484.1, showing homology to the secreted cement gland protein XAG-2.

SEQ ID NO: 219 is the determined cDNA sequence of 19470.1, showing no significant homology to any known gene.

SEQ ID NO: 220 is the determined cDNA sequence of 19469.1, showing homology to the human HLA-DM gene.

SEQ ID NO: 221 is the determined cDNA sequence of 19482.1, showing homology to the human pS2 protein gene.

SEQ ID NO: 222 is the determined cDNA sequence of B805P (19468.1), showing no significant homology to any known gene.

SEQ ID NO: 223 is the determined cDNA sequence of 19467.1, showing homology to human thrombospondin mRNA.

SEQ ID NO: 224 is the determined cDNA sequence of 19498.1, showing homology to the CDC2 gene involved in cell cycle control.

SEQ ID NO: 225 is the determined cDNA sequence of 19506.1, showing homology to human cDNA for TREB protein.

SEQ ID NO: 226 is the determined cDNA sequence of B806P (19505.1), showing no significant homology to any known gene.

SEQ ID NO: 227 is the determined cDNA sequence of 19486.1, showing homology to type I epidermal keratin.

SEQ ID NO: 228 is the determined cDNA sequence of 19510.1, showing homology to glucose transporter for glycoprotein.

SEQ ID NO: 229 is the determined cDNA sequence of 19512.1, showing homology to the human lysyl hydroxylase gene.

SEQ ID NO: 230 is the determined cDNA sequence of 19511.1, showing homology to human palimotoyl-protein thioesterase.

SEQ ID NO: 231 is the determined cDNA sequence of 19508.1, showing homology to human alpha enolase.

SEQ ID NO: 232 is the determined cDNA sequence of B807P (19509.1), showing no significant homology to any known gene.

SEQ ID NO: 233 is the determined cDNA sequence of B809P (19520.1), showing homology to clone 102D24 on chromosome 11q13.31.

SEQ ID NO: 234 is the determined cDNA sequence of 19507.1, showing homology toprosome beta-subunit.

SEQ ID NO: 235 is the determined cDNA sequence of 19525.1, showing homology to human pro-urokinase precursor.

SEQ ID NO: 236 is the determined cDNA sequence of 19513.1, showing no significant homology to any known gene.

SEQ ID NO: 237 is the determined cDNA sequence of 19517.1, showing homology to human PAC 128M19 clone.

SEQ ID NO: 238 is the determined cDNA sequence of 19564.1, showing homology to human cytochrome P450-IIB.

SEQ ID NO: 239 is the determined cDNA sequence of 19553.1, showing homology to human GABA-A receptor pi subunit.

SEQ ID NO: 240 is the determined cDNA sequence of B811P (19575.1), showing no significant homology to any known gene.

SEQ ID NO: 241 is the determined cDNA sequence of B810P (19560.1), showing no significant homology to any known gene.

SEQ ID NO: 242 is the determined cDNA sequence of 19588.1, showing homology to aortic carboxypetidase-like protein.

SEQ ID NO: 243 is the determined cDNA sequence of 19551.1, showing homology to human BCL-1 gene.

SEQ ID NO: 244 is the determined cDNA sequence of 19567.1, showing homology to human proteasome-related mRNA.

SEQ ID NO: 245 is the determined cDNA sequence of B803P (19583.1), showing no significant homology to any known gene.

SEQ ID NO: 246 is the determined cDNA sequence of B812P (19587.1), showing no significant homology to any known gene.

SEQ ID NO: 247 is the determined cDNA sequence of B802P (19392.2), showing homology to human chromosome 17.

SEQ ID NO: 248 is the determined cDNA sequence of 19393.2, showing homology to human nicein B2 chain.

SEQ ID NO: 249 is the determined cDNA sequence of 19398.2, human MHC class II DQ alpha mRNA.

SEQ ID NO: 250 is the determined cDNA sequence of B804P (19399.2), showing homology to human Xp22 BAC GSHB-184P14.

SEQ ID NO: 251 is the determined cDNA sequence of 19401.2, showing homology to human ikB kinase-b gene.

SEQ ID NO: 252 is the determined cDNA sequence of 20266, showing no significant homology to any known gene.

SEQ ID NO: 253 is the determined cDNA sequence of B826P (20270), showing no significant homology to any known gene.

SEQ ID NO: 254 is the determined cDNA sequence of 20274, showing no significant homology to any known gene.

SEQ ID NO: 255 is the determined cDNA sequence of 20276, showing no significant homology to any known gene.

SEQ ID NO: 256 is the determined cDNA sequence of 20277, showing no significant homology to any known gene.

SEQ ID NO: 257 is the determined cDNA sequence of B823P (20280), showing no significant homology to any known gene.

SEQ ID NO: 258 is the determined cDNA sequence of B821P (20281), showing no significant homology to any known gene.

SEQ ID NO: 259 is the determined cDNA sequence of B824P (20294), showing no significant homology to any known gene.

SEQ ID NO: 260 is the determined cDNA sequence of 20303, showing no significant homology to any known gene.

SEQ ID NO: 261 is the determined cDNA sequence of B820P (20310), showing no significant homology to any known gene.

SEQ ID NO: 262 is the determined cDNA sequence of B825P (20336), showing no significant homology to any known gene.

SEQ ID NO: 263 is the determined cDNA sequence of B827P (20341), showing no significant homology to any known gene.

SEQ ID NO: 264 is the determined cDNA sequence of 20941, showing no significant homology to any known gene.

SEQ ID NO: 265 is the determined cDNA sequence of 20954, showing no significant homology to any known gene.

SEQ ID NO: 266 is the determined cDNA sequence of 20961, showing no significant homology to any known gene.

SEQ ID NO: 267 is the determined cDNA sequence of 20965, showing no significant homology to any known gene.

SEQ ID NO: 268 is the determined cDNA sequence of 20975, showing no significant homology to any known gene.

SEQ ID NO: 269 is the determined cDNA sequence of 20261, showing homology to Human p120 catenin.

SEQ ID NO: 270 is the determined cDNA sequence of B822P (20262), showing homology to Human membrane glycoprotein 4F2.

SEQ ID NO: 271 is the determined cDNA sequence of 20265, showing homology to Human Na, K-ATPase Alpha 1.

SEQ ID NO: 272 is the determined cDNA sequence of 20267, showing homology to Human heart HS 90, partial cds.

SEQ ID NO: 273 is the determined cDNA sequence of 20268, showing homology to Human mRNA GPI-anchored protein p137.

SEQ ID NO: 274 is the determined cDNA sequence of 20271, showing homology to Human cleavage stimulation factor 77 kDa subunit.

SEQ ID NO: 275 is the determined cDNA sequence of 20272, showing homology to Human p190-B.

SEQ ID NO: 276 is the determined cDNA sequence of 20273, showing homology to Human ribophorin.

SEQ ID NO: 277 is the determined cDNA sequence of 20278, showing homology to Human ornithine amino transferase.

SEQ ID NO: 278 is the determined cDNA sequence of 20279, showing homology to Human S-adenosylmethionine synthetase.

SEQ ID NO: 279 is the determined cDNA sequence of 20293, showing homology to Human x inactivation transcript.

SEQ ID NO: 280 is the determined cDNA sequence of 20300, showing homology to Human cytochrome p450.

SEQ ID NO: 281 is the determined cDNA sequence of 20305, showing homology to Human elongation factor-1 alpha.

SEQ ID NO: 282 is the determined cDNA sequence of 20306, showing homology to Human epithelial ets protein.

SEQ ID NO: 283 is the determined cDNA sequence of 20307, showing homology to Human signal transducer mRNA.

SEQ ID NO: 284 is the determined cDNA sequence of 20313, showing homology to Human GABA-A receptor pi subunit mRNA.

SEQ ID NO: 285 is the determined cDNA sequence of 20317, showing homology to Human tyrosine phosphatase.

SEQ ID NO: 286 is the determined cDNA sequence of 20318, showing homology to Human cathepsine B proteinase.

SEQ ID NO: 287 is the determined cDNA sequence of 20320, showing homology to Human 2-phosphopyruvate-hydratase-alpha-enolase.

SEQ ID NO: 288 is the determined cDNA sequence of 20321, showing homology to Human E-cadherin.

SEQ ID NO: 289 is the determined cDNA sequence of 20322, showing homology to Human hsp86.

SEQ ID NO: 290 is the determined cDNA sequence of B828P (20326), showing homology to Human x inactivation transcript.

SEQ ID NO: 291 is the determined cDNA sequence of 20333, showing homology to Human chromatin regulator, SMARCA5.

SEQ ID NO: 292 is the determined cDNA sequence of 20335, showing homology to Human sphingolipid activator protein 1.

SEQ ID NO: 293 is the determined cDNA sequence of 20337, showing homology to Human hepatocyte growth factor activator inhibitor type 2.

SEQ ID NO: 294 is the determined cDNA sequence of 20338, showing homology to Human cell adhesion molecule CD44.

SEQ ID NO: 295 is the determined cDNA sequence of 20340, showing homology to Human nuclear factor (erythroid-derived)-like 1.

SEQ ID NO: 296 is the determined cDNA sequence of 20938, showing homology to Human vinculin mRNA.

SEQ ID NO: 297 is the determined cDNA sequence of 20939, showing homology to Human elongation factor EF-1-alpha.

SEQ ID NO: 298 is the determined cDNA sequence of 20940, showing homology to Human nestin gene.

SEQ ID NO: 299 is the determined cDNA sequence of 20942, showing homology to Human pancreatic ribonuclease.

SEQ ID NO: 300 is the determined cDNA sequence of 20943, showing homology to Human transcobalamin I.

SEQ ID NO: 301 is the determined cDNA sequence of 20944, showing homology to Human beta-tubulin.

SEQ ID NO: 302 is the determined cDNA sequence of 20946, showing homology to Human HS1 protein.

SEQ ID NO: 303 is the determined cDNA sequence of 20947, showing homology to Human cathepsin B.

SEQ ID NO: 304 is the determined cDNA sequence of 20948, showing homology to Human testis enhanced gene transcript.

SEQ ID NO: 305 is the determined cDNA sequence of 20949, showing homology to Human elongation factor EF-1-alpha.

SEQ ID NO: 306 is the determined cDNA sequence of 20950, showing homology to Human ADP-ribosylation factor 3.

SEQ ID NO: 307 is the determined cDNA sequence of 20951, showing homology to Human IFP53 or WRS for tryptophanyl-tRNA synthetase.

SEQ ID NO: 308 is the determined cDNA sequence of 20952, showing homology to Human cyclin-dependent protein kinase.

SEQ ID NO: 309 is the determined cDNA sequence of 20957, showing homology to Human alpha-tubulin isoform 1.

SEQ ID NO: 310 is the determined cDNA sequence of 20959, showing homology to Human tyrosine phosphatase-61 bp deletion.

SEQ ID NO: 311 is the determined cDNA sequence of 20966, showing homology to Human tyrosine phosphatase.

SEQ ID NO: 312 is the determined cDNA sequence of B830P (20976), showing homology to Human nuclear factor NF 45.

SEQ ID NO: 313 is the determined cDNA sequence of B829P (20977), owing homology to Human delta-6 fatty acid desaturase.

SEQ ID NO: 314 is the determined cDNA sequence of 20978, showing homology to Human nuclear aconitase.

SEQ ID NO: 315 is the determined cDNA sequence of clone 23176.

SEQ ID NO: 316 is the determined cDNA sequence of clone 23140.

SEQ ID NO: 317 is the determined cDNA sequence of clone 23166.

SEQ ID NO: 318 is the determined cDNA sequence of clone 23167.

SEQ ID NO: 319 is the determined cDNA sequence of clone 23177.

SEQ ID NO: 320 is the determined cDNA sequence of clone 23217.

SEQ ID NO: 321 is the determined cDNA sequence of clone 23169.

SEQ ID NO: 322 is the determined cDNA sequence of clone 23160.

SEQ ID NO: 323 is the determined cDNA sequence of clone 23182.

SEQ ID NO: 324 is the determined cDNA sequence of clone 23232.

SEQ ID NO: 325 is the determined cDNA sequence of clone 23203.

SEQ ID NO: 326 is the determined cDNA sequence of clone 23198.

SEQ ID NO: 327 is the determined cDNA sequence of clone 23224.

SEQ ID NO: 328 is the determined cDNA sequence of clone 23142.

SEQ ID NO: 329 is the determined cDNA sequence of clone 23138.

SEQ ID NO: 330 is the determined cDNA sequence of clone 23147.

SEQ ID NO: 331 is the determined cDNA sequence of clone 23148.

SEQ ID NO: 332 is the determined cDNA sequence of clone 23149.

SEQ ID NO: 333 is the determined cDNA sequence of clone 23172.

SEQ ID NO: 334 is the determined cDNA sequence of clone 23158.

SEQ ID NO: 335 is the determined cDNA sequence of clone 23156.

SEQ ID NO: 336 is the determined cDNA sequence of clone 23221.

SEQ ID NO: 337 is the determined cDNA sequence of clone 23223.

SEQ ID NO: 338 is the determined cDNA sequence of clone 23155.

SEQ ID NO: 339 is the determined cDNA sequence of clone 23225.

SEQ ID NO: 340 is the determined cDNA sequence of clone 23226.

SEQ ID NO: 341 is the determined cDNA sequence of clone 23228.

SEQ ID NO: 342 is the determined cDNA sequence of clone 23229.

SEQ ID NO: 343 is the determined cDNA sequence of clone 23231.

SEQ ID NO: 344 is the determined cDNA sequence of clone 23154.

SEQ ID NO: 345 is the determined cDNA sequence of clone 23157.

SEQ ID NO: 346 is the determined cDNA sequence of clone 23153.

SEQ ID NO: 347 is the determined cDNA sequence of clone 23159.

SEQ ID NO: 348 is the determined cDNA sequence of clone 23152.

SEQ ID NO: 349 is the determined cDNA sequence of clone 23161.

SEQ ID NO: 350 is the determined cDNA sequence of clone 23162.

SEQ ID NO: 351 is the determined cDNA sequence of clone 23163.

SEQ ID NO: 352 is the determined cDNA sequence of clone 23164.

SEQ ID NO: 353 is the determined cDNA sequence of clone 23165.

SEQ ID NO: 354 is the determined cDNA sequence of clone 23151.

SEQ ID NO: 355 is the determined cDNA sequence of clone 23150.

SEQ ID NO: 356 is the determined cDNA sequence of clone 23168.

SEQ ID NO: 357 is the determined cDNA sequence of clone 23146.

SEQ ID NO: 358 is the determined cDNA sequence of clone 23170.

SEQ ID NO: 359 is the determined cDNA sequence of clone 23171.

SEQ ID NO: 360 is the determined cDNA sequence of clone 23145.

SEQ ID NO: 361 is the determined cDNA sequence of clone 23174.

SEQ ID NO: 362 is the determined cDNA sequence of clone 23175.

SEQ ID NO: 363 is the determined cDNA sequence of clone 23144.

SEQ ID NO: 364 is the determined cDNA sequence of clone 23178.

SEQ ID NO: 365 is the determined cDNA sequence of clone 23179.

SEQ ID NO: 366 is the determined cDNA sequence of clone 23180.

SEQ ID NO: 367 is the determined cDNA sequence of clone 23181.

SEQ ID NO: 368 is the determined cDNA sequence of clone 23143.

SEQ ID NO: 369 is the determined cDNA sequence of clone 23183.

SEQ ID NO: 370 is the determined cDNA sequence of clone 23184.

SEQ ID NO: 371 is the determined cDNA sequence of clone 23185.

SEQ ID NO: 372 is the determined cDNA sequence of clone 23186.

SEQ ID NO: 373 is the determined cDNA sequence of clone 23187.

SEQ ID NO: 374 is the determined cDNA sequence of clone 23190.

SEQ ID NO: 375 is the determined cDNA sequence of clone 23189.

SEQ ID NO: 376 is the determined cDNA sequence of clone 23202.

SEQ ID NO: 378 is the determined cDNA sequence of clone 23191.

SEQ ID NO: 379 is the determined cDNA sequence of clone 23188.

SEQ ID NO: 380 is the determined cDNA sequence of clone 23194.

SEQ ID NO: 381 is the determined cDNA sequence of clone 23196.

SEQ ID NO: 382 is the determined cDNA sequence of clone 23195.

SEQ ID NO: 383 is the determined cDNA sequence of clone 23193.

SEQ ID NO: 384 is the determined cDNA sequence of clone 23199.

SEQ ID NO: 385 is the determined cDNA sequence of clone 23200.

SEQ ID NO: 386 is the determined cDNA sequence of clone 23192.

SEQ ID NO: 387 is the determined cDNA sequence of clone 23201.

SEQ ID NO: 388 is the determined cDNA sequence of clone 23141.

SEQ ID NO: 389 is the determined cDNA sequence of clone 23139.

SEQ ID NO: 390 is the determined cDNA sequence of clone 23204.

SEQ ID NO: 391 is the determined cDNA sequence of clone 23205.

SEQ ID NO: 392 is the determined cDNA sequence of clone 23206.

SEQ ID NO: 393 is the determined cDNA sequence of clone 23207.

SEQ ID NO: 394 is the determined cDNA sequence of clone 23208.

SEQ ID NO: 395 is the determined cDNA sequence of clone 23209.

SEQ ID NO: 396 is the determined cDNA sequence of clone 23210.

SEQ ID NO: 397 is the determined cDNA sequence of clone 23211.

SEQ ID NO: 398 is the determined cDNA sequence of clone 23212.

SEQ ID NO: 399 is the determined cDNA sequence of clone 23214.

SEQ ID NO: 400 is the determined cDNA sequence of clone 23215.

SEQ ID NO: 401 is the determined cDNA sequence of clone 23216.

SEQ ID NO: 402 is the determined cDNA sequence of clone 23137.

SEQ ID NO: 403 is the determined cDNA sequence of clone 23218.

SEQ ID NO: 404 is the determined cDNA sequence of clone 23220.

SEQ ID NO: 405 is the determined cDNA sequence of clone 19462.

SEQ ID NO: 406 is the determined cDNA sequence of clone 19430.

SEQ ID NO: 407 is the determined cDNA sequence of clone 19407.

SEQ ID NO: 408 is the determined cDNA sequence of clone 19448.

SEQ ID NO: 409 is the determined cDNA sequence of clone 19447.

SEQ ID NO: 410 is the determined cDNA sequence of clone 19426.

SEQ ID NO: 411 is the determined cDNA sequence of clone 19441.

SEQ ID NO: 412 is the determined cDNA sequence of clone 19454.

SEQ ID NO: 413 is the determined cDNA sequence of clone 19463.

SEQ ID NO: 414 is the determined cDNA sequence of clone 19419.

SEQ ID NO: 415 is the determined cDNA sequence of clone 19434.

SEQ ID NO: 416 is the determined extended cDNA sequence of B820P.

SEQ ID NO: 417 is the determined extended cDNA sequence of B821P.

SEQ ID NO: 418 is the determined extended cDNA sequence of B822P.

SEQ ID NO: 419 is the determined extended cDNA sequence of B823P.

SEQ ID NO: 420 is the determined extended cDNA sequence of B824P.

SEQ ID NO: 421 is the determined extended cDNA sequence of B825P.

SEQ ID NO: 422 is the determined extended cDNA sequence of B826P.

SEQ ID NO: 423 is the determined extended cDNA sequence of B827P.

SEQ ID NO: 424 is the determined extended cDNA sequence of B828P.

SEQ ID NO: 425 is the determined extended cDNA sequence of B829P.

SEQ ID NO: 426 is the determined extended cDNA sequence of B830P.

SEQ ID NO: 427 is the determined cDNA sequence of clone 266B4.

SEQ ID NO: 428 is the determined cDNA sequence of clone 22892.

SEQ ID NO: 429 is the determined cDNA sequence of clone 266G3.

SEQ ID NO: 430 is the determined cDNA sequence of clone 22890.

SEQ ID NO: 431 is the determined cDNA sequence of clone 264B4.

SEQ ID NO: 432 is the determined cDNA sequence of clone 22883.

SEQ ID NO: 433 is the determined cDNA sequence of clone 22882.

SEQ ID NO: 434 is the determined cDNA sequence of clone 22880.

SEQ ID NO: 435 is the determined cDNA sequence of clone 263G1.

SEQ ID NO: 436 is the determined cDNA sequence of clone 263G6.

SEQ ID NO: 437 is the determined cDNA sequence of clone 262B2.

SEQ ID NO: 438 is the determined cDNA sequence of clone 262B6.

SEQ ID NO: 439 is the determined cDNA sequence of clone 22869.

SEQ ID NO: 440 is the determined cDNA sequence of clone 21374.

SEQ ID NO: 441 is the determined cDNA sequence of clone 21362.

SEQ ID NO: 442 is the determined cDNA sequence of clone 21349.

SEQ ID NO: 443 is the determined cDNA sequence of clone 21309.

SEQ ID NO: 444 is the determined cDNA sequence of clone 21097.

SEQ ID NO: 445 is the determined cDNA sequence of clone 21096.

SEQ ID NO: 446 is the determined cDNA sequence of clone 21094.

SEQ ID NO: 447 is the determined cDNA sequence of clone 21093.

SEQ ID NO: 448 is the determined cDNA sequence of clone 21091.

SEQ ID NO: 449 is the determined cDNA sequence of clone 21089.

SEQ ID NO: 450 is the determined cDNA sequence of clone 21087.

SEQ ID NO: 451 is the determined cDNA sequence of clone 21085.

SEQ ID NO: 452 is the determined cDNA sequence of clone 21084.

SEQ ID NO: 453 is a first partial cDNA sequence of clone 2BT1-40.

SEQ ID NO: 454 is a second partial cDNA sequence of clone 2BT1-40.

SEQ ID NO: 455 is the determined cDNA sequence of clone 21063.

SEQ ID NO: 456 is the determined cDNA sequence of clone 21062.

SEQ ID NO: 457 is the determined cDNA sequence of clone 21060.

SEQ ID NO: 458 is the determined cDNA sequence of clone 21053.

SEQ ID NO: 459 is the determined cDNA sequence of clone 21050.

SEQ ID NO: 460 is the determined cDNA sequence of clone 21036.

SEQ ID NO: 461 is the determined cDNA sequence of clone 21037.

SEQ ID NO: 462 is the determined cDNA sequence of clone 21048.

SEQ ID NO: 463 is a consensus DNA sequence of B726P (referred to as B726P-spliced_seq_B726P).

SEQ ID NO: 464 is the determined cDNA sequence of a second splice form of B726P (referred to as 27490.seq_B726P).

SEQ ID NO: 465 is the determined cDNA sequence of a third splice form of B726P (referred to as 27068.seq_B726P).

SEQ ID NO: 466 is the determined cDNA sequence of a second splice form of B726P (referred to as 23113.seq_B726P).

SEQ ID NO: 467 is the determined cDNA sequence of a second splice form of B726P (referred to as 23103.seq_B726P).

SEQ ID NO: 468 is the determined cDNA sequence of a second splice form of B726P (referred to as 19310.seq_B726P).

SEQ ID NO: 469 is the predicted amino acid sequence encoded by the upstream ORF of SEQ ID NO: 463.

SEQ ID NO: 470 is the predicted amino acid sequence encoded by SEQ ID NO: 464.

SEQ ID NO: 471 is the predicted amino acid sequence encoded by SEQ ID NO: 465.

SEQ ID NO: 472 is the predicted amino acid sequence encoded by SEQ ID NO: 466.

SEQ ID NO: 473 is the predicted amino acid sequence encoded by SEQ ID NO: 467.

SEQ ID NO: 474 is the determined cDNA sequence for an alternative splice form of B726P.

SEQ ID NO: 475 is the amino acid sequence encoded by SEQ ID NO: 474.

SEQ ID NO: 476 is the isolated cDNA sequence of B720P.

SEQ ID NO: 477 is the full-length cDNA sequence of B720P.

SEQ ID NO: 478 is the amino acid sequence encoded by SEQ ID NO: 477.

SEQ ID NO: 479 is the determined cDNA sequence for clone 19465.

DETAILED DESCRIPTION OF THE INVENTION

As noted above, the present invention is generally directed to compositions and methods for using the compositions, for example in the therapy and diagnosis of cancer, such as breast cancer. Certain illustrative compositions described herein include breast tumor polypeptides, polynucleotides encoding such polypeptides, binding agents such as antibodies, antigen presenting cells (APCs) and/or immune system cells (e.g., T cells). A "breast tumor protein," as the term is used herein, refers generally to a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer.

Therefore, in accordance with the above, and as described further below, the present invention provides illustrative polynucleotide compositions having sequences set forth in SEQ ID NO: 1–175, 178, 180, 182–468, 474, 476 and 477, illustrative polypeptide compositions having amino acid sequences set forth in SEQ ID NO: 176, 179, 181, 469–473 and 475, antibody compositions capable of binding such polypeptides, and numerous additional embodiments employing such compositions, for example in the detection, diagnosis and/or therapy of human breast cancer.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.*

25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=–4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO: 1–175, 178, 180, 182–468, 474, 476 and 477, or any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et *al., Proc. Natl. Acad. Sci. USA* 94:2150–2155, 1997). Alternatively, polynucleotides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that arc 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem*. 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol*. 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J*. 6:307–311. Alternatively, plant promoters such as the small subunit of RUBISCO or heat shock promoters may be used (Coruzzi, G. et al. (1984) *EMBO J*. 3:1671–1680; Broglie, R. et al. (1984) *Science* 224:838–843; and Winter, J. et al. (1991) *Results Probl. Cell Differ*. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci*. 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci*. 81:3655–3659). In addition, transcription enhancers, such as the *Rous sarcoma* virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ*. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidinc (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transfonnants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide.

An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl.

Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNaseH while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonucleaseH (RNaseH, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within +1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein PV1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV docs not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-viral Vectors

In order to effect expression of the oligonuclcotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodicster bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozyrnes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No.92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in Vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having an amino acid sequence disclosed in SEQ ID NO: 176, 179, 181, 469–473 and 475, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO: 1–175, 178, 180, 182–468, 474, 476 and 477, or to active fragments, or to variants thereof, or to one or more nucleic acid sequences which hybridize to one or more of these sequences under conditions of moderate to high stringency. Particularly illustrative polypeptides include an amino acid sequence disclosed in SEQ ID NO: 176, 179, 181, 469–473 and 475.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml–100 $\mu$g/ml, preferably 200 ng/ml–25 $\mu$g/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be $CD4^+$ and/or $CD8^+$. Breast tumor protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic, acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidylglycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocepsule-, and Microparticle-mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of adivalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Immunogenic Compositions

In certain preferred embodiments of the present invention, immunogenic compositions, or vaccines, are provided. The immunogenic compositions will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and immunogenic compositions within the scope of the present invention may also contain other compounds, which may be biologically active or inactive. For example, one or more immunogenic portions of other tumor antigens may be present, either incorporated into a fusion polypeptide or as a separate compound, within the composition.

Illustrative immunogenic compositions may contain DNA encoding one or more of the polypeptides as described above, such that the polypeptide is generated in situ. As noted above, the DNA may be present within any of a variety of delivery systems known to those of ordinary skill in the art, including nucleic acid expression systems, .bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. No.4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. It will be apparent that an immunogenic composition may comprise both a polynucleotide and a polypeptide component. Such immunogenic compositions may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the immunogenic compositions provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffinan, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any immunogenic composition provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and immunogenic compositions to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a immunogenic composition or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as breast cancer. Within such methods, pharmaceutical compositions and immunogenic compositions are typically administered to a patient. As used herein, a "patient" refers to any warm-blooded animal, preferably a human. A patient may or may not be afflicted with cancer. Accordingly, the above pharmaceutical compositions and immunogenic compositions may be used to prevent the development of a cancer or to treat a patient afflicted with a cancer. A cancer may be diagnosed using criteria generally accepted in the art, including the presence of a malignant tumor. Pharmaceutical compositions and immunogenic compositions may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and immunogenic compositions may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such immunogenic compositions should also be capable of causing an immune response that leads to an improved clinical outcome (e.g., more frequent remissions, complete or partial or longer disease-free survival) in treated patients as compared to non-treated patients. In general, for pharmaceutical compositions and immunogenic compositions comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnosis

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about I hour and about 1 day. In general, contacting a well of a plastic microtiter plate (such as polystyrene or polyvinylchloride) with an amount of binding, agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^+$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 μg/ml). It may be desirable to incubate another aliquot of a T cell sample in the absence of breast tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–175, 178, 180, 182–468, 474, 476 and 477. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time.

In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 118 1.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO: 464–468, with the predicted amino acid sequences encoded by SEQ ID NO: 464–467 being provided in SEQ ID NO: 470–473, respectively. Using standard computer techniques, a 3,681 bp consensus DNA sequence (SEQ ID NO: 463) was created that contains two large open reading frames. The downstream ORF encodes the amino acid sequence of SEQ ID NO: 181. The predicted amino acid sequence encoded by the upstream ORF is provided in SEQ ID NO: 469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO: 474, with the corresponding amino acid sequence being provided in SEQ ID NO: 475.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 and 479 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245, 246 and 479, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

One of the cDNA clones isolated by PCR subtraction as described above (SEQ ID NO: 476; referred to as B720P) which was shown by microarray to be over-expressed in breast tumor tissues, was found to be identical to a known keratin gene. The full-length cDNA sequence of B720P is provided in SEQ ID NO: 477, with the corresponding amino acid sequence being provided in SEQ ID NO: 478.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO: 216) was over-expressed in a few breast tumors, with no over-expression in any normal tissues tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1 (SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clone 19587.1 (SEQ ID NO: 246) showed low level over-expression in some breast tumors and no significant over-expression in normal tissues.

Clone 19520.1 (SEQ ID NO: 233), showing homology to clone 102D24 on chromosome 11q13.31, was found to be over-expressed in breast tumors and in SCID tumors. Clone 19517.1 (SEQ ID NO: 237), showing homology to human PAC 128M19 clone, was found to be slightly over-expressed in the majority of breast tumors tested. Clone 19392.2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO: 405–415. Comparison of these sequences to those in the public database, as outlined above, revealed homologies between the sequences of SEQ ID NO: 408, 411, 413 and 414 and previously isolated ESTs. The sequences of SEQ ID NO: 405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO: 316–404. Comparison of these sequences with those in the public database, as described above, revealed no significant homologies to the sequence of SEQ ID NO: 366. The sequences of SEQ ID NO: 321–325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO: 427–439. The determined cDNA sequences of 22 clones identified using the modified Gemtools analysis are provided in SEQ ID NO: 440–462, wherein SEQ ID NO: 453 and 454 represent two partial, non-overlapping, sequences of the same clone.

Comparison of the clone sequences of SEQ ID NO: 436 and 437 (referred to as 263G6 and 262B2) with those in the public databases, as described above, revealed no significant homologies to previously identified sequences. The sequences of SEQ ID NO: 427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2BT1-59, 2BT1-52 and 2BT1-40, respectively) showed some homology to previously isolated expressed sequences tags (ESTs). The sequences of SEQ ID NO: 428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained by PCR-based Subtraction Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO: 416–426, respectively.

EXAMPLE 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO: 181) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., *J. Exp. Med.* 186:859–865, 1997) using IFN-gamma treated autologous fibroblasts transduced to express either B726P or an irrelevant, control, antigen as antigen presenting cells (APC). Of approximately 96 lines, one line (referred to as 6-2B) was identified that appeared to specifically recognize B726P-transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

EXAMPLE 5

Preparation and Characterization of Antibodies Against Breast Tumor Polypeptides Polyclonal antibodies against the breast tumor antigen B726P were prepared as follows.

The downstream ORF of B726P (SEQ ID NO: 181) expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2 L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the calorimetric reaction was stopped with 100 microliters of 1N $H_2SO_4$ and read immediately at 450 nm. The polyclonal antibodies showed immunoreactivity to B726P.

From the foregoing, it will be appreciated that, although specific embodiments of the invention have been described herein for the purposes of illustration, various modifications may be made without deviating from the spirit and scope of the invention.

What is claimed:

1. An isolated polypeptide consisting of the amino acid sequence set forth in SEQ ID NO: 179 or 473.

2. A fusion protein comprising at least one polypeptide according to claim 1.

3. A fusion protein according to claim 2, wherein a polynucleotide sequence encoding the fusion protein comprises an expression enhancer that increases expression of the fusion protein in a host cell transfected with the polynucleotide sequence encoding the fusion protein.

4. A fusion protein according to claim 2, wherein the fusion protein comprises a T helper epitope that is not present within any one of the polypeptides set forth in SEQ ID NO: 179 and 473.

5. A fusion protein according to claim 2, wherein the fusion protein comprises an affinity tag.

6. A composition comprising a polypeptide according to claim 1, in combination with a physiologically acceptable carrier.

7. An immunogenic composition comprising a polypeptide according to claim 1, in combination with an immunostimulant.

8. An immunogenic composition according to claim 7, wherein the immunostimulant is an adjuvant.

9. An immunogenic composition according to claim 7, wherein the immunostimulant induces a Type I response.

* * * * *